US012589145B2

(12) United States Patent
Taylor et al.

(10) Patent No.: US 12,589,145 B2
(45) **Date of Patent: \*Mar. 31, 2026**

(54) SYSTEMS TO PRODUCE B CELLS GENETICALLY MODIFIED TO EXPRESS SELECTED ANTIBODIES

(71) Applicant: Fred Hutchinson Cancer Center, Seattle, WA (US)

(72) Inventors: Justin J. Taylor, Seattle, WA (US); Howell F. Moffett, Seattle, WA (US)

(73) Assignee: Fred Hutchinson Cancer Center, Seattle, WA (US)

( \* ) Notice: Subject to any disclaimer, the term of this patent is extended or adjusted under 35 U.S.C. 154(b) by 118 days.

This patent is subject to a terminal disclaimer.

(21) Appl. No.: 18/166,151

(22) Filed: Feb. 8, 2023

(65) Prior Publication Data

US 2023/0250159 A1      Aug. 10, 2023

Related U.S. Application Data

(63) Continuation of application No. 16/757,707, filed as application No. PCT/US2018/056789 on Oct. 19, 2018, now Pat. No. 11,578,118.

(60) Provisional application No. 62/623,371, filed on Jan. 29, 2018, provisional application No. 62/580,303, filed on Nov. 1, 2017, provisional application No. 62/575,275, filed on Oct. 20, 2017.

(51) Int. Cl.

| | |
|---|---|
| *A61K 40/46* | (2025.01) |
| *A61K 39/12* | (2006.01) |
| *A61K 40/13* | (2025.01) |
| *A61K 40/24* | (2025.01) |
| *C07K 16/082* | (2026.01) |
| *C07K 16/085* | (2026.01) |
| *C07K 16/087* | (2026.01) |
| *C07K 16/10* | (2006.01) |
| *C07K 16/1282* | (2026.01) |
| *C07K 16/24* | (2006.01) |
| *C12N 5/0781* | (2010.01) |
| *C12N 15/86* | (2006.01) |
| *C12N 15/861* | (2006.01) |
| *C12N 15/90* | (2006.01) |

(52) U.S. Cl.
CPC .............. *A61K 39/12* (2013.01); *A61K 40/13* (2025.01); *A61K 40/24* (2025.01); *A61K 40/46* (2025.01); *C07K 16/082* (2013.01); *C07K 16/085* (2013.01); *C07K 16/087* (2013.01); *C07K 16/089* (2023.08); *C07K 16/1018* (2013.01); *C07K 16/1027* (2013.01); *C07K 16/1045* (2013.01); *C07K 16/1282* (2013.01); *C07K 16/241* (2013.01); *C12N 5/0635* (2013.01); *C12N 15/86* (2013.01); *C12N 15/907* (2013.01); *A61K 2239/31* (2023.05); *A61K 2239/38* (2023.05); *C12N 15/861*

(2013.01); *C12N 2310/20* (2017.05); *C12N 2510/00* (2013.01); *C12N 2750/14143* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 5,604,090 | A | 2/1997 | Alexander et al. |
| 7,981,632 | B2 | 7/2011 | Schmidt |
| 8,637,024 | B2 | 1/2014 | Ho et al. |
| 8,637,035 | B2 | 1/2014 | Wu et al. |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |
| 8,895,308 | B1 | 11/2014 | Zhang et al. |
| 8,906,616 | B2 | 12/2014 | Zhang et al. |
| 8,932,814 | B2 | 1/2015 | Cong et al. |
| 8,945,839 | B2 | 2/2015 | Zhang |
| 8,993,233 | B2 | 3/2015 | Zhang et al. |
| 8,999,641 | B2 | 4/2015 | Zhang et al. |
| 9,403,900 | B2 | 8/2016 | Williamson et al. |
| 9,469,685 | B2 | 10/2016 | Ahmed et al. |
| 9,512,204 | B2 | 12/2016 | Maynard et al. |

(Continued)

FOREIGN PATENT DOCUMENTS

| | | |
|---|---|---|
| CN | 102686609 | 9/2012 |
| CN | 105899658 | 8/2016 |

(Continued)

OTHER PUBLICATIONS

Pelletier et al., Nucleic Acids Research, 1997, 25(20): 3995-4003. (Year: 1997).*

(Continued)

*Primary Examiner* — Nicole Kinsey White

(74) *Attorney, Agent, or Firm* — C. Rachal Winger; Janina Malone; Lee & Hayes PC

(57)      ABSTRACT

Systems and methods to genetically modify B cells to express selected antibodies are described. The systems and methods can be used to: obviate the need for classical vaccinations; provide protection against infectious agents for which no vaccinations are currently available; provide protection against infectious agents when patients are otherwise immune-suppressed; and/or provide a benefit provided by a therapeutic antibody, such as in the treatment of autoimmune disorders.

20 Claims, 110 Drawing Sheets

Specification includes a Sequence Listing.

(56) References Cited

U.S. PATENT DOCUMENTS

| | | | |
|---|---|---|---|
| 2001/0034062 A1 | 10/2001 | Koenig | |
| 2002/0106729 A1* | 8/2002 | Bleck | C07K 16/3061 |
| | | | 435/456 |
| 2002/0146422 A1 | 10/2002 | Bachmann et al. | |
| 2003/0083474 A1 | 5/2003 | Schmidt | |
| 2005/0069552 A1* | 3/2005 | Bleck | C07K 16/00 |
| | | | 435/7.1 |
| 2007/0020279 A1 | 1/2007 | Johnson | |
| 2007/0243194 A1* | 10/2007 | Hariharan | A61P 35/04 |
| | | | 536/23.53 |
| 2012/0102582 A1 | 4/2012 | Haynes et al. | |
| 2012/0167237 A1 | 6/2012 | Bradley et al. | |
| 2012/0207673 A1 | 8/2012 | Christ et al. | |
| 2013/0078249 A1 | 3/2013 | Ast et al. | |
| 2014/0356908 A1 | 12/2014 | Grosveld et al. | |
| 2015/0056171 A1 | 2/2015 | Burack et al. | |
| 2016/0159866 A1 | 6/2016 | Ichtchenko et al. | |
| 2016/0159874 A1 | 6/2016 | Tavernier et al. | |

FOREIGN PATENT DOCUMENTS

| | | | |
|---|---|---|---|
| JP | 2015502149 A | 1/2015 | |
| JP | 2017505780 A | 2/2017 | |
| WO | WO2006115800 | 11/2006 | |
| WO | WO2011085247 A2 | 7/2011 | |
| WO | WO2013148256 A2 | 10/2013 | |
| WO | WO2014018423 A2 | 1/2014 | |
| WO | WO2014093595 A1 | 6/2014 | |
| WO | WO2014093622 A2 | 6/2014 | |
| WO | WO2014093635 A1 | 6/2014 | |
| WO | WO2014093655 A2 | 6/2014 | |
| WO | WO2014093661 A2 | 6/2014 | |
| WO | WO2014093694 A1 | 6/2014 | |
| WO | WO2014093701 A1 | 6/2014 | |
| WO | WO2014093709 A1 | 6/2014 | |
| WO | WO2014093712 A1 | 6/2014 | |
| WO | WO2014093718 A1 | 6/2014 | |
| WO | WO2014145599 A2 | 9/2014 | |
| WO | WO2014204723 A1 | 12/2014 | |
| WO | WO2014204724 A1 | 12/2014 | |
| WO | WO2014204725 A1 | 12/2014 | |
| WO | WO2014204726 A1 | 12/2014 | |
| WO | WO2014204727 A1 | 12/2014 | |
| WO | WO2014204728 A1 | 12/2014 | |
| WO | WO2014204729 A1 | 12/2014 | |
| WO | WO2015065964 A1 | 5/2015 | |
| WO | WO2015089351 A1 | 6/2015 | |
| WO | WO2015089354 A1 | 6/2015 | |
| WO | WO2015089364 A1 | 6/2015 | |
| WO | WO2015089419 A2 | 6/2015 | |
| WO | WO2015089427 A1 | 6/2015 | |
| WO | WO2015089462 A1 | 6/2015 | |
| WO | WO2015089465 A1 | 6/2015 | |
| WO | WO2015089473 A1 | 6/2015 | |
| WO | WO2015089486 A2 | 6/2015 | |
| WO | WO2016205711 A1 | 12/2016 | |
| WO | WO2017106657 A1 | 6/2017 | |
| WO | WO2017127807 A1 | 7/2017 | |
| WO | WO-2017176806 A1 * | 10/2017 | A61K 39/4612 |

OTHER PUBLICATIONS

Chen et al., Adv Drug Deliv Rev., 2013, 65(10):1357-1369. (Year: 2013).*
Lee et al., Mol Biol Cell., 1999, 10(7):2209-2219. (Year: 1999).*
Office Action Dated Jun. 21, 2023 for Eurasian Application No. 202090990, 2 pages.
Office Action Dated Jun. 6, 2023 for Japanese Application No. 2020-522004, 6 pages.
Israeli Office Action mailed Jan. 28, 2024 for Israeli Application No. 274082, a foreign counterpart to U.S. Pat. No. 11,578,118, 4 pages.
Canadian Office Action mailed Feb. 20, 2024 for Canadian Application No. 3,079,681, a foreign counterpart to U.S. Pat. No. 11,578,118, 4 pages.
Office Action for European Application No. 18869188.5, Dated Sep. 30, 2024, 6 pages.
Office Action for Israeli Application No. 274082, Dated Sep. 18, 2024, 4 pages.
Office Action for Japanese Application No. 2023-190846, Dated Oct. 29, 2024, 9 pages.
Schmidt & Skerra, "The Strep-tag system for one-step purification and high-affinity detection or capturing of proteins," Nature Protocols, vol. 2, No. 6, 2007, pp. 1528-1535.
Schnepp & Johnson, "Adeno-associated virus delivery of broadly neutralizing antibodies," Curr. Opin. HIV AIDS, vol. 9, No. 3, 2014, pp. 250-256.
Schumann, et al., "Generation of knock-in primary human T cells using Cas9 ribonucleoproteins," PNAS, vol. 112, No. 33, 2015, pp. 10437-10442.
Skaricic, et al., "Genetic delivery of an anti-RSV antibody to protect against pulmonary infection with RSV," Virology, vol. 378, No. 1, 2008, pp. 79-85.
Snijder, et al., "An Antibody Targeting the Fusion Machinery Neutralizes Dual-Tropic Infection and Defines a Site of Vulnerability on Epstein-Barr Virus," Immunity, vol. 48, No. 4, 2018, pp. 799-811.
Sternberg & Doudna, "Expanding the Biologist's Toolkit with CRISPR-Cas9," Mol. Cell, vol. 58, No. 4, 2015, pp. 568-574.
Stewart-Jones, et al., "A Cysteine Zipper Stabilizes a Pre-Fusion F Glycoprotein Vaccine for Respiratory Syncytial Virus," PLoS One, vol. 10, No. 6, 2015, 16 pages.
Swanson, et al., "A monomeric uncleaved respiratory syncytial virus F antigen retains prefusion-specific neutralizing epitopes," J Virol., vol. 88, No. 20, 2014, pp. 11802-11810.
Symington & Gautier, "Double-strand break end resection and repair pathway choice," Annu. Rev. Genet., vol. 45, 2011, pp. 247-271.
Taylor, et al., "A germinal center-independent pathway generates unswitched memory B cells early in the primary response," Journal of Experimental Medicine, vol. 209, No. 3, 2012, pp. 597-606.
Taylor, et al., "Apoptosis and antigen affinity limit effector cell differentiation of a single naïve B cell," Science, vol. 347, No. 6223, 2015, pp. 784-787.
Taylor, et al., "Hapten-specific naïve B cells are biomarkers of vaccine efficacy against drugs of abuse," J. Immunol. Methods, vol. 405, 2014, pp. 74-86.
Taylor, et al., "Heterogeneity in the differentiation and function of memory B cells," Trends Immunol., vol. 33, No. 12, 2012, pp. 590-597.
The IMpact-RSV Study Group, "Palivizumab, a humanized respiratory syncytial virus monoclonal antibody, reduces hospitalization from respiratory syncytial virus infection in high-risk infants. The IMpact-RSV Study Group," Pediatrics, vol. 102, No. 3 Pt. 1, 1998, pp. 531-537.
The PREVENT Study Group, "Reduction of respiratory syncytial virus hospitalization among premature infants and Infants with bronchopulmonary dysplasia using respiratory syncytial virus immune globulin prophylaxis." Pediatrics, vol. 99, No. 1, 1997, pp. 93-99.
Watson, et al., "The Individual and Population Genetics of Antibody Immunity," Cell Press, vol. 38, No. 7, 2017, pp. 459-470.
Widjaja, et al., "Recombinant Soluble Respiratory Syncytial Virus F Protein That Lacks Heptad Repeat B, Contains a GCN4 Trimerization Motif and Is Not Cleaved Displays Prefusion-Like Characteristics," PLoS One, vol. 10, No. 6, 2015, 19 pages.
Wilcox, et al., "Bezlotoxumab for Prevention of Recurrent Clostridium difficile Infection," New England Journal of Medicine, vol. 376, No. 4, 2017, pp. 305-317.
Williams, et al., "Evaluation of the response to a booster dose of hepatitis B vaccine in previously immunized healthcare workers," Vaccine, No. 19, No. 28-29, 2001, pp. 4081-4085.
Wolfe, et al., "DNA Recognition by Cys2His2 Zinc Finger Proteins," Annual Review of Biophysics and Biomolecular Structure, vol. 29, 2000, pp. 183-212.

(56) References Cited

OTHER PUBLICATIONS

Yassine, et al., "Hemagglutinin-stem nanoparticles generate heterosubtypic influenza protection," Nature Medicine, vol. 21, No. 9, 2015, pp. 1065-1070.

Zetsche, et al., "Cpf1 Is a Single RNA-Guided Endonuclease of a Class 2 CRISPR-Cas System," Cell, vol. 163, No. 3, 2015, pp. 759-771.

Chinese Office Action mailed Sep. 29, 2023 for Chinese Patent Application No. 201880080021.5, a foreign counterpart to U.S. Pat. No. 11,578,118, 24 pages.

Office Action for Ukranian Application No. a2020 02980, Dated May 10, 2024, 19 pages.

Office Action Dated Mar. 3, 2023, for Chinese Application No. 201880080021.5, 15 pages.

Aurnhammer, et al., "Universal Real-Time PCR for the Detection and Quantification of Adeno-Associated Virus Serotype 2-Derived Inverted Terminal Repeat Sequences," Human Gene Therapy Methods, vol. 23, No. 1, 2012, pp. 18-28.

Bauer & Jilg, "Hepatitis B surface antigen-specific T and B cell memory in individuals who had lost protective antibodies after hepatitis B vaccination," Vaccine, vol. 24, No. 5, 2006, pp. 572-577.

Bibikova, et al., "Enhancing Gene Targeting with Designed Zinc Finger Nucleases," Science, vol. 300, No. 5620, 2003, 1 page.

Bibikova, et al., "Targeted Chromosomal Cleavage and Mutagenesis in *Drosophila* Using Zinc-Finger Nucleases," Genetics, vol. 161, No. 3, 2002, pp. 1169-1175.

Bird, et al., "Single-chain antigen-binding proteins," Science, vol. 242, No. 4877, 1988, pp. 423-426.

Blanco, et al., "New insights for development of a safe and protective RSV vaccine," Hum. Vaccin., vol. 6, No. 6, 2010, op. 482-492.

Boch, et al., "Breaking the Code of DNA Binding Specificity of TAL-Type III Effectors," Science, vol. 326, No. 5959, 2009, pp. 1509-1512.

Broadbent, et al., "Respiratory syncytial virus, an ongoing medical dilemma: an expert commentary on respiratory syncytial virus prophylactic and therapeutic pharmaceuticals currently in clinical trials," Influenza Other Respir. Viruses, vol. 9, No. 4, 2015, pp. 169-178.

Choi, et al., "Production of Recombinant Adeno-Associated Viral Vectors for In Vitro and In Vivo Use," Molecular Biology, vol. 78, No. 1, 2007, 24 pages.

Christian, et al., "Targeting DNA Double-Strand Breaks with TAL Effector Nucleases," Genetics, vol. 186, No. 2, 2010, pp. 757-761.

Correia, et al., "Proof of principle for epitope-focused vaccine design," Nature, vol. 507, No. 7491, 2014, pp. 201-206.

Delpy, et al., "B Cell Development Arrest Upon Insertion of a neo Gene Between JH and EMu: Promoter Competition Results in Transcriptional Silencing of Germline JH and Complete V(D)J Rearrangements," Journal of Immunology, vol. 169, No. 12, 2002, pp. 6875-6882.

Deng, et al., "Pharmacokinetics and Exposure-Response Analysis of RG7667, a Combination of Two Anticytomegalovirus Monoclonal Antibodies, in a Phase 2a Randomized Trial To Prevent Cytomegalovirus Infection in High-Risk Kidney Transplant Recipients," Antimicrobial Agents and Chemotherapy, vol. 62, No. 2, 12 pages.

Dole, et al., "A First-in-Human Study To Assess the Safety and Pharmacokinetics of Monoclonal Antibodies against Human Cytomegalovirus in Healthy Volunteers," Antimicrobial Agents and Chemotherapy, vol. 60, No. 5, 2016, pp. 2881-2887.

Donnelly, et al., "Analysis of the aphthovirus 2A/2B polyprotein 'cleavage' mechanism indicates not a proteolytic reaction, but a novel translational effect: a putative ribosomal 'skip'," Journal of General Virology, vol. 82, No. 2, 2001, pp. 1013-1025.

Office Action Dated Nov. 24, 2022 for Eurasian Application No. 202090990, 5 pages.

Elliott, et al., "Gene conversion tracts from double-strand break repair in mammalian cells," Molecular and Cellular Biology, vol. 18, No. 1, 1998, pp. 93-101.

Extended European Search Report Dated Nov. 9, 2021 for European Patent Application No. 18869188.5, 12 pages.

Garg, et al., "Vaccination with the RSV fusion protein formulated with a combination adjuvant induces long-lasting protective immunity," J Gen. Virol., vol. 95, Part 5, 2014, pp. 1043-1054.

Haasken, et al., "Macrophage Scavenger Receptor 1 (Msr1, SR-A) Influences B Cell Autoimmunity by Regulating Soluble Autoantigen Concentration," Journal of Immunology, vol. 191, No. 3, 2013, pp. 1055-1062.

Hamilton, et al., "General Approach for Tetramer-Based Identification of Autoantigen-Reactive B Cells: Characterization of La- and snRNP-Reactive B Cells in Autoimmune BXD2 Mice," Journal of Immunology, vol. 194, No. 10, 2015, pp. 5022-5034.

Haryadi, et al., "Optimization of heavy chain and light chain signal peptides for high level expression of therapeutic antibodies in CHO cells," PLOS One, vol. 10, No. 2, 2015, 16 pages.

Helmreich, et al., "The secretion of antibody by isolated lymph node cells," J. Biol. Chem., vol. 236, No. 2, 1961, pp. 464-473.

Hibi and Dosch, "Limiting dilution analysis of the B cell compartment in human bone marrow," Eur. J. Immunol., vol. 16, No. 2, 1986, pp. 139-145.

Hsiau, et al., "Inference of CRISPR Edits from Sanger Trace Data," bioRxiv, 2018, 17 pages.

Isu, et al., "DNA targeting specificity of RNA-guided Cas9 nucleases," Nat. Biotechnol., vol. 31, No. 9, 2013, pp. 827-832.

Invitation to Pay Additional Fees Dated Dec. 10, 2018 for International Application No. PCT/US2018/056789, 2 pages.

Office Action Dated Oct. 18, 2022 for Japanese Application No. 2020-522004, 15 pages.

Kay, et al., "Evidence for gene transfer and expression of factor IX in haemophilia B patients treated with an AAV vector," Nature Genetics, vol. 24, No. 257, 2000, pp. 257-261.

Kim, et al., "Establishment and characterization of BALB/c lymphoma lines with B cell properties," J. Immunol., vol. 122, No. 2, 1979, pp. 549-554.

Kim, et al., "Hybrid restriction enzymes: zinc finger fusions to Fok I cleavage domain," PNAS USA, vol. 93, No. 3, 1996, pp. 1156-1160.

Koerber, et al., "An improved single-chain Fab platform for efficient display and recombinant expression," J. Mol. Biol., vol. 427, No. 2, 2015, pp. 576-586.

Li, et al., "A role for the IgH intronic enhancer Eu in enforcing allelic exclusion," Journal of Experimental Medicine, vol. 206, No. 1, 2009, pp. 153-167.

Love, et al., "Individual VH promoters vary in strength, but the frequency of rearrangement of those VH genes does not correlate with promoter strength nor enhancer-independence," Mol. Immun., vol. 37, No. 1-2, 2000, pp. 29-39.

Luo, et al., "Engineering human hematopoietic stem/progenitor cells to produce a broadly neutralizing anti-HIV antibody after in vitro maturation to human B lymphocytes," Blood, vol. 113, No. 7, 2009, pp. 1422-1431.

Malkin, et al., "Safety and immunogenicity of a live attenuated RSV vaccine in healthy RSV-seronegative children 5 to 24 months of age," PLoS One, vol. 8, No. 10, 2013, 10 pages.

Mcguire, et al., "Specifically modified Env immunogens activate B-cell precursors of broadly neutralizing HIV-1 antibodies in transgenic mice," Nature Communications, vol. 7, No. 10618, 2016, 10 pages.

McHeyzer-Williams, et al., "Molecular programming of B cell memory," Nat. Rev. Immunol., vol. 12, No. 1, 2011, pp. 24-34.

McLellan, et al., "Structure-Based Design of a Fusion Glycoprotein Vaccine for Respiratory Syncytial Virus," Science, vol. 342, No. 6158, 2013, pp. 592-598.

Meissner & Kimberlin, "RSV immunoprophylaxis: does the benefit justify the cost?," Pediatrics, vol. 132, No. 5, 2013, pp. 915-918.

Miller, et al., "A TALE nuclease architecture for efficient genome editing," Nature Biotechnology, vol. 29, No. 2, 2011, pp. 143-148.

Miller, et al., "An improved zinc-finger nuclease architecture for highly specific genome editing," Nature Biotechnology, vol. 25, No. 7, 2007, pp. 778-785.

(56)  References Cited

OTHER PUBLICATIONS

Miller, et al., "Repetitive zinc-binding domains in the protein transcription factor IIIA from Xenopus oocytes," EMBO J., vol. 4, No. 6, 1985, pp. 1609-1614.

Moscou & Bogdanove, "A Simple Cipher Governs DNA Recognition by TAL Effectors," Science, vol. 326, No. 5959, 2009, 1 page.

Munir, et al., "Nonstructural Proteins 1 and 2 of Respiratory Syncytial Virus Suppress Maturation of Human Dendritic Cells," Journal of Virology, vol. 82, No. 17, 2008, pp. 8780-8796.

Murphy, et al., "Enhanced pulmonary histopathology is observed in cotton rats immunized with formalin-inactivated respiratory syncytial virus (RSV) or purified F glycoprotein and challenged with RSV 3-6 months after immunization," Vaccine, vol. 8, No. 5, 1990, pp. 497-502.

Nakai, et al., "Adeno-associated viral vector-mediated gene transfer of human blood coagulation factor IX into mouse liver," Blood, vol. 91, No. 12, 1998, pp. 4600-4607.

Nanton, et al., "Direct visualization of endogenous Salmonella-specific B cells reveals a marked delay in clonal expansion and germinal center development," Eur. J. Immunol., vol. 45, No. 2, 2015, pp. 428-441.

Pape, et al., "Different B cell populations mediate early and late memory during an endogenous immune response," Science, vol. 331, No. 6021, 2011, pp. 1203-1207.

Search Report and Written Opinion Dated Feb. 15, 2019 for International Application No. PCT/US2018/056789, 17 pages.

Chinese Office Action Dated Mar. 22, 2024 for Chinese Application No. 201880080021.5, a foreign counterpart to U.S. Pat. No. 11,578,118, 10 pages.

Examination Report for Australian Application No. 2018351072, Dated Jun. 18, 2024, 6 pages.

Office Action for Eurasian Application No. 202490247, Dated Jul. 4, 2024, 9 pages.

Fife, et al., "Inhibition of T cell activation and autoimmune diabetes using a B cell surface-linked CTLA-4 agonist" J. Clin. Invest., vol. 116, No. 8, 2006, pp. 2252-2261.

Li, et al., "A role for the IgHintronic enhancer E in enforcing allelic exclusion", The Journal of Experimental Medicine, vol. 1.206, No. 1, Dec. 29, 2008, pp. 153-167.

Chen, et al., "Mutations of the intronic IgH enhancer and its flanking sequences differentially affect accessibility of the JH locus", The EMBO Journal, vol. 12, No. 12, 1993, pp. 4635-4645.

Yeo and Burge, "Maximum entropy modeling of short sequence motifs with applications to RNA splicing signals," J Comput Biol. 2004, vol. 11, No. 2-3, pp. 377-394.

* cited by examiner

FIG. 6A

Antibody genes

IgH

IgL

FIG. 6B

Antibody protein

Light chain (IgL)

Heavy chain (IgH)

VDJ recombination (2000kb)          Class switch recombination (100kb)

FIG. 11A

Human Eμ intronic enhancer sequence:

GTAGTTGAAAAGTGGTCTTGAAAAATACTAAAATGAAGGCCACTCTATCAGAATATCAAAGT
GTTTCTCCTTAATCACAAAGAGAAAACGAGTTAACCTAAAAAGATTGTGAACACAGTCATTA
TGAAAATAATGCTCTGAGGTATCGAAAAAGTATTTGAGATTAATTATCACATGAAGGGATAA
CAAGCTAATTTAAAAAACTTTTTGAATACAGTCATAAACTCTCCCTAAGACTGTTTAATTTCT
TAAACATCTTACTTTAAAAATGAATGCAGTTTAGAAGTTGATATGCTGTTTGCACAAACTAGC
AGTTGATAAGCTAAGATTGGAAATGAAATTCAGATAGTTAAAAAAAGCCTTTTCAGTTTCGG
TCAGCCTCGCCTTATTTTAGAAACGCAAATTGTCCAGGTGTTGTTTTGCTCAGTAGAGCACT
TTCAGATCTGGGCCTGGGCAAAACCACCTCTTCACAACCAGAAGTGATAAATTTACCAATT
GTGTTTTTTGCTTCCTAAAATAGACTCTCGCGGTGACCTGCTTCCTGCCACCTGCTGTGG
GTGCCGGAGACCCCCATGCAGCCATCTTGACTCTAATTCATCATCTGCTTCCAGCTTCGCT
CAATTAATTAAAAAAATAAACTTGATTTATGATGGTCAAAACGCAGTCCCGCATCGGGGCCG
ACAGCACTGTGCTAGTATTTCTTAGCTGAGCTTGCTTTGGCCTCAATTCCAGACACATATCA
CTCATGGGTGTTAATCAAATGATAAGAATTTCAAATACTTGGACAGTTAAAAAAATTAATATA
CTTGAAAATCTCTCACATTTTTAAGTCA (SEQ ID NO: 85)

Human Intronic Region 1 to Target for Genetic Construct Insertion:

CTACATGGACGTCTGGGGCAAAGGGACCACGGTCACCGTCTCCTCAGGTAAGAATGGCCA
CTCTAGGGCCTTTGTTTTCTGCTACTGCCTGTGGGGTTTCCTGAGCATTGCAGGTTGGTCC
TCGGGGCATGTTCCGAGGGGACCTGGGCGGACTGGCCAGGAGGGGATGGGCACTGGGG
TGCCTTGAGGATCTGGGAGCCTCTGTGGATTTTCCGATGCCTTTGGAAAATGGGACTCAG
GTTGGGTGCGTCTGATGGAGTAACTGAGCCTGGGGGCTTGGGGAGCCACATTTGGACGA
GATGCCTGAACAAACCAGGGGTCTTAGTGATGGCTGAGGAATGTGTCTCAGGAGCGGTGT
CTGTAGGACTGCAAGATCGCTGCACAGCAGCGAATCGTGAAATATTTTCTTTAGAATTATGA
GGTGCGCTGTGTGTCAACCTGCATCTTAAATTCTTTATTGGCTGGAAAGAGAACTGTCGGA
GTGGGTGAATCCAGCCAGGAGGGACGCGTAGCCCCGGTCTTGATGAGAGCAGGGTTGGG
GGCAGGGGTAGCCCAGAAACGGTGGCTGCCGTCCTGACAGGGGCTTAGGGAGGCTCCAG
GACCTCAGTGCCTTGAAGCTGGTTTCCATGAGAAAAGGATTGTTTATCTTAGGAGGCATGC
TTACTGTTAAAAGACAGGATATGTTTGAAGTGGCTTCTGA GAAAAATGGTTAAGAAAATTAT
(SEQ ID NO: 1)

FIG. 11B

Human_Region_1_gRNA_1      GGTCCTCGGGGCATGTTCCGAGG (SEQ ID NO: 5)

Human_Region_1_gRNA_2      GGGCATGTTCCGAGGGGACCTGG (SEQ ID NO: 6)

Human_Region_1_gRNA_3      GCATTGCAGGTTGGTCCTCGGGG (SEQ ID NO: 7)

Human_Region_1_gRNA_4      TCCTCGGGGCATGTTCCGAGGGG (SEQ ID NO: 8)

Human_Region_1_gRNA_5      GGCATGTTCCGAGGGGACCTGGG (SEQ ID NO: 9)

Human_Region_1_gRNA_6      GTCTCAGGAGCGGTGTCTGTAGG (SEQ ID NO: 10)

Human_Region_1_gRNA_7      AGCATTGCAGGTTGGTCCTCGGG (SEQ ID NO: 11)

Human_Region_1_gRNA_8      CCTGGGCGGACTGGCCAGGAGGG (SEQ ID NO: 12)

Human_Region_1_gRNA_9      ACTGGGGTGCCTTGAGGATCTGG (SEQ ID NO: 13)

Human_Region_1_gRNA_10     CCCCAGTGCCCATCCCCTCCTGG (SEQ ID NO: 14)

Human_Region_1_gRNA_11     CTAAGACCCCTGGTTTGTTCAGG (SEQ ID NO: 15)

Human_Region_1_gRNA_12     TGTGGATTTTCCGATGCCTTTGG (SEQ ID NO: 16)

Human_Region_1_gRNA_13     AGGACCAACCTGCAATGCTCAGG (SEQ ID NO: 17)

Human_Region_1_gRNA_14     CTCAGGTTGGGTGCGTCTGATGG (SEQ ID NO: 18)

Human_Region_1_gRNA_15     CCCTCCTGGCCAGTCCGCCCAGG (SEQ ID NO: 19)

Human_Region_1_gRNA_16     GGCCAGGAGGGGATGGGCACTGG (SEQ ID NO: 20)

Human_Region_1_gRNA_17     GAGATGCCTGAACAAACCAGGGG (SEQ ID NO: 21)

Human_Region_1_gRNA_18     AGGGGTCTTAGTGATGGCTGAGG (SEQ ID NO: 22)

Human_Region_1_gRNA_19     ATGGGCACTGGGGTGCCTTGAGG (SEQ ID NO: 23)

Human_Region_1_gRNA_20     TTCCGATGCCTTTGGAAAATGGG (SEQ ID NO: 24)

FIG. 11B (cont'd)

Human _1_gRNA_1     GGUCCUCGGGGCAUGUUCCG (SEQ ID NO: 290)

Human _1_gRNA_2     GGGCAUGUUCCGAGGGGACC (SEQ ID NO: 291)

Human _1_gRNA_3     GCAUUGCAGGUUGGUCCUCG (SEQ ID NO: 88)

Human _1_gRNA_4     UCCUCGGGGCAUGUUCCGAG (SEQ ID NO: 292)

Human _1_gRNA_5     GGCAUGUUCCGAGGGGACCU (SEQ ID NO: 293)

Human _1_gRNA_6     GUCUCAGGAGCGGUGUCUGU (SEQ ID NO: 89)

Human _1_gRNA_7     AGCAUUGCAGGUUGGUCCUC (SEQ ID NO: 294)

Human _1_gRNA_8     CCUGGGCGGACUGGCCAGGA (SEQ ID NO: 295)

Human _1_gRNA_9     ACUGGGGUGCCUUGAGGAUC (SEQ ID NO: 296)

Human _1_gRNA_10     CCCCAGUGCCCAUCCCUCC (SEQ ID NO: 297)

Human _1_gRNA_11     CUAAGACCCCUGGUUUGUUC (SEQ ID NO: 298)

Human _1_gRNA_12     UGUGGAUUUUCCGAUGCCUU (SEQ ID NO: 299)

Human _1_gRNA_13     AGGACCAACCUGCAAUGCUC (SEQ ID NO: 300)

Human _1_gRNA_14     CUCAGGUUGGGUGCGUCUGA (SEQ ID NO: 301)

Human _1_gRNA_15     CCCUCCUGGCCAGUCCGCCC (SEQ ID NO: 302)

Human _1_gRNA_16     GGCCAGGAGGGGAUGGGCAC (SEQ ID NO: 303)

Human _1_gRNA_17     GAGAUGCCUGAACAAACCAG (SEQ ID NO: 304)

Human _1_gRNA_18     AGGGGUCUUAGUGAUGGCUG (SEQ ID NO: 305)

Human _1_gRNA_19     AUGGGCACUGGGGUGCCUUG (SEQ ID NO: 306)

Human _1_gRNA_20     UUCCGAUGCCUUUGGAAAAU (SEQ ID NO: 307)

FIG. 12A

Human Intronic Region 2 to Target for Genetic Construct Insertion

CTCACTTTAGGATAAGTTTTAGGTAAAATGTGCATCATTATCCTGAATTATTTCAGTTAAGCA
TGTTAGTTGGTGGCATAAGAGAAAACTCAATCAGATAGTGCTGAAGACAGGACTGTGGAGA
CACCTTAGAAGGACAGATTCTGTTCCGAATCACCGATGCGGCGTCAGCAGGACTGGCCTA
GCGGAGGCTCTGGGAGGGTGGCTGCCAGGCCCGGCCTGGGCTTTGGGTCTCCCCGGAC
TACCCAGA GCTGGGATGCGTGGCTTCTGCTGCCGGGCCGACTGGCTGCTCAGGCCCCA
GCCCTTGTTAATGGACTTGGAGGAATGATTCCATGCCAAAGCTTTGCAAGGCTCGCAGTGA
CCAGGCGCCCGACATGGTAAGAGACAGGCAGCCGCCGCTGCTGCATTTGCTTCTCTTAAA
ACTTTGTATTTGACGTCTTATTTCCACTAGAAGGGGAACTGGTCTTAATTGCTTGATGAAGA
GCAGGAGACTCATTTATGTGAGTCTTTTGAGTGACCATTGTCTGGGTCACTCCCATTTAACT
TTCCCTAAAGCCCATTTGAAGGAGAGGTCGCACGAGCTGCTCCACAACCTCTGAATGGGG
ATGGCATGGGTAATGATGCTTGAGAACATACCAAGCCCCACTGGCATCGCCCTTGTCTAAG
TCATTGACTGTAGGTCATCATCGCACCCTTGAAAGTAGCCCATGCCTTCCAAAGCGATTTAT
GGTAAATGGCAGAATTTTAAGTGGCAAATTCAGATAAAATGCATTTCTTGGTTGTTTCCAAT
GATGACTGTT ATCTAGAGGGAATTTAAAGGCAGGGGTTTACTGCAGACTCAGAAGGGAGG
GGATGCTCCGGGAAGGTGGAGGCTCTGAGCATCTCAATACCCTCCTCTTGGTGCAGAAGA
TATGCTGCCACTTCTAGAGCAAGGGGACCTGCTCATTTTTATCACAGCACAGGCTCCTAAA
TTCTTGGTCTCATTCTCAAGATGTTTTAATGACTTTAAAGCAGCAAAGAAATATTCCACCCA
GGTAGTGGAGGGTGGTAATGATTGGTAATGCTTTGGAACCAAAACCCAGGTGGCGCTGGG
GCAGGAC TGCAGGGAACTGGGGTATCAAGTAGAGGGAGACAAAAGATGGAAGCCAGC
CTGGCTGTGCAGGAACCCGGCAATGAGATGGCTTTAGCTGAGACAAGCAGGTCTGGTGG
GCTGACCATTTCTGGCCATGACAACTCCATCCAGCTTTCAGAAATGGACTCAGATGGGCAA
AACTGACCTAAGCTGACCTAGACTAAACAAGGCTGAAC (SEQ ID NO: 2)

FIG. 12B

Human_region2_gRNA_1     CTGACGCCGCATCGGTGATT<u>CGG</u> (SEQ ID NO: 25)

Human_region2_gRNA_2     TTAGACAAGGGCGATGCCAGT<u>GG</u> (SEQ ID NO: 26)

Human_region2_gRNA_3     CGTGCGACCTCTCCTTCAAA<u>TGG</u> (SEQ ID NO: 27)

Human_region2_gRNA_4     AGCATATCTTCTGCACCAAG<u>AGG</u> (SEQ ID NO: 28)

Human_region2_gRNA_5     ATATTCCACCCAGGTAGTGG<u>AGG</u> (SEQ ID NO: 29)

Human_region2_gRNA_6     GTGCGACCTCTCCTTCAAAT<u>GGG</u> (SEQ ID NO: 30)

Human_region2_gRNA_7     AGGTCCCCTTGCTCTAGAAG<u>TGG</u> (SEQ ID NO: 31)

Human_region2_gRNA_8     CTCTAGATAACAGTCATCAT<u>TGG</u> (SEQ ID NO: 32)

Human_region2_gRNA_9     TTGTCTAAGTCATTGACTGT<u>AGG</u> (SEQ ID NO: 33)

Human_region2_gRNA_10     CCAAAGCGATTTATGGTAAA<u>TGG</u> (SEQ ID NO: 34)

Human_region2_gRNA_11     TCTTTTGAGTGACCATTGTC<u>TGG</u> (SEQ ID NO: 35)

Human_region2_gRNA_12     CCATTTACCATAAATCGCTT<u>TGG</u> (SEQ ID NO: 36)

Human_region2_gRNA_13     AGGGCGATGCCAGTGGGGCT<u>TGG</u> (SEQ ID NO: 37)

Human_region2_gRNA_14     AGCTAAAGCCATCTCATTGC<u>CGG</u> (SEQ ID NO: 38)

Human_region2_gRNA_15     CCACAACCTCTGAATGGGGA<u>TGG</u> (SEQ ID NO: 39)

Human_region2_gRNA_16     TTAATTGCTTGATGAAGAGC<u>AGG</u> (SEQ ID NO: 40)

Human_region2_gRNA_17     TAGACAAGGGCGATGCCAGT<u>GGG</u> (SEQ ID NO: 41)

Human_region2_gRNA_18     AAGCTGACCTAGACTAAACA<u>AGG</u> (SEQ ID NO: 42)

Human_region2_gRNA_19     GCAGGAACCCGGCAATGAGA<u>TGG</u> (SEQ ID NO: 43)

Human_region2_gRNA_20     TCTGTTCCGAATCACCGATG<u>CGG</u> (SEQ ID NO: 44)

FIG. 12B (cont'd)

Human_2_gRNA_1     CUGACGCCGCAUCGGUGAUU (SEQ ID NO: 308)

Human_2_gRNA_2     UUAGACAAGGGCGAUGCCAG (SEQ ID NO: 309)

Human_2_gRNA_3     CGUGCGACCUCUCCUUCAAA (SEQ ID NO: 310)

Human_2_gRNA_4     AGCAUAUCUUCUGCACCAAG (SEQ ID NO: 311)

Human_2_gRNA_5     AUAUUCCACCCAGGUAGUGG (SEQ ID NO: 312)

Human_2_gRNA_6     GUGCGACCUCUCCUUCAAAU (SEQ ID NO: 313)

Human_2_gRNA_7     AGGUCCCUUGCUCUAGAAG (SEQ ID NO: 314)

Human_2_gRNA_8     CUCUAGAUAACAGUCAUCAU (SEQ ID NO: 315)

Human_2_gRNA_9     UUGUCUAAGUCAUUGACUGU (SEQ ID NO: 316)

Human_2_gRNA_10     CCAAAGCGAUUUAUGGUAAA (SEQ ID NO: 317)

Human_2_gRNA_11     UCUUUUGAGUGACCAUUGUC (SEQ ID NO: 318)

Human_2_gRNA_12     CCAUUUACCAUAAAUCGCUU (SEQ ID NO: 319)

Human_2_gRNA_13     AGGGCGAUGCCAGUGGGGCU (SEQ ID NO: 320)

Human_2_gRNA_14     AGCUAAAGCCAUCUCAUUGC (SEQ ID NO: 321)

Human_2_gRNA_15     CCACAACCUCUGAAUGGGGA (SEQ ID NO: 322)

Human_2_gRNA_16     UUAAUUGCUUGAUGAAGAGC (SEQ ID NO: 323)

Human_2_gRNA_17     UAGACAAGGGCGAUGCCAGU (SEQ ID NO: 324)

Human_2_gRNA_18     AAGCUGACCUAGACUAAACA (SEQ ID NO: 325)

Human_2_gRNA_19     GCAGGAACCCGGCAAUGAGA (SEQ ID NO: 326)

Human_2_gRNA_20     UCUGUUCCGAAUCACCGAUG (SEQ ID NO: 327)

FIG. 13A

Mouse Eμ intronic enhancer sequence:

AGTCTAGATAATTGCATTCATTTAAAAAAAAAGTCTTTCTCCTAAAATGAATACTCAGAAAGT
GGTCTTGAAAAAGATTTGTGAAGCCGTTTTGACCAGAATGTCAAAGTCTTAATAGTAAGGCA
AAACAAACAACTAAAAAAGATCATGAACAAAGTCACTGTAAATGCTTCGGGTATTGGAAAAG
AATTGAATGGAGACCAATAATCAGAGGGAAGAATAATAGAGTAATTTTAAGAAGTTTTCTAA
ATATATTAGAAATTAAAGACACTAAAGTCCTTCAATTTCTTACATAACCTAATTTTGAAAATGA
ATTCTAAATACATTTTAGAAGTCGATAAACTTAAGTTTGGGGAAACTAGAACTACTCAAGCT
AAAATTAAAAGGTTGAACTCAATAAGTTAAAAGAGGACCTCTCCAGTTTCGGCTGAATCCTC
AACTTATTTTAGAAATGCAAATTACCCAGGTGGTGTTTGCTCAGCCTGGACTTTCGGTTTG
GTGGGGCTGGACAGAGTGTTTCAAAACCACTTCTTCAAACCACAGCTACAAGTTTACCTAG
TGGTTTTATTTTCCCTTCCCCAAATAGCCTTGCCACATGACCTGCTTCCTGCCAGCTGCTGC
AGGTGTTCTGGTTCTGATCGGCCATCTTGACTCCAACTCAACATTGCTCAATTCATTTAAAA
ATATTTGAAACTTAATTTATTATTGTTAAAAGTCAGTTCTGAATAGGTTATGAGAGAGCCTCA
CTCCCATTCCTCGGTTAAACTTTAAGTAATATCAGTTCTACACAAACAAGACCTCAAACTGA
TTGACAAGAATTTTGGACATTTAAAAAAATGAGTACTTGAAAACCCTCTCACATTTTAAAGTC
ACAGTATTTAACTATTTTTCCTAGGAACCAACTTAAGAGTAAAAGCAACATCTTCTAATATTC
CATACACATACTTCTGTGTTCCTTTGAAAGCTGGACTTTTGCAGGCTCCACCAGACCTCTCT
AGACA (SEQ ID NO: 86)

Mouse Intronic Region 1 to Target for Genetic Construct Insertion:

GGACTACTGGGGTCAAGGAACCTCAGTCACCGTCTCCTCAGGTAAGAATGGCCTCTCCAG
GTCTTTATTTTTAACCTTTGTTATGGAGTTTTCTGAGCATTGCAGACTAATCTTGGATATTTG
TCCCTGAGGGAGCCGGCTGAGAGAAGTTGGGAAATAAACTGTCTAGGGATCTCAGAGCCT
TTAGGACAGATTATCTCCACATCTTTGAAAAACTAAGAATCTGTGTGATGGTGTTGGTGGAG
TCCCTGGATGATGGGATAGGGACTTTGGAGGCTCATTTGAAGAAGATGCTAAAACAATCCT
ATGGCTGGAGGGATAGTTGGGGCTGTAGTTGGAGATTTTCAGTTTTTAGAATAAAAGTATTA
GTTGTGGAATATACTTCAGGACCACCTCTGTGACAGCATTTATACAGTATCCGATGCATAG
GGACAAAGAGTGGAGTGGGGCACTTTCTTTAGATTTGTGAGGAATGTTCCGCACTAGATTG
TTTAAAACTT CATTTGTTGGAAGGAGAGCTGTCTTAGTGATTGAGTCAAGGGAGAAAGGC
ATCTAGCCTCGGTCTCAAAAGGGTAGTTGCTG (SEQ ID NO: 3)

FIG. 13B

Mouse_Region_1_gRNA_1     CAACTACCCTTTTGAGACCGAGG (SEQ ID NO: 45)

Mouse_Region_1_gRNA_2     TTATACAGTATCCGATGCATAGG (SEQ ID NO: 46)

Mouse_Region_1_gRNA_3     TATACAGTATCCGATGCATAGGG (SEQ ID NO: 47)

Mouse_Region_1_gRNA_4     CATCTAGCCTCGGTCTCAAAGG (SEQ ID NO: 48)

Mouse_Region_1_gRNA_5     CACTCTTTGTCCCTATGCATCGG (SEQ ID NO: 49)

Mouse_Region_1_gRNA_6     ATCTAGCCTCGGTCTCAAAAGGG (SEQ ID NO: 50)

Mouse_Region_1_gRNA_7     AAGTTTTAAACAATCTAGTGCGG (SEQ ID NO: 51)

Mouse_Region_1_gRNA_8     AAGATGCTAAACAATCCTATGG (SEQ ID NO: 52)

Mouse_Region_1_gRNA_9     TGCTAAACAATCCTATGGCTGG (SEQ ID NO: 53)

Mouse_Region_1_gRNA_10     AAGTCCCTATCCCATCATCCAGG (SEQ ID NO: 54)

Mouse_Region_1_gRNA_11     GGGAGAAAGGCATCTAGCCTCGG (SEQ ID NO: 55)

Mouse_Region_1_gRNA_12     TGAGCATTGCAGACTAATCTTGG (SEQ ID NO: 56)

Mouse_Region_1_gRNA_13     TTAGTTGTGGAATATACTTCAGG (SEQ ID NO: 57)

Mouse_Region_1_gRNA_14     TGGTGGAGTCCCTGGATGATGGG (SEQ ID NO: 58)

Mouse_Region_1_gRNA_15     GTGGAGATAATCTGTCCTAAAGG (SEQ ID NO: 59)

Mouse_Region_1_gRNA_16     AGTCCCTATCCCATCATCCAGGG (SEQ ID NO: 60)

Mouse_Region_1_gRNA_17     ATCTTGGATATTTGTCCCTGAGG (SEQ ID NO: 61)

Mouse_Region_1_gRNA_18     GGGATAGTTGGGGCTGTAGTTGG (SEQ ID NO: 62)

Mouse_Region_1_gRNA_19     CAGGTAAGAATGGCCTCTCCAGG (SEQ ID NO: 63)

Mouse_Region_1_gRNA_20     TCTCTCAGCCGGCTCCCTCAGGG (SEQ ID NO: 64)

FIG. 13B (cont'd)

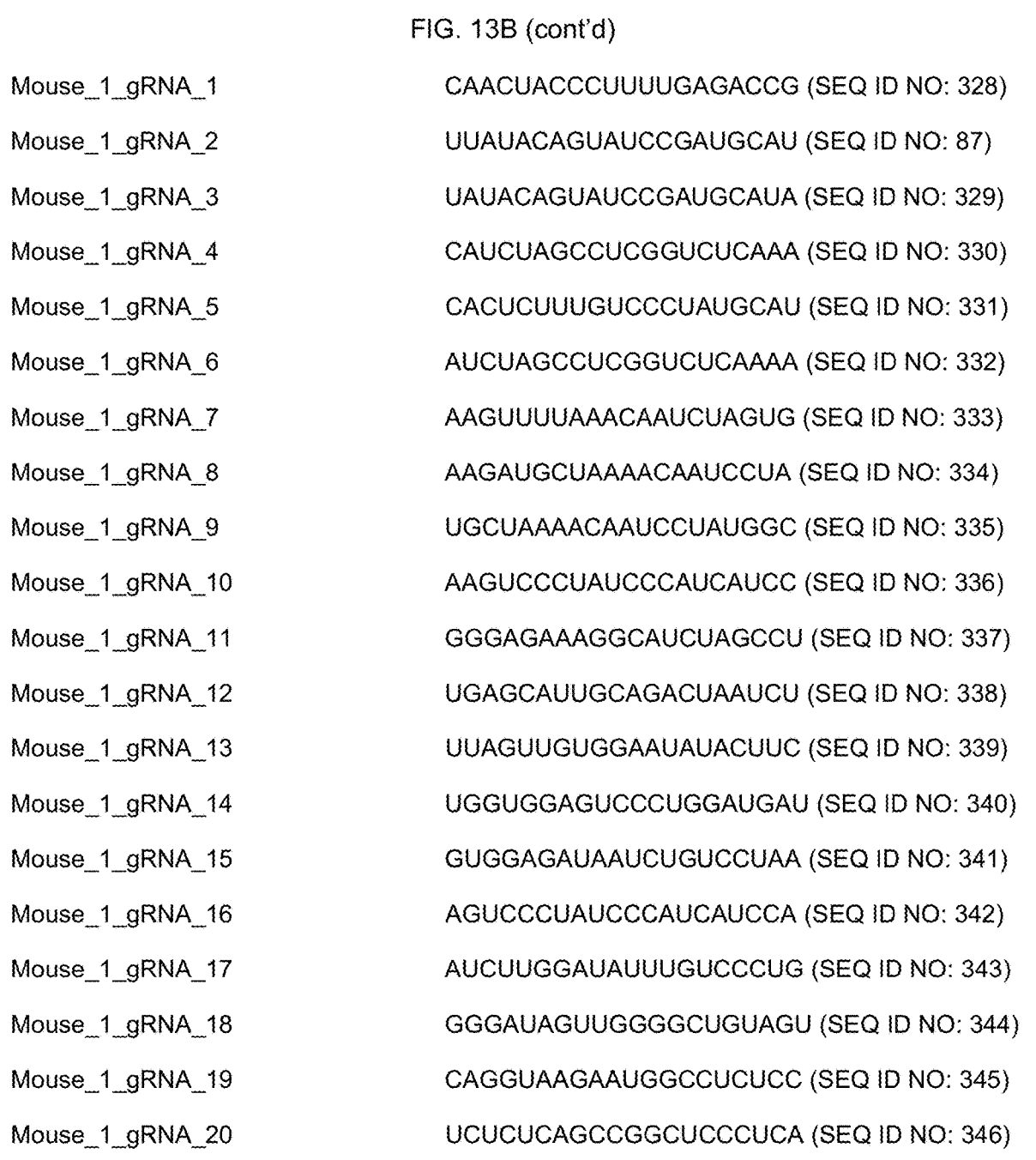

Mouse_1_gRNA_1          CAACUACCCUUUUGAGACCG (SEQ ID NO: 328)

Mouse_1_gRNA_2          UUAUACAGUAUCCGAUGCAU (SEQ ID NO: 87)

Mouse_1_gRNA_3          UAUACAGUAUCCGAUGCAUA (SEQ ID NO: 329)

Mouse_1_gRNA_4          CAUCUAGCCUCGGUCUCAAA (SEQ ID NO: 330)

Mouse_1_gRNA_5          CACUCUUUGUCCCUAUGCAU (SEQ ID NO: 331)

Mouse_1_gRNA_6          AUCUAGCCUCGGUCUCAAAA (SEQ ID NO: 332)

Mouse_1_gRNA_7          AAGUUUUAAACAAUCUAGUG (SEQ ID NO: 333)

Mouse_1_gRNA_8          AAGAUGCUAAAACAAUCCUA (SEQ ID NO: 334)

Mouse_1_gRNA_9          UGCUAAAACAAUCCUAUGGC (SEQ ID NO: 335)

Mouse_1_gRNA_10         AAGUCCCUAUCCCAUCAUCC (SEQ ID NO: 336)

Mouse_1_gRNA_11         GGGAGAAAGGCAUCUAGCCU (SEQ ID NO: 337)

Mouse_1_gRNA_12         UGAGCAUUGCAGACUAAUCU (SEQ ID NO: 338)

Mouse_1_gRNA_13         UUAGUUGUGGAAUAUACUUC (SEQ ID NO: 339)

Mouse_1_gRNA_14         UGGUGGAGUCCUGGAUGAU (SEQ ID NO: 340)

Mouse_1_gRNA_15         GUGGAGAUAAUCUGUCCUAA (SEQ ID NO: 341)

Mouse_1_gRNA_16         AGUCCCUAUCCCAUCAUCCA (SEQ ID NO: 342)

Mouse_1_gRNA_17         AUCUUGGAUAUUUGUCCCUG (SEQ ID NO: 343)

Mouse_1_gRNA_18         GGGAUAGUUGGGGCUGUAGU (SEQ ID NO: 344)

Mouse_1_gRNA_19         CAGGUAAGAAUGGCCUCUCC (SEQ ID NO: 345)

Mouse_1_gRNA_20         UCUCUCAGCCGGCUCCCUCA (SEQ ID NO: 346)

FIG. 14A

Mouse Intronic Region 2 to Target for Genetic Construct Insertion

TTATTTCAGTTGAACATGCTGGTTGGTGGTTGAGAGGACACTCAGTCAGTCAGTGACGTGA
AGGGCTTCTAAGCCAGTCCACATGCTCTGTGTGAACTCCCTCTGGCCCTGCTTATTGTTGA
ATGGGCCAAAGGTCTGAGACCAGGCTGCTGCTGGGTAGGCCTGGACTTTGGGTCTCCCAC
CCAGACCTGGGAATGTATGGTTGTGGCTTCTGCCACCCATCCACCTGGCTGCTCATGGAC
CAGCCAGCCTCGGTGGCTTTGAAGGAACAATTCCACACAAAGACTCTGGACCTCTCCGAA
ACCAGGCACCGCAAATGGTAAGCCAGAGGCAGCCACAGCTGTGGCTGCTGCTCTTAAAGC
TTGTAAACTGTTTCTGCTTAAGAGGGACTGAGTCTTCAGTCATTGCTTTAGGGGGAGAAAG
AGACATTTGTGTGTCTTTTGAGTACCGTTGTCTGGGTCACTCACATTTAACTTTCCTTGAAA
AACTAGTAAAAGAAAAATGTTGCCTGTTAACCAATAATCATAGAGCTCATGGTACTTTGAGG
AAATCTTAGAAAGCGTGTATACAATTGTCTGGAATTATTTCAGTTAAGTGTATTAGTTGAGGT
ACTGATGCTGTCTCTACTTCAGTTATACATGTGGGTTTGAATTTTGAATCTATTCTGGCTCTT
CTTAAGCAGAAAATTTAGATAAAATGGATACCTCAGTGGTTTTTAATGGTGGGTTTAATATA
GAAGGAATTTAAATTGGAAGCTAATTTAGAATCAGTAAGGAGGGACCCAGGCTAAGAAGGC
AATCCTGGGATTCTGGAAGAAAAGATGTTTTTAGTTTTTATAGAAAACACTACTACATTCTTG
ATCTACAACTCAATGTGGTTTAATGAATTTGAAGTTGCCAGTAAATGTACTTCCTGGTTGTTA
AAGAATGGTATCAAAGGACAGTGCTTAGATCCGAGGTGAGTGTGAGAGGACAGGGGCTGG
GGTATGGATACGCAGAAGGAAGGCCACAGCTGTACAGAATTGAGAAAGAATAGAGACCTG
CAGTTGAGGCCAGCAGGTCGGCTGGACTAACTCTCCAGCCACAGTAATGACCCAGACAGA
GAAAGCCAGACTCATAAAGCTTGCTGAGCAAAATTAAGGGAACAAGGTTGAGAGCCCTAGT
AAGCGAGGCTCTAAAAAGCACAGCTGAGCTGAGATGGGTGGGCTTCTCTGAGTGCTTCTA
AAATGCGCTAAACTGAGGTGATTACTCTGAGGTAAGCAAAGCTGGGCTTGAGCCAAAATGA
AGTAGACTGTAATGAACTGGAATGAGCTGGGCCGCTAAGCTAAACTAGGCTGGCTTAACC
GAGATGAGCCAAACTGGAATGAACTTCATTAATCTAGGTTGAATAGAGCTAAACTCTACTGC
CTACACTGGACTGTTCTGAGCTGAGATGAGCTGGGGTGAGCTCAGCTATGCTACGCTGTG
TTGGGGTGAGCTGATCTGAAATGAGATACTCTGGAGTAGCTGAGATGGGGTGAGATGGGG
TG (SEQ ID NO: 4)

FIG. 14B

MOUSE_REGION_2_gRNA__1     CCGAAACCAGGCACCGCAAA<u>TGG</u> (SEQ ID NO: 65)

MOUSE_REGION_2_gRNA__2     CACCGCAAATGGTAAGCCAG<u>AGG</u> (SEQ ID NO: 66)

MOUSE_REGION_2_gRNA__3     GGCTTACCATTTGCGGTGCC<u>TGG</u> (SEQ ID NO: 67)

MOUSE_REGION_2_gRNA__4     TGCGGTGCCTGGTTTCGGAG<u>AGG</u> (SEQ ID NO: 68)

MOUSE_REGION_2_gRNA__5     CAGCTATGCTACGCTGTGTT<u>GGG</u> (SEQ ID NO: 69)

MOUSE_REGION_2_gRNA__6     AAGGACAGTGCTTAGATCCG<u>AGG</u> (SEQ ID NO: 70)

MOUSE_REGION_2_gRNA__7     TCAGTCAGTCAGTGACGTGA<u>AGG</u> (SEQ ID NO: 71)

MOUSE_REGION_2_gRNA__8     CATGCTGGTTGGTGGTTGAG<u>AGG</u> (SEQ ID NO: 72)

MOUSE_REGION_2_gRNA__9     TCTTTTGAGTACCGTTGTCT<u>GGG</u> (SEQ ID NO: 73)

MOUSE_REGION_2_gRNA__10     TGGCCCATTCAACAATAAGC<u>AGG</u> (SEQ ID NO: 74)

MOUSE_REGION_2_gRNA__11     CTGGGCCGCTAAGCTAAACT<u>AGG</u> (SEQ ID NO: 75)

MOUSE_REGION_2_gRNA__12     GCCAGCCTAGTTTAGCTTAG<u>CGG</u> (SEQ ID NO: 76)

MOUSE_REGION_2_gRNA__13     TGAAGTAGACTGTAATGAAC<u>TGG</u> (SEQ ID NO: 77)

MOUSE_REGION_2_gRNA__14     GACCTGGGAATGTATGGTTG<u>TGG</u> (SEQ ID NO: 78)

MOUSE_REGION_2_gRNA__15     GGTATGGATACGCAGAAGGA<u>AGG</u> (SEQ ID NO: 79)

MOUSE_REGION_2_gRNA__16     GTTGAGAGCCCTAGTAAGCG<u>AGG</u> (SEQ ID NO: 80)

MOUSE_REGION_2_gRNA__17     GCCGCTAAGCTAAACTAGGC<u>TGG</u> (SEQ ID NO: 81)

MOUSE_REGION_2_gRNA__18     TCAGCTATGCTACGCTGTGT<u>TGG</u> (SEQ ID NO: 82)

MOUSE_REGION_2_gRNA__19     TTTTAGAGCCTCGCTTACTA<u>GGG</u> (SEQ ID NO: 83)

MOUSE_REGION_2_gRNA__20     CTCTATGATTATTGGTTAAC<u>AGG</u> (SEQ ID NO: 84)

FIG. 14B (cont'd)

MOUSE_2_gRNA__1          CCGAAACCAGGCACCGCAAA (SEQ ID NO: 347)

MOUSE_2_gRNA__2          CACCGCAAAUGGUAAGCCAG (SEQ ID NO: 348)

MOUSE_2_gRNA__3          GGCUUACCAUUUGCGGUGCC (SEQ ID NO: 349)

MOUSE_2_gRNA__4          UGCGGUGCCUGGUUUCGGAG (SEQ ID NO: 350)

MOUSE_2_gRNA__5          CAGCUAUGCUACGCUGUGUU (SEQ ID NO: 351)

MOUSE_2_gRNA__6          AAGGACAGUGCUUAGAUCCG (SEQ ID NO: 352)

MOUSE_2_gRNA__7          UCAGUCAGUCAGUGACGUGA (SEQ ID NO: 353)

MOUSE_2_gRNA__8          CAUGCUGGUUGGUGGUUGAG (SEQ ID NO: 354)

MOUSE_2_gRNA__9          UCUUUUGAGUACCGUUGUCU (SEQ ID NO: 355)

MOUSE_2_gRNA__10         UGGCCCAUUCAACAAUAAGC (SEQ ID NO: 356)

MOUSE_2_gRNA__11         CUGGGCCGCUAAGCUAAACU (SEQ ID NO: 357)

MOUSE_2_gRNA__12         GCCAGCCUAGUUUAGCUUAG (SEQ ID NO: 358)

MOUSE_2_gRNA__13         UGAAGUAGACUGUAAUGAAC (SEQ ID NO: 359)

MOUSE_2_gRNA__14         GACCUGGGAAUGUAUGGUUG (SEQ ID NO: 360)

MOUSE_2_gRNA__15         GGUAUGGAUACGCAGAAGGA (SEQ ID NO: 361)

MOUSE_2_gRNA__16         GUUGAGAGCCCUAGUAAGCG (SEQ ID NO: 362)

MOUSE_2_gRNA__17         GCCGCUAAGCUAAACUAGGC (SEQ ID NO: 363)

MOUSE_2_gRNA__18         UCAGCUAUGCUACGCUGUGU (SEQ ID NO: 364)

MOUSE_2_gRNA__19         UUUUAGAGCCUCGCUUACUA (SEQ ID NO: 365)

MOUSE_2_gRNA__20         CUCUAUGAUUAUUGGUUAAC (SEQ ID NO: 366)

Repair Templates

Physically linked with
Strep-Tag

FIG. 23A
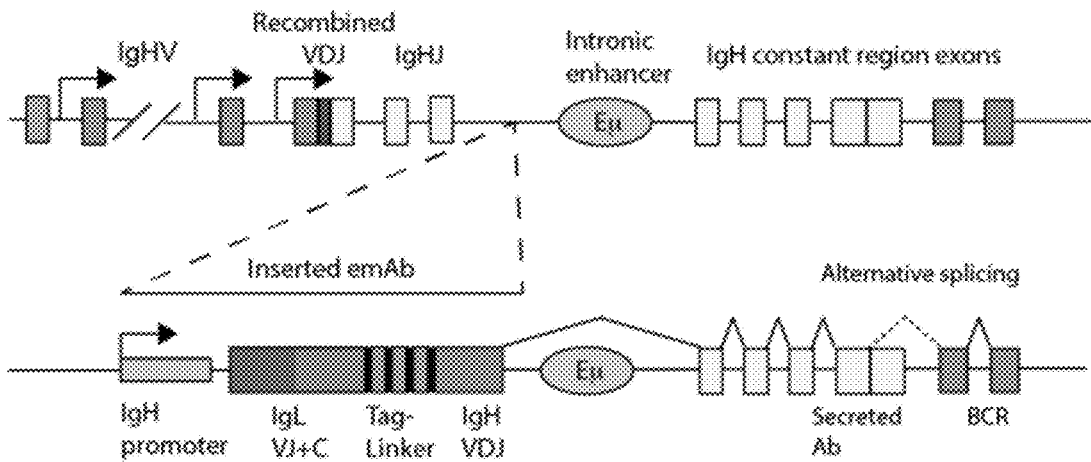
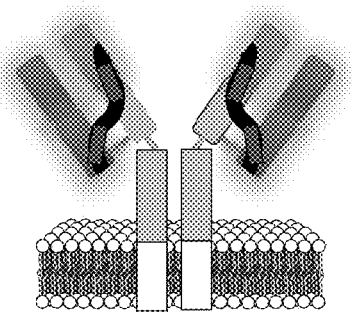
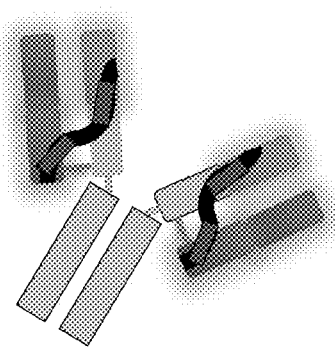

FIG. 25A sgRNA sequences:

Mouse: sgRNA-mIgH_3: UUAUACAGUAUCCGAUGCAU (SEQ ID NO: 87)
Human: sgRNA-hIgH-6: GCAUUGCAGGUUGGUCCUCG (SEQ ID NO: 88)
        sgRNA-hIgH-7: GUCUCAGGAGCGGUGUCUGU (SEQ ID NO: 89)

Mouse (for sgRNA-mIgH_3) Genome Homology Regions:
Upstream: CATCGGATACTGTATAAATGCTGTCACAGAGGTGGT (SEQ ID NO: 90)
Downstream: CATAGGGACAAAGAGTGGAGTGGGGCACTTTCTTTA (SEQ ID NO: 91)

Human (for sgRNA-hIgH-7) Genome Homology Regions:
GACACCGCTCCTGAGACACATTCCTCAGCCATCACT (SEQ ID NO: 92)
TGTAGGACTGCAAGATCGCTGCACAGCAGCGAATCG (SEQ ID NO: 93)

Human (for sgRNA-hIgH-6) Genome Homology Regions:
GGGACCAACCTGCAATGCTCAGGAAACCCACAGGCA (SEQ ID NO: 94)
TTCGGGGCATGTTCCGAGGGGACCTGGGCGGACTGGC (SEQ ID NO: 95)

Splicing oligonucleotides (homology to genome indicated in bold):

Mouse (for sgRNA-mIgH_3):
Upstream:CTTCGAGACATGTACAGACCATTTAGATGTAGTATCAAAGCCTAATATCTCAATCTT
AAAATAGAATCCTAACCTGAGACACTCACTTGTC**CATCGGATACTGTATAAATGCTGTCACA
GAGGTGGT** (SEQ ID NO: 96)
Downstream:CTTCTCCCATTCTAAATGCATGTTGGGGGGATTCTGGGCCTTCAGGACCA**CATA
GGGACAAAGAGTGGAGTGGGGCACTTTCTTTA** (SEQ ID NO: 97)

Human (for sgRNA-hIgH-7):
Upstream:GTGCACAGCGCTCTTCCCGCTGCAGAACAAACCCCAACCCCAGGATGCACTCCTC
ACTGTGAACCCACATTTTATTGGCCTAAAGATTACG**GACACCGCTCCTGAGACACATTCCTC
AGCCATCACT** (SEQ ID NO: 98)
Downstream:GTCTGGGGATAGCGGGGAGCCAGGTGTACTGGGCCAGGCAAGGGCTTTGGTG
TAGGACTGCAAGATCGCTGCACAGCAGCGAATCG (SEQ ID NO: 99)

Human (for sgRNA-hIgH-6):
Upstream:GTGCACAGCGCTCTTCCCGCTGCAGAACAAACCCCAACCCCAGGATGCACTCCTC
ACTGTGAACCCACATTTTATTGGCCTAAAGATTACG**GGGACCAACCTGCAATGCTCAGGAAA
CCCCACAGGCA** (SEQ ID NO: 100)
Downstream:GTCTGGGGATAGCGGGGAGCCAGGTGTACTGGGCCAGGCAAGGGCTTTGGTT
CGGGGCATGTTCCGAGGGGACCTGGGCGGACTGGC (SEQ ID NO: 101)

FIG. 25B
human anti-RSV emAb AAV (2531 bp)

TGTGACGCCCCGGAGACACAGAAGGTCTCTGGGTGGGTTTTGTGCGTGGCTGGGTTTTGTGGCGTGAGGATGGCACATTCTGCCATTGTGATTACTACTACTACTACTACTACATGGACGTCTGGG
                                        Human T7 Upstream Homology
        20          40          60          80          100

GCAAAGGGACCAGGTGTCTCAGGTAAGAATGGCCACTCTAGGGCCTTGTTTTCTGCTACTGCCTGTGGGGTTCCTGAGCATTGCCAGGTGGTCCTCG
                                        Human T7 Upstream Homology
        120          140          160          180          200

GGGCCATGTTTTCCGAGGGGACCTGGGCCAGGAGCGGGACTGGCCAGGAGGGGATGGGCACTGGGGTGCCTTGAGGATCTGGGAGGCCTTGTGTGGATTTTCCGATGCCTTTGGAAAATG
                                        Human T7 Upstream Homology
        220          240          260          280          300          320

GGACTCAGGTTGGGTGCCTTCTGATGGAGTAACTGAGCCCTCGGGGCCTTGGGGAGCAGGCCACATTTGGGACGAGATGCTGAACAAACCAGGGGTCTTAGTGATGGCTGAGGA
                                        Human T7 Upstream Homology
        340          360          380          400          420

ATGTGTGTCTCAGGAGCGGGTGTCTGATCGTAATCGTAATCTTTAGGCCAATAAAATGTGGGTTCACAGTGAGGAGTGCATCCTGGGGTTGGGGTTTGTTGTTCTGCAGCGGGAAGAGC
                                        IgVH1-69 Promoter
        440          460          480          500          520

FIG. 25B (cont'd)

GCTGTGCACAGAAAGCTTAGAAATGGGGCAAGAGATGCTTTCCTCAGGCAGGATTTAGGGCTTGGTCTTCTCAGCATCCACACTTGTACAGGCTGATGTGGCATCTG
───────────────────────────────────── IgVH1-69 Promoter ───────────────────────────────────
540                560                580                600                620                640

TGTTTTTCTTCTCATCCTAGATCAGGCTTTGAGCTGTGAAATACCCTGCCTCATGCAAATAACCTGAGGTCTTCTGAGATAAATATAGATATATTGGTGCC
───────────────────────────────────── IgVH1-69 Promoter ───────────────────────────────────
660                680                700                720                740

CTGAGGTTTAAACGgccgccaccatggctgctacccgcagcagcaacaagcctgctgctccctggttgctgctctccctggttgctcctgctctgcccgacatcc
                                        M A T G S R T S L L L A F G L L C L P W L Q E G S A D I
                                        ─────────────────── hRSV-light chain ───────────────
                                        ▶────────────── signalpeptide2 ──────────────▶
700                780                800                820                840 agatgacacagagcccctagcagcactgtctgctgccagtgtggcgcgacagagtgaccatcacagtcaagtgccagcctgagctgggctacatgcactggtatcagcaaaag
Q M T Q S P S T L S A S V G D R V T I T C K C Q L S W G K H H W Q K
─────────────────────────────────── hRSV-light chain ─────────────────────────────────────
───────────────────────────────────── hRSV-light-variable ────────────────────────────────
860                880                900                920                940                960

FIG. 25B (cont'd)

cccggcaagcccctaagctgctgatctacgatacctccaagctggcctctggcgtgcctccagattttctggcagcggcagcggaaccgagttcaccctgaccat
P  G  K  A  P  K  L  L  I  Y  D  T  S  K  L  A  S  G  V  P  S  R  F  S  G  S  G  S  G  T  E  F  T  L  T  I hRSV-light chain
hRSV-Light-variable 980        1,000        1,020        1,040        1,060 ctcaagcctgagcctgcagcctgaagattttgccacctactactgtcaacaaggcagcggctacccCttcacattt ggccagcggaacaaagtggaaatcaagcggactgtgg
S  S  L  Q  P  E  D  F  A  T  Y  Y  C  Q  Q  G  S  G  Y  P  F  T  F  G  Q  G  T  K  L  E  I  K  R  T  V hRSV-light chain
hRSV-Light-variable 1,080        1,100        1,120        1,140        1,160 ccgctcctagccgtgttcatctttccacctagcgacgagcagctgaagtctggcactgcctctgtcgtgtgcctgctgaacaacttctaccctcgagaggccaaggtg
A  A  P  S  V  F  I  F  P  P  S  D  E  Q  L  K  S  G  T  A  S  V  V  C  L  L  N  N  F  Y  P  R  E  A  K  V hRSV-light chain
hRSV-LightConstant 1,180        1,200        1,220        1,240        1,260        1,280

FIG. 25B (cont'd)

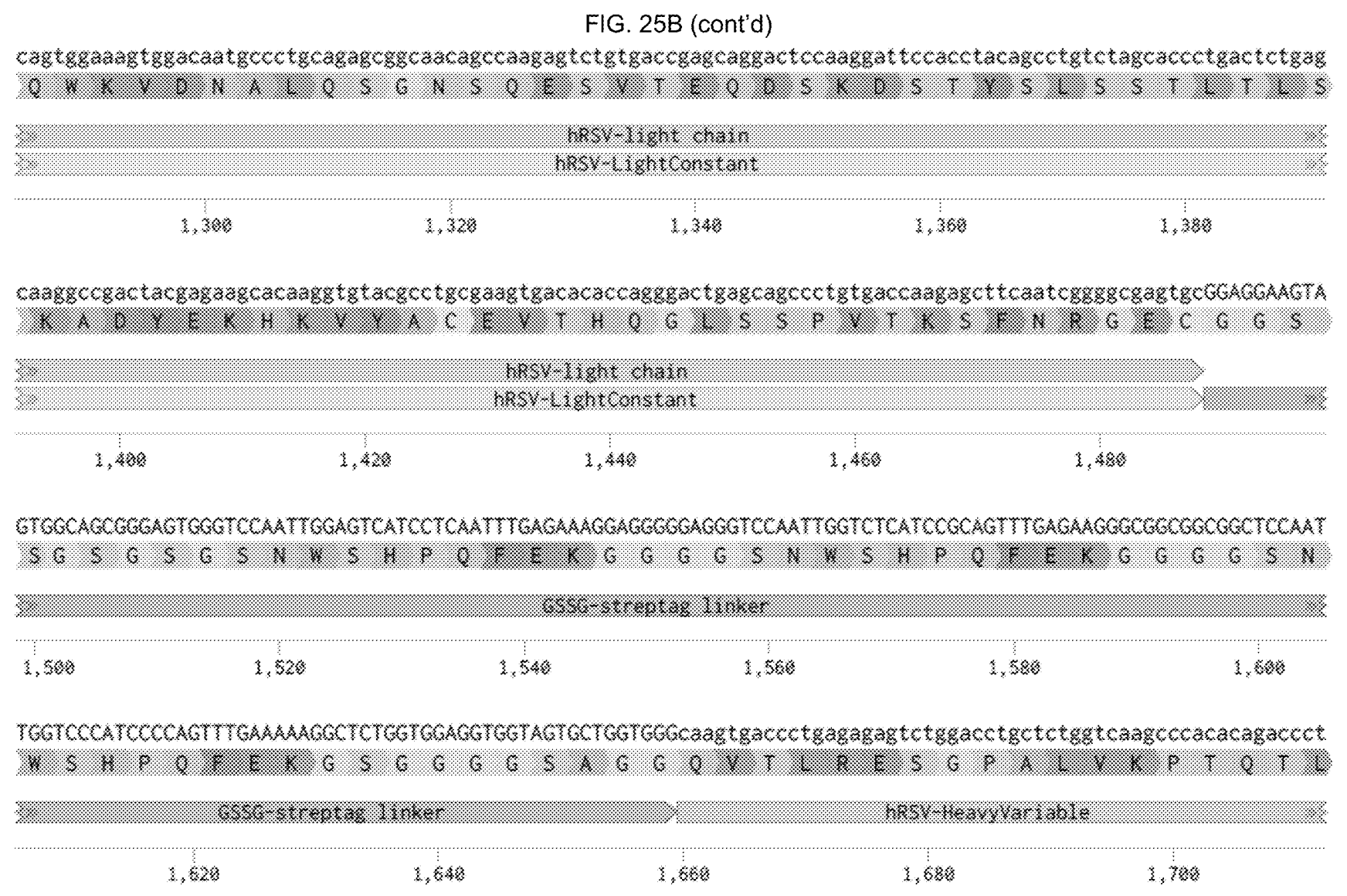

cagtggaaagtggacaatgccctgcagagcggcaacagccaagtctgtgaccgacgagcagcaggattccacctacagcctgtctagcacctgtgaccctgag
Q  W  K  V  D  N  A  L  Q  S  G  N  S  Q  E  S  V  T  E  Q  D  S  K  D  S  T  Y  S  L  S  S  T  L  T  L  S hRSV-light chain
hRSV-LightConstant 1,300          1,320          1,340          1,360          1,380 caaggccgactacgagaagcacaaggtgtacgcctgcgaagtgacacaccagggactgagcagccctgtgaccaagagcttcaatcggggcgagtgcGGAGGAAGTA
K  A  D  Y  E  K  H  K  V  Y  A  C  E  V  T  H  Q  G  L  S  S  P  V  T  K  S  F  N  R  G  E  C  G  G  S hRSV-light chain
hRSV-LightConstant 1,400          1,420          1,440          1,460          1,480

GTGGCAGGGGGAGTGGGGGTCCAATTGGAGTCATCCCTCAATTTGAGAAAAGGAGGGGGAGGGTCCAATTGGTCTCATCCGCAGTTTGAGAAGGGCGGGGGCGGGTCCAAT
S  G  G  S  G  G  S  N  W  S  H  P  Q  F  E  K  G  G  G  S  N  W  S  H  P  Q  F  E  K  G  G  G  S  N

GSSG-streptag linker 1,500          1,520          1,540          1,560          1,580          1,600

TGGTCCCATCCCCAGTTTGAAAAAGGCTCTGGTGGAGGCGGGAGTGGGGGAGGCGGGGGTAGTGGTGGCGGCcaagtgacctgctgtgagaggagtctggaccctgagagaggagagtctggacccCacagaccct
W  S  H  P  Q  F  E  K  G  S  G  G  G  G  S  A  G  G  G  V  T  L  R  E  S  G  P  A  L  V  K  P  T  Q  T  L GSSG-streptag linker          hRSV-HeavyVariable 1,620          1,640          1,660          1,680          1,700

FIG. 25B (cont'd)

gacactgacctgcacctcagcgcttagctgctggcacaagcggcatggcgtcggctggattagagcagccctgagatggctgcggcattt
T L T C T P S G R S L S S T S G M S V G W R Q P P K A L E W L A D I hRSV-HeavyVariable 1,720    1,740    1,760    1,780    1,800 ggtgggacgacaagaaggactacaacccagcctgagtcccggctgacatcagcaaggacaagaccagcaaggtggtgctgaaagtgccaacatggcccct
W D D K K D Y N P S L K S R L T I S K D T S K V V L K V P T W P P hRSV-HeavyVariable 1,820    1,840    1,860    1,880    1,900    1,920 gccgacaccgccactactactgtgccagatccatgatcaccaactggtacttcgacgtgtggggccggcaccacACCGTCTCTTCAGGTAAGTCTGCTGTCTG
A D T A V Y C A R S M I T N W Y F D V W G A G T T V S S (SEQ ID NO: 126)

hRSV-HeavyVariable

Splice 1,940    1,960    1,980    2,000    2,020

GGGGATTAGCGGGGGAGCCAGGTGTACTGGGACTGCAAGGGCTTTGGATCGTGGGCCAGGCAAGGGCTTTGGATCGTGGGCCAGATCGCTGCACAGCAGGAATCGTGCTAGGACTGCAAGATCGCTGCACAGCAGCGAATCGTGAAATATTTCTTTAGAATTATG

Human T7 Downstream Homology 2,040    2,060    2,080    2,100    2,120    2,140

FIG. 25B (cont'd)

AGGTGCGCTGTGTGTCAACCTGCATCTTAAATTCTTTATTGGCTGGAAAGAGAACTGTCGGAGTGGTGAATCAGCCAGGAGGGAGGACGGCTAGCCCCGGTCTTGATG

Human T7 Downstream Homology 2,160        2,180        2,200        2,220        2,240

AGAGCAGGGTTGGGGGCAGGGGTAGCCCAGGAAAACGGTGCCTGCCGTGTCCTGACACAGGGGCTTAGGGAGGCTCCAGGGACCTCAGTGCCTTGAAGCTGGTTTCCATGAGAA

Human T7 Downstream Homology 2,260        2,280        2,300        2,320        2,340

AAGGATTGTTTATCTTTAGGAGGCCATGTTTACTGTTAAAAGACAGGATATGTTTGAAGTGGCTTCTGAGAGAAAAATGGTTAAGAAAATTATGACTTAAAAATGTGAGAG

Human T7 Downstream Homology 2,360        2,380        2,400        2,420        2,440        2,460

ATTTTCAAGTATATTAATTTTTTTTTAACTGTCCAAGTATTTGAAATTCTTATCATTGATTAACACCCATG (SEQ ID NO: 102)

Human T7 Downstream Homology 2,470        2,480        2,490        2,500        2,510        2,520        2,530

FIG. 25B (cont'd)

>Human T7 upstream homology region in human anti-RSV emAb AAV

TGTGACGCCCGGAGACAGAAGGTCTCTGGGTGGCTGGGTTTTGTGGGGTGAGGATGGACATTCTGCCATTGTGATTACTACTA
CTACTACTACATGACGTCTGGGCAAAGGACCACGGTCACCGGTCCTCAGTAAGAATGGCCACTCTAGGGCCTTTGTTT
CTGCTACTGCCTGTGGGTTCCTGAGCATTGCAGGTTGGTCCTGGGGCATGTCCGAGGGGACCTGGGCGGACTGGCCAG
GAGGGGGATGGGCACTGGGGTGCCTGGGGATCTGGAGGAGCCTCTGTGGATTTTCCGATGCCTTTGGAAAATGGGACTCAGGTTG
GGTGCGTCTGATGGAGTAACTGAGCCTGGGGGCTTGGGGAGCCACATTTGGACGAGATGCCTGAACAAACCAGGGGTCTTAGT
GATGGCTGAGGAATGTGTCTCAGGAGCGGGTGTCT (SEQ ID NO: 110)

>IgVH1-69 promoter in human anti-RSV emAb AAV

GTAATCTTTAGGCCAATAAAATGTGGGTTCACAGTGAGGAGTGCATCCTGGGGTTGGGGTTTGTTCTGCAGCGGGAAGAGCGCT
GTGCACAGAGAAAGCTTAGAAATGGGGCAAGAGAGATGCTTTCCTCAGGCAGGATTTAGGGCTCTCAGCATCCCACACTTG
TACAGTCGATGTGGCATCTGTGTTTCTTTCTCATCCTAGATCAGGCTTTGAGCTGTGAAATACCCTGCCTCATGCATATGCAAAT
AACCTGAGGTCTTCTGAGATAAAATATAGATATATTGGTGCCCTGAG (SEQ ID NO: 111)

>Signal peptide coding sequence in human anti-RSV emAb AAV

ATGGCTACCGGCAGCAGCAGAACAAGCCTGCTGCTCGCTTTTGGACTGCTGCTCGTCTCCCCTGGTTGCAAGAAGGCAGCGGCC (SEQ ID
NO: 112)

>hRSV light chain coding sequence in human anti-RSV emAb AAV

ATGGCTACCGGCAGCAGCAGAACAAGCCTGCTGCTCGCTTTTGGACTGCTGCTCGTCTCCCCTGGTTGCAAGAAGGCAGCGGCCGACAT
CCAGATGACACAGAGCCCTAGCACACTGTCTGCCAGCGTGGGCGACAGAGTGACCATCACATGCAAGGCCAGCCAGCGGTGG
GCTACATGCACTGGTATCAGCAAAAGCCCGGCAAGGCCCCTAAGCTGCTGATCTACGATACCTCCAAGCTGGCCTCTGGCGTG
CCCTCCAGATTTTCTGGCAGCGGCAGCGGCACCGAGTTCACCCTGACCATCTCAAGCCTGCAGCCTGACGACTTCGCTACGTAC
TACTGCTTCCAAGGCAGCGGCTACCCCTTCACCATTTGGCGGCGGAACAAAGCTGGAAATCAAGCGGACTGTGGCCGCTCCTAG
CGTGTTCATCTTTCCACCTAGCGACGAGCAGCTGAAGTCTGGCACTGCTTCTGTGGTGTGTGCTGCTGGTGTGACGGCAAGAAGTCTGTGACCCTCG
AGAGGCCAAGGTGCAGTGGAAAGTGGACAATGCCCTGCAGAGCGGCAACAGCCAAGAGAAGCACAGAGAAGGACTCCAAG
GATTCCACCTACAGCCTGAGCAGCACCCTGACCCTGTCTAAGGCCGACTACGAGAAGCACAAGGTGTACGCCTGCGAAGTGAC
ACACCAGGGGACTGAGCAGCACCCTGTGACCAAGAGCTTCAATCGGGGCGAGTGC (SEQ ID NO: 113)

FIG. 25B (cont'd)

>hRSV variable light chain coding sequence in human anti-RSV emAb AAV
GACATCCAGATGACATGACACAGAGCCCTAGCACACTGTCTGCCAGCGTGGGCGACAGAGTGACCATCACATGCAAGTGCCAGCTGAG
CGTGGGCTACATGCACTGGTATCAGCAAAAGCCCGGCAAGGCCCCTAAGCTGCTGATCTACGATACCTCCAAGCTGCCCTCTG
GCGTGCCCTCCAGATTTTCTGGCAGCGGCAGCGGGAACCGAGTTCACCCTGACCATCTCAAGCCTGCAGCCTGACGACTTCGCT
ACGTACTACTGCTTCCAAGCAGCAGCGGCTACCCCTTCACATTTGGCGGCGGAACAAAGCTGGAAATCAAGCGG (SEQ ID NO: 114)

>kappa constant light chain coding sequence in human anti-RSV emAb AAV
ACTGTGGCCGCTCCTCCTAGCGTGTTCATCTTTCCACCTAGCGACGAGCAGCTGAAGTCTGGCACTGCCTCTGTCGTGTGCCTGCTG
AACAACTTCTACCCTCGAGAGGCCAAGGTGCAGTGGAAAGTGGACAATGCCCTGCAGAGCGGCAACAGCCAAGAGTCTGTGAC
CGAGCAGGACTCCAAGGATTCCACCTACAGCCTGCTGAGCACCCTGACTCTGAGCAAGGCAGACTACGAGAAGCACAAGGTGT
ACGCCTGCGAAGTGACACACCAGGGACTGAGCAGCCCTGTGACCAAGAGCTTCAATCGGGGCGAGTGC (SEQ ID NO: 115)

>GSSG-streptag linker coding sequence in human anti-RSV emAb AAV
GGAGGAAGTAGTGGCAGCGGGAGTGGGTCCAATTGGAGTCATCCTCAATTTGAGAAAGGAGGGGAGGGTCCAATTGGTCTCA
TCCGCAGTTTGAGAGGGACGGGGGCGGGCGGTCCAATTGGTCCCATCCCCAGTTTGAAAAAGGCTCTGGTGGAGGTGGTAGTGCTG
GTGGG (SEQ ID NO: 116)

>hRSV variable heavy chain coding sequence in human anti-RSV emAb AAV
CAAGTGACCCTGAGAGAGTCTGGACCTGCTCTGGTCAAGCCCACACAGACCCTGACACTGACCTGCACCTTCAGCGGCTTTAG
CCTGAGCACAAGCGGCATGAGCGTCGGCTGGATTAGACAGCCTCCTGGCAAGCCCTGGCCGACATTTGGTGG
GACGACAAGAAGGACTACAACCCCAGCCTGAAGTCCCGGCTGACCATCAGCAAGGACACCAGCAAGAACCAGGTGGTGCTGAA
AGTGACCAACATGGACCCTGCCGACACGCCGCCACCTACTGTGCCAGATCACTGATCACCAACACCGTCTCTTCA (SEQ ID NO: 117)

>signal peptide amino acid sequence in human anti-RSV emAb AAV
MATGSRTSLLLAFGLLCLPWLQEGSA (SEQ ID NO: 118)

FIG. 25B (cont'd)

>hRSV light chain amino acid sequence in human anti-RSV emAb AAV
MATGSRTSLLLAFGLLCLPWLQEGSADIQMTQSPSTLSASVGDRVTITCKCQLSVGYMHWYQQKPGKAPKLLIYDTSKLASGVPSRFS
GSGSGTEFTLTISSLQPDDFATYYCFQGSSYPFTFGGGTKLEIKRTVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKSFNRGEC (SEQ ID NO: 119)

>hRSV variable light chain amino acid sequence in human anti-RSV emAb AAV
DIQMTQSPSTLSASVGDRVTITCKCQLSVGYMHWYQQKPGKAPKLLIYDTSKLASGVPSRFSGSGSGTEFTLTISSLQPDDFATYYCF
QGSSYPFTFGGGTKLEIKR (SEQ ID NO: 120)

>kappa constant light chain amino acid sequence in human anti-RSV emAb AAV
TVAAPSVFIFPPSDEQLKSGTASVVCLLNNFYPREAKVQWKVDNALQSGNSQESVTEQDSKDSTYSLSSTLTLSKADYEKHKVYACEV
THQGLSSPVTKSFNRGEC (SEQ ID NO: 121)

>GSSG-streptag linker amino acid sequence in human anti-RSV emAb AAV
GGSSGSGGSGSNWSHPQFEKGGGGSNWSHPQFEKGGGGSNWSHPQFEKGSSGGGSAGG (SEQ ID NO: 122)

>hRSV variable heavy chain amino acid sequence in human anti-RSV emAb AAV
QVTLRESGPALVKPTQTLTLTCTFSGFSLSTSGMSVGWIRQPPGKALEWLADIWWDDKKD
YNPSLKSRLTISKDTSKNQVVLKVTNMDPADTATYYCARSMITNWYFDVWGAGTTTVSS (SEQ ID NO: 123)

>splice junction with flanking sequence in human anti-RSV emAb AAV
CAGGTAAGTCTGCTGTCTGGGGATAGCGGGGGAGCCAGGTGACTGGGCCCAGGCAAGGGCTTTGGATC (SEQ ID NO: 124)

>Human T7 downstream homology in human anti-RSV emAb AAV
GTAGGACTGCAAGATCGCTGCACAGCAGCGAATCGTGAAATATTTCTTTAGAATTATGAGGTGCGCTGTGTGTCAACCTGCATC
TTAAATTCTTTATTGGCTGGAAGAAGAGAACTGTCGGAGTGGGTGAATCCAGCAGCAGGACGCGTAGCCCCGGTCTTGATGAGA
GCAGGGTTGGGGCCAGGGGTAGCCAGAAAACGGTGGCTGCGCCGTCCTGACAGGGGCTTAGGGAGGCTCAGGAGGCTCAGTGC
CTTGAAGCTGGTTTCCATGAGAAAAGGATTGTTTATCTTAGGAGGCATGCTTACTGTTAAAAGACAGGATATGTTGAAGTGGCTT
CTGAGAAAAATGGTTAAGAAGAAATTATGACTTAAAAAAATGTGAGAGATTTTCAAGTATTATTAATCTGTCCAAGTATTTGAAA
TTCTTATCATTTGATTAACACCCCATG (SEQ ID NO: 125)

FIG. 25B (cont'd)

>hRSV light chain coding sequence without signal sequence in human anti-RSV emAb AAV
GACATCCAGATGACACAGAGCCCTAGCACTCTGTCTGCCAGCGTGGGCGACAGAGTGACCATCACATGCAAGTGCCAGCTGAG
CGTGGGCTACACATGCACTGGTATCAGCAAAAGCCCGGCAAGGCCCCTAAGCTGCTGATCTACGATACCTCCAAGCTGGCCTCTG
GCGTGCCCTCCAGATTTTCTGGCAGCGGCAGCGGCTACCCCTTCACCTTCACCATCTCAGCCTGACCATCTCAGCCTGACGACTTCGCT
ACGTACTACTGCTTCCAAGGCAGCGGCTACCCCTTCACCTTCACCATTTGGCGGCGGAACAAAGCTGGAAATCAAGCGGACTGTGGCCGC
TCCTAGCGTGTTCATCTTTCCACCTAGCGACGAGCAGCTGAAGTCTGGCCAACTCTGTGTGCCTGCCTGTGTGCCTGCTGAACAACTTCTA
CCCCTCGAGAGGCCAAGGTGCAGTGGAAAGTGGACAACGCCCTGCAGAGCGGCAACAGCCAAGAGTCTGTGACCGAGCAGGAC
TCCAAGGATTCCACCTACAGCCTGTCTAGCACCCTGACCCTGAGCAAAGCCGACTACGAGAAGCACAAGGTGTACGCCCTGCGA
AGTGACACACCAGGGACTGAGCGCCCTGTGACCAAGAGCTTCAATCGGGGCGAGTGC (SEQ ID NO: 280)

>hRSV light chain amino acid sequence without signal peptide in human anti-RSV emAb AAV
DIQMTQSPSTLSASVGDRVTITCKCQLSVGYMHWYQQKPGKAPKLLIYDTSKLASGVPSRFSGSGSGTEFTLTISSLQPDDFATYYCF
QGSGYPFTFGGGTKLEIKRTVAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 285)

FIG. 25C mouse anti-RSV emAb AAV (3134 bp)

CCAGGGGTGATTCTAGTCAGACTCTGGGGTTTTGTCGGGTATAGAGGAAAAATCCACTATTGTGATTACTACTATGCTATGGGGTCAAGGAACCTCAGTCA mB3 Balb/C Upstream 20　　　　40　　　　60　　　　80　　　　100

CCGTCTCCTCAGGTAAGAATGGCCTCTCCTTCAGGTCTTTATTTTAACCTTGTTATGGAGTTTTCTGAGCATTGCAGACTAATCTTGGATATTTGTCCCTGAGCGAGC mB3 Balb/C Upstream 120　　　　140　　　　160　　　　180　　　　200

CGGCTGAGACAAGTTGGGAAATAAACTGTCTAGGGATCTCAGAGCCTTTAGGACAGATTATCTCCACATCTTTGAAAAACTAAGAATCTGTGTGATGGTGTTGGTGG mB3 Balb/C Upstream 220　　　　240　　　　260　　　　280　　　　300　　　　320

AGTCCCTGGGATGGGATAGGGACTTTGGGAGGCTCATTTGAGGGGAGATGCTAAAACAATCCTATGGCTGGAGGCATAGTTGGGGGCTGTAGTTGGGAGATTTTCAGTT mB3 Balb/C Upstream 340　　　　360　　　　380　　　　400　　　　420

TTTAGAATAAAAGTATTAGTTGTGTGGAATATACTTCAGGACCACCTCTGTGACAGCATTTATACAGTATCCGATGGATGGACAAGTGAGTGTCTCTCAGGTTAGGATTCTA mB3 Balb/C Upstream　　　　　　　　　　JS58N10 Promoter 440　　　　460　　　　480　　　　500　　　　520

GCTCCGTGGGCTACATGCACTGGTATCAGCAGAAGTCTAGCACAGAGAAGCCCAAGCTGGAATCTTACGGACACCTCCAAGCTGGCCTCTGGCGTGCCAGGCAGATTTCT

S S V G Y M H W Y Q Q K S S T S P K L W I Y D T S K L A S G V P G R F S mRSV-kappal mPalivizumab  variable light chain 980          1,000          1,020          1,040          1,060

GGAAGCGGCAGCGGCAACAGCTACAGCCTGACTATCAGCTCCATCCAGGCCGAGGATGTGGCTACTACTACTGCTTCAGAGAGGCAGGCTACCCCTTCACATTTGG

G S G S G N S Y S L T I S S I Q A E D V A T Y Y C F R G S G W P F T F G mRSV-kappal mPalivizumab  variable light chain 1,080          1,100          1,120          1,140          1,160

CCAGGGCACCAAGCTGGAAATCAAGCGGACAGTGGCCGCTCCTAGCGTGTTCATCTTTCCACCTAGCAGCGAGCAGCTGACATCTGGCGGAGCCTCTGTCGTGTGCTTCC

Q G T K L E I K R T V A A P S V F I F P P S S E Q L T S G G A S V V C F mRSV-kappal m IgL constant 1,180          1,200          1,220          1,240          1,260          1,280

FIG. 25C (cont'd)

TGAACAACTTCTACCTAAGGACATCAAGTGGAAGACTGACGGCTCCGAGAGATCGACAGCAACGGGCGGTGCTGAACTCTTGGACCGACCAGGACAGCAGGATAGC
E N N F Y P K D I N W K T D G S E R Q N G V L N S W T D Q D S K D S mRSV-kappaL
m IgL constant 1,300    1,320    1,340    1,360    1,380

ACCTACAGCATGAGCAGCACTCTGACCCTGACGAAGGACGAGTACGAGAGGCACAACTCCTACACATGCGAGGCCACACAAGACCAGCACATCCCAATCGTGAA
T Y S M S S T L T L T K D E Y E R H N S W T C E A T H K T S T S P I V K mRSV-kappaL
m IgL constant 1,400    1,420    1,440    1,460    1,480

GTCCTTCAACCGGAACGAGTGCGGAGGAAGTAGTGGCAGCGGCGGGAGTGGCAGCGGCGGGAGTGGCAGGAGGGGGTCCATTGAGAAGGAGGGGGGTCCATC
S F N R N E C G G S S G S G G S G S G G S I E K E G G G S N W S H mRSV-kappaL
m IgL constant
GSSG-streptag linker 1,500    1,520    1,540    1,560    1,580    1,600

CGCAGTTTGAGAAGGGGCGGCGGCGGCTCCAATTGGTCCCATCCCCAGTTTGAAAAAGGCTCTGGTGGAGGTGGTAGTGCTGGTGGTGGCAGGTGGCAGGTGGAACTGCAAGAAAGC
P Q F E K G G G S N W S H P Q F E K G G G S A G G G V E L Q E S

GSSG-streptag linker 1,620    1,640    1,660    1,680    1,700

FIG. 25C (cont'd)

```
GGCCCTGGCCATCCTGCAGCCTTCTCAGACACTGAGCTTGACCTGTACCTGTAGCTTCAGCGGCTTCAGCCTGAGCACAAGCGGCATGTCTTGTGGCTGGATCAGACAGCCTTC
 G  P  G  I  L  Q  P  S  Q  T  L  S  L  T  C  S  F  S  G  F  S  L  S  T  S  G  M  S  W  G  W  I  R  Q  P  S
                              mPalizimab variable heavy chain
      1,720        1,740        1,760        1,780        1,800
```

```
TGGCGAAGGACTGGAATGGCTGGCCGACATTTGGTGGGACGACGACAAGGACTACAACCCAGCTGAAGTCAGACTCAGAGCAGCAACC
 G  E  G  L  E  W  L  A  D  I  W  W  D  D  D  K  D  Y  N  P  S  L  K  S  R  L  T  I  S  K  D  T  S  S  N
                              mPalizimab variable heavy chain
   1,820        1,840        1,860        1,880        1,900        1,920
```

```
AGGTGTTCCTGAAGATCACCGGCGTGGACACAGCCGATACCGCCACCTATTACTGCGCCAGATCCATGATCACCAACTGGTACTTCGAGGTGTGGGGCCGTGGCACC
 Q  V  F  L  K  I  T  G  V  D  T  A  D  T  A  T  Y  Y  C  A  R  S  M  I  T  N  W  Y  F  D  V  W  G  A  G  T
                              mPalizimab variable heavy chain
      1,940        1,960        1,980        2,000        2,020
```

```
ACAGTGACCGTCTCCTCAGGTGAGTCCTAACTTCTCCCATTCTAAATGCATGTTGGGGGGATTCTGGGCCTTCAGGACCACCATGTACCAAAGCCATAACGATCGG
 T  V  S  S  (SEQ ID NO: 141)
          Splice
              IntronSplice                              Extra Sequence
   2,040        2,060        2,080        2,100        2,120        2,140
```

FIG. 25C (cont'd)

TGGGAGTATTCATTGTGGTCAAGATCCATAGGGACAAAGAGTGGAGTGGGGCACTTTCTTTAGATTGTGTGAGGAATGTTCCGCACTAGATTGTTAAAACTTCATTT

Extra Sequence 2,160    2,180    2,200    2,220    2,240

GTTGGAAGGAGAGCTGTCTTAGTGATTGAGTCAAGGCATCAGCCTCCGGTCTCAAAAGGGTAGTTGCTGTCTAGAGAGGTCTGCGTGGAGCCTGCAAAAG mB3 Balb/C Downstream 2,260    2,280    2,300    2,320    2,340

TCCAGCTTTCAAAGGAACACAGAAGTATGTGTATGGAATATTAGAAGATGTTGCTTTACTCTTAAGTTGGTTCCTAGGAAAATAGTTAAATACTGTGACTTTAAA mB3 Balb/C Downstream 2,360    2,380    2,400    2,420    2,440    2,460

ATGTGAGAGGGTTTTCAACTACTCATTTTTTTAAATGTCCAAAATTTTTGTCAATCAGTTTGAGGTCTTGTGTTGTGTAGAACTGATATTACTTAAAGTTTAACCGAG mB3 Balb/C Downstream 2,480    2,500    2,520    2,540    2,560

GAATGGCAGTGAGGCTCTCTCATAACCTATTCAGAACTGACTTTTAACAATAATAAATTAAGTTAAAATATTTTAAATGAATTGAGCAATGTGTTGAGTTGGGAGTCA mB3 Balb/C Downstream 2,580    2,600    2,620    2,640    2,660

FIG. 25C (cont'd)

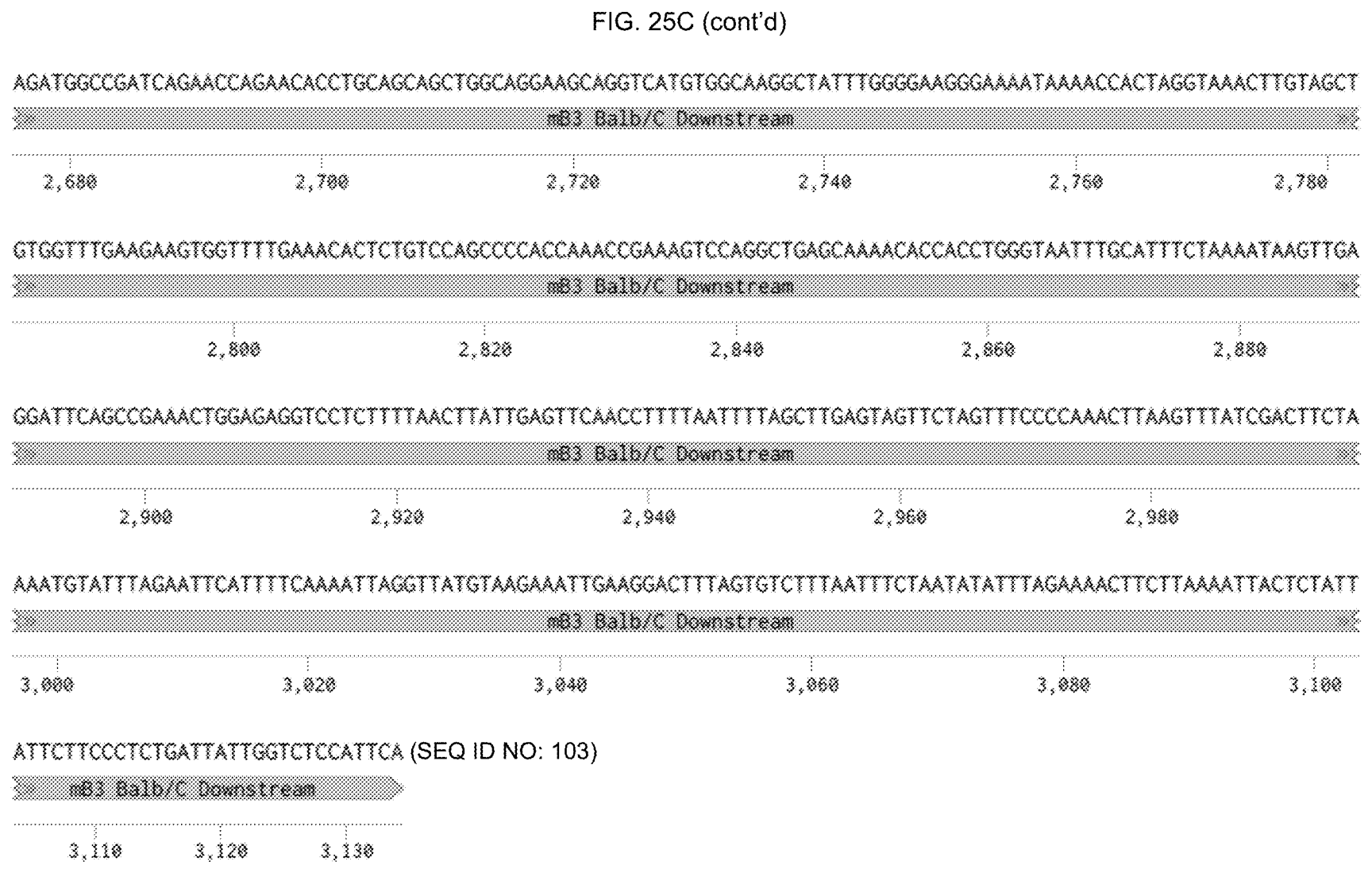

AGATGGCCGATCAGAGAACCAGAGAACCACCTGCAGCAGCAGGTCATGTGGCAAGGCTATTTGGGGAAGGGAAATAAAACCACTAGGTAAACTTGTGTAGCT mB3 Balb/C Downstream 2,680    2,700    2,720    2,740    2,760    2,780

GTGGTTTGAAGAAGTGGTTTGAAACACTCTGTCCAGCCCACCAAAACGAAGTCCAGGCTGAGCAAAACACCACCTGGGTAATTGCATTTCTAAAAATAAGTTGA mB3 Balb/C Downstream 2,800    2,820    2,840    2,860    2,880

CGAATTCAGCCGAAACTGGACAGAGGTCCTCTTTTTAACTTATTGAGTTCAACCTTTTAGCTTGAGTAGTTCTAGTTCCCAAACTTAAGTTATCGACTTCTA mB3 Balb/C Downstream 2,900    2,920    2,940    2,960    2,980

AAATGTATTTAGAATTCATTTCAAAATTAGTTATGTAAGGACTTTAGTGTCTTTAATTTCTAATATATTTAGAAAACTTCTTAAAATTACTCTATT mB3 Balb/C Downstream 3,000    3,020    3,040    3,060    3,080    3,100

ATTCTTCCCTCTGATTATTGGTGTCTCCATTCA (SEQ ID NO: 103)

mB3 Balb/C Downstream 3,110    3,120    3,130

FIG. 25C (cont'd)

>Mouse mB3 Balb/C upstream region in mouse anti-RSV emAb AAV
CCAGGGGTGATTCAGTCAGACTCTGGGGTTTTGTCGGGTATAGAGAGGAAAAATCCACTATTGTGATTACTATGCTATGGACTAC
TGGGGTCAAGGAACCTCAGTCACCGTCTCCTCAGGTAAGAATGGCCTCTCCAGGTCTTTATTTTAACCTTTGTTATGGAGTTTTC
TGAGCATTGCAGACTAATCTTGGATATTTGTCCCTGAGGGAGCCGGCTGAGAGAAGTTGGGAAATAAACTGTCTAGGGATCTCA
GAGCCTTTAGGACAGAGATTATCTCCACATCTTTGAAAAACTAAGAATCTGTGTGATGGTGTTGGTGGAGTCCCTGGATGATGGAT
AGGGACTTTGGAGGCTCATTTGAGGGAGATGCTAAAACAATCCTATGGCTGGAGGGATAGTTGGGGCTGTAGTTGGAGATTTTC
AGTTTTTAGAATAAAAAGTATTAGTTGTGGAATAATACTTCAGGACCACCTCTGTGACAGCATTTATACAGTATCCGATG (SEQ ID
NO: 127)

>J558H10 promoter in mouse anti-RSV emAb AAV
GACAAGTGAGTGTCTCAGGTTAGGATTCTATTTTAAGATTGAGATATTAGGCTTTGATACTACATCTAAATGGTCTGTACATGTCT
CGAAGAAAGTTCTTCAGACAGAGTTAGGACTTAGGACTTGGATCCAGGAGTTAGGACTTGGACTCAGGAGGACTCTAGTTTCTTCTTC
TCCAGCTGGAATGTCCTTATGTAAGAAGAAAGCCTTGCCTCATGAGTATGCAAATCATGTGCGACTGTGATGATTAATATAGGGATAT
CCACACCAAACATCATATGAGCCCTATCTTCTCTACAGACACTGAATCTCAAGGTCCTTACA (SEQ ID NO: 128)

>Signal peptide coding sequence in mouse anti-RSV emAb AAV
ATGGAAACCGACACACTGCTGCTGCTGGGGTGTGCTGCTTCTTTGGGTGCCCGGAAGCACAGGC (SEQ ID NO: 129)

>mRSV kappa light chain coding sequence in mouse anti-RSV emAb AAV
ATGGAAACCGACACACTGCTGCTGCTGGGGTGTGCTGCTTCTTTGGGTGCCCGGAAGCACAGGC
GACATCCAGCTGACACAGAGCCCTGACCATCATGTCTGCTAGCACAGAAGTGACAATGACCTGTTCCGCCAGCAGCTC
CGTGGGCTACACTGCACTGATTCAGCAGAAGTCTAGCACACAGGCCCCCAAGCCCTGTGGATCTGTGATCTACAGCACCAGCAACCTCCAAGCTGGGCT
GCGTGCCAGGCAGATTTTCTGGAAGCGGCAACAGCGGCAGCGGCAACAGCCTGACTATCAGCTCACATTTGGCCAGGCACCAAGCTGGAAATCAAGGCCGATGCCGCTCC
ACCTACTACTGCTTCAGAGGCAGCGGCTACCCCTTCACATTTGGCCAGGCAGCTGACATCTGGCGGACATCTGGCGGAGCCTCTGGCGGAGACTCTGAACAACTTCTACCCT
TACCGTGTCTATCTTTCCACCTAGCAGCGAGCAGCTGAAGAGTGGAAGATCAAGCTCAAGGTGCTGCTCCGAGAGACAAAGGACGACGAGTACGAGCGGCCA
GGATAGCAGCACCTACAGCCTCAGCAGCACCCTGACCCTGAGCAAAGCAGACTACGAGAAGCACAAAGTCTACGCCTGCGAAGTCACCCATCAGGGCCTGAGCAGCCCTGTGACAAAGAGCTTCAAAAAGTCCTGAACCGGAGAGGAGTGC
CACACAAGACCAGCAGCACATCCCCAATCGTGAAGTCCTTCAACCGGAACGAGTGC (SEQ ID NO: 130)

FIG. 25C (cont'd)

>mPalivizumab variable light chain coding sequence in mouse anti-RSV emAb AAV
GACATCCAGCTGACACAGAGCCCTGCCATCATGTCTGCTAGCCCTGGCGAGAAAGTGACAATGACCTGTTCCGCCAGCAGCTC
CGTGGGCTACACTGCACTGGTATCAGCAGAAGTCTAGCAGCAGCCCCAAGCTGTGGATCTACGACACCTCCAAGCTGGCCTCTG
GCGTGCCAGGCAGATTTTCTGGAAGCGGCAGCGGCAACAGCTACAGCCTGACTATCAGCTCCCTGCCAGGCCGAGGATGTGGCT
ACCTACTACTGCTTCAGAGGCAGCGGCGGCTACCCCTTCACATTTGGCCAGGGCACCAAGCTGGAAATCAAG (SEQ ID NO: 131)

>mIgL kappa constant light chain coding sequence in mouse anti-RSV emAb AAV
GCCGATGCCGCTCCTACCGTGTCTATCTTTCCACCTAGCAGCGAGCAGCTGACATCTGGGCGGAGCCTCTGTCTGTGTCTTCCTG
AACAACTTCTACCCTAAGGACATCAACGTCAAGTGGAAGATCGACGGCTCCGAGAGACAGAACGGCGTGCTGAACTCTTGGACC
GACCAGGACAGCAAGGATAGCACCTACAGCCTGAGCAGCACTCTGACCCTGAGCAAAGGACGAGTACGAGAGGCACAACTCCTA
CACATGCGAGGCCACACAGAGACCAGCACATCCCAATCGTGAAGTCCTTCAACCGGAACGGCGGC (SEQ ID NO: 132)

>GSSG-streptag linker coding sequence in mouse anti-RSV emAb AAV is SEQ ID NO: 116

>mPalivizumab variable heavy chain coding sequence in mouse anti-RSV emAb AAV
CAGGTGGAACTGCAAGAAGCGGGCCCTGGCATCCTGCAGCCTTCTCAGACACTGAGCCTGACCTGTAGCTTCAGCGGCTTCAG
CCTGAGCACAGCAGGCGTCATGTCTGTCGGCATCGGGCCATGGCCTTCTGCGGCCATCAGCGGCCTGAGACTGGCGCCAGCAGCCTTCTGGCGAAGGCCAGCAGCATTGGTGGG
ACGACAAGAAGGACTACAACCCCAGCCTGAAGTCCAGACTGACCATCAGCAAGGACACAAGCAAGAACCAGGTGTTCCTGAAG
ATCACCGGCGTGGACACAGCCGATACCGCCACCTATTACTGCGCCACCTATTACTGCGCCAGATCCATGATCACCAACTGGTACTTCGACGTGTGGGG
CGCTGGCACCACAGTGACCGTCTCCTCA (SEQ ID NO: 133)

>Signal peptide amino acid sequence in mouse anti-RSV emAb AAV
METDTLLLWLLLWVPGSTG (SEQ ID NO: 134)

>mRSV kappa light chain amino acid sequence in mouse anti-RSV emAb AAV
METDTLLLWLLLWVPGSTGDIQLTQSPAIMSASPGEKVTMTCSASSSVGYMHWYQQKSSTSPKLWIYDTSKLASGVPGRFSGSGSG
NSYSLTISSIQAEDVATYYCFRGSGYPFTFGQGTKLEIKADAAPTVSIFPPSSEQLTSGGASVVCFLNNFYPKDINVKWKIDGSERQNGV
LNSWTDQDSKDSTYSMSSTLTLTKDEYERHNSYTCEATHKTSTSPIVKSFNRNEC (SEQ ID NO: 135)

FIG. 25C (cont'd)

>mPalivizumab variable light chain amino acid sequence in mouse anti-RSV emAb AAV
DIQLTQSPAIMSASPGEKVTMTCSASSSVGYMHWYQQKSSTSPKLWIYDTSKLASGVPGRFSGSGSGNSYSLTISSIQAEDVATYYCF
RGSGYPFTFGQGTKLEIK (SEQ ID NO: 136)

>mIgL kappa constant light chain amino acid sequence in mouse anti-RSV emAb AAV
ADAAPTVSIFPPSSEQLTSGGASVVCFLNNFYPKDINVKWKIDGSERQNGVLNSWTDQDSKDSTYSMSSTLTLTKDEYERHNSYTCEA
THKTSTSPIVKSFNRNEC (SEQ ID NO: 137)

>GSSG-streptag linker amino acid sequence in mouse anti-RSV emAb AAV is SEQ ID NO: 122

>mPalivizumab variable heavy chain amino acid sequence mouse anti-RSV emAb AAV
QVELQESGPGILQPSQTLSLTCSFSGFSLSTSGMSVGWIRQPSGEGLEWLADIWWDDKKDYNPSLKSRLTISKDTSSNQVFLKITGVD
TADTATYYCARSMITNWYFDVWGAGTTVTVSS (SEQ ID NO: 138)

>splice junction with flanking sequence in mouse anti-RSV emAb AAV
CAGGTGAGTCCTAACTTCTCTCCCATTCTAAATGCATGTTGGGGGGATTCTGGGCCTTCAGGACCA (SEQ ID NO: 139)

>Mouse mB3 Balb/C downstream region in mouse anti-RSV emAb AAV
CATAGGGACAAAGAGTGGGAGTGGGGCACTTTCTTTAGATTTGTGAGGAATGTTCCGCACTAGATTCCCGCCACTAGATTGTTAAAACTTCATTGTTG
GAAGGAGAGCTGTCTTAGTGATTGAGTCAAGGGAGGAGAAAGGCATCTAGCCTCGGTCTCAAAAGGGTAGTTGCTGTCTAGAGAGGT
CTGGTGGAGCCTGCAAAAGTCCAGCTTCAAAGGAACACAGAAGTATGTGTATGGAATATTAGAAGATGTTGCTTTACTCTTAA
GTTGGTTCCTAGGAAAAAATAGTTAAATACTGTGACTTTAAAATGTGAGAGGGTTTCAAGTACTCATTTTTTAAATGTCCAAAATT
TTTGTCAATCAGTTGAGGTTTGTGGTAGAGACAATAAATAAGTTAAAATATTTTAAAATGAATTGAGCAATGTTGAGTTGGAGTCAAGATG
CCTATTCAGAACTGACTTTAACAATAATAAGTTAACAATAAATAAGTTAGCAGGAAGCAGGTCATGTGGCAGGGAAGGAAAATAAAACC
GCCGATCAGAACCAGAACCACCTGCAGCAGCACCTGCAGGAAGCTGGCAGGTCATGTGGCAGGGAAGGAAAATAAAACC
ACTAGGTAAACTTGTAGCTGTGGTTTGAAGAAGTGGTTTGAAGAAACACTCTGTCAGCCCCACCAAACCGAAAGTCCAGGCTGAG
CAAAACACCACCTGGGTAATTTGCATTTCTAAAATAAGTTGAGGATTCAGCGGAAACTGGGAGGAGTCCTCTTTAACTTATTGAGT
TCAACCTTTTTAATTTAGCTTGAGTAGTTCTAGTTCTAGTTCCCCAAACTTAAGTTTATCGACTTCTCAAAATGTATTTAGAATTCATTTCAA
AATTAGGTTATGTAAGAAATTGAAGGACTTTAGTGTCTTTAAATTCTAATATATTTAGAAAACTTCTTAAAATTACTCTATTATTCTTC
CCTCTGATTATTGGTCTCCATTCA (SEQ ID NO: 140)

FIG. 25C (cont'd)

>mRSV kappa light chain coding sequence without signal sequence in mouse anti-RSV emAb AAV
GACATCCAGCTGACACAGAGCCCTGCCATCATGTCTGCTAGCCTGTCTGCTAGCAGGTGACAATGACCTGTTCCGCCAGCAGCTC
CGTGGGCTACACATGCACTGGTATCAGCAGAAGTCTAGCACAAGCCCCAAGCTGTGGATCTACGACACCTCCAAGCTGGCCTCTG
GCGTGCCAGGCAGATTTTCTGGAAGCGGCAGCGGGCTACCCCTTCACATTTGCCAGGGCACCAAGCTGGAAATCAAGGCGCGCTCC
ACCTACTACTGCTTCAGAGGCAGCGGGCTACCCCTTCACATTTGGCCAGGGCACCAAGCTGGAAATCAAGGCGCGCTCC
TACCGGTGTCTATCTTTCCACCTAGCCAGCGACTGAACATCTGGGCGGAGCCTCTGCGTGTCGTCGTTCCTGAACAACTTCTACCCT
AAGGACATCAACGTCAAGTGGAAGATCGACGGCTCCGAGAGACAGAACGGCGTGCTGAACTCTTGGACCGACCAGGACAGCAA
GGATAGCACCTACAGCATGAGCAGCACCCTGACCCTGACCCTGACCACTCTGAAGTCCTTCAACCGGAACGAGTGC (SEQ ID NO: 281)
CACACAAGACCAGCACATCCCCAATCGTGAAGTCCTTCAACCGGAACGAGTGC (SEQ ID NO: 281)

>mRSV kappa light chain amino acid sequence without signal peptide in mouse anti-RSV emAb AAV
DIQLTQSPAIMSASPGEKVTMTCSASSSVGYMHWYQQKSSTSPKLWIYDTSKLASGVPGRFSGSGSGNSYSLTISSIQAEDVATYYCF
RGSGYPFTFGQGTKLEIKADAAPTVSIFPPSSEQLTSGGASVVCFLNNFYPKDINVKWKIDGSERQNGVLNSWTDQDSKDSTYSMSST
LTLTKDEYERHNSYTCEATHKTSTSPIVKSFNRNEC (SEQ ID NO: 286)

FIG. 25D ms-emAb-RSV-dsDNA (1736 bp)

ACCACCTCTGTGACAGCATTTATACAGTATCCGATGGATGGACAAGTGAGTGTCTCAGGTTAGGATTCTATTTAAGATTGAGATATTAGGCTTTGATACTACACTA

Upstream homology (F primer)       JS58H10 Promoter 20          40          60          80          100

AATGGTCTGTACATGTCTCGGAAGAAAGTTCTTCAGACACAGAGTTAGGACTTGGATCCAGGAGGAGTTAGGACTTGGACTTGGACTCTAGTTTCTTCTTCTCCA

JS58H10 Promoter 120         140         160         180         200

GCTGGAATGTGTCCTTATGTGTAAGAAAAAGCCTTGCCTCATGAGTATGCAAATCATGTCGACTGTGATGATTAATATATGGGATATCCACACCAAACATCATATGAGCCCT

JS58H10 Promoter 220         240         260         280         300         320

ATCTTCTCTACAGACACTGAATCTCAAGGTCCTTACAATGGAAAACGACACTGCTGCTGTGGTGCTGCTTCTTTGGGTGCCCGGAAGCACAGCGGACATCCAGC

M  E  T  D  T  L  L  L  W  V  L  L  L  W  V  P  G  S  T  G  D  I  Q

JS58H10 Promoter       mRSV-kappal

Mouse Ig Kappa Signal peptide 340         360         380         400         420

FIG. 25D (cont'd)

TGACACAGAGCCCTGCCATCATGTCTGCTAGCCCTGGCGAGAAAGTGACAATGACCTGTTCCCCAGCAGCTCCGTGGCTACATGCACTGGTATCAGCAGAAGTCT

L  T  Q  S  P  A  T  M  S  A  S  P  G  E  K  V  T  M  T  C  S  A  S  S  S  V  G  Y  M  H  W  Y  Q  K  S mRSV-kappal
mPalivizumab   variable light chain 440     460     480     500     520

AGCACAAGGCCCCCAAGCTGTGGATCTACGACACCTCCAAGCTGGCCTCTGGCGTGCCAAGCTGGCCTGGGCGTGCCAAGCAGTGGCCAGATTTTCTGGAAGCGGCAGCGGCAACAGTGTACAGCCTGACTATCAG

S  T  S  P  K  L  W  I  Y  D  T  S  K  L  A  S  G  V  P  G  R  F  S  G  S  G  S  G  N  S  V  Q  S  L  T  I  S mRSV-kappal
mPalivizumab   variable light chain 540     560     580     600     620

CTCCATCCAGGCCGAGGATGTGGCTACCTACTACTGCTTCCAGGGCAGCGGCTACCCCTTCACATTTGGCCAGGGCACCAAGCTGGAAATCAAGCGGGCCGATGCCGCTC

S  I  Q  A  E  D  V  A  T  Y  Y  C  F  Q  G  S  G  Y  P  F  T  F  G  Q  G  T  K  L  E  I  K  R  A  D  A  A mRSV-kappal
mPalivizumab   variable light chain 660     680     700     720     740

FIG. 25D (cont'd)

CTACCGTGTCTATCTTTCCACCTAGCAGCAGCTGACATCTGGGCAGCCTCTGTCGTGTGCTTCCTGAACAACTTCTACCCTAAGGACATCAAGTCAAGTGG
P  T  V  S  I  F  P  P  S  S  E  Q  L  T  S  G  G  A  S  V  V  C  F  L  N  N  F  Y  P  K  D  I  N  V  K  W mRSV-kappa
m IgL constant 760   780   800   820   840   960

AAGATCGACGGCTCCGAGAGACAGAACGGCGTGCTGAACTCTTGGACTGATCAGGACAGCAAGGATAGCACCTACAGCATGAGCAGCACTCTGACCCTGACAAAGGA
K  I  D  G  S  E  R  Q  N  G  V  L  N  S  W  T  D  Q  D  S  K  D  S  T  Y  S  M  S  S  T  L  T  L  T  K  D mRSV-kappa
m IgL constant 860   880   900   920   940

CGAGTACGAGAGAGGCACAACTCTGAGGCCCACAAGACCAGCACATCCCAATCGTGAAGTCTTCAACCGTGAGGAAGAGTAGTGGCA
E  Y  E  R  H  N  S  Y  T  C  E  A  T  H  K  T  S  T  S  P  I  V  K  S  F  N  R  N  E  C  G  G  S  S  G mRSV-kappa
m IgL constant 980   1,000   1,020   1,040   1,060

GCGGGAGTGGGTCCAATTGGAGTCATCCTCAATTTGAGAAGAAGGAGGGGGAGGGTCCAATTGGTCTCATCCCAGTTTGGAGAAGGGGCGGCGGGGCTCCAATTGGTCC
S  G  G  S  N  W  S  H  P  Q  F  E  K  G  G  G  S  N  W  S  H  P  Q  F  E  K  G  G  G  S  N  W  S

GSSG-streptag linker 1,080   1,100   1,120   1,140   1,160

FIG. 25D (cont'd)

CATCCCCAGTTTGAAAAAGGCTCTGGTGGTGGAGGTGGCAGCGGCGGAGGCGGTGGGCAGGTGGGGCAGGTGGGAACTGCAAGAAAGCGGCCTCGGCATCCTGGCCTTCTCAGACACTGAGCCT

H  P  Q  F  E  K  G  S  G  G  G  G  S  G  G  G  G  S  G  G  Q  V  E  L  Q  E  S  G  P  G  I  L  Q  P  S  Q  T  L  S  L

GSG-streptag linker          mPalivizumab variable heavy chain 1,180            1,200            1,220            1,240            1,260            1,280

GACCTGTAGCTTCAGCGGCTTCAGCCTGAGCACAAGCGGCATGTCTGTCGGCTGGATCAGACAGCCTTCTGGCGAAGGACTGGAATGGCTGGCCGACATTTGGTGGG

T  C  S  G  F  S  L  S  T  S  G  M  S  V  G  W  N  R  Q  P  S  G  E  G  L  E  W  L  A  D  I  W  W mPalivizumab variable heavy chain 1,300            1,320            1,340            1,360            1,380

ACGACAAGAAGGACTACAACCCCAGCCTGAAGTCACGCCTGACCATCAGCAGGACCAGCCAGGGACAGCAGCCTACAACCAGGTGTTCCTGAAGATCACGGGGCGTGGACAGCGGAT

D  D  K  D  Y  N  P  S  L  K  S  R  L  T  I  S  K  D  T  S  S  N  Q  V  F  L  K  I  T  G  V  D  T  A  D mPalivizumab variable heavy chain 1,400            1,420            1,440            1,460            1,480

ACCGCCACCTATTACTGCGCCAGATCCATGATCACCAACTGGTACTTCGACGTGTGGGGCCTGCGCACCAACAGTGACCGCGTTCCTCAGGTGAGTCTAACTTCTCCC

T  A  T  Y  Y  C  A  R  S  M  I  T  N  W  Y  F  D  V  W  G  A  G  T  T  V  T  V  S  S (SEQ ID NO: 144)

mPalivizumab variable heavy chain          IntronSplice 1,500            1,520            1,540            1,560            1,580            1,600

FIG. 25D (cont'd)

ATTCTAAATGCATGTTGGGGGATTCTGGGCCTTCAGGACCACCATGTACCAAAGCCATAACGATCGGTGGGAGTATTCATTGTGGTCAAGATCCATAGGGACAAA

Intronsplice    Extra Sequence 1,620    1,640    1,660    1,680    1,700

GAGTGGGAGTGGGGCACTTTCTTTA (SEQ ID NO: 104)

>Upstream homology sequence (F primer) in ms-emAb-RSV-dsDNA
ACCACCTCTGTGACAGCATTTATACAGTATCCGATGGAT (SEQ ID NO: 142)

>J558H10 promoter in ms-emAb-RSV-dsDNA is SEQ ID NO: 128

>Signal peptide coding sequence in ms-emAb-RSV-dsDNA is SEQ ID NO: 129

>mPalivizumab light chain coding sequence in ms-emAb-RSV-dsDNA is SEQ ID NO: 130

>mPalivizumab variable light chain coding sequence in ms-emAb-RSV-dsDNA is SEQ ID NO: 131

>mPalivizumab kappa constant light chain coding sequence in ms-emAb-RSV-dsDNA is SEQ ID NO: 132

>GSSG-streptag linker coding sequence in ms-emAb-RSV-dsDNA is SEQ ID NO: 116

>mPalivizumab variable heavy chain coding sequence in ms-emAb-RSV-dsDNA is SEQ ID NO: 133

>Signal peptide amino acid sequence in ms-emAb-RSV-dsDNA is SEQ ID NO: 134

>mPalivizumab light chain amino acid sequence in ms-emAb-RSV-dsDNA is SEQ ID NO: 135

>mPalivizumab variable light chain amino acid sequence in ms-emAb-RSV-dsDNA is SEQ ID NO: 136

>mPalivizumab kappa constant light chain amino acid sequence in ms-emAb-RSV-dsDNA is SEQ ID NO: 137

>GSSG-streptag linker amino acid sequence in ms-emAb-RSV-dsDNA is SEQ ID NO: 122

>mPalivizumab variable heavy chain amino acid sequence in ms-emAb-RSV-dsDNA is SEQ ID NO: 138

>splice junction with flanking sequence in in ms-emAb-RSV-dsDNA is SEQ ID NO: 139

>Downstream homology sequence in ms-emAb-RSV-dsDNA
ATCCATAGGGACAAAGAGTGGAGTGGGGCACTTTCTTTA (SEQ ID NO: 143)

>mPalivizumab light chain coding sequence without signal sequence in ms-emAb-RSV-dsDNA is SEQ ID NO: 281

>mPalivizumab light chain amino acid sequence without signal peptide in ms-emAb-RSV-dsDNA is SEQ ID NO: 286

FIG. 25E
hu-emAb-VRC01-AAV (2551 bp)

TGTGAGCCCGGAGACAGAAGGTCTCTGGGTGTCGCCTGGGTTTTGTGGGGTGAGGATGGACATTCTGCCATTGTGATTACTACTACTACTACTACATGGAGGTCTGGG

Human T7 Upstream Homology 20    40    60    80    100

GCAAAGGGACCACGGTCACCGTCTCCTCAGGTAAGAATGGCCACTCTAGGCCTTGTTTTCTGCTACTGCTGTGGGGTTTCCTGAGGCATTGCAGGTTGGTCTCG

Human T7 Upstream Homology 120    140    160    180    200

GGGCATGTTCCGAGGGGACCTGGGCCGACTGGGCCAGGAGGGGATGGCACTGGGGTGCCTTGGGGGTCTCGTGTTGGATCTGGGAGCCTCTGTGTTGGATTTTCCGATGCCTTTGGAAAATG

Human T7 Upstream Homology 220    240    260    280    300    320

GGACTCAGGTTGGGTGCGTCTGATGGAGTAACTGAGCCTGGGGGCTTGGGGAGCCTGGGGCCACATTTGGACCGAGATGCCTGAACAAACCAGGGGTCTTAGTGATGGCTGAGGA

Human T7 Upstream Homology 340    360    380    400    420

ATGTGTCTCAGGAGCGGGTGTCTGATCGTAATCTTTAGGCCAATAAAATGTGGGTTCACAGTGAGGAGTGCATCCTGGGGTTGGGCTTTGTTCTGCAGCGGGAAGAGC

IGVH1-69 promoter 440    460    480    500    520

FIG. 25E (cont'd)

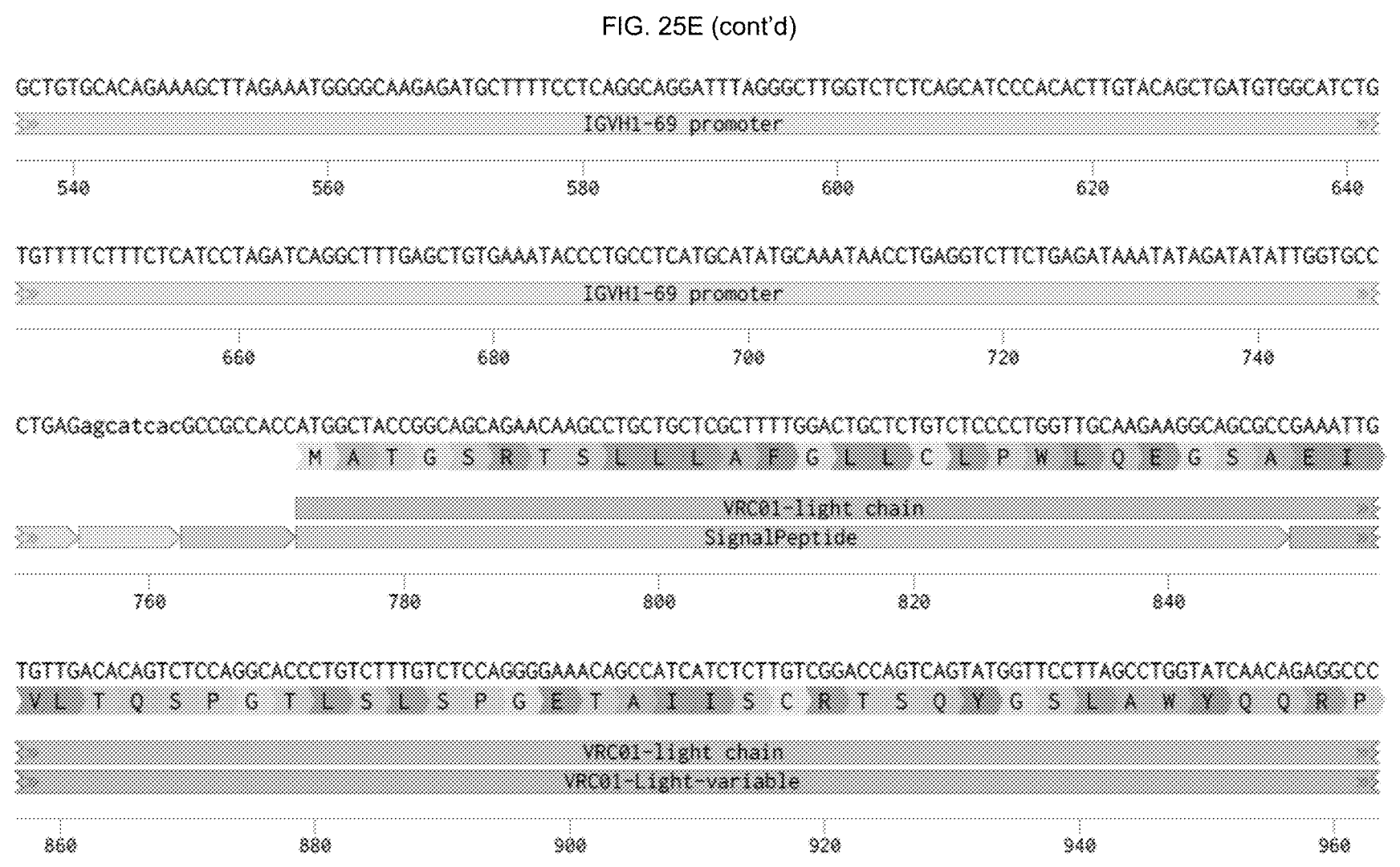

GCTGTGCACAGAGAAAGCTTAGAAATGGGGCAAGAGATGCTTTCCTCAGGCAGGATTTAGGGCTTGGTCTCTCAGCTACAGATCCCACACTTGTACAGCTGATGTGGCCATCTG
540          560          580          620          640
IGVH1-69 promoter TGTTTTCTTTCTTCATCCTAGATCAGGCTTTGAGCTGTGAAATACCTGCCTCATGCATATGCAAATAACCTGAGGTCTTTCTGACATAAATATAGATATATTGGTGCC
660          680          700          720          740
IGVH1-69 promoter CTGAGagcatcacgGCGCCGCCACCATGGCTACCGGTTCCCTGCTGCTCTTTGCACTGCTCCTCCCTGGTTGCAAGAAGCAGGCGGCCGAAATTG
760          780          800          820
M  A  T  G  S  R  T  S  L  L  L  A  F  G  L  L  C  L  P  W  L  Q  E  G  S  A  E  I
VRC01-light chain
SignalPeptide TGTTGACACAGTCTCCAGGCACCCTGTCTTTGTCTCCAGGGGAAAGAGCCACCATCTCTTGTCGGGCCAGTCAGTATGGTTCCTTAGCCTGGTATCAACAGAGGCCC
860          880          900          920          940          960
V  L  T  Q  S  P  G  T  L  S  L  S  P  G  E  T  A  I  I  S  C  R  T  S  Q  Y  G  S  L  A  W  Y  Q  Q  R  P
VRC01-light chain
VRC01-light-variable

FIG. 25E (cont'd)

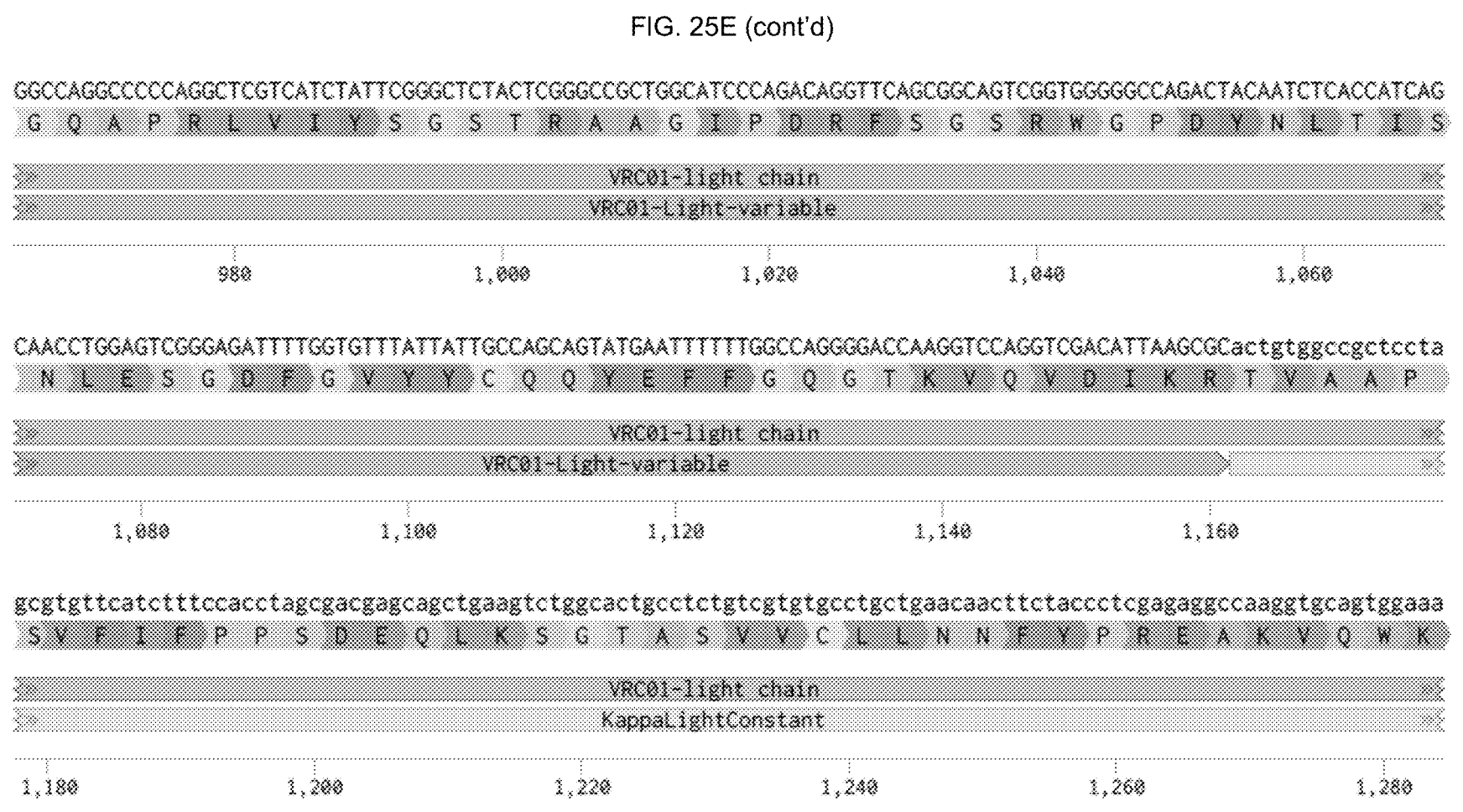

GGCCAGGCCCCAGGCTCGTCATCTATTGGGCTCTACTCGGGCTCCAGGCGCTGGCATCCCAGACACAGGTTCAGGCGGCAGTCGGTGGGGGGCCAGACTACAATTCCACCATCAG
 G  Q  A  P  R  L  V  I  Y  S  G  S  T  R  A  A  G  I  P  D  R  F  S  G  S  R  N  G  P  D  W  N  L  T  I  S

VRC01-light chain
VRC01-Light-variable 980          1,000          1,020          1,040          1,060

CAACCTGGAGTCGGGAGATTTTGGTGTGTTTATTATTGCCAGCAGTATGAATTTTTTGGCCAGGGGACCAAGGTCGACATTAAGCGCactgtggccgctccta
 N  L  E  S  G  D  F  G  V  F  Y  Y  C  Q  Q  Y  E  F  F  G  Q  G  T  K  V  D  I  K  R  T  V  A  P VRC01-light chain
VRC01-Light-variable 1,080          1,100          1,120          1,140          1,160 gcgtgttcatctttccacctagcgacgagcagctgaagtctggaactgcctctgtcgtgtgcctgctgaataacttctacccctgcgaggccaaggtgcagtggaag
 A  V  F  I  F  P  P  S  D  E  Q  L  K  S  G  T  A  S  V  V  C  L  L  N  N  F  Y  P  C  E  A  K  V  Q  W  K VRC01-light chain
KappaLightConstant 1,180          1,200          1,220          1,240          1,260          1,280

FIG. 25E (cont'd)

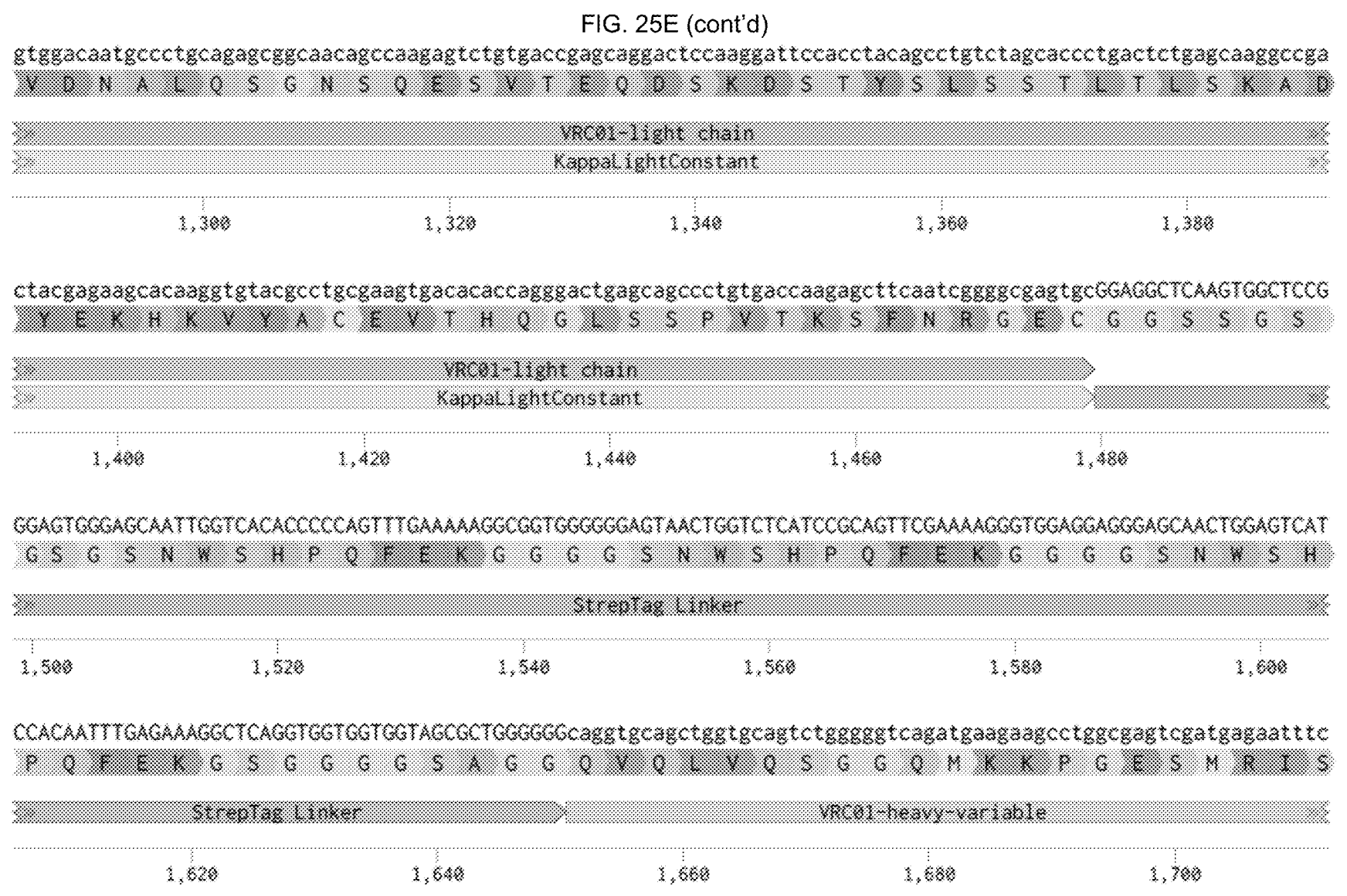

gtggacaatgccctgcagagctggcaacagccaagagtctgtgaccgagcgagcaggactccaactacagcctgctctagcacctgacctctgagcaagccga
V D N A L Q S G N S Q E S V T E Q D S K D S T Y S L S S T L T L S K A D VRC01-light chain
KappaLightConstant 1,300    1,320    1,340    1,360    1,380 ctacgaggagcacaaggtgtacgcctgcgaagtgacacaccaggactgagcagccctgtgaccagcttcaatcggggccagtgcGGAGCTCAAGTGGCTCCG
Y E K H K V Y A C E V T H Q G L S S P V T K S F N R G Q C G G S G S VRC01-light chain
KappaLightConstant 1,400    1,420    1,440    1,460    1,480

GGAGTGGGAGCAATTGGTCACACCCCCAGTTTCAAAAAGGCGGTGGGGGAGTAACTGGTCTCATCCGCAGTTCGAAAAGGGTGGAGGGGGAGCAACTGGAGTCAT
G S G N W S H P Q F E K G G G S G S N W S H P Q F E K G G G S N W S H

StreptTag Linker 1,500    1,520    1,540    1,560    1,580    1,600

CCACAATTTGAGAAAGGCTCAGGTGGTGGTGGTAGCGGTGGGGGCaggtcagctgtcagtggttgtcagtgctcggggggtcagatgaagaagcctcggggtcagatgaagaagcctcggagtcgatgaggaattc
P Q F E K G S G G G G S A G G G Q V Q L V Q S G G Q M K K P G E S M R I S StreptTag Linker      VRC01-heavy-variable 1,620    1,640    1,660    1,680    1,700

FIG. 25E (cont'd)

ttgtcgggctctctggatatgaattattgattgtacgctaaattggttcgtctgctccgccccggaaaaaggcctgagtggatgggatggtgaagcctcgagtggcg
C R A S G Y E F I D C T L N W I R L A P G K R P E W M G W L K P R G G 1,720    1,740    1,760    1,780    1,800

VRC01-heavy-variable cggtcaactacgcacgtccacttcaggcagagtgaccatgacgactcgagacgtttattccgacacagccttttgggagctgcgctcgttgacagtagacgacggcc
A V N Y A R P L Q G R V T M T R D V Y S D T A F L E L R S L T V D D T A 1,820    1,840    1,860    1,880    1,900    1,920

VRC01-heavy-variable gtctactttgtactagggaaaaactgtgattacaattgggacttcgaacactgggccccgggcaccccgtcatcgtctcatcaGGTGAGTTGGCTTTCCTTCT (SEQ ID NO: 152)
V Y F V L G K N C D Y N W D F E H W G R G T P V I V S S 1,940    1,960    1,980    2,000    2,020

VRC01-heavy-variable    Splice

GCCTCCTTTCTCTGGGCCCAGCGTCCTCTGACCTGGAGCTGGGAGATAATGTCCGGCGGCTCCTTATCGTAGGACTGCAAGATCGCTGCACAGCAGCGAATCGTGAA

Flanking sequence 2,040    2,060    2,080    2,100    2,120    2,140

FIG. 25E (cont'd)

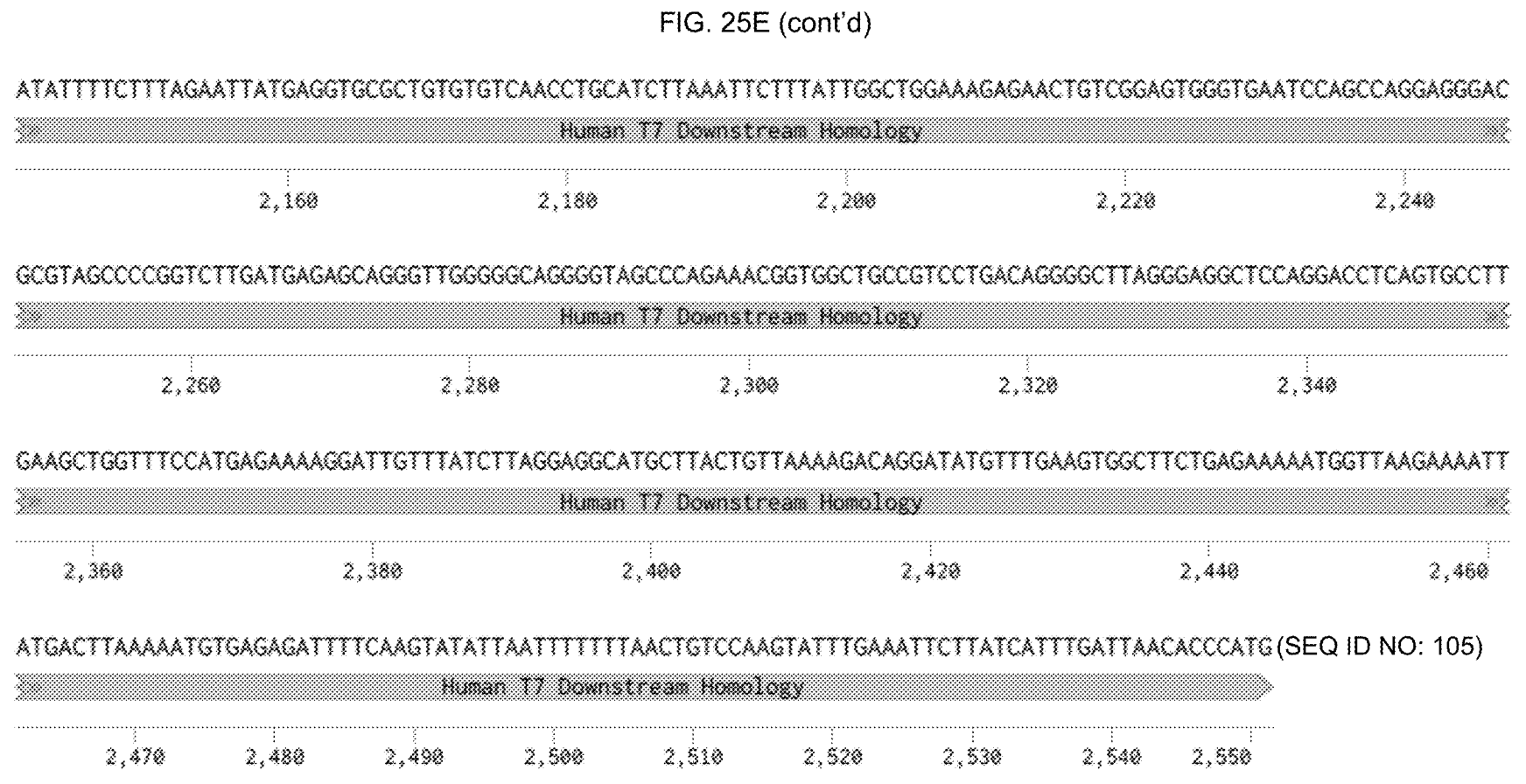

ATATTTTCTTTAGAATTATGAGGTGCGCTGTGTGTGTCAACCTGCATCTTAAATTCTTTATTGGCTGGAAAGAGAACTGTCGGAGTGGGTGAATCCAGCCAGGAGGGAC

Human T7 Downstream Homology 2,160    2,180    2,200    2,220    2,240

GCGGTAGCCCCGGTCTTGATGAGAGCAGGGTTGGGGCCAGGGGTAGCCCAGAAACGGTGGCTGGCGTCCTGCCGTCCTGACAGGGGGTCCCAGGAGGCTCCAGGACCTCAGTGCCTT

Human T7 Downstream Homology 2,260    2,280    2,300    2,320    2,340

CAAGCTGGTTCCATGACGAAAAAGGATTGTTTATCTTAGGAGGCATGCTTACTCGTTAAAAGACAGGATATGTTTGAAGTGGGCTTCTGAGAAAATGGTTAAGAAAATT

Human T7 Downstream Homology 2,360    2,380    2,400    2,420    2,440    2,460

ATCACTTAAAAATGTGAGAGATTTCAAGTATATTAATTTTTTTTAACTGTCCAAGTATTTGAAATTCTTATCATTTGATTAACACCATG(SEQ ID NO: 105)

Human T7 Downstream Homology 2,470    2,480    2,490    2,500    2,510    2,520    2,530    2,540    2,550

FIG. 25E (cont'd)

>Human T7 upstream homology in Hu-emAb-VRC01-AAV is SEQ ID NO: 110

>IgVH1-69 promoter in Hu-emAb-VRC01-AAV is SEQ ID NO: 111

>Signal peptide coding sequence in Hu-emAb-VRC01-AAV is SEQ ID NO: 112

>VRC01 light chain coding sequence in Hu-emAb-VRC01-AAV
ATGGCTACCGGCAGCAGCAGAACAAGCCTGCTGCTGCTGCTTTGGACTGCTGCTGTCCCCTGGTTGCAAGAAGGCAGGCGGCGAAATT
GTGTTGACACAGTCTCCAGGCACCCTGTCTCTGTCTCCAGGGGAAACAGCCATCATCTCTTGTCGGACCAGTCAGTATGGTTCC
TTAGCCTGGTATCAACAGAGGCCCGGCCAGGCCCGGCTCGTCACTCTATTCGGGCTCATCTCATCAGCAACCTGGCATCCCAGA
CAGGTTCAGCGGCAGTCGGTGGGGCCAGACTACAATCTCACCATCAGCAACCTGGAGTCGGGGGAGATTTTGGTGTTTATTATTG
CCAGCAGTATGAATTTTTGGCCAGGGGACCAAGGTGGAGGTCCTCACCTAGCGTGTTCATCTT
TCCACCTAGCGACGAGCAGCTGAAGTGCCTGCACTGCCTCTGTGTGTGTCCAAGAACTTCTACCCTGCCAAGGCCAAGG
TGCAGTGGAAAGTGGACAATGCCCTGCCAGAGCGGCCAACAGCCAAGAGTCTGTGACCGAGCAGGATTCCACCTAC
AGCCTGTCTAGCACCCTGACTCTGAGCAAGGCCGACTACGAGAAGCACAAGGTGTACGCCTGCGAAGTGACACACCAGGGACT
GAGCAGCAGCCCCTGTGACCAAGAGCTTCAATCGGGGCGAGTGC (SEQ ID NO: 145)

>VRC01 variable light chain coding sequence in Hu-emAb-VRC01-AAV
GAAATTGTGTTGACACAGTCTCCAGGCACCCTGTCTCTGTCTCCAGGGGAAACAGCCATCATCTCTTGTCGGACCAGTCAGTATG
GTTCCTTAGCCTGGTATCAACAGAGGCCCGGCCAGGCCCGGCTCGTCATCTATTCGGGCTCTACTCGGGCCGCTGGCATC
CCAGACAGGTTCAGCGGCAGTCGGTGGGGCCAGACTACAATCTCACCATCAGCAACCTGGACATTAAGGC (SEQ ID NO: 146)
TTATTGCCAGCAGTATGAATTTTTGGCCAGGGGACCAAGGTGGAGGTCCTCACCTAGCGTG >Kappa constant light chain coding sequence in Hu-emAb-VRC01-AAV is SEQ ID NO: 115

>GSSG-streptag linker coding sequence in Hu-emAb-VRC01-AAV is SEQ ID NO: 116

>VRC01 variable heavy chain coding sequence in Hu-emAb-VRC01-AAV
CAGGTGCAGCTGGTGCAGTCTGGGGGTCAGATGAAGAAGCCTGGCGAGTCGATGAGGAATTTCTGTGTCGGGCCTTCTGGGATATGA
ATTTATTGATTGTACGCTAAATTGGATTCGTCTGGCCCCGGAAAAAGGCCTGAGTGGCTGAAGCCTCGAGGTGG
CGCGGTCAACTACGCACGTCCACTTCAGGGCAGGAGTGACCATGAGACGTTTATTCCGACACAGCCTTTTGGGAGCTGCG
CTCGTTGACAGTAGAGCGACACGGCCGTCTACTTTTGTACTAGGGGGAAAAACTGTGATTACAATTGGGACTTCGAACACTGGGG
CCGGGGCACCCGGTCATCGTCTCTCATCA (SEQ ID NO: 147)

FIG. 25E (cont'd)

>Signal peptide amino acid sequence in Hu-emAb-VRC01-AAV is SEQ ID NO: 118

>VRC01 light chain amino acid sequence in Hu-emAb-VRC01-AAV
MATGSRTSLLLAFGLLCLPWLQEGSAEIVLTQSPGTLSLSPGETAIISCRTSQYGSLAWYQQRPGQAPRLVIYSGSTRAAGIPDRFSGS
RWGPDYNLTISNLESGDFGVYYCQQYEFFGQGTKVQVDIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 148)

>VRC01 variable light chain amino acid sequence in Hu-emAb-VRC01-AAV
EIVLTQSPGTLSLSPGETAIISCRTSQYGSLAWYQQRPGQAPRLVIYSGSTRAAGIPDRFSGSRWGPDYNLTISNLESGDFGVYYCQQ
YEFFGQGTKVQVDIKR (SEQ ID NO: 149)

>Kappa constant light chain amino acid sequence in Hu-emAb-VRC01-AAV is SEQ ID NO: 121

>GSSG-streptag linker amino acid sequence in Hu-emAb-VRC01-AAV is SEQ ID NO: 122

>VRC01 variable heavy chain amino acid sequence in Hu-emAb-VRC01-AAV
QVQLVQSGGQMKKPGESMRISCRASGYEFIDCTLNWIRLAPGKRPEWMGWLKPRGGAVNYARPLQGRVTMTRDVYSDTAFLELRSL
TVDDTAVYFCTRGKNCDYNWDFEHWGRGTPVIVSS (SEQ ID NO: 150)

>splice junction with flanking sequence in constructs of the disclosure
CAGGTGAGTTGGCTTTCCTTCCTTCTGCCCTTCCTTCTGCGCCCTTGGGCCCAGCTGCCTCCTCTGACCTGGAGCTGGGAGATAATGTCCGGGGGCT
CCTT (SEQ ID NO: 151)

>Human T7 downstream homology in Hu-emAb-VRC01-AAV is SEQ ID NO: 125

FIG. 25E (cont'd)

>VRC01 light chain coding sequence without signal sequence in Hu-emAb-VRC01-AAV
GAAATTGTGTTGACACAGTCTCCAGGCACCCTGTCTTTGTCTCCAGGGGAAACAGCCATCATCTCTTGTCGGACCAGTCAGTATG
GTTCCTTAGCTGGTATCAACAGAGGCCCGGCCCAGCCCCAGGGCTCGTCATCTATTCGGGGCTCACTCGGGCCGCTGGCATC
CCAGACAGGTTCAGCGGCAGTCGGTGGGGCCAGACTACAATCTCACCATCAGCAACTGGGAGTCGGGAGATTTGGTGTTTA
TTATTGCCAGCAGTATGAATTTTTGGCCAGGGGACCAAGGTCCAGGTCACTGCCTCTCTGTGTGCACTGTGGCACTGTGGTGTT
CATCTTTCCACCTGACCGCGAGCAGCGACAATGCCCTGCCAGAGCGGCAACAGCCAAGAGTCTGTGACCAGGATTCCA
CAAGGTCAGTGGAAGTGGACAAGGTGCCCTGCGAGCAGGCCGACTACGAGGTGTACGCCTGCGAAGTGACACACCAG
CCTCAGCCTGTCTCAGCACCCTGACCAAGAGCTTCAATCGGGGCGAGTGC (SEQ ID NO: 282)
GGACTGAGCAGCCCTGTGACCAAGAGCTTCAATCGGGGCGAGTGC (SEQ ID NO: 282)

>VRC01 light chain amino acid sequence without signal peptide in Hu-emAb-VRC01-AAV
EIVLTQSPGTLSLSPGETAIISCRTSQYGSLAWYQQRPGQAPRLVIYSGSTRAAGIPDRFSGSRWGPDYNLTISNLESGDFGVYYCQQ
YEFFGQGTKVQVDIKRTVAAPSVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC (SEQ ID NO: 287)

FIG. 25F
hu-emAb-Medi8852-AAV (2544 bp)

TGTGACGCCCCGGAGACACAGAAGGTCTCTGGGTGCTGGGTTTTGTGGGGTGAGGATGGACATTCTGCCATTGTGATTACTACTACTACTACATGGACGTCTGGG

Human T7 Upstream Homology

GCAAAGGGACCACGGTCACCGTCTCCTCAGGTAAGAATGGCCACTCTAGGGCCTTTGTTTTCTGCTACTGCCTGTGTGGGTTTCCTGAGGCCATGTTCCGAGGGGACC

Human T7 Upstream Homology

TGGGCGGACTGGCCAGGAGGGATGGCACTGGGTGCCTTGAGGATCTGGAGCTTCTGTGTGGATTTTCCGATGCCTTGGAAAATGGACTCAGGTTGGGTGCGTC

Human T7 Upstream Homology

TGATGGAGTAACTGAGCTTGGGGGCTTGGGGAGCCACATTTGGACACGAGATGCCTGAACAAACCAGGGGTCTTAGTGATGGCTGAGGAATGTGTCTCAGGAGCCGGTGT

Human T7 Upstream Homology

CTCGATCGTAATCTTTAGGCCAATAAAATGTGGGTTCACAGTGAGGAGTGCATCCTGGGGTTGGGGTTTGTTCTGCCAGTGGGGAAGAGCCGCTGTGCACAGAAAGCTTAG

IgVH1-69 Promoter

FIG. 25F (cont'd)

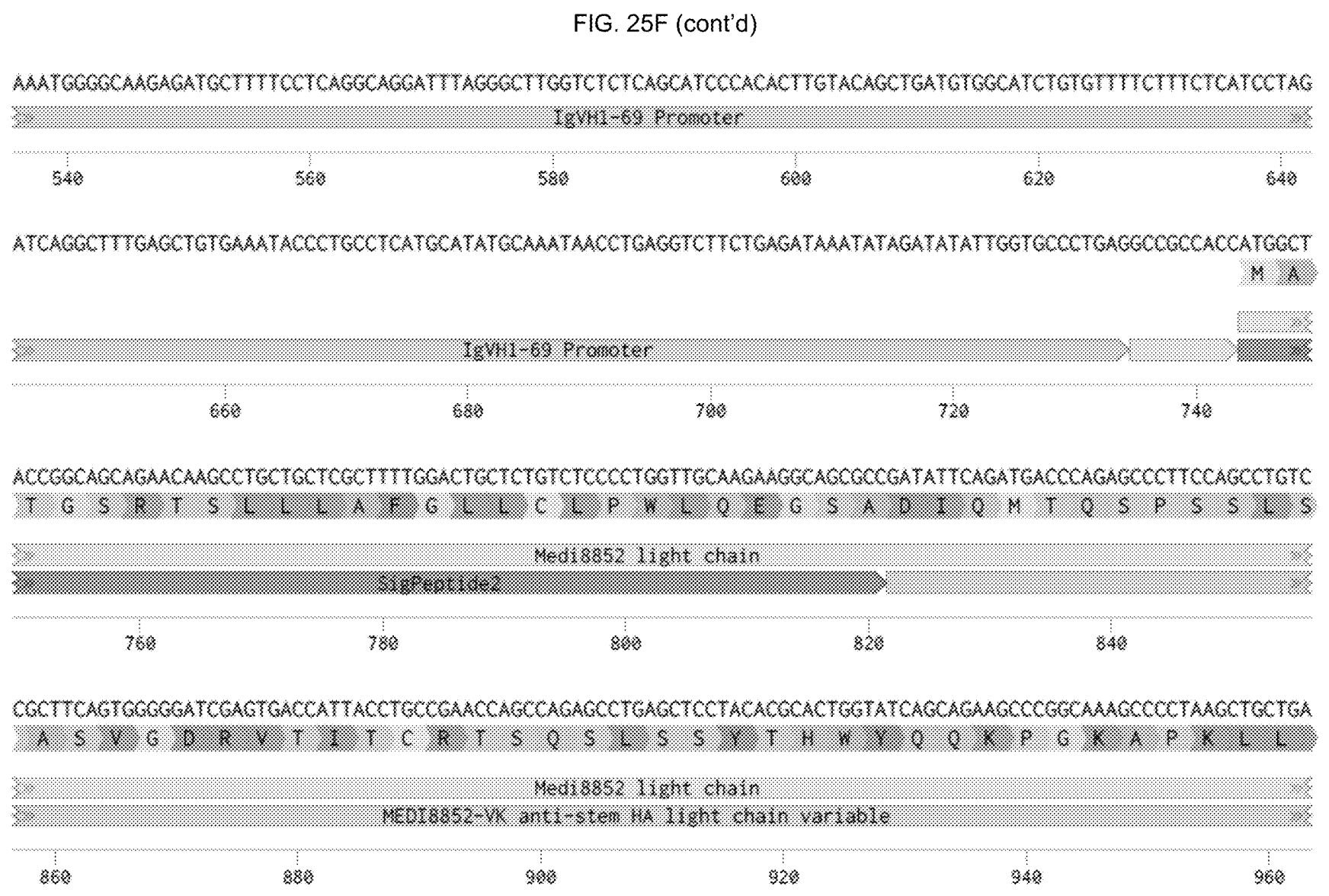

AAATGGGGCAAGAGATGCTTTCCTCAGGCAGGATTTAGGGCTTGGTCTCTCAGCATCCCACACTTGTACAGCTGATGTGGCATCGTGTTTTCTTCTCATCCTAG

IghV1-69 Promoter 540 560 580 600 620 640

ATCAGGCTTTGAGCTGTGAAATACCCTGCCTCATGCGATATGCAAATAACCTGAGGTCTTCTGAGATAAATATAGATATATTGGTGCCCTGAGCGCCGCCACCATGGCT

M A

IgHV1-69 Promoter 660 680 700 720 740

ACCCGGCAGCAGAACAGCCTGCTCGCTTTTGGACTGCTCTGTCTCCCTGGTTCCAAGAGGCAGCCCGATATTCAGATGACCCAGAGCCCTTCCAGCTGTC

T G S R T S L L L A F G L L C L P W L Q E G S A D I Q M T Q S P S S L S

Medi8852 light chain 760 780 800 820 840

CGCTTCAGTGGGGGGATCAGTGACCATTACCTGCCGAGCCAGTGACGTGGTATCAGCAGAAGCCCGGCAAAGCCCCTAAGCTGCTGA

A S V G D R V T I T C R T S Q S L S S S T H W Y Q Q K P G K A P K L L

Medi8852 light chain

MEDI8852-VK anti-stem H4 light chain variable 860 880 900 920 940 960

FIG. 25F (cont'd)

TCTAGCGCCGCTTCTAGTCGGGGGTCCGGAGTGCCAAGCCGGTTCTCCGGATCTGGGAGTGGGAACCGACTTTACCTGACAATTCAAGCCTGCAGCCCGAGGATTTC
A A S R G S G V P S R F S G S G S G T D F T L T I S S L Q P E D F

Medi8852 light chain
MEDI8852-VK anti-stem HA light chain variable 980          1,000          1,020          1,040          1,060

GCTACATACTACTGTGTCAGCAGAGCAGAGAACTTTCGGGCAGGGCACTAAGGTGGAGATCAAAcggactgtggccgctcctagcgtgttcatctttccacctagcgacga
A T Y Y C Q Q S R T E G Q G T K V E I K R T V A A P S V F I F P P S D E

Medi8852 light chain
MEDI8852-VK anti-stem HA light chain variable          KappaLightConstant 1,080          1,100          1,120          1,140          1,160 gcagctgaagtctggaactgcctctgtcgtgtgcctgctgaacaacttctaccctcgagaggccaaggtgcagtggaaggtggacaatgccctgcagagcggcaaca
Q L K S G T A S V V C L L N N F Y P R E A K V Q W K V D N A L Q S G N

Medi8852 light chain
KappaLightConstant 1,180          1,200          1,220          1,240          1,260          1,280

FIG. 25F (cont'd)

gccaagagtctgtgaccgagcaggactccaagcctacagcctgtctagcacctgactctgagcaaggccgactacgagaagcacaaggtgtacgcctgc
S Q E S V T E Q D S K D S T W S L S S T L T L S K A D Y E K H K V Y A C Med18852 light chain
KappaLightConstant 1,300     1,320     1,340     1,360     1,380 gaagtgacacaccaggggctgagcagccctgtgaccaagagcttcaatcgggggcgagtgccGAGGAAGTAGTGGCAGCCGGAGTGGGTCCAATTGGAGTCATCTCA
E V T H Q G L S S P V T K S F N R G E C G G S S G S G S G S G N N S H P Q GSSG-streptag linker 1,400     1,420     1,440     1,460     1,480

Med18852 light chain
KappaLightConstant

ATTTGAGAAAGGAGGCGGAGGGTCTCATCCCAGTTGGTTGGTTCAATTGGTTGAGAAGGGCGGGCGGCGGGTCCAATTGGTTCCAATTGGTTGAAAAGGCTCTGGTGGAG
F E K G G G G S N W S H P Q F E K G G G G S N W S H P Q F E K G G G G

GSSG-streptag linker 1,500     1,520     1,540     1,560     1,580     1,600

GTGGTAGTGCCTGGTGGTGGCAGGTCCAGTGCAGCAGAGCGGCCCCGGACTGGTCAAGCCTTCACAGACACTGAGCCTGACATGCGCCATTAGCGGAGATAGCGTGAGC
G G S A G G Q V Q L V Q S G P G L V K P S Q T L S L T C A I S G D S V S

MEDI8852 anti-stem HA varible heavy region 1,620     1,640     1,660     1,680     1,700

FIG. 25F (cont'd)

TCCTACAATGCCGTGTGGAACTGGATCAGGCAGTCTCCAAGTGGAGGACTGGAGTGGCTGGGAGTCGGACGAACATACTATAGATCCGGGTGGTACAATGACTATGCTGAATC
S Y N A V W N W I R Q S P S R G L E W L G V G R T Y Y R S G W N D Y A E S

MEDI8852 anti-stem HA varible heavy region 1,720          1,740          1,760          1,780          1,800

AGTGAAAGCCGAATTACTATCAACCCGATACCAGTTCTCTCTGCAGTCAGAATCAGTTCTCTCTGCAGTGTGAACAGTGTGACCCTGAGGACGCACAGCGTGTACTACTGCGCCAGAA
V K S R I T I N P D T S K N Q F S L Q L N S V T P E D T A V Y Y C A R

MEDI8852 anti-stem HA varible heavy region 1,820          1,840          1,860          1,880          1,900          1,920

GCGGCCATCACCGTCTTTGGCGTCAATGTGGATGCTTTCGATATGTGGGGCAGGGGACTATGGTCACCGTGTCTTCAGGTGGCTTCCTTCTGCCTCCT
S G H I T V F G V N V D A F D M W G Q G T M V T V S S

MEDI8852 anti-stem HA varible heavy region (SEQ ID NO: 160)

Splice          Flanking sequence 1,940          1,960          1,980          2,000          2,020

TTCTCTGGGCCCAGCGTCCTCTCGACCTGGAGCTGGGAGATAATGTCCGGGGGCCTCCTTATCGTAGGACTGCAAGATCGGTGCCACAGCAGCGAATGCGTGAAATATTTT
Flanking sequence                          Human T7 Downstream Homology 2,040          2,060          2,080          2,100          2,120          2,140

FIG. 25F (cont'd)

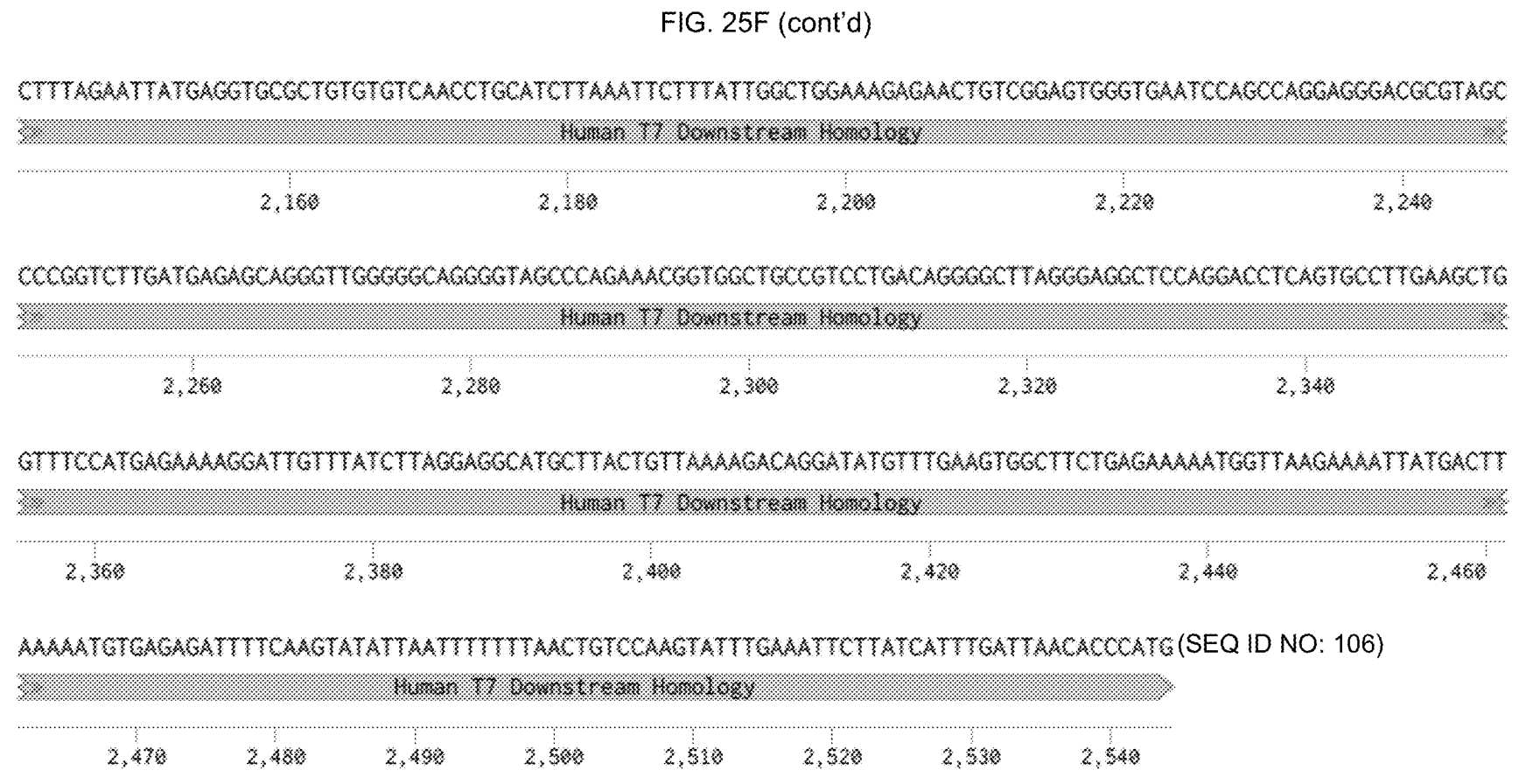

CTTTAGAATTATGAGGTGCGCTGTGTGTCAACCTGCATCTTAAATTCTTTATTGGCTGGAAGAACTGTCGGAGTGGGTGAATCCAGCCAGGAGGGACGCGTAGC

Human T7 Downstream Homology 2,160　　2,180　　2,200　　2,220　　2,240

CCCGGTCTTGATGAGAGCAGGGTGGGGGCAGGGGTAGCCCAGAAACGGTGGCTGCGTCCTGACAGGGGCTTAGGGAGGCTCCAGGACCTCAGTGCCTTGAAGCTG

Human T7 Downstream Homology 2,260　　2,280　　2,300　　2,320　　2,340

GTTTCCATGCAGAAAAGGATTGTTTATCTTAGGCAGGCATGCTTACTGTTAAAAGACAGGATATGTTTGAAGTGGCTTCTGAGAAAAATGGTTAAGAAAATTATGACTT

Human T7 Downstream Homology 2,360　　2,380　　2,400　　2,420　　2,440　　2,460

AAAAATGTGAGAGATTTCAAGTATATTAATTAATTTTTTTTAACTGTCCAAGTATTTGAATTCTTATCATTGATTAACACCCATG (SEQ ID NO: 106)

Human T7 Downstream Homology 2,470　　2,480　　2,490　　2,500　　2,510　　2,520　　2,530　　2,540

FIG. 25F (cont'd)

>human T7 upstream homology region in constructs of disclosure
TGTGACGCGCCGGAGACAGAGGTCTCTGGGTGGCTGGGTTTTGTGGGGTGAGGATGGACATTCTGCCATTGTGATTACTACTA
CTACTACTACGAGCGTCTGGGGCAAAGGGACCACGGTCACCGTCTCTCAGGTAAGAATGGCCACTCTAGGGCCTTTGTTT
CTGCTACTGCCTGTGTGGGGTTTCCTGAGGGCATGTCCGAGGGGACCTGGGCGGACCTGGCCAGGAGGGGGATGGGCACTGGGGT
GCCTTGAGGATCTGGGAGCCTCTGTGATTTTCCGATGCCTTTGGAAAATGGGACTCAGGTTGGGTGCGTCTGATGGAGTAACT
GAGCCTGGGGGCTTGGGGAGGCCACATTTGGACGAGATGCCTGAACAAACCAGGGGTCTTAGTGATGGCTGAGGAATGTGTCTC
AGGAGCGGGTGTCT (SEQ ID NO: 153)

>IgVH1-69 promoter in hu-emAb-Medi8852-AAV is SEQ ID NO: 111

>Signal peptide coding sequence in hu-emAb-Medi8852-AAV is SEQ ID NO: 112

>Medi8852 light chain coding sequence in hu-emAb-Medi8852-AAV
ATGGCTACCGGCAGCAGCAGAACAAGCCTGCTGCTCTGTCTCCCCTGGTTGCAAGAAGGCAGCGCCGATATT
CAGATGACCCAGAGCCCTTCCAGCTTGTCCGATCGAGTGACCATTACCTGCGAGCCCAGAGCCTGAG
CTCCTACACGCACTGGTATCAGCAGAAGCCCGGCAAAGCCCTTTACCCTGAGCTGCTATCGCGGGGGTCCGGAG
TGCCAAGCCGGTTCTCCGGAGTGGAGTGGCAGGGCACTAAGGTGGAGATCAAAACGGACTGTGGCCGCTGTTCATC
ACTACTGTCAGCAGCAGCAGAACTTTCGGGCAGGAAGTCTGGCACTGCTGAGTGCCACTGCTGAACAACTTCACCCTGAGAGGCCAAG
TTTCCACCTAGCGACGACGCAGCAGCTGCCTGCAGAGCGGGCAACAGCCAAGATCTGTGACGGAGGATCCAAGGATTCCACCTA
GTGCAGTGGAAAGTGGACAATGCCCTGCAGAGCGGGCAACAGCCAAGATCTGTGACGGAGGCCAAGGTTGTACGCCTGCGAAGTGACACACCAGGGAC
TGAGCAGCCCTGTGACCAAGAGCTTCAATCGGGGGACGGGGAGTGC (SEQ ID NO: 154)

>MEDI8852-VK anti-stem HA variable light chain coding sequence in hu-emAb-Medi8852-AAV
GATATTCAGATGACCCAGAGCCCTTCCAGCTTGTCCGCTTCAGTGGGGGATCGAGTGACCATTACCTGCGAACCAGCCAGAG
CCTGAGCTCCTACACGCACTGGTATCAGCAGAAGCCCGGCAAAGCCCTAAGCTGCTACGCGGCCTTCTAGTCGGGGGGT
CCGGAGTGCCAAGCCGGTTCTCCGGAGTGGAGTGGCAGGGCACTAAGGTGGAGATCAAA (SEQ ID NO: 155)

>Kappa constant light chain coding sequence in hu-emAb-Medi8852-AAV is SEQ ID NO: 115

>GSSG-streptag linker coding sequence in hu-emAb-Medi8852-AAV is SEQ ID NO: 116

FIG. 25F (cont'd)

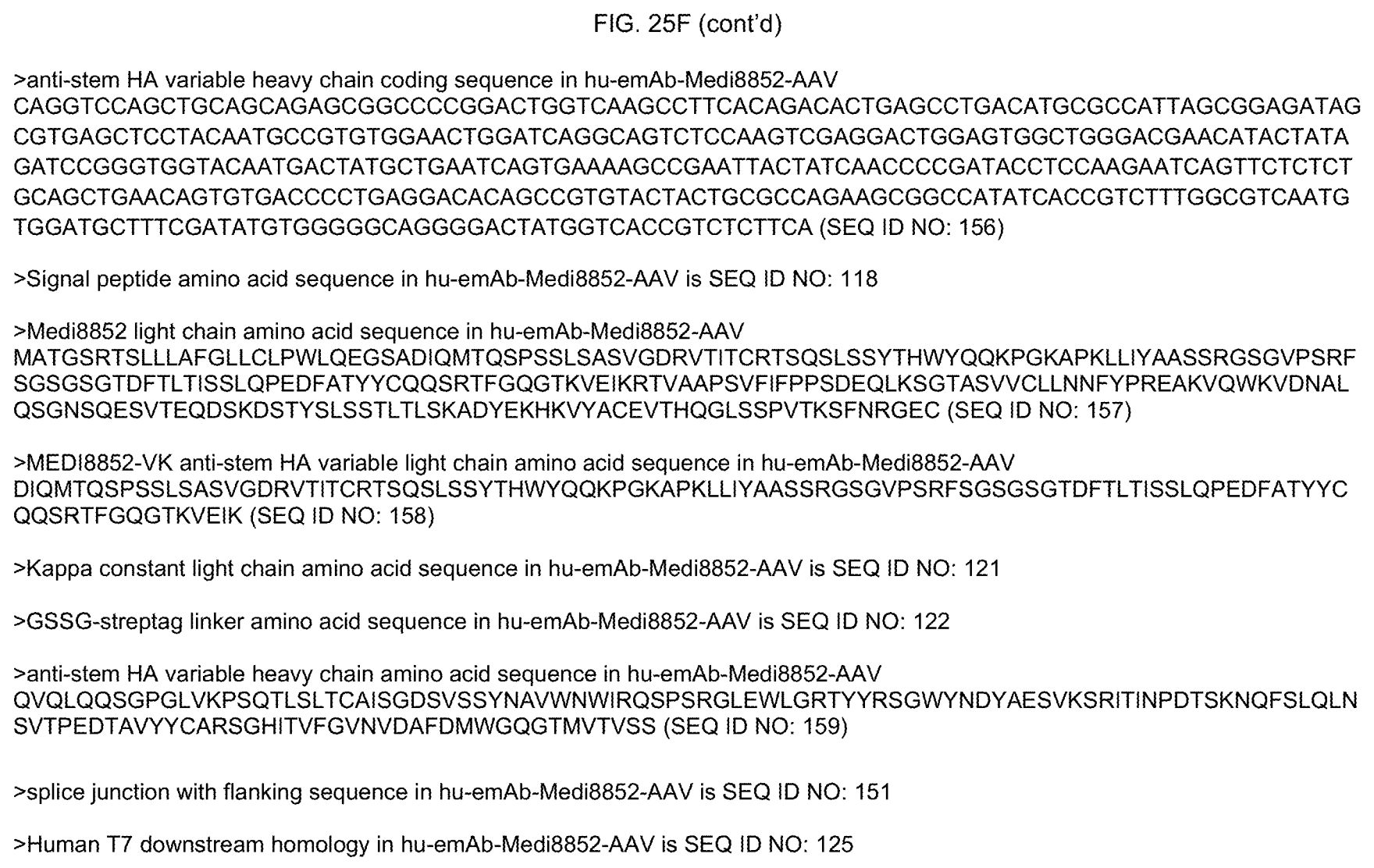

>anti-stem HA variable heavy chain coding sequence in hu-emAb-Medi8852-AAV

CAGGTCCAGCTGCAGCAGAGCGGCCCCGGACTGGTCAAGCCTTCACAGACACTGAGCCTGACATGCGCCATTAGCGGGAGATAG
CGTGAGCTCCTACAATGCCGTGTGGAACTGGATCAGGCAGTCTCCAAGTCGAGGACTGGAGTGGCTGGGACGAACATACTATA
GATCCGGGTGGTACAATGACTATGCTGAATCAGTGAAAAGCCGAATTACTATCAACCCCGATACCTCCAAGAATCAGTTCTCT
GCAGCTGAACAGTGTGACCCCTGAGGACACAGCCGTGTACTACTGCGCCAGAAGCGGCCATATCACCGTGCTCTTTGGCGTCAATG
TGGATGCTTTCGATATGTGGGGGCAGGGGACTATGGTCACCGTGTCTTCA (SEQ ID NO: 156)

>Signal peptide amino acid sequence in hu-emAb-Medi8852-AAV is SEQ ID NO: 118

>Medi8852 light chain amino acid sequence in hu-emAb-Medi8852-AAV

MATGSRTSLLLAFGLLCLPWLQEGSADIQMTQSPSSLSASVGDRVTITCRTSQSLSSYTHWYQQKPGKAPKLLIYAASSRGGSGVPSRF
SGSGSGTDFTLTISSLQPEDFATYYCQQSRTFGQGTKVEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC (SEQ ID NO: 157)

>MEDI8852-VK anti-stem HA variable light chain amino acid sequence in hu-emAb-Medi8852-AAV DIQMTQSPSSLSASVGDRVTITCRTSQSLSSYTHWYQQKPGKAPKLLIYAASSRGGSGVPSRFSGSGSGTDFTLTISSLQPEDFATYYC
QQSRTFGQGTKVEIK (SEQ ID NO: 158)

>Kappa constant light chain amino acid sequence in hu-emAb-Medi8852-AAV is SEQ ID NO: 121

>GSSG-streptag linker amino acid sequence in hu-emAb-Medi8852-AAV is SEQ ID NO: 122

>anti-stem HA variable heavy chain amino acid sequence in hu-emAb-Medi8852-AAV

QVQLQQSGPGLVKPSQTLSLTCAISGDSVSSYNAVWNWIRQSPSRGLEWLGRTYYRSGWYNDYAESVKSRITINPDTSKNQFSLQLN
SVTPEDTAVYYCARSGHITVFGVNVDAFDMWGQGTMVTVSS (SEQ ID NO: 159)

>splice junction with flanking sequence in hu-emAb-Medi8852-AAV is SEQ ID NO: 151

>Human T7 downstream homology in hu-emAb-Medi8852-AAV is SEQ ID NO: 125

FIG. 25F (cont'd)

>Medi8852 light chain coding sequence without signal sequence in hu-emAb-Medi8852-AAV
GATATTCAGATGACCCAGAGAGCCCTTCCAGCTTCCAGCCTGTCCGCTTCAGTGGGGGATCGAGTGAGTCGACCATTACCTGCCGAACCAGCCAGAG
CCTGAGCTCCTACACGCCACTGGTATCAGCAGAAGCCCGGCAAGCCCCTAAGCTGCTGATCTACGCCGCTTCTAGTCGGGGGT
CCGGAGTGCCAAGCCGGTTCTCCGGATCTGGGAGTGGAACCGACTTTACCCTGACAATTTCAGCCTGCAGCCCGAGGATTTC
GCTACATACTACTGTCAGCAGAGCAGAACTTTCGGGCAGGGCACTAAGGTGGAGATCAAACGGACTGTGCCGCTCCTAGCGT
GTTCATCTTTCCACCTAGCGACGAGCAGTTGAAGTCTGGCACTGCCTCTGTCGTGTGCCTGCTGAACAACTTCTACCCTCGAGA
GGCCAAGGTGCAGTGGAAAGTGGACAATGCCCTGCAGAGCGGCAAGCCCGACTACGAGCAAGGTGTACGCCTGCGAAGTGACACA
TCCACCTACAGCCTGTCTGCAGCACCCTGACCAAGAGCTTCAATCGGGGGCGGAGTGC (SEQ ID NO: 283)

>Medi8852 light chain amino acid sequence without signal peptide in hu-emAb-Medi8852-AAV
DIQMTQSPSSLSASVGDRVTITCRTSQSLSSYTHWYQQKPGKAPKLLIYAASSRGSGVPSRFSGSGSGTDFTLTISSLQPEDFATYYC
QQSRTFGQGTKVEIKRTVAAPSVFIFPPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC (SEQ ID NO: 288)

FIG. 25G
hu-emAb-AMM01-AAV (2555 bp)

TGTCACGACCCCGGAGAACAGAAGGTCTCTGGGTTTTTGTGGGTGGCTGGGTTTTGTGGGTGAGGATGGACATTCTGCCATTGTGATTACTACTACTACTACTACTACATGGACGTGTCTGGG

Human T7 Upstream Homology 20              40              60              80              100

GCAAAGGGACCACGGTCACCGTCTCCTCAGGTAAGAATGGCCACTCTAGGGCCTTGTTTTCTGCTACTGCCTGTGGGGTTCCTGAGGGCATGGTTCCGAGGGGACC

Human T7 Upstream Homology 120             140             160             180             200

TGGGCGGACTGGCCAGGAGGGGATGGCACTGGGGTGCCTTGAGGATCTGGGAGCCTCTGTGGATTTTCCGATGCCTTGGAAAATGGGACTCAGGTTGGGGTGCCGTC

Human T7 Upstream Homology 220             240             260             280             300             320

TGATGGAGTAACTGAGCCTTGGGGAGCCACATTTGGACGAGAGATGCCTGAACAAACCAGGGGTCTTAGTGATGGCTGAGGAATGTGTCTCAGGAGCCGGTGT

Human T7 Upstream Homology 340             360             380             400             420

CTCGATCGTAATCTTTAGGCCAATAAAATGTGGGTTCACAGTGAGGAGTGCATCCTGGGGGTTGGGGTTTGTTCTGCAGCGGGGAAGAGCGCTGTGCACAGAAAGCTTAG

IgVH1-69 Promoter 440             460             480             500             520

FIG. 25G (cont'd)

```
AAATGGGGGCAAGAGATGCTTTCCTCAGGCAGGATTTAGGGCTTGGTCTCTCAGCATCCCACACTTGTACAGCTGATGTGGCATCTGTGTTTCTTTCTCATCCTAG
                                         IgVH1-69 Promoter
     540          560          580          600          620          640

ATCAGGCTTTGAGGCTGTGAAATACCCTGCCTCATGCAAATAACCTGAGGTCTTCTGAGATAAATATAGATATTGTGCCTGACagcatcacgGCGGCCA
                                IgVH1-69 Promoter
     660          680          700          720          740

CCATGGCTACCGGCAGCCAGAACAAGCCTGCTGCTGTCTCGCTTTGGACTGCTGCTGCTCCCCTGGTTGCAAGAAGGCCAGCCtcctatgagctgactcagccacccctca
 M  A  T  G  S  R  T  S  L  L  L  A  P  G  L  L  L  L  P  W  L  Q  E  G  S  A  S  E  L  T  Q  P  P  S
                             AMM01 light chain
                  Signal peptide
     760          780          800          820          840 gtgtcagtgggccccgggccagaggccccacaattacctgtgggggacacaacatcggaagctaaaaatgtccactgtaccagcagaagccaggccaggcccctgtcct
 W  S  V  A  P  G  Q  R  A  T  I  T  C  G  G  N  N  I  G  A  K  N  V  H  W  Y  Q  Q  K  P  G  Q  A  P  V  L
                             AMM01 light chain
                             AMM01 Lambda Variable
     860          880          900          920          940          960
```

FIG. 25G (cont'd)

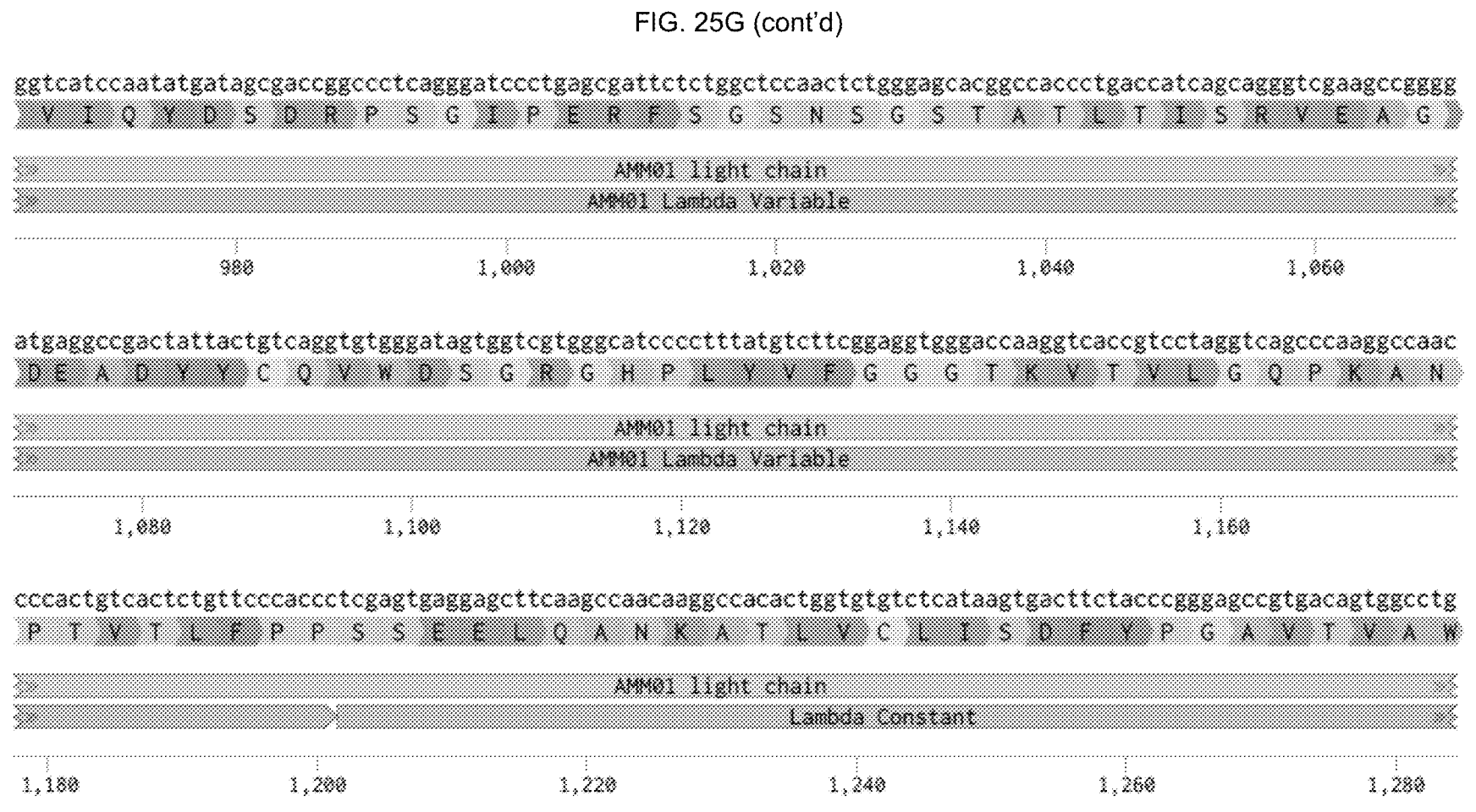

ggtcatccaatatgatagccgacgccctgagccgattcctgctccaactctgggagcacggcacgccacccctgaccatcagcagggtcgaggcccggg

V I Q W D S D R P S G I P E R F S G S N S G S T A T L T I S R V E A G

AMM01 light chain
AMM01 Lambda Variable 980     1,000     1,020     1,040     1,060 atgaggccgactattactgtcagtcgtgggatagtagtggtcgtccccttttatgtcttcggaagtggagtcgggaccaaggtcaccgtcctaggtcagcccaaggccaac

D E A D Y Y C Q V W D S S G R G H P L Y V F G G G T K V T V L G Q P K A N

AMM01 light chain
AMM01 Lambda Variable 1,080     1,100     1,120     1,140     1,160 cccactgtcactctgttcccaccctcgagtgaggagcttcaagccaacaaggccacactggtgtgtctcataagtgacttctacccgggagccgtgacagtggcctg

P T V T L F P P S S E E L Q A N K A T L V C L I S D F Y P G A V T V A W

AMM01 light chain
Lambda Constant 1,180     1,200     1,220     1,240     1,260     1,280

FIG. 25G (cont'd)

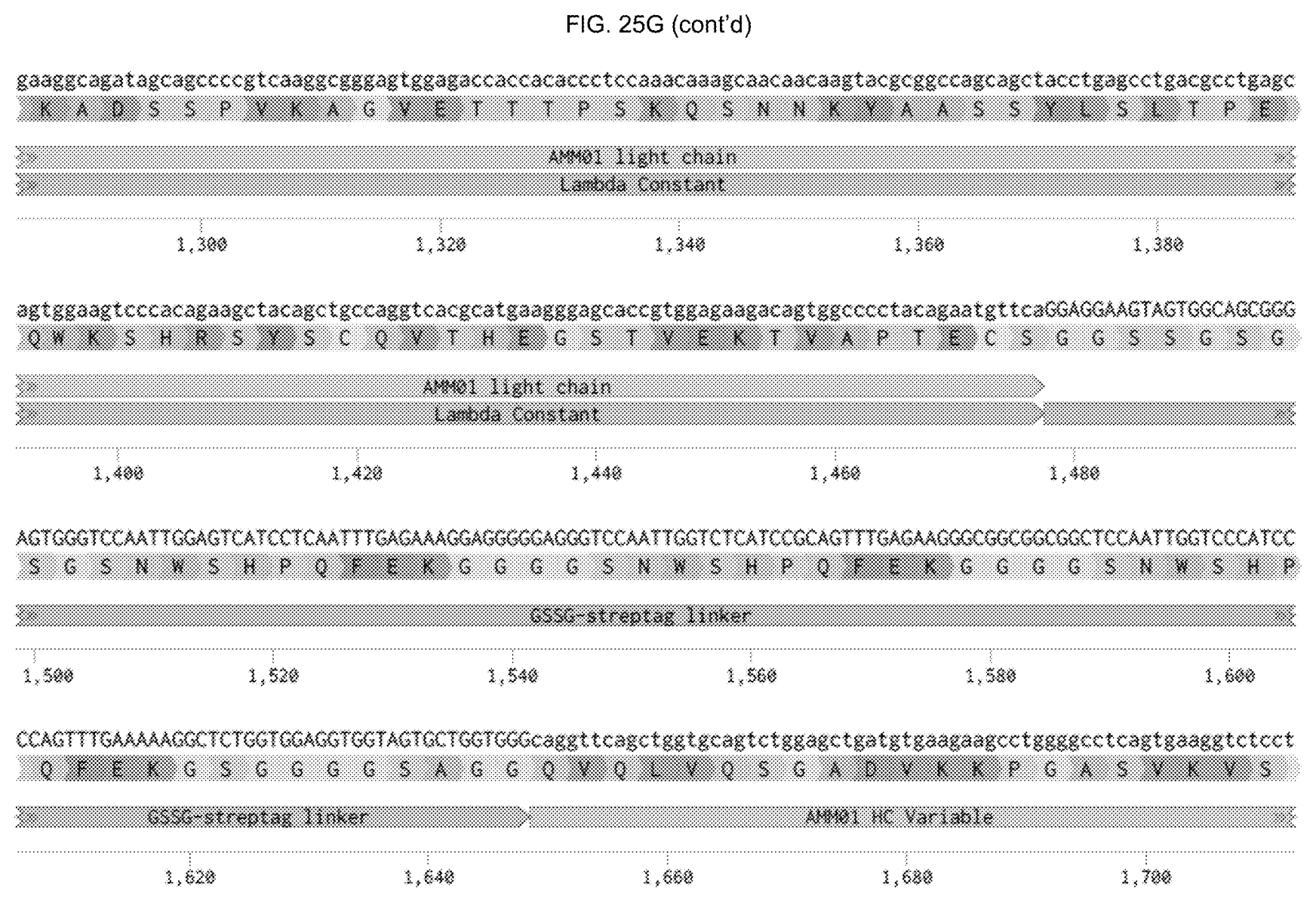

```
gaaggcagatagcagcgcccgtcaggtcaggagtggagggaccaccaccctccaaacaagcaacaacaagtacggcggccagagcagcagctacctggcctgagcctgagc
  K   A   D   S   S   P   V   K   A   G   V   E   T   T   T   P   S   K   Q   S   N   N   K   Y   A   A   S   S   Y   L   S   L   T   P   E
```

AMM01 light chain
Lambda Constant 1,300    1,320    1,340    1,360    1,380

```
agtggaagtcccacagagaagctacagctgccaggtcacgcatgaaggggagcaccgtggagaagacagtgcccctacagagaatgttcaGGAGGAAGTAGTGGCAGCGGG
  Q   W   K   S   H   R   S   Y   S   C   Q   V   T   H   E   G   S   T   V   E   K   T   V   A   P   T   E   C   S   G   G   S   S   G   S   G
```

AMM01 light chain
Lambda Constant 1,400    1,420    1,440    1,460    1,480

```
AGTGGGGTCAATTGGAGTCATCCTCAATTTGAGAAAGGAGGAGGGGGGTCAATTGGTGTCATCGGCAGTTTGAGAAAGGGGGGGTCCAATTGGTCCATCC
  S   G   G   S   N   W   S   H   P   Q   F   E   K   G   G   G   S   N   W   S   H   P   Q   F   E   K   G   G   G   S   N   W   S   H   P
```

GGSG-streptag linker 1,500    1,520    1,540    1,560    1,580    1,600

```
CCAGTTTGAAAAGGCTCTGGTGGCGAGGTGGTAGTGCTGGTGGcaggttcagctgggtgtgcagtctgggcctggcagtctggggctggagctgtatgttgaagaagcctgggcctcagtgaaggtctcct
  Q   F   E   K   G   S   G   G   G   S   A   G   G   Q   V   Q   L   V   Q   S   G   A   D   V   K   K   P   G   A   S   V   K   V   S
```

GGSG-streptag linker     AMM01 HC Variable 1,620    1,640    1,660    1,680    1,700

FIG. 25G (cont'd)

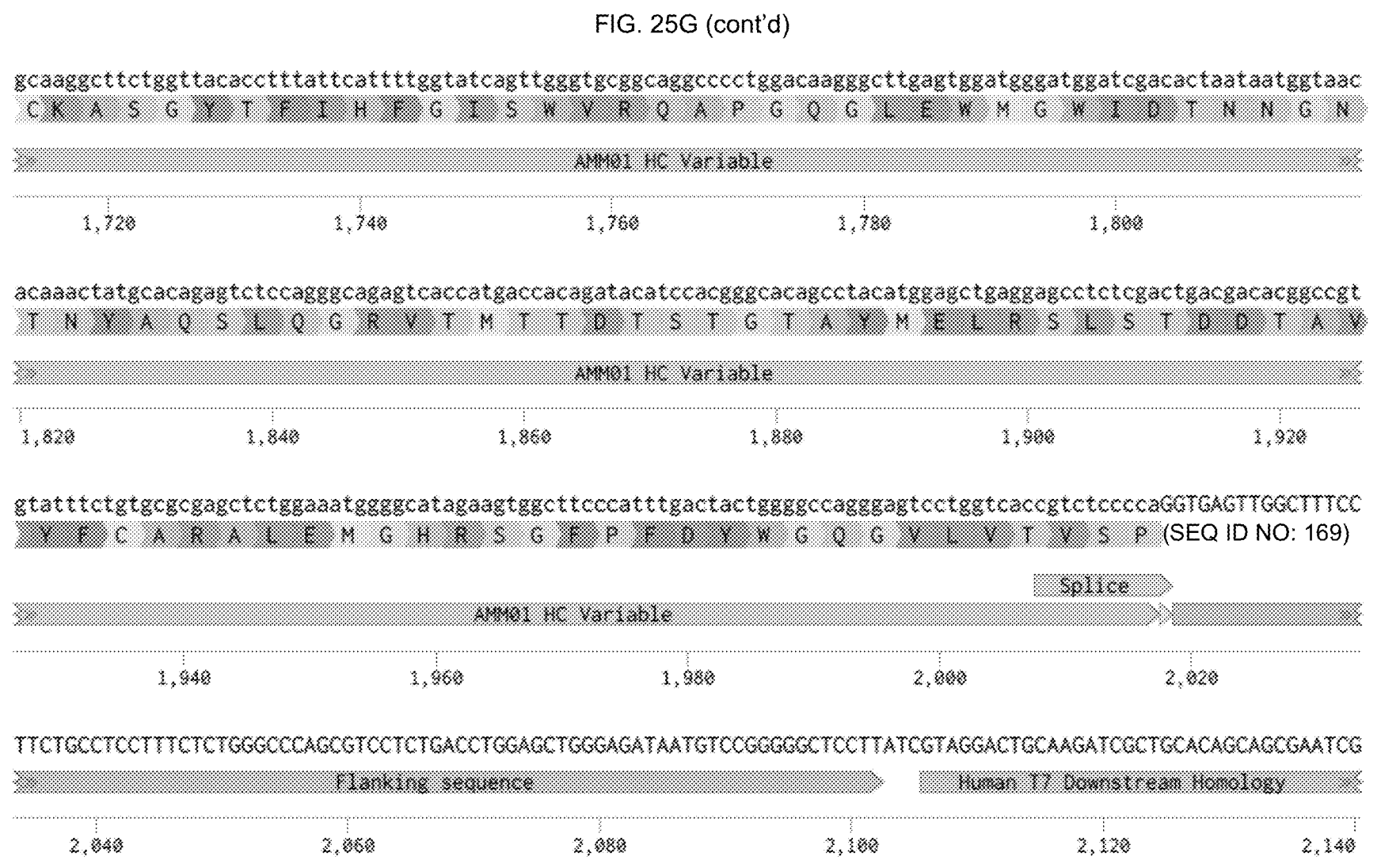

```
gcaaggcttctggttacacctttattcattttggtatcattggtgtggctcaggcccccctggacaaggctcaggccagatggagtgggatggatcgcacactaataatgtaac
  C  K  A  S  G  Y  T  F  T  H  F  G  I  S  W  V  R  Q  A  P  G  Q  G  L  E  W  M  G  W  I  D  T  N  N  G  N
```
AMM01 HC Variable
```
         1,720          1,740          1,760          1,780          1,800
```

```
acaaactatgcacagaagtctccaggcagagtcaccatgaccacagatacatccacgggcacctacatggagctgaggagcctctcgctgacgacacggccgt
  T  N  Y  A  Q  K  S  Q  G  R  V  T  M  T  T  D  T  S  T  G  T  A  Y  M  E  L  R  S  L  S  L  T  D  T  A  V
```
AMM01 HC Variable
```
  1,820         1,840          1,860          1,880          1,900          1,920
```

```
gtatttctgtgcgcgagctctggaaatgggcatagaagtggcttcccattgactactgggccagggaccctggtcaccgtctcccagGTGAGTTGGCTTTCC (SEQ ID NO: 169)
  Y  F  C  A  R  A  L  E  M  G  H  R  S  G  F  P  F  D  Y  W  G  Q  G  T  L  V  T  V  S  P
```
AMM01 HC Variable
```
  1,940         1,960          1,980          2,000          2,020
```
Splice

```
TTCTGCCTCCTTTCTCTGGGCCCCAGGCGTCCTCTGACCTGGAGCTGGAGATAATGTCCGGGGGGTCCTTATCGTAGGACTGCAAGATCGCTGCACAGCAGCGAATCG
```
Flanking sequence       Human T7 Downstream Homology
```
  2,040         2,060          2,080          2,100          2,120          2,140
```

FIG. 25G (cont'd)

```
TGAAATATTTTCTTTAGAATTATGAGGTGCGGCTGTGTGTCAACCTGCATCTTAAATTCTTTATTGGCTGGAAAGAGAACTGTCGGAGTGGGTGAATCCAGCCAGGAG
Human T7 Downstream Homology
      2,160      2,180      2,200      2,220      2,240

GGACGCGGTAGCCCCGGTCTTGATCGAGCAGGGTGGGGGCAGGGGTAGCCCAGAAACGGGTGGCTGCCGTGTCCTGACCAGGGCTTAGGGAGGCTTCCAGGACCTCAGTG
Human T7 Downstream Homology
      2,260      2,280      2,300      2,320      2,340

CCTTGAAGCTGGTTCCATGAGAAAAGGATTGTTTATCTTACTGTTAAAAGACAGGATATGTTTGAAGTGGCTTCTGAGAAAATGGTTAAGAA
Human T7 Downstream Homology
      2,360      2,380      2,400      2,420      2,440      2,460

AATTATGACTTAAAAAATGTGAGAGATTTCAAGTATATTAATTTTTTTAACTGTCCAAGTATTTGAAATTCTTATCATTGATTAACACCCATG(SEQ ID NO: 107)
Human T7 Downstream Homology
  2,470      2,480      2,490      2,500      2,510      2,520      2,530      2,540      2,550
```

FIG. 25G (cont'd)

>human T7 upstream homology region in hu-emAb-AMM01-AAV is SEQ ID NO: 153

>IgVH1-69 promoter in hu-emAb-AMM01-AAV is SEQ ID NO: 111

>Signal peptide coding sequence in hu-emAb-AMM01-AAV is SEQ ID NO: 112

>AMM01 light chain coding sequence in hu-emAb-AMM01-AAV
ATGGCTACCGGCAGCAGCAGAACAAGCCTGCTCGCTTTTGGACTGCTCTGTCTCCCCTGGTTGCAAGAAGGCAGGCGCCTCCTAT
GAGCTGACTCAGCCACCCTCAGTGTCAGTGGCCCCCGGGGCAGAGGGCCACAATTACCTGTGGGGGACCACAACATCGGAGCTA
AAAATGTCCACTGGTACCAGCAGAAGCCAGGCCAGGCACGCGCCACCCTGGTCATCCAATATGATAGCGAAGCCCCTCAGGGATC
CCTGAGCGCGATTCTCTGGCTCCAACTCTGGGAGCACGGTCGGGATAGTGGTCGTGGGACCAAGGTCACCGTCCTAGGTCAGC
ATTACTGTCAGGTGTGGGATAGTGGTCGTGGGATCCCCTTTATGTCTTCGGAGGTGGGACCAAGGCCAACAAGGCCACAACCACC
CCAAGGCCAACCCACTGTCACTCTGTTCCCACCCTCGAGTGAGGAGCTTCAAGCCAACAAGGCCACAAGGCCAGCAGTGGAGCAGTCCCACAGAAGCTACA
GTGACTTCTACCCGGGAGCCGTGACAGTACGCGGCAACAACAAGTACGCGGGAGGGAGCACCGTGGAGGAGCACCGTG
GCTGCCAGGTGTCACGCGTCAGTGTTCA (SEQ ID NO: 161)

>AMM01 lambda variable light chain coding sequence in hu-emAb-AMM01-AAV
TCCTATGAGCTGACTCAGCCACCCTCAGTGTCAGTGGCCCCCGGGGCAGAGGGCCACAATTACCTGTGGGGGACCACAACATCGG
AGCTAAAAATGTCCACTGGTACCAGCAGAAGCCAGGCCAGGCACGCGCCACCCTGGTCATCCAATATGATAGCGAAGCCCCTCAG
GGATCCCTGAGCGCGATTCTCTGGCTCCAACTCTGGGAGCACGGTCGGGGATGAGGC
CGACTATTACTGTCAGGTGTGGGATAGTGGTCGTGGGATCCCCTTTATGTCTTCGGAGGTGGGACCAAGGTCACCGTCCTAGG
TCAGCCCAAGGCCAACCCCACTGTCACTCTGTTCCCACCC (SEQ ID NO: 162)

>lambda constant light chain coding sequence in hu-emAb-AMM01-AAV
TCGAGTGAGGAGCTTCAAGCCAACAAGGCCACAACCACCCACTGTGTGTCTCATAAGTGACTTCTACCCGGGAGCCGTGACAGTGGCCTG
GAAGGCAGATAGCAGCCCCGTCAAGGCGGGAGTGGAGACCACCAAACCCTCCAAACAAAGCAACAACAAGTACGCGGGCCAGC
AGCTACCTGAGCCTGACGCCTGAGCGAGTGGAAGTCCCACAGAAGCTACACAGGTCACGCGCATGAAGGGAGCACCGTGG
AGAAGACAGTGGCCCCTACAGAATGTTCA (SEQ ID NO: 163)

>GSSG-streptag linker coding sequence in hu-emAb-AMM01-AAV is SEQ ID NO: 116

FIG. 25G (cont'd)

>AMM01 variable heavy chain coding sequence in hu-emAb-AMM01-AAV
CAGGTTCAGCTGGTGCAGTCTGGAGCTGAGGTGAAGAAGCCTGGGGCCTCAGTGAAGGTCTCCTGCAAGGCTTCTGGTTACAC
CTTTATTCATTTGGTATCAGTCAGGTGCGGCAGGCCCCTGGACAAGGGCTTGAGTGGATGGATCGACACTAATAATGG
TAACACAAACTATGCACAGAGTCTCCAGGGCAGAGTCACCATGACCACAGATACATCCACGGCACAGCCTACATGGAGCTGAG
GAGCCTCTCGACTGACGACACGGCCGTGTATTTCTGTGCGCGAGCTCTGGAAATGGGGCATAGAAGTGGCTTCCCATTTGACTA
CTGGGGCCAGGGAGTCCTGGTCACCGTCTCCCCA (SEQ ID NO: 164)

>Signal peptide amino acid sequence in hu-emAb-AMM01-AAV is SEQ ID NO: 118

>AMM01 light chain amino acid sequence in hu-emAb-AMM01-AAV
MATGSRTSLLLAFGLLCLPWLQEGSASYELTQPPSVSVAPGQRATITCGGHNIGAKNVHWYQQKPGQAPVLVIQYDSDRPSGIPERFS
GSNSGSTATLTISRVEAGDEADYYCQVWDSGRGHPLYVFGGGTKVTVLGQPKANPTVTLFPPSSEELQANKATLVCLISDFYPGAVTV
AWKADSSPVKAGVETTTPSKQSNNKYAASSYLSLTPEQWKSHRSYSCQVTHEGSTVEKTVAPTECS (SEQ ID NO: 165)

>AMM01 variable light chain amino acid sequence in hu-emAb-AMM01-AAV
SYELTQPPSVSVAPGQRATITCGGHNIGAKNVHWYQQKPGQAPVLVIQYDSDRPSGIPERFSGSNSGSTATLTISRVEAGDEADYYCQ
VWDSGRGHPLYVFGGGTKVTVLGQPKANPTVTLFPP (SEQ ID NO: 166)

>AMM01 lambda constant light chain amino acid sequence in hu-emAb-AMM01-AAV
SSEELQANKATLVCLISDFYPGAVTVAWKADSSPVKAGVETTTPSKQSNNKYAASSYLSLTPEQWKSHRSYSCQVTHEGSTVEKTVA
PTECS (SEQ ID NO: 167)

>GSSG-streptag linker amino acid sequence in hu-emAb-AMM01-AAV is SEQ ID NO: 122

>AMM01 variable heavy chain amino acid sequence in hu-emAb-AMM01-AAV
QVQLVQSGADVKKPGASVKVSCKASGYTFIHFGISWVRQAPGQGLEWMGWIDTNNGNTNYAQSLQGRVTMTTDTSTGTAYMELRSL
STDDTAVYFCARALEMGHRSGFPFDYWGQGVLVTVSP (SEQ ID NO: 168)

>splice junction with flanking sequence in hu-emAb-AMM01-AAV is SEQ ID NO: 151

>Human T7 downstream homology in hu-emAb-AMM01-AAV is SEQ ID NO: 125

FIG. 25G (cont'd)

>AMM01 light chain coding sequence without signal sequence in hu-emAb-AMM01-AAV
TCCTATGAGCTGACTCAGCCACCCTCAGTGTCAGTGGCCCCGGGCAGAGGGCCACAATTACCTGTGGGGGACACAACATCGG
AGCTAAAAATGTCCACTGGTACCAGCAGAAGCCAGGCCAGCCCCCTGTCCTGGTCATCCAATATGATAGCGACCGGCCCTCAG
GGATCCCTGAGCGATTCTCTGGCTCCAACTCTGGGAGCACGGCCACCCTGACCATCAGCAGGGTCGAAGCCGGGGATGAGGC
CGACTATTACTGTCAGGTGTGGGATAGTGGTCGTGGGCATCCCCTTTATGTCTTCGGAGGTGGGACCAAGGCCACACTGGTGTCT
TCAGCCCAAGGCCAACCCCACTGTCACTCTGTTCCCACCCTCGAGTGAGGAGCTTCAAGCCAACAAGGCCACCCTGGTGTGCC
CATAAGTGACTTCTACCCGGGAGCCGTGACAGTGGCCTGGAAGGCAGCAGATAGCAGCCCCGTCAAGGCGGGAGTGGAGACCACC
ACACCCTCCAAACAAAGCAACAACAAGTACGGCGGCCAGCTACCTGAGCCTGAGCAGTGGAAGTCCCACAGAAG
CTACAGCTGCCAGGTCACGCATGAAGGGAGCACCGTGGAGAAGACAGTGGCCCCTACAGAATGTTCA (SEQ ID NO: 284)

>AMM01 light chain amino acid sequence without signal peptide in hu-emAb-AMM01-AAV
SYELTQPPSVSVAPGQRATITCGGHNIGAKNVHWYQQKPGQAPVLVIQYDSDRPSGIPERFSGSNSGSTATLTISRVEAGDEADYYCQ
VWDSGRGHPLYVFGGGTKVTVLGQPKANPTVTLFPPSSEELQANKATLVCLISDFYPGAVTVAWKADSSPVKAGVETTTPSKQSNNK
YAASSYLSLTPEQWKSHRSYSCQVTHEGSTVEKTVAPTECS (SEQ ID NO: 289)

FIG. 25H
Balb/C mRSV-Splice integration (2261 bp)

FIG. 25H (cont'd)

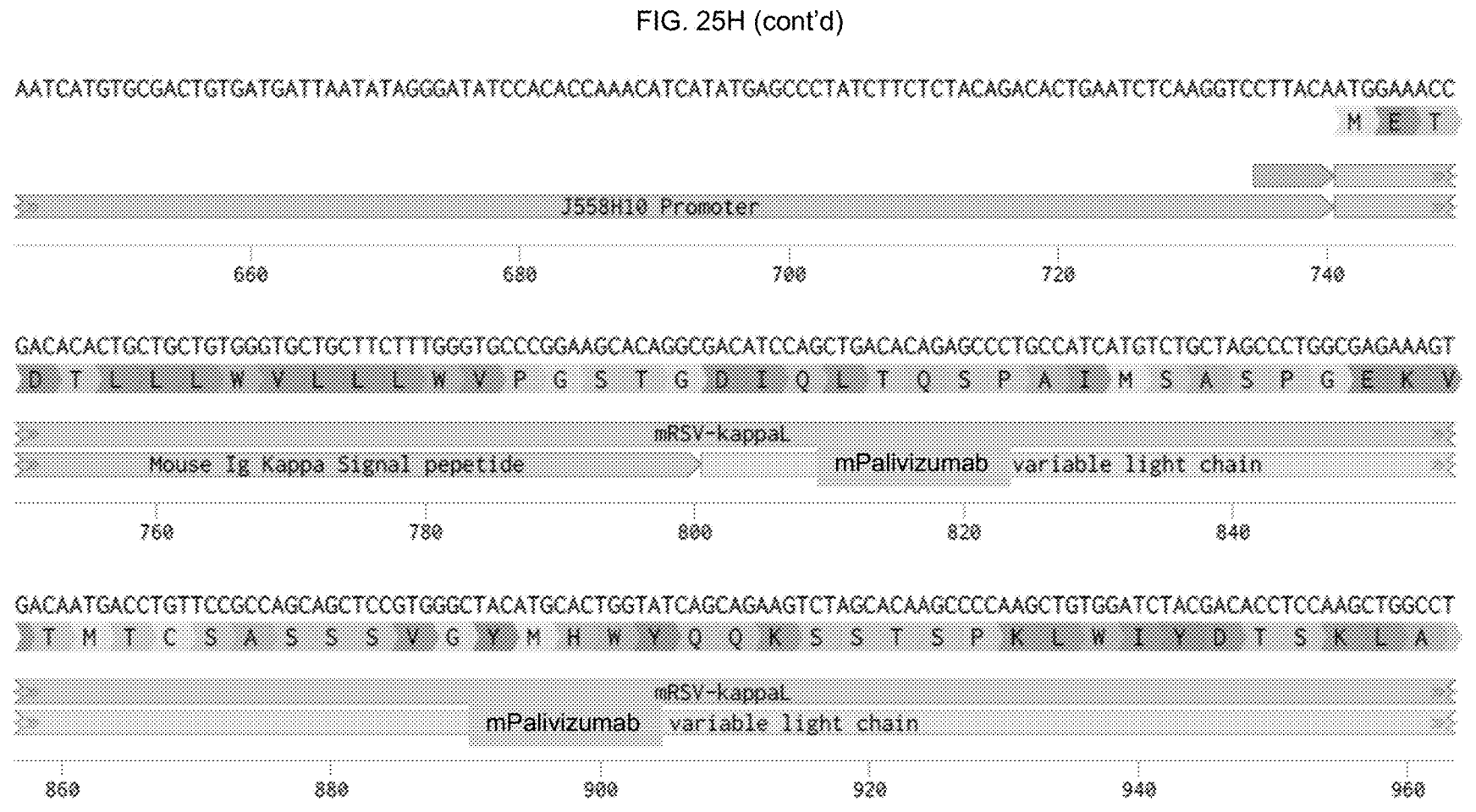

AATCATGTGCGACTGTGATGATTAATATAGGGATATCCACCAAACATCATATGAGCCCTATCTTCTCTACAGACACTGAATCTCAAGGTCCTTACAATGGAAACC
M E T

J558H10 Promoter 660    680    700    720    740

GACACACTGCTGCTGTGGGTGCTGCTTCTTTGGGTGCCGGGAAGCAGACAGGGGACATCCAGCTGACACAGAGCCTGCCATCATGTCTGCTAGCCTGGGAGAAGT
D T L L L W V L L L W V P G S T G D I Q L T Q S P A I M S A S P G E K V

Mouse Ig Kappa Signal peptide    mRSV-Kappa1    mPalivizumab variable light chain 760    780    800    820    840

GACAATGACCTGTTCCCCCAGCAGTCCGTGGGCTACATGCACTGGTATCAGCAGCAGAGTCTAGCACAACAAGCCCCAAGCTCTAGCCCATCTACGACACTCCAAGTGGCCT
T M T C S A S S S V G Y M H W Y Q Q K S S P K L W I D T S K L A mRSV-Kappa1    mPalivizumab variable light chain 860    880    900    920    940    960

FIG. 25H (cont'd)

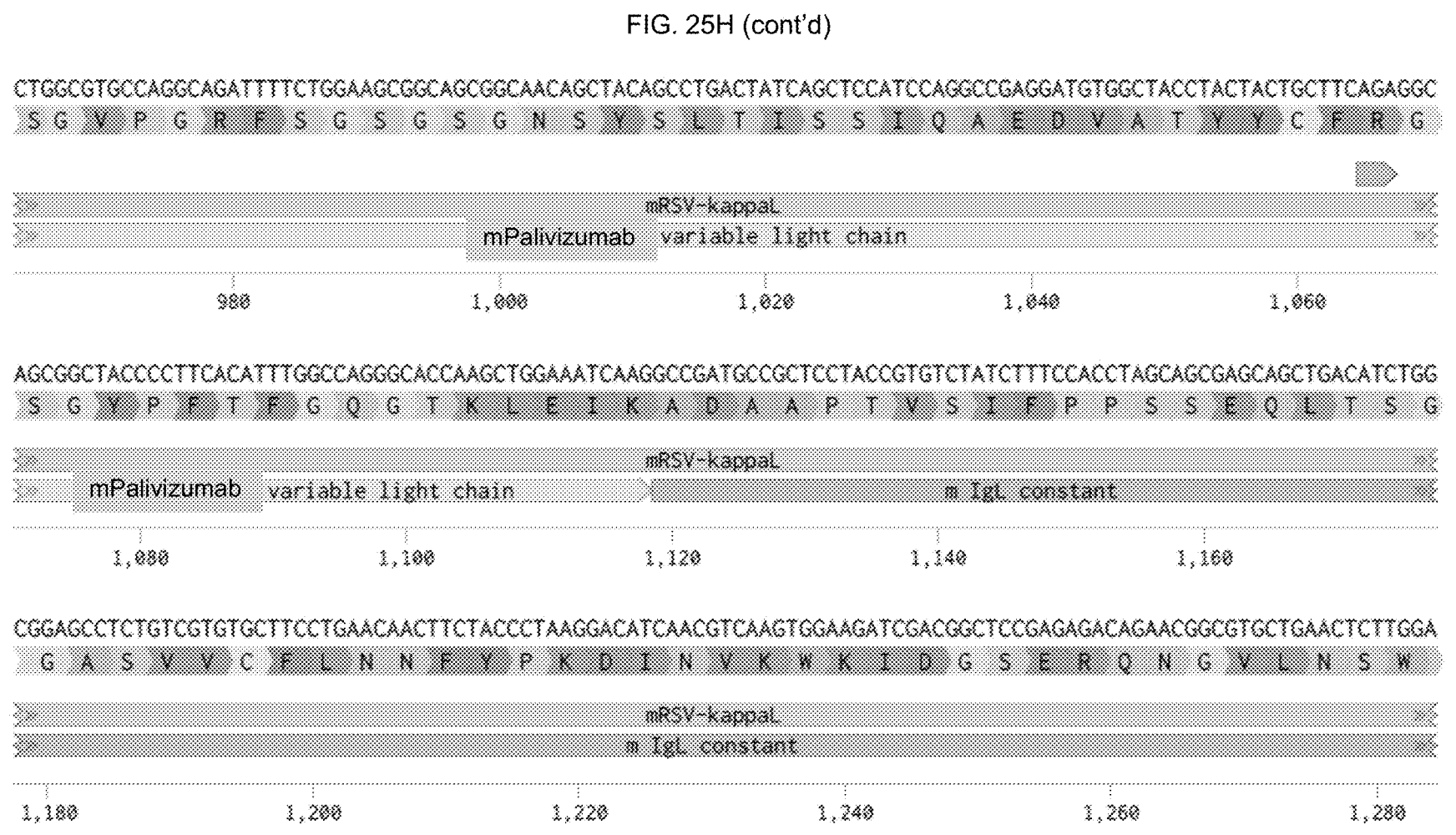

CTGGCCGTGCCAGGCAGATTTTCTGGAAGCGGCAGCGGCAACAGCTACAGCTACCTGACTATCAGCTCCATCCAGGCCGAGGATGTGGCTACCTACTGCTTCAGAGGC

S G W P G R F S G S G S G N S Y S Y L T I S S I Q A E D V A T Y C F R G mRSV-kappa1
mPalivizumab variable light chain 980        1,000        1,020        1,040        1,060

AGCGGGCTACCCCTTCACATTGGCCAGGGCACCAAGCTGGAAATCAAGCGTACGGTAGCGCTCCTACGGTGTCATCTTCCACCTAGCAGCCAGCTGACATCTGG

S G Y P F T F G Q G T K L E I K R A D A A P T V S I F P P S S E Q L T S G mRSV-kappa1
mPalivizumab variable light chain
m Igl constant 1,080        1,100        1,120        1,140        1,160

CGGCAGCCTCTGTCGTGTGCTTCCTGAACAACTTCTACCCTAAGGACATCAATGTCAAGTGGAAGATCGACGGCTCCGAGAGGACAGAATCGGGTGCTGAACTCTTGGA

G A S V V C F L N N F Y P K D I N V K W K I D G S E R Q N G V L N S W mRSV-kappa1
m Igl constant 1,180        1,200        1,220        1,240        1,260        1,280

FIG. 25H (cont'd)

```
CGGACCAGGACGAAGGATAGCACCTACAGCATGAGCAGCACTCTGACCCTGACAAGGACGAGTACCGAGAGGCACAACTCCTACACATGGCGAGGCCCACACACAAG
 T  D  Q  D  S  T  Y  S  M  S  S  T  L  T  L  T  K  D  E  Y  E  R  H  N  S  Y  T  W  R  G  P  H  T  K
                    mRSV-kappa1
                    m IgL constant
          1,300              1,320              1,340              1,360              1,380

ACCAGCACATCCCAATCGTGAAGTCCTTCAACCGGAACGGAGTCGCCGAGGAAGTAGTGGCAGCGGGGAGTGGTCCAATTGGAGTCATCCTCCAATTTGAGAAAGGAGG
 T  S  S  P  I  V  K  S  F  N  R  N  E  C  G  G  S  G  S  G  S  G  S  N  W  S  H  P  Q  F  E  K  G  G
          mRSV-kappa1                                      GSSg-streptag linker
          m IgL constant
          1,400              1,420              1,440              1,460              1,480

GGGAGGGTCCAATTGGTGTCATCCGCCAGTTTGAGAAGGGCGGCGGCGGCGGGCCTCCAATTGGTGTCCATCCCAGTTGGTCCCATCCCAGTTTGAAAAGGCTCTGGTGGAGGTGGTGTAGTGGTGGTG
 G  G  G  S  N  W  S  H  P  Q  F  E  K  G  G  G  G  S  N  W  S  H  P  Q  F  E  K  G  G  G  G  S  A  G
                              GSSg-streptag linker
          1,500              1,520              1,540              1,560              1,580              1,600

GGCAGGTGGAACTGCAAGAAAGCGGGCCCTGGCATCCTGCAGCCTTCTCAGACACTGAGCCTGACCTGTAGCTTCAGCGGCTTCAGCCTGAGCACAAGCGGCATGTCT
 G  Q  V  E  L  Q  E  S  G  P  G  I  L  Q  P  S  Q  T  L  S  L  T  C  S  F  S  G  F  S  L  S  T  S  G  M  S
                    mPalivizumab  variable heavy chain
          1,620              1,640              1,660              1,680              1,700
```

FIG. 25H (cont'd)

GTCGGCTGGATCAGACAGCCTTCTGGGCGAAGGACTGGAATGGCTGGCCGACATTTGGTGGGACGACAAGAGGACTACAACCCAGCTGCGAAGTCAGACTGACCAT
V G W I R Q P S G E G L E W L A D I W W D D K R T T T N P S L K S R L T T mPalivizumab variable heavy chain 1,720    1,740    1,760    1,780    1,800

CAGCAAGGACACCAGCAGCAACCAGGTGTTCCTGAAGATCACCGGCGTGGACACAGCCGATACCGCCACCTATTACTGCGCCAGATCGATCACCAACTGGTACT
S K D T S S N Q V F L K I T G V D T A D T A T Y Y C A R S M I T N W Y mPalivizumab variable heavy chain 1,820    1,840    1,860    1,880    1,900    1,920

TCGACGTGTGGGGCGCTGGCACCACAGTGACCGTCTCCTCAGGTGAGTCTCCAACTTCTCCATTCTAAATGCATGTTGGGGGGATTCTGGGCCTTCAGGACCACATA
F D V W G A G T T V T V S S (SEQ ID NO: 172)

Splice mPalivizumab variable heavy chain    IntronSplice 1,940    1,960    1,980    2,000    2,020

CGGACAAAGAGTGGAGTGGGCACTTTCTTAGATTTGTGAGGAATGTTCCGCACTAGATTGTTTAAAACTTCATTGTTGGAAGGAGAGCTGTCTTAGTGATTGAG
Flanking Genomic 2,040    2,060    2,080    2,100    2,120    2,140

TCAAGGGAGGAAGGCATCTAGCCTCGGTCTCAAAAGGGTAGTTGCTGTCTAGAGAGGTCTGGTGGAGCCTGCAAAGTCCAGCTTTCAAAGGAACACAGAAGTATGT 2,160          2,180          2,200          2,220          2,240

GTATGGAATATTAG (SEQ ID NO: 108)

>upstream flanking genomic DNA in Balb/C mRSV-Splice Integration
AGGACCACCTCTGTGACAGCATTTATACAGTATCCGATG (SEQ ID NO: 170)

>J558H10 promoter in Balb/C mRSV-Splice Integration is SEQ ID NO: 128

>Signal peptide coding sequence in Balb/C mRSV-Splice Integration is SEQ ID NO: 129

>mPalivizumab light chain coding sequence in Balb/C mRSV-Splice Integration is SEQ ID NO: 130

>mPalivizumab variable light chain coding sequence in Balb/C mRSV-Splice Integration is SEQ ID NO: 131

>mPalivizumab kappa constant light chain coding sequence in Balb/C mRSV-Splice Integration is SEQ ID NO: 132

>GSSG-streptag linker coding sequence in Balb/C mRSV-Splice Integration is SEQ ID NO: 116

>mPalivizumab variable heavy chain coding sequence in Balb/C mRSV-Splice Integration is SEQ ID NO: 133

>Signal peptide amino acid sequence in Balb/C mRSV-Splice Integration is SEQ ID NO: 134

>mPalivizumab light chain amino acid sequence in Balb/C mRSV-Splice Integration is SEQ ID NO: 135

>mPalivizumab variable light chain amino acid sequence in Balb/C mRSV-Splice Integration is SEQ ID NO: 136

>mPalivizumab kappa constant light chain amino acid sequence in Balb/C mRSV-Splice Integration is SEQ ID NO: 137

>GSSG-streptag linker amino acid sequence in Balb/C mRSV-Splice Integration is SEQ ID NO: 122

>mPalivizumab variable heavy chain amino acid sequence in Balb/C mRSV-Splice Integration is SEQ ID NO: 138

>splice junction with flanking sequence in in Balb/C mRSV-Splice Integration is SEQ ID NO: 139

>downstream flanking genomic DNA in Balb/C mRSV-Splice Integration
CATAGGGACAAAGAGTGGAGTGGGGCACTTTCTTTAGATTT (SEQ ID NO: 171)

>mPalivizumab light chain coding sequence without signal sequence in Balb/C mRSV-Splice Integration is SEQ ID NO: 281

>mPalivizumab light chain amino acid sequence without signal peptide in Balb/C mRSV-Splice Integration is SEQ ID NO: 286

FIG. 25I
TT-hRSV-T7-integrated (1707 bp)

GTCTTAGTGATGGCTGAGGAATGTGTCTCAGGACGGGTGTCCGTAATCTTTAGGCCAATAAAATGTGGGTTCACAGTGAGGAGTGCATCCTGGGGTTGGGGTTTGTT
Flanking Genome
hRSV gRNA T7
IgVH1-69 Promoter
20          40          60          80          100

CTGCAGCGGGAAGAGCGCTGTGCACAGAGAAAGCTTAGAAATGGGGCAAGAGATGCTTTTCCTCAGGCAGGATTTAGGGCTTGGTCTCTCAGCATCCCACACTTGTACA
hRSV gRNA T7
IgVH1-69 Promoter
120         140         160         180         200

GCTCGATGTGGCATCTGTGTGTTTTTCTTCATCGTAGATCAGGCTTTGAGCTGTGAAATACCCTGCCTCATGCAAATAACCTGAGGTCTTCTGAGATAAAATA
hRSV gRNA T7
IgVH1-69 Promoter
220         240         260         280         300         320

TAGATATATTGGTGCCCTGAGGTTTAAACgccgccaccatggctaccggcagcagaacaagcctgctgctcgctttttggactgctgctccctgttgcaagaa
                                                M  A  T  G  S  R  T  S  L  L  L  A  F  G  L  L  C  L  P  W  L  Q  E
hRSV gRNA T7
340         360         380         400         420

FIG. 25I (cont'd)

```
ggcagcgccgacatccagatgacacagagcccctagcacactgtctgccagcgtgggcgacagagtgaccatcacatgcaagtgccagctggctggctacatgca
 G  S  A  D  I  Q  M  T  Q  S  P  S  T  L  S  A  S  V  G  D  R  V  T  I  T  C  K  C  Q  L  A  G  Y  M  H
        440              460              480              500              520
``` hRSV gRNA T7
hRSV-Light-variable

```
ctggtatcagcaaaagcccggcaaagcccctaagctgctgatctacgatgctgctgctctccaagctggccctctgcgtgccctccagatttctggcagcggcagcggaaccg
 W  Q  Q  K  P  G  K  A  P  K  L  L  I  Y  D  A  A  A  L  Q  S  G  V  P  S  R  F  S  G  S  G  S  G  T
        540              560              580              600              620              640
``` hRSV gRNA T7
hRSV-Light-variable

```
agttcaccctgaccatctccagcctgcagcctgacgactactactgctaccaccagggcagcggctggcccttcacatttggcggcggaggaacaaagctggaa
 E  F  T  L  T  I  S  S  L  Q  P  D  D  F  A  T  Y  Y  C  Y  H  Q  G  S  G  W  P  F  T  F  G  G  G  T  K  L  E
        660              680              700              720              740
``` hRSV gRNA T7
hRSV-Light-variable

FIG. 25I (cont'd)

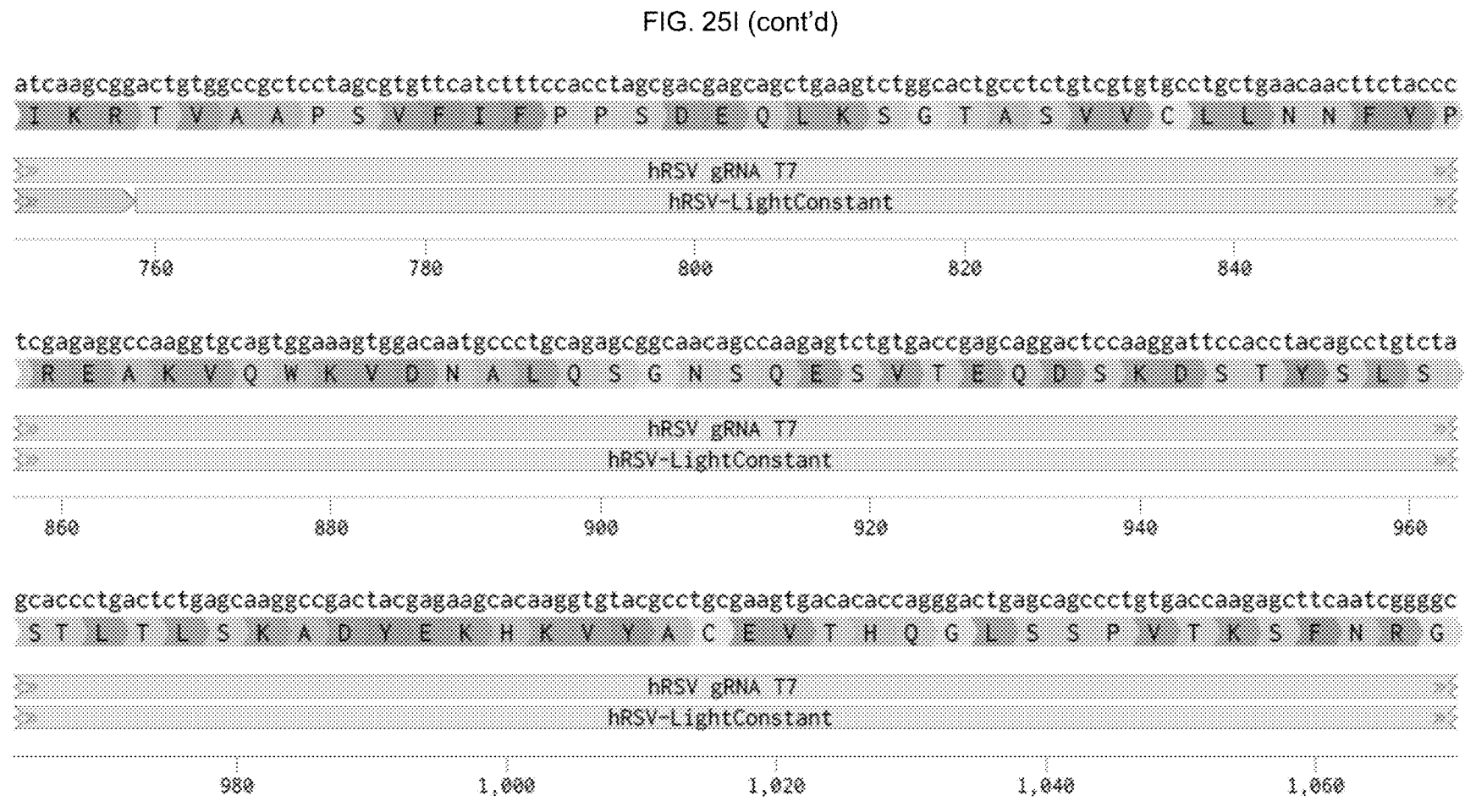

atcaagcggactgtggccgctcctagcgtcttcatctttccacctagtgttccactgctgctcctgtcgtctgtgctgctgaacaacttctaccc
 I  K  R  T  V  A  A  P  S  V  F  I  F  P  P  S  D  E  Q  L  K  S  G  T  A  S  V  V  C  L  L  N  N  F  Y  P hRSV gRNA T7
hRSV-LightConstant 760        780        800        820        840 tcgagaggccaaggtgcagtggaaagtggacaatgccctgcagagcggcaacagccaggagagcgtgaccgagcaggacagcaaggacagcacctactccctgagcagcaccctgtccta
 R  E  A  K  V  Q  W  K  V  D  N  A  L  Q  S  G  N  S  Q  E  S  V  T  E  Q  D  S  K  D  S  T  Y  S  L  S hRSV gRNA T7
hRSV-LightConstant 860        880        900        920        940        960 gcaccctgactctgagcaaggccgactacgagaagcacaaggtgtacgcctgcgaagtgacccaccagggcctgtctagccctgtgaccaagagcttcaatcggggc
 S  T  L  T  L  S  K  A  D  Y  E  K  H  K  V  Y  A  C  E  V  T  H  Q  G  L  S  S  P  V  T  K  S  F  N  R  G hRSV gRNA T7
hRSV-LightConstant 980        1,000       1,020       1,040       1,060

FIG. 25I (cont'd)

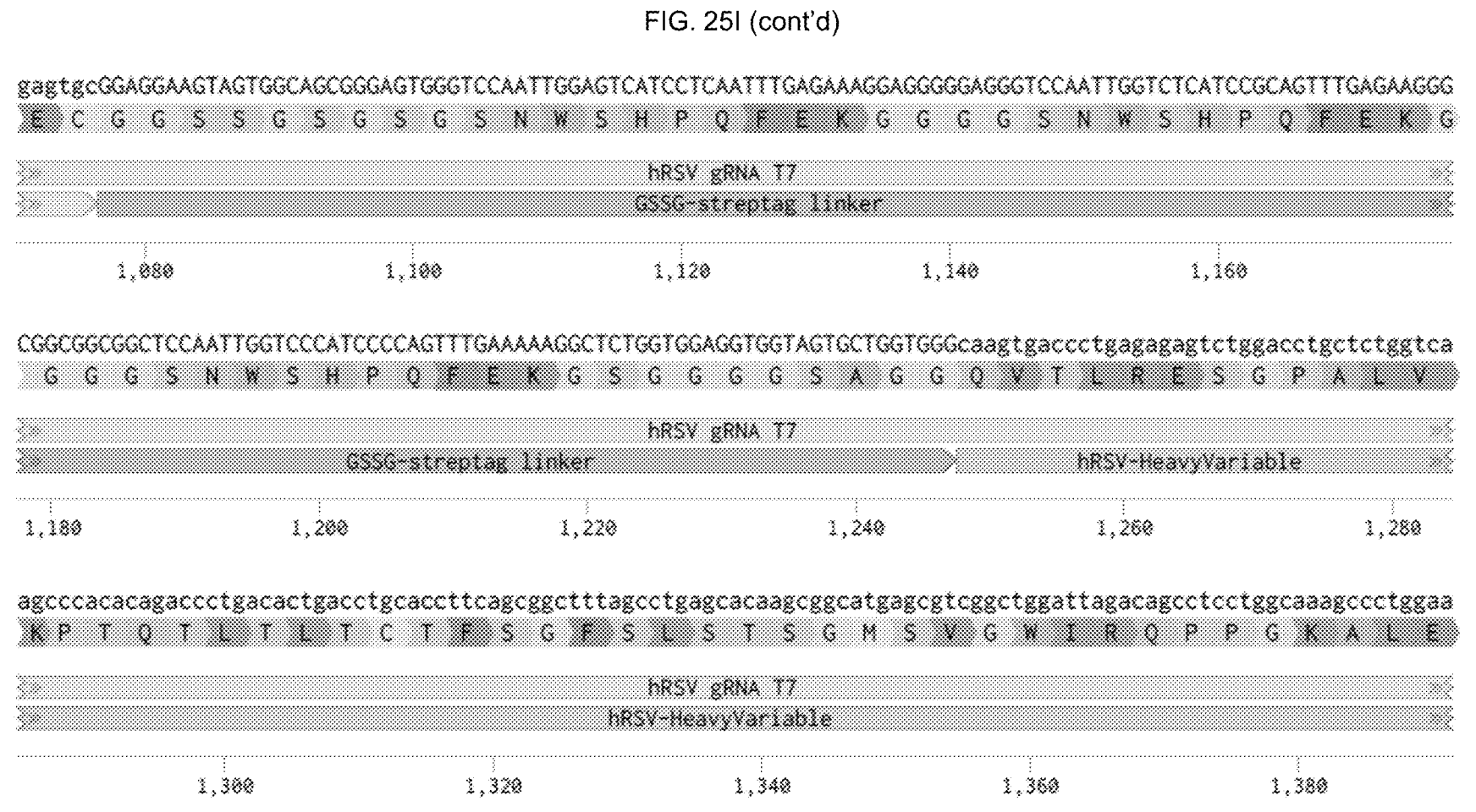

gagtgcggaggaagtagtggcagcgggagtgggtccaattggagtcatccctcaattggagtcatccctcaattggtctcatccggcagtttgagaaggg
E C G G S S G S G S N W S H P Q F E K G G G S N W S H P Q F E K G
1,080    1,100    1,120    1,140    1,160 hRSV gRNA T7
GSSG-streptag linker

CGGCGGGCCTCCAATTGGTCCCAGTTTGAAAAAGGCTCTGGTGGTGGAGGTGGTAGTGGTGGTGGCcaagtgaccctgagagagttctggacctgctctggtca
G G G S N W S H P Q F E K G G G S G G G G S G G G A G G Q V T L R E S G P A L V
1,180    1,200    1,220    1,240    1,260    1,280 hRSV gRNA T7
GSSG-streptag linker
hRSV-Heavyvariable agcccacacagagaccctgacctgcacctttagcggcggctttagcctgagcacacaagcggcatgagcgtcggctggattagacagcctcctggcaaaagccctgaa
K P T Q T L T C T F S G G F S L S T S G M S V G W I R Q P P G K A L E
1,300    1,320    1,340    1,360    1,380 hRSV gRNA T7
hRSV-Heavyvariable

FIG. 25I (cont'd)

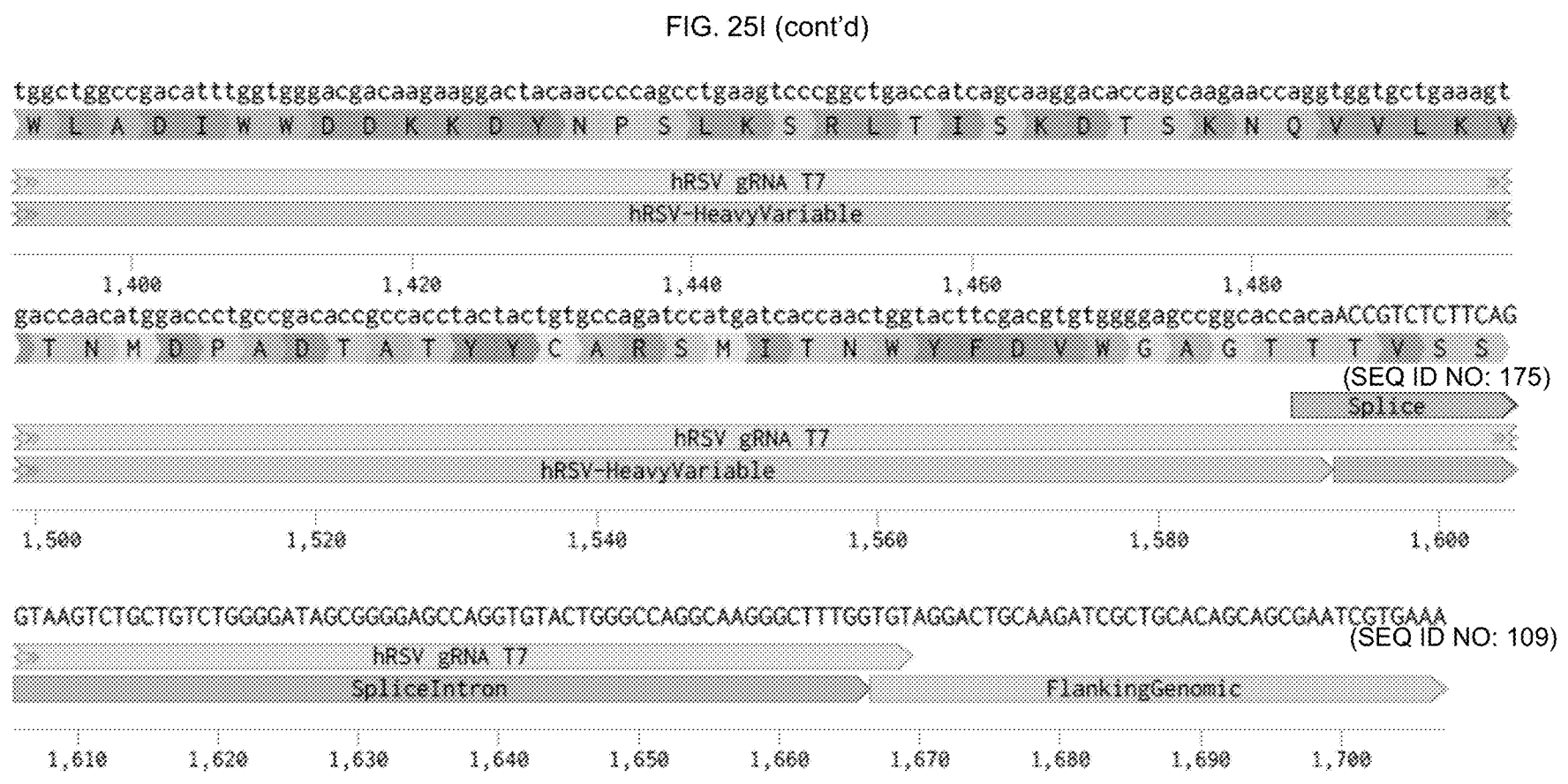

tggctggccgacatttggtgggacgacaagaaggactacaaccccagcctgaagtcccggctgaccatcagcaaggacaccaagcaagagaaccagtggtggtgctgaaagt
W  L  A  D  I  W  W  D  D  K  D  Y  N  P  S  L  K  S  R  L  T  I  S  K  D  T  S  K  Q  V  V  L  K  V hRSV gRNA T7
hRSV-HeavyVariable 1,400                    1,420                    1,440                    1,460                    1,480 gaccaacatggacccctgccgacacaccgccacctactactgtgccagatccatgatcaccaactggtacttcgacgtgtggggccggtgcaccacaACCGTCTCTTCAG
T  N  M  D  P  A  D  T  A  T  Y  Y  C  A  R  S  M  I  T  N  W  Y  F  D  V  W  G  A  G  T  T  V  S  S
(SEQ ID NO: 175)

hRSV gRNA T7                                                                              Splice
hRSV-HeavyVariable 1,500                    1,520                    1,540                    1,560                    1,580                    1,600

GTAAGTCTCGTCGTCTCGGGGATAGCGGGGGAGCCAGGTGTACTGGGCCAGGCAAGGGCTTTGGTGTGTAGGACTGCAAGATCGTCGCACAGCAGCGAATCGTGAAA
(SEQ ID NO: 109)

hRSV gRNA T7                                                              FlankingGenomic
SpliceIntron 1,610      1,620      1,630      1,640      1,650      1,660      1,670      1,680      1,690      1,700

FIG. 25I (cont'd)

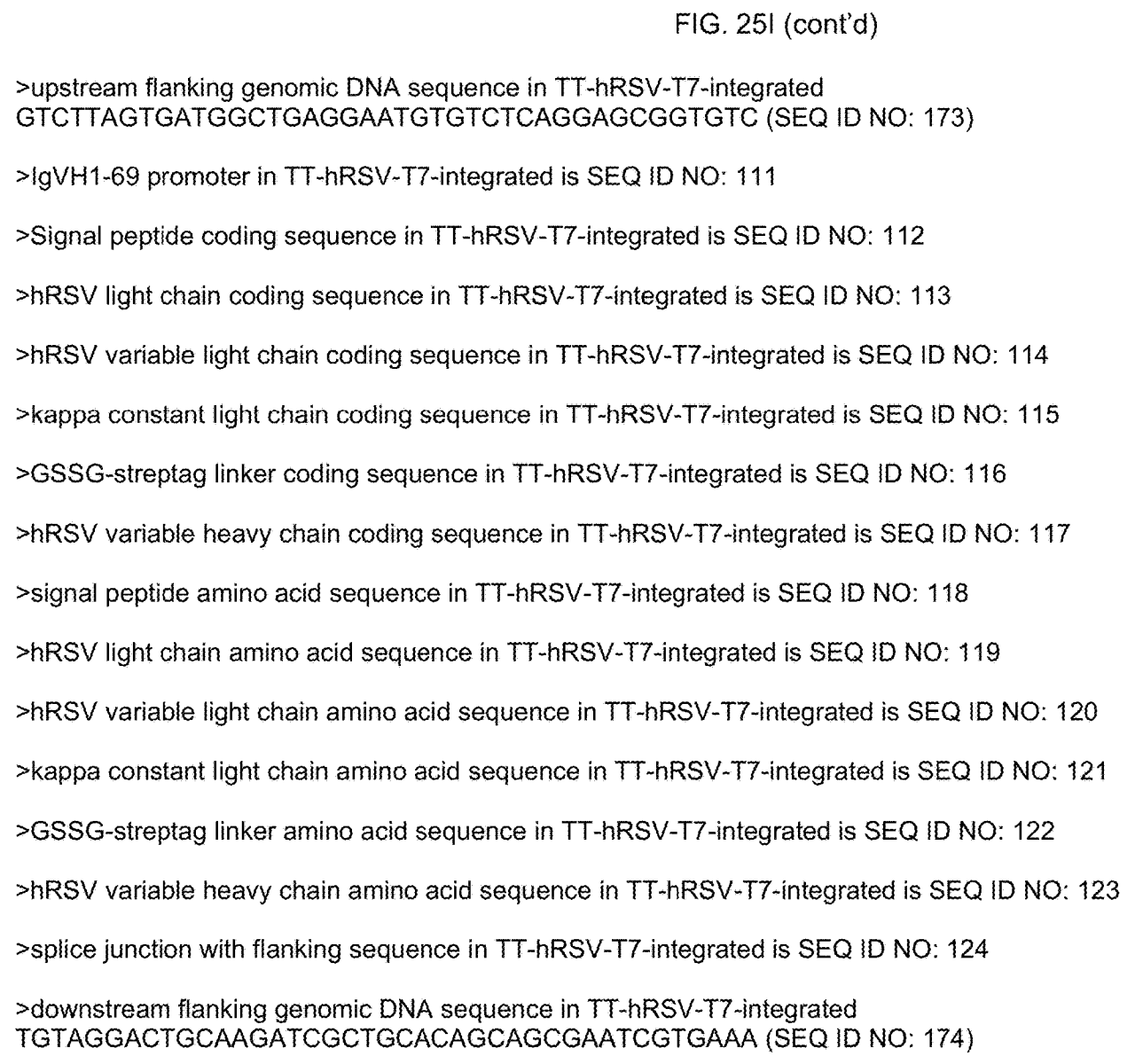

>upstream flanking genomic DNA sequence in TT-hRSV-T7-integrated
GTCTTAGTGATGGCTGAGGAATGTGTCTCAGGAGCGGGTGTC (SEQ ID NO: 173)

>IgVH1-69 promoter in TT-hRSV-T7-integrated is SEQ ID NO: 111

>Signal peptide coding sequence in TT-hRSV-T7-integrated is SEQ ID NO: 112

>hRSV light chain coding sequence in TT-hRSV-T7-integrated is SEQ ID NO: 113

>hRSV variable light chain coding sequence in TT-hRSV-T7-integrated is SEQ ID NO: 114

>kappa constant light chain coding sequence in TT-hRSV-T7-integrated is SEQ ID NO: 115

>GSSG-streptag linker coding sequence in TT-hRSV-T7-integrated is SEQ ID NO: 116

>hRSV variable heavy chain coding sequence in TT-hRSV-T7-integrated is SEQ ID NO: 117

>signal peptide amino acid sequence in TT-hRSV-T7-integrated is SEQ ID NO: 118

>hRSV light chain amino acid sequence in TT-hRSV-T7-integrated is SEQ ID NO: 119

>hRSV variable light chain amino acid sequence in TT-hRSV-T7-integrated is SEQ ID NO: 120

>kappa constant light chain amino acid sequence in TT-hRSV-T7-integrated is SEQ ID NO: 121

>GSSG-streptag linker amino acid sequence in TT-hRSV-T7-integrated is SEQ ID NO: 122

>hRSV variable heavy chain amino acid sequence in TT-hRSV-T7-integrated is SEQ ID NO: 123

>splice junction with flanking sequence in TT-hRSV-T7-integrated is SEQ ID NO: 124

>downstream flanking genomic DNA sequence in TT-hRSV-T7-integrated
TGTAGGACTGCAAGATCGCTGCACAGCAGCGAATCGTGAAA (SEQ ID NO: 174)

FIG. 25I (cont'd)

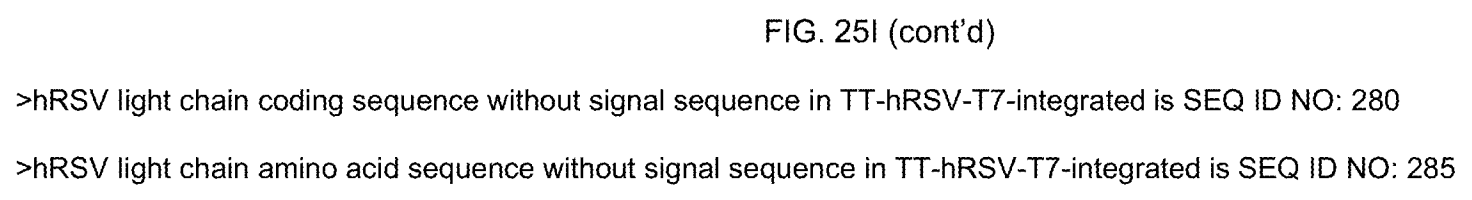

>hRSV light chain coding sequence without signal sequence in TT-hRSV-T7-integrated is SEQ ID NO: 280

>hRSV light chain amino acid sequence without signal sequence in TT-hRSV-T7-integrated is SEQ ID NO: 285

FIG. 27A
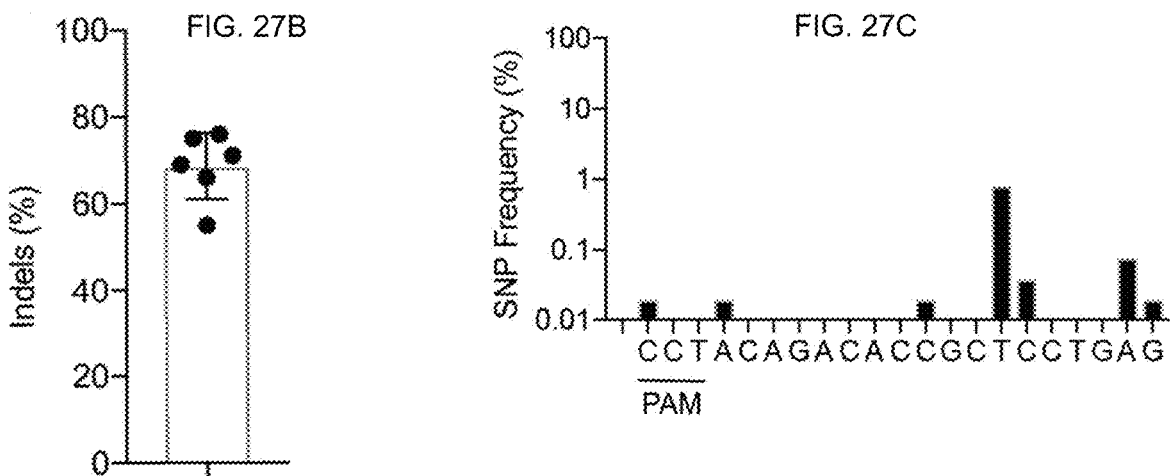
FIG. 27B
FIG. 27C
FIG. 27D
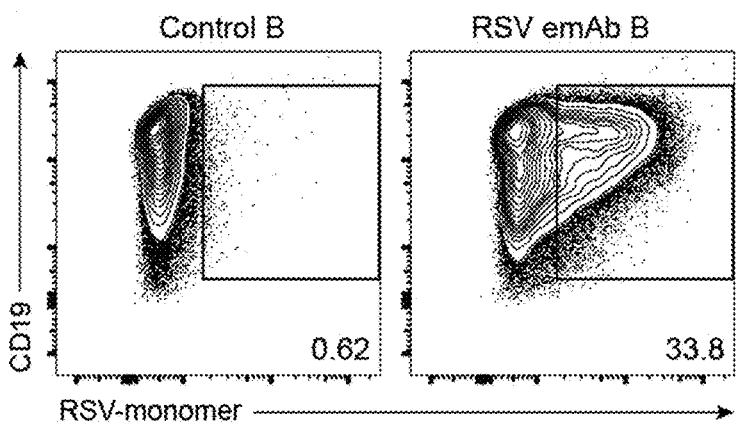

FIG. 27E
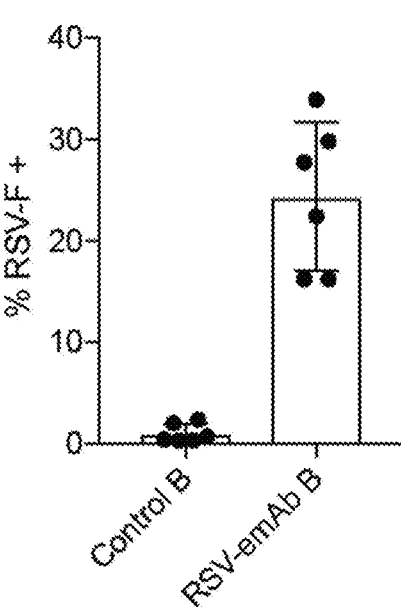
FIG. 27F
FIG. 27G
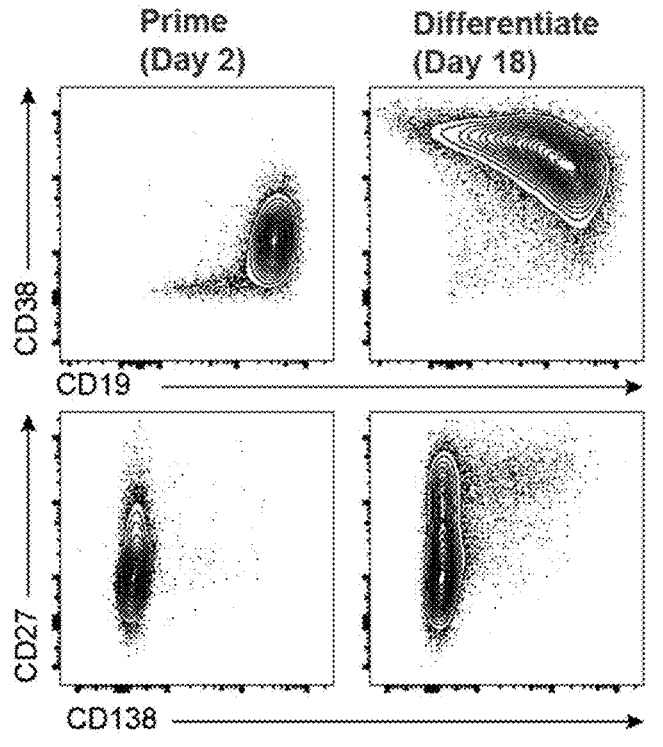
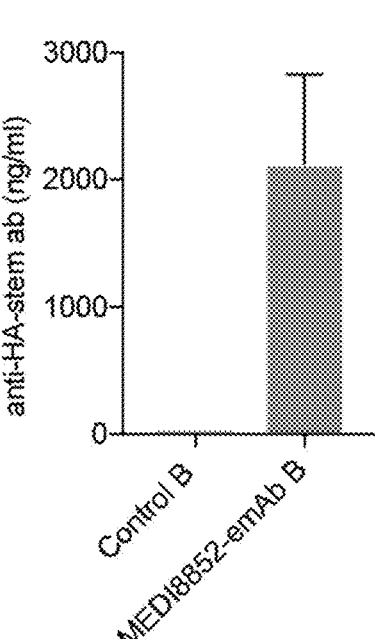

RAMOS IgH alleles

B cell IgH alleles

FIG. 30A
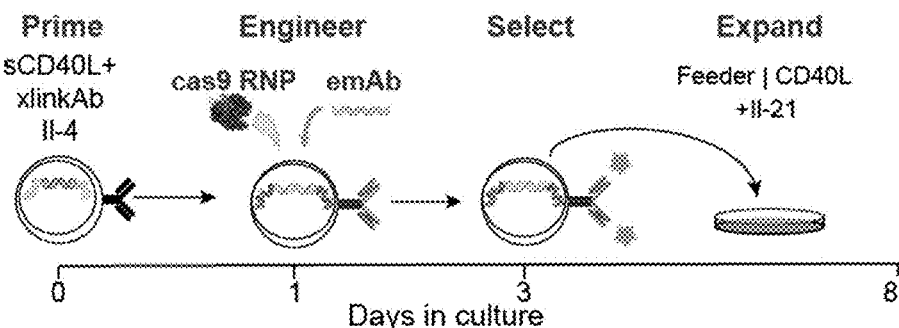
FIG. 30B
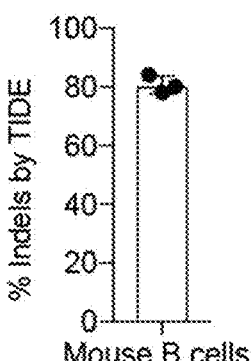
FIG. 30C

| Day 0 | Day 6 | Day 7 | Day 12 |

$1.5 \times 10^7$ emAb B cells

Blood draw for emAb in serum

Intranasal challenge with $10^6$ PFV RSV

Viral titer in lung

SEQUENCE LISTING

```
Sequence total quantity: 366
SEQ ID NO: 1            moltype = DNA  length = 722
FEATURE                 Location/Qualifiers
source                  1..722
                        mol_type = genomic DNA
                        organism = Homo sapiens
SEQUENCE: 1
ctacatggac gtctggggca aagggaccac ggtcaccgtc tcctcaggta agaatggcca   60
ctctagggcc tttgtttct gctactgcct gtggggtttc ctgagcattg caggttggtc  120
ctcggggcat gttccgaggg gacctgggcg gactggccag gaggggatgg gcactggggt  180
gccttgagga tctgggagcc tctgtggatt ttccgatgcc tttggaaaat gggactcagg  240
ttgggtgcgt ctgatggagt aactgagcct ggggggcttgg ggagccacat ttggacgaga  300
tgcctgaaca aaccaggggt cttagtgatg gctgaggaat gtgtctcagg agcggtgtct  360
gtaggactgc aagatcgctg cacagcagcg aatcgtgaaa tattttcttt agaattatga  420
ggtgcgctgt gtgtcaacct gcatcttaaa ttctttattg gctggaaaga gaactgtcgg  480
agtgggtgaa tccagccagg agggacgcgt agccccggtc ttgatgagag cagggttggg  540
ggcaggggta gcccagaaac ggtggctgcc gtcctgacag gggcttaggg aggctccagg  600
acctcagtgc cttgaagctg gtttccatga gaaaaggatt gtttatctta ggaggcatgc  660
ttactgttaa aagacaggat atgtttgaag tggcttctga gaaaaatggt taagaaaatt  720
at                                                                  722

SEQ ID NO: 2            moltype = DNA  length = 1308
FEATURE                 Location/Qualifiers
source                  1..1308
                        mol_type = genomic DNA
                        organism = Homo sapiens
SEQUENCE: 2
ctcactttag gataagtttt aggtaaaatg tgcatcatta tcctgaatta tttcagttaa   60
gcatgttagt tggtggcata agagaaaact caatcagata gtgctgaaga caggactgtg  120
gagacacctt agaaggacag attctgttcc gaatcaccga tgcggcgtca gcaggactgg  180
cctagcggag gctctgggag ggtggctgcc aggcccggcc tgggctttgg gtctccccgg  240
actacccaga gctgggatgc gtggcttctg ctgccgggcc gactggctgc tcaggcccca  300
gcccttgtta atggacttgg aggaatgatt ccatgccaaa gctttgcaag gctcgcagtg  360
accaggcgcc cgacatggta agagacaggc agccgccgct gctgcatttg cttctcttaa  420
aactttgtat ttgacgtctt atttccacta gaaggggaac tggtcttaat tgcttgatga  480
agagcaggag actcatttat gtgagtcttt tgagtgacca ttgtctgggt cactcccatt  540
taactttccc taaagcccat ttgaaggaga ggtcgcacga gctgctccac aacctctgaa  600
tggggatggc atgggtaatg atgcttgaga acataccaag ccccactggc atcgcccttg  660
tctaagtcat tgactgtagg tcatcatcgc acccttgaaa gtagcccatg ccttccaaag  720
cgatttatgg taaatggcag aattttaagt ggcaaattca gataaaatgc atttcttggt  780
tgtttccaat gatgactgtt atctagaggg aatttaaagg caggggttta ctgcagactc  840
agaagggagg ggatgctccg ggaaggtgga ggctctgagc atctcaatac cctcctcttg  900
gtgcagaaga tatgctgcca cttctagagc aaggggacct gctcattttt atcacagcac  960
aggctcctaa attcttggtc tcattctcaa gatgtttaa tgactttaaa gcagcaaaga  1020
aatattccac ccaggtagtg gagggtggta atgattggta atgctttgga accaaaaccc  1080
aggtggcgct ggggcaggac tgcagggaac tggggtatca agtagaggga gacaaaagat  1140
ggaagccagc ctggctgtgc aggaacccgg caatgagatg gctttagctg agacaagcag  1200
```

-continued

```
gtctggtggg ctgaccattt ctggccatga caactccatc cagctttcag aaatggactc   1260
agatgggcaa aactgaccta agctgaccta gactaaacaa ggctgaac                1308

SEQ ID NO: 3          moltype = DNA   length = 582
FEATURE               Location/Qualifiers
source                1..582
                      mol_type = genomic DNA
                      organism = Mus musculus
SEQUENCE: 3
ggactactgg ggtcaaggaa cctcagtcac cgtctcctca ggtaagaatg gcctctccag   60
gtctttattt ttaacctttg ttatggagtt ttctgagcat tgcagactaa tcttggatat   120
ttgtccctga gggagccggc tgagagaagt tgggaaataa actgtctagg gatctcagag   180
cctttaggac agattatctc cacatctttg aaaaactaag aatctgtgtg atggtgttgg   240
tggagtccct ggatgatggg ataggggactt tggaggctca tttgaagaag atgctaaaac   300
aatcctatgg ctggagggat agttggggct gtagttggag attttcagtt tttagaataa   360
aagtattagt tgtggaatat acttcaggac cacctctgtg acagcattta tacagtatcc   420
gatgcatagg gacaaagagt ggagtgggc actttctttta gatttgtgag gaatgttccg   480
cactagattg tttaaaactt catttgttgg aaggagagct gtcttagtga ttgagtcaag   540
ggagaaaggc atctagcctc ggtctcaaaa gggtagttgc tg                      582

SEQ ID NO: 4          moltype = DNA   length = 1528
FEATURE               Location/Qualifiers
source                1..1528
                      mol_type = genomic DNA
                      organism = Mus musculus
SEQUENCE: 4
ttatttcagt tgaacatgct ggttggtggt tgagaggaca ctcagtcagt cagtgacgtg   60
aagggcttct aagccagtcc acatgctctg tgtgaactcc ctctggccct gcttattgtt   120
gaatgggcca aaggtctgag accaggctgc tgctgggtag gcctggactt tgggtctccc   180
acccagacct gggaatgtat ggttgtggct tctgccaccc atccacctgg ctgctcatgg   240
accagccagc ctcggtggct ttgaaggaac aattccacac aaagactctg gacctctccg   300
aaaccaggca ccgcaaatgg taagccagag gcagccacag ctgtggctgc tgctcttaaa   360
gcttgtaaac tgtttctgct taagagggac tgagtcttca gtcattgctt tagggggaga   420
aagagacatt tgtgtgtctt ttgagtaccg ttgtctgggt cactcacatt taactttcct   480
tgaaaaacta gtaaaagaaa aatgttgcct gttaaccaat aatcatagag ctcatggtac   540
tttgaggaaa tcttagaaag cgtgtataca attgtctgga attatttcag ttaagtgtat   600
tagttgaggt actgatgctg tctctacttc agttatacat gtgggtttga attttgaatc   660
tattctggct cttcttaagc agaaaattta gataaaatgg atacctcagt ggttttttaat   720
ggtgggttta atatagaagg aatttaaatt ggaagctaat ttagaatcag taaggaggga   780
cccaggctaa gaaggcaatc ctgggattct ggaagaaaag atgttttttag tttttataga   840
aaacactact acattcttga tctacaactc aatgtggttt aatgaatttg aagttgccag   900
taaatgtact tcctggttgt taaagaatgg tatcaaagga cagtgcttag atccgaggtg   960
agtgtgaagag gacagggggct ggggtatgga tacgcagaag gaaggccaca gctgtacaga   1020
attgagaaag aatagagacc tgcagttgag gccagcaggt cggctggact aactctccag   1080
ccacagtaat gacccagaca gagaaagcca gactcataaa gcttgctgag caaaattaag   1140
ggaacaaggt tgagagccct agtaagcgag gctctaaaaa gcacagctga gctgagatgg   1200
gtgggcttct ctgagtgctt ctaaaatgcg ctaaactgag gtgattactc tgaggtaagc   1260
aaagctgggc ttgagccaaa atgaagtaga ctgtaatgag ctggaatgag ctgggccgct   1320
aagctaaact aggctggctt aaccgagatg agccaaactg gaatgaactt cattaatcta   1380
ggttgaatag agctaaactc tactgcctac actggactgt tctgagctga gatgagctgg   1440
ggtgagctca gctatgctac gctgtgttgg ggtgagctga tctgaaatga gatactctgg   1500
agtagctgag atggggtgag atggggtg                                      1528

SEQ ID NO: 5          moltype = DNA   length = 23
FEATURE               Location/Qualifiers
source                1..23
                      mol_type = genomic DNA
                      organism = Homo sapiens
SEQUENCE: 5
ggtcctcggg gcatgttccg agg                                           23

SEQ ID NO: 6          moltype = DNA   length = 23
FEATURE               Location/Qualifiers
source                1..23
                      mol_type = genomic DNA
                      organism = Homo sapiens
SEQUENCE: 6
gggcatgttc cgaggggacc tgg                                           23

SEQ ID NO: 7          moltype = DNA   length = 23
FEATURE               Location/Qualifiers
source                1..23
                      mol_type = genomic DNA
                      organism = Homo sapiens
SEQUENCE: 7
gcattgcagg ttggtcctcg ggg                                           23

SEQ ID NO: 8          moltype = DNA   length = 23
FEATURE               Location/Qualifiers
```

-continued

```
source                    1..23
                          mol_type = genomic DNA
                          organism = Homo sapiens
SEQUENCE: 8
tcctcggggc atgttccgag ggg                                              23

SEQ ID NO: 9             moltype = DNA   length = 23
FEATURE                  Location/Qualifiers
source                    1..23
                          mol_type = genomic DNA
                          organism = Homo sapiens
SEQUENCE: 9
ggcatgttcc gaggggacct ggg                                              23

SEQ ID NO: 10            moltype = DNA   length = 23
FEATURE                  Location/Qualifiers
source                    1..23
                          mol_type = genomic DNA
                          organism = Homo sapiens
SEQUENCE: 10
gtctcaggag cggtgtctgt agg                                              23

SEQ ID NO: 11            moltype = DNA   length = 23
FEATURE                  Location/Qualifiers
source                    1..23
                          mol_type = genomic DNA
                          organism = Homo sapiens
SEQUENCE: 11
agcattgcag gttggtcctc ggg                                              23

SEQ ID NO: 12            moltype = DNA   length = 23
FEATURE                  Location/Qualifiers
source                    1..23
                          mol_type = genomic DNA
                          organism = Homo sapiens
SEQUENCE: 12
cctgggcgga ctggccagga ggg                                              23

SEQ ID NO: 13            moltype = DNA   length = 23
FEATURE                  Location/Qualifiers
source                    1..23
                          mol_type = genomic DNA
                          organism = Homo sapiens
SEQUENCE: 13
actggggtgc cttgaggatc tgg                                              23

SEQ ID NO: 14            moltype = DNA   length = 23
FEATURE                  Location/Qualifiers
source                    1..23
                          mol_type = genomic DNA
                          organism = Homo sapiens
SEQUENCE: 14
ccccagtgcc catcccctcc tgg                                              23

SEQ ID NO: 15            moltype = DNA   length = 23
FEATURE                  Location/Qualifiers
source                    1..23
                          mol_type = genomic DNA
                          organism = Homo sapiens
SEQUENCE: 15
ctaagacccc tggtttgttc agg                                              23

SEQ ID NO: 16            moltype = DNA   length = 23
FEATURE                  Location/Qualifiers
source                    1..23
                          mol_type = genomic DNA
                          organism = Homo sapiens
SEQUENCE: 16
tgtggatttt ccgatgcctt tgg                                              23

SEQ ID NO: 17            moltype = DNA   length = 23
FEATURE                  Location/Qualifiers
source                    1..23
                          mol_type = genomic DNA
                          organism = Homo sapiens
SEQUENCE: 17
aggaccaacc tgcaatgctc agg                                              23

SEQ ID NO: 18            moltype = DNA   length = 23
```

-continued

```
FEATURE           Location/Qualifiers
source            1..23
                  mol_type = genomic DNA
                  organism = Homo sapiens
SEQUENCE: 18
ctcaggttgg gtgcgtctga tgg                                        23

SEQ ID NO: 19     moltype = DNA   length = 23
FEATURE           Location/Qualifiers
source            1..23
                  mol_type = genomic DNA
                  organism = Homo sapiens
SEQUENCE: 19
ccctcctggc cagtccgccc agg                                        23

SEQ ID NO: 20     moltype = DNA   length = 23
FEATURE           Location/Qualifiers
source            1..23
                  mol_type = genomic DNA
                  organism = Homo sapiens
SEQUENCE: 20
ggccaggagg ggatgggcac tgg                                        23

SEQ ID NO: 21     moltype = DNA   length = 23
FEATURE           Location/Qualifiers
source            1..23
                  mol_type = genomic DNA
                  organism = Homo sapiens
SEQUENCE: 21
gagatgcctg aacaaaccag ggg                                        23

SEQ ID NO: 22     moltype = DNA   length = 23
FEATURE           Location/Qualifiers
source            1..23
                  mol_type = genomic DNA
                  organism = Homo sapiens
SEQUENCE: 22
aggggtctta gtgatggctg agg                                        23

SEQ ID NO: 23     moltype = DNA   length = 23
FEATURE           Location/Qualifiers
source            1..23
                  mol_type = genomic DNA
                  organism = Homo sapiens
SEQUENCE: 23
atgggcactg gggtgccttg agg                                        23

SEQ ID NO: 24     moltype = DNA   length = 23
FEATURE           Location/Qualifiers
source            1..23
                  mol_type = genomic DNA
                  organism = Homo sapiens
SEQUENCE: 24
ttccgatgcc tttggaaaat ggg                                        23

SEQ ID NO: 25     moltype = DNA   length = 23
FEATURE           Location/Qualifiers
source            1..23
                  mol_type = genomic DNA
                  organism = Homo sapiens
SEQUENCE: 25
ctgacgccgc atcggtgatt cgg                                        23

SEQ ID NO: 26     moltype = DNA   length = 23
FEATURE           Location/Qualifiers
source            1..23
                  mol_type = genomic DNA
                  organism = Homo sapiens
SEQUENCE: 26
ttagacaagg gcgatgccag tgg                                        23

SEQ ID NO: 27     moltype = DNA   length = 23
FEATURE           Location/Qualifiers
source            1..23
                  mol_type = genomic DNA
                  organism = Homo sapiens
SEQUENCE: 27
cgtgcgacct ctccttcaaa tgg                                        23
```

-continued

```
SEQ ID NO: 28          moltype = DNA   length = 23
FEATURE                Location/Qualifiers
source                 1..23
                       mol_type = genomic DNA
                       organism = Homo sapiens
SEQUENCE: 28
agcatatctt ctgcaccaag agg                                            23

SEQ ID NO: 29          moltype = DNA   length = 23
FEATURE                Location/Qualifiers
source                 1..23
                       mol_type = genomic DNA
                       organism = Homo sapiens
SEQUENCE: 29
atattccacc caggtagtgg agg                                            23

SEQ ID NO: 30          moltype = DNA   length = 23
FEATURE                Location/Qualifiers
source                 1..23
                       mol_type = genomic DNA
                       organism = Homo sapiens
SEQUENCE: 30
gtgcgacctc tccttcaaat ggg                                            23

SEQ ID NO: 31          moltype = DNA   length = 23
FEATURE                Location/Qualifiers
source                 1..23
                       mol_type = genomic DNA
                       organism = Homo sapiens
SEQUENCE: 31
aggtcccctt gctctagaag tgg                                            23

SEQ ID NO: 32          moltype = DNA   length = 23
FEATURE                Location/Qualifiers
source                 1..23
                       mol_type = genomic DNA
                       organism = Homo sapiens
SEQUENCE: 32
ctctagataa cagtcatcat tgg                                            23

SEQ ID NO: 33          moltype = DNA   length = 23
FEATURE                Location/Qualifiers
source                 1..23
                       mol_type = genomic DNA
                       organism = Homo sapiens
SEQUENCE: 33
ttgtctaagt cattgactgt agg                                            23

SEQ ID NO: 34          moltype = DNA   length = 23
FEATURE                Location/Qualifiers
source                 1..23
                       mol_type = genomic DNA
                       organism = Homo sapiens
SEQUENCE: 34
ccaaagcgat ttatggtaaa tgg                                            23

SEQ ID NO: 35          moltype = DNA   length = 23
FEATURE                Location/Qualifiers
source                 1..23
                       mol_type = genomic DNA
                       organism = Homo sapiens
SEQUENCE: 35
tcttttgagt gaccattgtc tgg                                            23

SEQ ID NO: 36          moltype = DNA   length = 23
FEATURE                Location/Qualifiers
source                 1..23
                       mol_type = genomic DNA
                       organism = Homo sapiens
SEQUENCE: 36
ccatttacca taaatcgctt tgg                                            23

SEQ ID NO: 37          moltype = DNA   length = 23
FEATURE                Location/Qualifiers
source                 1..23
                       mol_type = genomic DNA
                       organism = Homo sapiens
SEQUENCE: 37
agggcgatgc cagtggggct tgg                                            23
```

-continued

```
SEQ ID NO: 38              moltype = DNA   length = 23
FEATURE                    Location/Qualifiers
source                     1..23
                           mol_type = genomic DNA
                           organism = Homo sapiens
SEQUENCE: 38
agctaaagcc atctcattgc cgg                                            23

SEQ ID NO: 39              moltype = DNA   length = 23
FEATURE                    Location/Qualifiers
source                     1..23
                           mol_type = genomic DNA
                           organism = Homo sapiens
SEQUENCE: 39
ccacaacctc tgaatgggga tgg                                            23

SEQ ID NO: 40              moltype = DNA   length = 23
FEATURE                    Location/Qualifiers
source                     1..23
                           mol_type = genomic DNA
                           organism = Homo sapiens
SEQUENCE: 40
ttaattgctt gatgaagagc agg                                            23

SEQ ID NO: 41              moltype = DNA   length = 23
FEATURE                    Location/Qualifiers
source                     1..23
                           mol_type = genomic DNA
                           organism = Homo sapiens
SEQUENCE: 41
tagacaaggg cgatgccagt ggg                                            23

SEQ ID NO: 42              moltype = DNA   length = 23
FEATURE                    Location/Qualifiers
source                     1..23
                           mol_type = genomic DNA
                           organism = Homo sapiens
SEQUENCE: 42
aagctgacct agactaaaca agg                                            23

SEQ ID NO: 43              moltype = DNA   length = 23
FEATURE                    Location/Qualifiers
source                     1..23
                           mol_type = genomic DNA
                           organism = Homo sapiens
SEQUENCE: 43
gcaggaaccc ggcaatgaga tgg                                            23

SEQ ID NO: 44              moltype = DNA   length = 23
FEATURE                    Location/Qualifiers
source                     1..23
                           mol_type = genomic DNA
                           organism = Homo sapiens
SEQUENCE: 44
tctgttccga atcaccgatg cgg                                            23

SEQ ID NO: 45              moltype = DNA   length = 23
FEATURE                    Location/Qualifiers
source                     1..23
                           mol_type = genomic DNA
                           organism = Mus musculus
SEQUENCE: 45
caactaccct tttgagaccg agg                                            23

SEQ ID NO: 46              moltype = DNA   length = 23
FEATURE                    Location/Qualifiers
source                     1..23
                           mol_type = genomic DNA
                           organism = Mus musculus
SEQUENCE: 46
ttatacagta tccgatgcat agg                                            23

SEQ ID NO: 47              moltype = DNA   length = 23
FEATURE                    Location/Qualifiers
source                     1..23
                           mol_type = genomic DNA
                           organism = Mus musculus
SEQUENCE: 47
```

-continued

```
tatacagtat ccgatgcata ggg                                                 23

SEQ ID NO: 48              moltype = DNA   length = 23
FEATURE                    Location/Qualifiers
source                     1..23
                           mol_type = genomic DNA
                           organism = Mus musculus
SEQUENCE: 48
catctagcct cggtctcaaa agg                                                 23

SEQ ID NO: 49              moltype = DNA   length = 23
FEATURE                    Location/Qualifiers
source                     1..23
                           mol_type = genomic DNA
                           organism = Mus musculus
SEQUENCE: 49
cactctttgt ccctatgcat cgg                                                 23

SEQ ID NO: 50              moltype = DNA   length = 23
FEATURE                    Location/Qualifiers
source                     1..23
                           mol_type = genomic DNA
                           organism = Mus musculus
SEQUENCE: 50
atctagcctc ggtctcaaaa ggg                                                 23

SEQ ID NO: 51              moltype = DNA   length = 23
FEATURE                    Location/Qualifiers
source                     1..23
                           mol_type = genomic DNA
                           organism = Mus musculus
SEQUENCE: 51
aagttttaaa caatctagtg cgg                                                 23

SEQ ID NO: 52              moltype = DNA   length = 23
FEATURE                    Location/Qualifiers
source                     1..23
                           mol_type = genomic DNA
                           organism = Mus musculus
SEQUENCE: 52
aagatgctaa aacaatccta tgg                                                 23

SEQ ID NO: 53              moltype = DNA   length = 23
FEATURE                    Location/Qualifiers
source                     1..23
                           mol_type = genomic DNA
                           organism = Mus musculus
SEQUENCE: 53
tgctaaaaca atcctatggc tgg                                                 23

SEQ ID NO: 54              moltype = DNA   length = 23
FEATURE                    Location/Qualifiers
source                     1..23
                           mol_type = genomic DNA
                           organism = Mus musculus
SEQUENCE: 54
aagtccctat cccatcatcc agg                                                 23

SEQ ID NO: 55              moltype = DNA   length = 23
FEATURE                    Location/Qualifiers
source                     1..23
                           mol_type = genomic DNA
                           organism = Mus musculus
SEQUENCE: 55
gggagaaagg catctagcct cgg                                                 23

SEQ ID NO: 56              moltype = DNA   length = 23
FEATURE                    Location/Qualifiers
source                     1..23
                           mol_type = genomic DNA
                           organism = Mus musculus
SEQUENCE: 56
tgagcattgc agactaatct tgg                                                 23

SEQ ID NO: 57              moltype = DNA   length = 23
FEATURE                    Location/Qualifiers
source                     1..23
                           mol_type = genomic DNA
                           organism = Mus musculus
```

```
SEQUENCE: 57
ttagttgtgg aatatacttc agg                                                       23

SEQ ID NO: 58           moltype = DNA   length = 23
FEATURE                 Location/Qualifiers
source                  1..23
                        mol_type = genomic DNA
                        organism = Mus musculus
SEQUENCE: 58
tggtggagtc cctggatgat ggg                                                       23

SEQ ID NO: 59           moltype = DNA   length = 23
FEATURE                 Location/Qualifiers
source                  1..23
                        mol_type = genomic DNA
                        organism = Mus musculus
SEQUENCE: 59
gtggagataa tctgtcctaa agg                                                        23

SEQ ID NO: 60           moltype = DNA   length = 23
FEATURE                 Location/Qualifiers
source                  1..23
                        mol_type = genomic DNA
                        organism = Mus musculus
SEQUENCE: 60
agtccctatc ccatcatcca ggg                                                        23

SEQ ID NO: 61           moltype = DNA   length = 23
FEATURE                 Location/Qualifiers
source                  1..23
                        mol_type = genomic DNA
                        organism = Mus musculus
SEQUENCE: 61
atcttggata tttgtccctg agg                                                        23

SEQ ID NO: 62           moltype = DNA   length = 23
FEATURE                 Location/Qualifiers
source                  1..23
                        mol_type = genomic DNA
                        organism = Mus musculus
SEQUENCE: 62
gggatagttg gggctgtagt tgg                                                        23

SEQ ID NO: 63           moltype = DNA   length = 23
FEATURE                 Location/Qualifiers
source                  1..23
                        mol_type = genomic DNA
                        organism = Mus musculus
SEQUENCE: 63
caggtaagaa tggcctctcc agg                                                        23

SEQ ID NO: 64           moltype = DNA   length = 23
FEATURE                 Location/Qualifiers
source                  1..23
                        mol_type = genomic DNA
                        organism = Mus musculus
SEQUENCE: 64
tctctcagcc ggctccctca ggg                                                        23

SEQ ID NO: 65           moltype = DNA   length = 23
FEATURE                 Location/Qualifiers
source                  1..23
                        mol_type = genomic DNA
                        organism = Mus musculus
SEQUENCE: 65
ccgaaaccag gcaccgcaaa tgg                                                        23

SEQ ID NO: 66           moltype = DNA   length = 23
FEATURE                 Location/Qualifiers
source                  1..23
                        mol_type = genomic DNA
                        organism = Mus musculus
SEQUENCE: 66
caccgcaaat ggtaagccag agg                                                        23

SEQ ID NO: 67           moltype = DNA   length = 23
FEATURE                 Location/Qualifiers
source                  1..23
                        mol_type = genomic DNA
```

-continued

```
                              organism = Mus musculus
SEQUENCE: 67
ggcttaccat ttgcggtgcc tgg                                                23

SEQ ID NO: 68           moltype = DNA   length = 23
FEATURE                 Location/Qualifiers
source                  1..23
                        mol_type = genomic DNA
                        organism = Mus musculus
SEQUENCE: 68
tgcggtgcct ggtttcggag agg                                                23

SEQ ID NO: 69           moltype = DNA   length = 23
FEATURE                 Location/Qualifiers
source                  1..23
                        mol_type = genomic DNA
                        organism = Mus musculus
SEQUENCE: 69
cagctatgct acgctgtgtt ggg                                                23

SEQ ID NO: 70           moltype = DNA   length = 23
FEATURE                 Location/Qualifiers
source                  1..23
                        mol_type = genomic DNA
                        organism = Mus musculus
SEQUENCE: 70
aaggacagtg cttagatccg agg                                                23

SEQ ID NO: 71           moltype = DNA   length = 23
FEATURE                 Location/Qualifiers
source                  1..23
                        mol_type = genomic DNA
                        organism = Mus musculus
SEQUENCE: 71
tcagtcagtc agtgacgtga agg                                                23

SEQ ID NO: 72           moltype = DNA   length = 23
FEATURE                 Location/Qualifiers
source                  1..23
                        mol_type = genomic DNA
                        organism = Mus musculus
SEQUENCE: 72
catgctggtt ggtggttgag agg                                                23

SEQ ID NO: 73           moltype = DNA   length = 23
FEATURE                 Location/Qualifiers
source                  1..23
                        mol_type = genomic DNA
                        organism = Mus musculus
SEQUENCE: 73
tcttttgagt accgttgtct ggg                                                23

SEQ ID NO: 74           moltype = DNA   length = 23
FEATURE                 Location/Qualifiers
source                  1..23
                        mol_type = genomic DNA
                        organism = Mus musculus
SEQUENCE: 74
tggcccattc aacaataagc agg                                                23

SEQ ID NO: 75           moltype = DNA   length = 23
FEATURE                 Location/Qualifiers
source                  1..23
                        mol_type = genomic DNA
                        organism = Mus musculus
SEQUENCE: 75
ctgggccgct aagctaaact agg                                                23

SEQ ID NO: 76           moltype = DNA   length = 23
FEATURE                 Location/Qualifiers
source                  1..23
                        mol_type = genomic DNA
                        organism = Mus musculus
SEQUENCE: 76
gccagcctag tttagcttag cgg                                                23

SEQ ID NO: 77           moltype = DNA   length = 23
FEATURE                 Location/Qualifiers
source                  1..23
```

-continued

```
                              mol_type = genomic DNA
                              organism = Mus musculus
SEQUENCE: 77
tgaagtagac tgtaatgaac tgg                                          23

SEQ ID NO: 78          moltype = DNA   length = 23
FEATURE                Location/Qualifiers
source                 1..23
                       mol_type = genomic DNA
                       organism = Mus musculus
SEQUENCE: 78
gacctgggaa tgtatggttg tgg                                          23

SEQ ID NO: 79          moltype = DNA   length = 23
FEATURE                Location/Qualifiers
source                 1..23
                       mol_type = genomic DNA
                       organism = Mus musculus
SEQUENCE: 79
ggtatggata cgcagaagga agg                                          23

SEQ ID NO: 80          moltype = DNA   length = 23
FEATURE                Location/Qualifiers
source                 1..23
                       mol_type = genomic DNA
                       organism = Mus musculus
SEQUENCE: 80
gttgagagcc ctagtaagcg agg                                          23

SEQ ID NO: 81          moltype = DNA   length = 23
FEATURE                Location/Qualifiers
source                 1..23
                       mol_type = genomic DNA
                       organism = Mus musculus
SEQUENCE: 81
gccgctaagc taaactaggc tgg                                          23

SEQ ID NO: 82          moltype = DNA   length = 23
FEATURE                Location/Qualifiers
source                 1..23
                       mol_type = genomic DNA
                       organism = Mus musculus
SEQUENCE: 82
tcagctatgc tacgctgtgt tgg                                          23

SEQ ID NO: 83          moltype = DNA   length = 23
FEATURE                Location/Qualifiers
source                 1..23
                       mol_type = genomic DNA
                       organism = Mus musculus
SEQUENCE: 83
ttttagagcc tcgcttacta ggg                                          23

SEQ ID NO: 84          moltype = DNA   length = 23
FEATURE                Location/Qualifiers
source                 1..23
                       mol_type = genomic DNA
                       organism = Mus musculus
SEQUENCE: 84
ctctatgatt attggttaac agg                                          23

SEQ ID NO: 85          moltype = DNA   length = 834
FEATURE                Location/Qualifiers
source                 1..834
                       mol_type = genomic DNA
                       organism = Homo sapiens
SEQUENCE: 85
gtagttgaaa agtggtcttg aaaaatacta aaatgaaggc cactctatca gaatatcaaa   60
gtgtttctcc ttaatcacaa agagaaaacg agttaaccta aaaagattgt gaacacagtc  120
attatgaaaa taatgctctg aggtatcgaa aaagtatttg agattaatta tcacatgaag  180
ggataacaag ctaatttaaa aaactttttg aatacagtca taaactctcc ctaagactgt  240
ttaatttctt aaacatctta ctttaaaaat gaatgcagtt tagaagttga tatgctgttt  300
gcacaaacta gcagttgata agctaagatt ggaaatgaaa ttcagatagt taaaaaaagc  360
cttttcagtt tcggtcagcc tcgccttatt ttagaaacga aaattgtcca ggtgttgttt  420
tgctcagtag agcactttca gatctgggcc tgggcaaaac cacctcttca caaccagaag  480
tgataaattt accaattgtg tttttttgct tcctaaaata gactctcgcg gtgacctgct  540
tcctgccacc tgctgtgggt gccggagacc cccatgcagc catcttgact ctaattcatc  600
atctgcttcc agcttcgctc aattaattaa aaaaataaac ttgatttatg atggtcaaaa  660
cgcagtcccc atcggggcc gacagcactg tgctagtatt tcttagctga gcttgctttg  720
```

-continued

```
gcctcaattc cagacacata tcactcatgg gtgttaatca aatgataaga atttcaaata  780
cttggacagt taaaaaaatt aatatacttg aaaatctctc acatttttaa gtca         834

SEQ ID NO: 86          moltype = DNA   length = 1002
FEATURE                Location/Qualifiers
source                 1..1002
                       mol_type = genomic DNA
                       organism = Mus musculus
SEQUENCE: 86
agtctagata attgcattca tttaaaaaaa aagtctttct cctaaaatga atactcagaa   60
agtggtcttg aaaaagattt gtgaagccgt tttgaccaga atgtcaaagt cttaatagta  120
aggcaaaaca aacaactaaa aaagatcatg aacaaagtca ctgtaaatgc ttcgggtatt  180
ggaaaagaat tgaatggaga ccaataatca gagggaagaa taatagagta attttaagaa  240
gtttctaaa tatattagaa attaaagaca ctaaagtcct tcaatttctt acataaccta   300
attttgaaaa tgaattctaa atacatttta gaagtcgata aacttaagtt tggggaaact  360
agaactactc aagctaaaat taaaaggttg aactcaataa gttaaaagag gacctctcca  420
gtttcggctg aatcctcaac ttattttaga aatgcaaatt acccaggtgg tgttttgctc  480
agcctggact ttcggtttgg tggggctgga cagagtgttt caaaaccact tcttcaaacc  540
acagctacaa gtttacctag tggtttttatt ttccccttccc caaatagcct tgccacatga  600
cctgcttcct gccagctgct gcaggtgttc tggttctgat cggccatctt gactccaact  660
caacattgct caattcattt aaaaatattt gaaacttaat ttattattgt taaaagtcag  720
ttctgaatag gttatgagag agcctcactc ccattcctcg gttaaacttt aagtaatatc  780
agttctacac aaacaagacc tcaaactgat tgacaagaat tttggacatt taaaaaaatg  840
agtacttgaa aaccctctca cattttaaag tcacagtatt taactatttt tcctaggaac  900
caacttaaga gtaaaagcaa catcttctaa tattccatac acatacttct gtgttccttt  960
gaaagctgga cttttgcagg ctccaccaga cctctctaga ca                    1002

SEQ ID NO: 87          moltype = RNA   length = 20
FEATURE                Location/Qualifiers
misc_feature           1..20
                       note = mouse sgRNA-mIgH_3 from FIG. 25A
source                 1..20
                       mol_type = other RNA
                       organism = synthetic construct
SEQUENCE: 87
ttatacagta tccgatgcat                                               20

SEQ ID NO: 88          moltype = RNA   length = 20
FEATURE                Location/Qualifiers
misc_feature           1..20
                       note = human sgRNA-hIgH-6 from FIG. 25A
source                 1..20
                       mol_type = other RNA
                       organism = synthetic construct
SEQUENCE: 88
gcattgcagg ttggtcctcg                                               20

SEQ ID NO: 89          moltype = RNA   length = 20
FEATURE                Location/Qualifiers
misc_feature           1..20
                       note = human sgRNA-hIgH-7 from FIG. 25A
source                 1..20
                       mol_type = other RNA
                       organism = synthetic construct
SEQUENCE: 89
gtctcaggag cggtgtctgt                                               20

SEQ ID NO: 90          moltype = DNA   length = 36
FEATURE                Location/Qualifiers
source                 1..36
                       mol_type = genomic DNA
                       organism = Mus musculus
SEQUENCE: 90
catcggatac tgtataaatg ctgtcacaga ggtggt                            36

SEQ ID NO: 91          moltype = DNA   length = 36
FEATURE                Location/Qualifiers
source                 1..36
                       mol_type = genomic DNA
                       organism = Mus musculus
SEQUENCE: 91
catagggaca aagagtggag tggggcactt tcttta                            36

SEQ ID NO: 92          moltype = DNA   length = 36
FEATURE                Location/Qualifiers
source                 1..36
                       mol_type = genomic DNA
                       organism = Homo sapiens
SEQUENCE: 92
```

-continued

```
gacaccgctc ctgagacaca ttcctcagcc atcact                         36

SEQ ID NO: 93          moltype = DNA   length = 36
FEATURE                Location/Qualifiers
source                 1..36
                       mol_type = genomic DNA
                       organism = Homo sapiens
SEQUENCE: 93
tgtaggactg caagatcgct gcacagcagc gaatcg                         36

SEQ ID NO: 94          moltype = DNA   length = 37
FEATURE                Location/Qualifiers
source                 1..37
                       mol_type = genomic DNA
                       organism = Homo sapiens
SEQUENCE: 94
gggaccaacc tgcaatgctc aggaaacccc acaggca                        37

SEQ ID NO: 95          moltype = DNA   length = 37
FEATURE                Location/Qualifiers
source                 1..37
                       mol_type = genomic DNA
                       organism = Homo sapiens
SEQUENCE: 95
ttcgggcat gttccgaggg gacctgggcg gactggc                         37

SEQ ID NO: 96          moltype = DNA   length = 127
FEATURE                Location/Qualifiers
misc_feature           1..127
                       note = upstream splicing oligonucleotide for mouse
                         sgRNA-mIgH_3
source                 1..127
                       mol_type = other DNA
                       organism = synthetic construct
SEQUENCE: 96
cttcgagaca tgtacagacc atttagatgt agtatcaaag cctaatatct caatcttaaa   60
atagaatcct aacctgagac actcacttgt ccatcggata ctgtataaat gctgtcacag  120
aggtggt                                                          127

SEQ ID NO: 97          moltype = DNA   length = 86
FEATURE                Location/Qualifiers
misc_feature           1..86
                       note = downstream splicing oligonucleotide for mouse
                         sgRNA-mIgH_3
source                 1..86
                       mol_type = other DNA
                       organism = synthetic construct
SEQUENCE: 97
cttctcccat tctaaatgca tgttggggggg attctgggcc ttcaggacca catagggaca   60
aagagtggag tggggcactt tcttta                                     86

SEQ ID NO: 98          moltype = DNA   length = 127
FEATURE                Location/Qualifiers
misc_feature           1..127
                       note = upstream splicing oligonucleotide for human
                         sgRNA-hIgH-7
source                 1..127
                       mol_type = other DNA
                       organism = synthetic construct
SEQUENCE: 98
gtgcacagcg ctcttcccgc tgcagaacaa accccaaccc caggatgcac tcctcactgt   60
gaacccacat tttattggcc taaagattac ggacaccgct cctgagacac attcctcagc  120
catcact                                                         127

SEQ ID NO: 99          moltype = DNA   length = 86
FEATURE                Location/Qualifiers
misc_feature           1..86
                       note = downstream splicing oligonucleotide for human
                         sgRNA-hIgH-7
source                 1..86
                       mol_type = other DNA
                       organism = synthetic construct
SEQUENCE: 99
gtctgggat agcggggagc caggtgtact gggccaggca agggctttgg tgtaggactg   60
caagatcgct gcacagcagc gaatcg                                     86

SEQ ID NO: 100         moltype = DNA   length = 128
FEATURE                Location/Qualifiers
misc_feature           1..128
```

```
                        note = upstream splicing oligonucleotide for human
                            sgRNA-hIgH-6
source                  1..128
                        mol_type = other DNA
                        organism = synthetic construct
SEQUENCE: 100
gtgcacagcg ctcttcccgc tgcagaacaa accccaaccc caggatgcac tcctcactgt  60
gaacccacat tttattggcc taaagattac ggggaccaac ctgcaatgct caggaaaccc  120
cacaggca                                                          128

SEQ ID NO: 101          moltype = DNA  length = 87
FEATURE                 Location/Qualifiers
misc_feature            1..87
                        note = downstream splicing oligonucleotide for human
                            sgRNA-hIgH-6
source                  1..87
                        mol_type = other DNA
                        organism = synthetic construct
SEQUENCE: 101
gtctggggat agcggggagc caggtgtact gggccaggca agggctttgg ttcggggcat  60
gttccgaggg gacctgggcg gactggc                                      87

SEQ ID NO: 102          moltype = DNA  length = 2531
FEATURE                 Location/Qualifiers
misc_feature            1..2531
                        note = human anti-RSV-emAb AAV
source                  1..2531
                        mol_type = other DNA
                        organism = synthetic construct
SEQUENCE: 102
tgtgacgccc ggagacagaa ggtctctggg tggctgggtt tttgtggggt gaggatggac  60
attctgccat tgtgattact actactacta ctacatggac gtctgggca aagggaccac  120
ggtcaccgtc tcctcaggta agaatggcca ctctagggcc tttgttttct gctactgcct  180
gtggggtttc ctgagcattg caggttggtc ctcggggcat gttccgaggg gacctgggcg  240
gactggccag gaggggatgg gcactggggt gccttgagga tctgtggagcc tctgtggatt  300
ttccgatgcc tttgggaaat gggactcagg ttgggtgcgt ctgatggagt aactgagcct  360
gggggcttgg ggagccacat ttggacgaga tgcctgaaca aaccagggg cttagtgatg  420
gctgaggaat gtgtctcagg agcggtgtct gatcgtaatc tttaggccaa taaatgtgg  480
gttcacagtg aggagtgcat cctgggttg gggtttgttc tgcagcggga agagcgcgtt  540
gcacagaaag cttagaaatg gggcaagaga tgcttttcct caggcaggat ttagggcttg  600
gtctctcagc atcccacact tgtacagctg atgtggcatc tgtgtttct ttctcatcct  660
agatcaggct ttgagctgtg aaataccctg cctcatgcat atgcaaataa cctgaggtct  720
tctgagataa atatagatat attggtgccc tgaggtttaa acgccgccac catggctacc  780
ggcagcagaa caagcctgct gctcgctttt ggactgctct gtctcccctg gttgcaagaa  840
ggcagcgccg acatccagat gacacagagc cctagcacac tgtctgccag cgtgggcgac  900
agagtgacca tcacatgcaa gtgccagctg agcgtgggct acatgcactg gtatcagcaa  960
aagcccggca aggcccctaa gctgctgatc tacgatacct ccaagctgac ctctggcgtg  1020
ccctccagat tttctggcag cggcagcgga accgagttca ccctgaccat ctcaagcctg  1080
cagcctgacg acttcgctac gtactactgc ttccaaggca gcggctaccc cttcacattt  1140
ggcggcggaa caaagctgga aatcaagcgg actgtggccg ctcctagcgt gttcatcttt  1200
ccacctagcg acgagcagct gaagtctggc actgcctctg tcgtgtgcct gctgaacaac  1260
ttctaccctc gagaggccaa ggtgcagtgg aaagtggaca atgccctgca gagcggcaac  1320
agccaagagt ctgtgaccga gcaggactcc aaggattcca cctacagcct gtctagcacc  1380
ctgactctga gcaaggccga ctacgagaag cacaaggtgt acgcctgcga agtgacacac  1440
cagggactga gcagccctgt gaccaagagc ttcaatcggg gcgagtgcgg aggaagtagt  1500
ggcagcggga gtgggtccaa ttggagtcat cctcaatttg agaaaggagg gggagggtcc  1560
aattggtctc atccgcagtt tgagaagggc ggcggcggct ccaattggtc ccatcccag  1620
tttgaaaaag gctctggtgg aggtggtagt gctggtgggc aagtgaccct gagagagtct  1680
ggacctgctc tggtcaagcc cacacagacc ctgacactga cctgcacctt cagcggcttt  1740
agcctgagca caagcggcat gagcgtcggc tggattagac agcctcctgg caagccctg  1800
gaatggctgg ccgacatttg tgtgggacgac aagaaggact acaacccag cctgaagtcc  1860
cggctgacca tcagcaagga caccagcaag aaccaggtgg tgctgaaagt gaccaacatg  1920
gaccctgccg acaccgccac ctactactgt gccagatcca tgatcaccaa ctggtacttc  1980
gacgtgtggg gagccggcac cacaaccgtc tcttcaggta agtctgctgt gtgggagtag  2040
cggggagcca ggtgtactgg gccaggcaag gctttggat cgtaggactg caagatcgtc  2100
gcacagcagc gaatcgtgaa atattttctt tagaattatg aggtgcgctg tgtgtcaacc  2160
tgcatcttaa attctttatt ggctggaag agaactgtcg gagtggggtga atccagccag  2220
gagggacgcg tagccccggt cttgatgaga gcagggttgg gggcagggt agcccagaaa  2280
cggtcgctgc cgtcctgaca ggggcttagg gaggctccag gacctcagtg cctttgaagct  2340
ggtttccatg agaaaaggat tgtttatctt aggaggcatg cttactgtta aaagacagga  2400
tatgtttgaa gtggcttctg agaaaaatgg ttaagaaaat tatgacttaa aaatgtgaga  2460
gattttcaag tatattaatt ttttaactg tccaagtatt tgaaattctt atcatttgat  2520
taacacccat g                                                      2531

SEQ ID NO: 103          moltype = DNA  length = 3134
FEATURE                 Location/Qualifiers
misc_feature            1..3134
                        note = mouse anti-RSV emAb AAV
source                  1..3134
```

-continued

```
                              mol_type = other DNA
                              organism = synthetic construct
SEQUENCE: 103
ccaggggtga ttctagtcag actctggggt ttttgtcggg tatagaggaa aaatccacta    60
ttgtgattac tatgctatgg actactgggg tcaaggaacc tcagtcaccg tctcctcagg   120
taagaatggc ctctccaggt cttttatttt aacctttgtt atggagtttt ctgagcattg   180
cagactaatc ttggatattt gtccctgagg gagccggctg agagaagttg ggaaataaac   240
tgtctaggga tctcagagcc tttaggacag attatctcca catctttgaa aaaactaagaa   300
tctgtgtgat ggtgttggtg gagtccctgg atgatgggat agggactttg gaggctcatt   360
tgagggagat gctaaaacaa tcctatggct ggagggatag ttggggctgt agttggagat   420
tttcagtttt tagaataaaa gtattagttg tggaatatac ttcaggacca cctctgtgac   480
agcatttata cagtatccga tggatgacaa gtgagtgtct caggttagga ttctatttta   540
agattgagat attaggcttt gatactacat ctaaatggtc tgtacatgtc tcgaagaaag   600
ttcttcagac agagttagga cttggatcca ggagttagac cttggactga ctcaggagga   660
ctctagtttc ttcttctcca gctggaatgt ccttatgtaa gaaaagcctt gcctcatgag   720
tatgcaaatc atgtgcgact gtgatgatta atatgggat atccacacca aacatcatat   780
gagccctatc ttctctacag acactgaatc tcaaggtcct tacaatggaa accgacacac   840
tgctgctgtg ggtgctgctt ctttgggtgc ccggaagcac aggcgacatc cagctgacac   900
agagccctgc catcatgtct gctagccctg cgagaaagt gacaatgacc tgttccgcca   960
gcagctccgt gggctacatg cactggtatc agcagaagtc tagcacaagc cccaagctgt  1020
ggatctacga cacctccaag ctggcctctg gcgtgccagg cagattttct ggaagcggca  1080
gcggcaacag ctacagcctg actatcagct ccatccagcc cgaggatgtg gctacctact  1140
actgcttcag aggcagcggc taccccttca catttggcca gggcaccaag ctggaaatca  1200
aggccgatgc cgctcctacc gtgtctatct tccacctag cagcgagcag ctgacatctg  1260
gcggagcctc tgtcgtgtgc ttcctgaaca acttctaccc taaggacatc aacgtcaagt  1320
ggaagatcga cggctccgag agacagaacg gcgtgctgaa ctcttggcac gaccaggaca  1380
gcaaggatag cacctacagc atgagcagca ctctgacct gacaaaggac gagtacgaga  1440
ggcacaactc ctacacatgc gaggccacac aaagaccag cacatcccca atcgtgaagt  1500
ccttcaaccg gaacgagtgc ggaggaagta gtggcagcgg gagtgggtcc aattggagtc  1560
atcctcaatt tgagaaagga gggggagggt ccaattggtc tcatccgacg tttgagaagg  1620
gcggcggcgg ctccaattgg tcccatcccc agtttgaaaa aggctctggt ggaggtggta  1680
gtgctggtgg gcaggtggaa ctgcaagaaa gcggccctgg catcctgcag ccttctcaga  1740
cactgagcct gacctgtagc ttcagcggct tcagcctgag cacaagcggc atgtctgtcg  1800
gctggatcag acagccttct ggcgaaggac tggaatggct ggccgacatt tggtgggacg  1860
acaagaagga ctacaacccc agcctgaagt ccagactgac catcagcaag gacaccagca  1920
gcaaccaggt gttcctgaag atcaccggc tggacacagc cgataccgcc acctattact  1980
gcgccagatc catgatcacc aactggtact tcgacgtgtg gggcgctggc accacagtga  2040
ccgtctcctc aggtgagtcc taacttctcc cattctaaat gcatgttggg gggattctgg  2100
gccttcagga ccaccatgta ccaaaagcca taacgatcgg tgggagtatt cattgtggtc  2160
aagatccata gggacaaaga gtgggagtggg gcactttctt tagatttgtg aggaatgttc  2220
cgcactagat tgtttaaaac ttcatttgtt ggaaggagag ctgtcttagt gattgagtca  2280
agggagaaag gcatctagcc tcggtctcaa aagggtagtg gctgtctaga gaggtctggt  2340
ggagcctgca aaagtccagc tttcaaagga cacagaagt atgtgatggg aattattagaa  2400
gatgttgctt ttactcttaa gttggttcct aggaaaaata gttaaatact gtgactttaa  2460
aatgtgagag ggttttcaag tactcatttt tttaaatgtc caaaatttt gtcaatcagt  2520
ttgaggtctt gtttgtgtag aactgatatt acttaaagtt taaccgagga atgggagtga  2580
ggctctctca taacctattc agaactgact tttaaacata ataaattaag tttaaaatat  2640
ttttaaatga attgagcaat gttgagtgg agtcaagatg gccgatcaga accagaaacac  2700
ctgcagcagc tggcaggaag caggtcatgt ggcaaggcta tttggggaag ggaaaataaa  2760
accactaggt aaacttgtag ctgtggtttg aagaagtggt tttgaaacac tctgtccagc  2820
cccaccaaac cgaaagtcca ggctgagcaa aacaccacct gggtaatttg catttctaaa  2880
ataagttgag gattcagccg aaactggaga ggtcctcttt taacttattg agttcaacct  2940
tttaatttta gcttgagtag ttctagtttc cccaaactta agtttatcga cttctaaaat  3000
gtatttagaa ttcattttca aaattaggtt atgtaagaaa ttgaaggact ttagtgtctt  3060
taatttctaa tatatttaga aaacttctta aaattactct attattcttc cctctgatta  3120
ttggtctcca ttca                                                    3134

SEQ ID NO: 104             moltype = DNA   length = 1736
FEATURE                    Location/Qualifiers
misc_feature              1..1736
                          note = ms-emAb-RSV-dsDNA
source                    1..1736
                          mol_type = other DNA
                          organism = synthetic construct
SEQUENCE: 104
accacctctg tgacagcatt tatacagtat ccgatggatg acaagtgagt gtctcaggtt    60
aggattctat tttaagattg agatattagg ctttgatact acatctaaat ggtctgtaca   120
tgtctcgaag aaagttcttc agacagagtt aggacttgga tccaggagtt aggacttgga   180
ctgactcagg aggactctag tttcttcttc tccagctgga atgtccttat gtaagaaaag   240
ccttgcctca tgagtatgca aatcatgtgc gactgtgatg attaatatag ggatatccac   300
accaaacatc atatgagccc tatcttctct acagacactg aatctcaagg tccttacaat   360
ggaaaccgac acactgctgc tgtgggtgct gcttctttgg gtgcccggaa gcacaggcga   420
catccagctg acacagagcc ctgccatcat gtctgctagc cctggcgaga aagtgacaat   480
gacctgttcc gccagcagct ccgtgggcta catgcactgg tatcagcagt agtcagctagc   540
aagcccaag ctgtggatct acgacacctc caagctggcc tctggcgtgc caggcagatt   600
ttctggaagc ggcagcggca acagctacag cctgactatc agctccatcc aggccgagga   660
tgtggctacc tactactgct tcagaggcag cggctacccc ttcacatttg ccagggcac   720
caagctggaa atcaaggccg atgccgctcc taccgtgtct atctttccac ctagcagcga   780
gcagctgaca tctggcggag cctctgtcgt gtgcttcctg aacaacttct accctaagga   840
```

```
catcaacgtc aagtggaaga tcgacggctc cgagagacag aacgcgtgc tgaactcttg   900
gaccgaccag gacagcaagg atagcaccta cagcatgagc agcactctga ccctgacaaa   960
ggacgagtac gagaggcaca actcctacac atgcgaggcc acacacaaga ccagcacatc  1020
cccaatcgtg aagtccttca accggaacga gtgcggagga agtagtggca gcgggagtgg  1080
gtccaattgg agtcatcctc aatttgagaa aggagggga gggtccaatt ggtctcatcc  1140
gcagtttgag aagggcggcg gcggctccaa ttggtcccat ccccagtttg aaaaaggctc  1200
tggtggaggt ggtagtgctg gtgggcaggt ggaactgcaa gaaagcggcc ctggcatcct  1260
gcagccttct cagacactga gcctgacctg tagcttcagc ggcttcagcc tgagcacaag  1320
cggcatgtct gtcggctgga tcagacagcc ttctggcgaa ggactggaat ggctggccga  1380
catttggtgg gacgacaaga aggactacaa ccccagcctg aagtccagac tgaccatcag  1440
caaggacacc agcagcaacc aggtgttcct gaagatcacc ggcgtggaca cagccgatac  1500
cgccacctat tactgcgcca gatccatgat caccaactgg tacttcgacg tgtgggcgc   1560
tggcaccaca gtgaccgtct cctcaggtga gtcctaactt ctcccattct aaatgcatgt  1620
tggggggatt ctgggccttc aggaccacca tgtaccaaaa gccataacga tcggtgggag  1680
tattcattgt ggtcaagatc catagggaca aagagtggag tggggcactt tcttta        1736
```

```
SEQ ID NO: 105            moltype = DNA  length = 2551
FEATURE                   Location/Qualifiers
misc_feature              1..2551
                          note = hu-emAb-VRC01-AAV
source                    1..2551
                          mol_type = other DNA
                          organism = synthetic construct
SEQUENCE: 105
tgtgacgccc ggagacagaa ggtctctggg tggctgggtt tttgtggggt gaggatggac   60
attctgccat tgtgattact actactacta ctacatggac gtctggggca aagggaccac  120
ggtcaccgtc tcctcaggta agaatggcca ctctagggcc tttgtttct gctactgcct  180
gtggggtttc ctgagcattg caggttggtc ctcggggcat gttccgaggg gacctgggcg  240
gactggccag gaggggatgg gcactggggt gccttgagga tctgggagcc tctgtggatt  300
ttccgatgcc tttggaaaat gggactcagg ttgggtgcgt ctgatggagt aactgagcct  360
gggggcttgg ggagccacat ttggacgaga tgcctgaaca aaccaggggt cttagtgatg  420
gctgaggaat gtgtctcagg agcggtgtct gatcgtaatc tttaggccaa taaaatgtgg  480
gttcacagtg aggagtgcat cctggggttg gggtttgttc tgcagcggga agagcgctgt  540
gcacagaaag cttagaaatg gggcaagaga tgcttttcct caggcaggat ttagggcttg  600
gtctctcagc atcccacact tgtacagctg atgtggcatc tgtgttttct ttctcatcct  660
agatcaggct ttgagctgtg aaataccctg cctcatgcat atgcaaataa cctgaggtct  720
tctgagataa atatagatat attggtgccc tgagagcatc acgccgccac catggctacc  780
ggcagcagaa caagcctgct gctcgctttt ggactgctct gtctccctg gttgcaagaa  840
ggcagcgcg aaattgtgtt gacacagtct ccaggcaccc tgtctttgtc tccaggggaa  900
acagccatca tctcttgtcg gaccagtcag tatggttcct tagcctggta tcaacagagg  960
cccggccagg ccccaggct cgtcatctat tcgggtctcta ctcgggccgc tggcatccca  1020
gacaggttca gcggcagtcg gtggggggcca gactacaatc tcaccatcag caacctggag 1080
tcgggatt ttggtgttta ttattgccag cagtatgaat tttttggcca ggggaccaag 1140
gtccaggtcg acattaagcg cactgtggcc gctcctagcg tgttcatctt tccacctagc 1200
gacgagcagc tgaagtctgg cactgcctct gtcgtgtgcc tgctgaacaa cttctaccct 1260
cgagaggcca aggtgcagtg gaaagtggac aatgccctgc agagcggcaa cagccaagag 1320
tctgtgaccg agcaggactc caaggattcc acctacagcc tgtctagcac cctgactctg 1380
agcaaggccg actacgagaa gcacaaggtg tacgcctgcg aagtgacaca ccagggactg 1440
agcagccctg tgaccaagag cttcaatcgg ggcgagtgcg gaggctcaag tggctccggg 1500
agtgggagca attggtcaca cccccagttt gaaaaaggcg gtggggggag taactggtct 1560
catccgcagt tcgaaaaggg tggaggaggg agcaactgga gtcatccaca atttgagaaa 1620
ggctcaggtg gtggtggtag cgctgggggg caggtgcagc tggtgcagtc tgggggtcag 1680
atgaagaagc tggcgagtc gatgagaatt tcttgtcggg cttctggata tgaatttatt 1740
gattgtacgc taaattggat tcgtctggcc cccggaaaaa ggcctgagtg gatgggatgg 1800
ctgaagcctc gaggtggcgc ggtcaactac gcacgtccac ttcagggcag agtgaccatg 1860
actcgagacg tttattccga cacagccttt ttggagctgc gctcgttgac agtagacgac 1920
acggccgtct acttttgtac taggggaaaa aactgtgatt acaattggga cttcgaacac 1980
tggggccggg gcaccccggt catcgtctca tcaggtgagt tggctttcct tctgcctcct 2040
ttctctgggc ccagcgtcct ctgacctgga gctgggagat aatgtccggg ggctccttat 2100
cgtaggactg caagatcgct gcacagcagc gaatcgtgaa atatttttt tagaattatg 2160
aggtgcgctg tgtgtcaacc tgcatcttaa attctttatt ggctggaaag agaactgtcg 2220
gagtgggtga atccagccag gagggacgcg tagccccggt cttgatgaga gcaggggttgg 2280
gggcagggggt agcccagaaa cggtggctgc cgtcctgaca ggggggcttagg gaggctccag 2340
gacctcagtg ccttgaagct ggtttccatg agaaaaggat tgtttatctt aggaggcatg 2400
cttactgtta aaagacagga tatgtttgaa gtggcttctg agaaaaatgg ttaagaaaat 2460
tatgacttaa aaatgtgaga gattttcaag tatattaatt tttttaactg tccaagtatt 2520
tgaaattctt atcatttgat taacacccat g                                 2551
```

```
SEQ ID NO: 106            moltype = DNA  length = 2544
FEATURE                   Location/Qualifiers
misc_feature              1..2544
                          note = hu-emAb-Medi8852-AAV
source                    1..2544
                          mol_type = other DNA
                          organism = synthetic construct
SEQUENCE: 106
tgtgacgccc ggagacagaa ggtctctggg tggctgggtt tttgtggggt gaggatggac   60
attctgccat tgtgattact actactacta ctacatggac gtctggggca aagggaccac  120
ggtcaccgtc tcctcaggta agaatggcca ctctagggcc tttgtttct gctactgcct  180
```

```
gtggggtttc ctgagggcat gttccgaggg gacctgggcg gactggccag gaggggatgg   240
gcactggggt gccttgagga tctgggagcc tctgtggatt ttccgatgcc tttggaaaat   300
gggactcagg ttgggtgcgt ctgatggagt aactgagcct gggggcttgg ggagccacat   360
ttggacgaga tgcctgaaca aaccagggg cttagtgatg gctgaggaat gtgtctcagg    420
agcggtgtct gatcgtaatc tttaggccaa taaaatgtgg gttcacagtg aggagtgcat   480
cctggggttg gggtttgttc tgcagcggga agagcgctgt gcacagaaag cttagaaatg   540
gggcaagaga tgcttttcct caggcaggat ttagggcttg gtctctcagc atcccacact   600
tgtacagctg atgtggcatc tgtgtttct ttctcatcct agatcaggct ttgagctgtg    660
aaataccctg cctcatgcat atgcaaataa cctgaggtct tctgagataa atatagatat   720
attggtgccc tgaggccgcc accatggcta ccggcagcag aacaagcctg ctgctcgctt   780
ttggactgct ctgtctcccc tggttgcaag aaggcagcgc cgatattcag atgacccaga   840
gcccttccag cctgtccgct tcagtggggg atcgagtgac cattacctgc cgaaccagcc   900
agagcctgag ctcctacacg cactggtatc agcagaagcc cggcaaagcc cctaagctgc   960
tgatctacgc cgcttctagt cgggggtccg gagtgccaag ccggttctcc ggatctggga  1020
gtggaaccga ctttaccctg acaatttcaa gcctgcagcc cgaggatttc gctacatact  1080
actgtcagca gagcagaact ttcgggcagg gcactaaggt ggagatcaaa cggactgtgg  1140
ccgctcctag cgtgttcatc tttccaccta gcgacgagca gctgaagtct ggcactgcct  1200
ctgtcgtgtg cctgctgaac aacttctacc ctcgagagc caaggtgcag tggaaagtgg  1260
acaatgccct gcagagcggc aacagccaag agtctgtgac cgagcaggac tccaaggatt  1320
ccacctacag cctgtctagc accctgactc tgagcaaggc cgactacgag aagcacaagg  1380
tgtacgcctg cgaagtgaca caccagggac tgagcagccc tgtgaccaag agcttcaatc  1440
ggggcgagtg cggaggaagt agtggcagcg ggagtgggtc caattggagt catcctcaat  1500
ttgagaaagg aggggagggg tccaattggt ctcatccgca gtttgagaag ggcggcggcg  1560
gctccaattg gtcccatccc cagtttgaaa aaggctctgg tggaggtggt agtgctggtg  1620
ggcaggtcca gctgcagcag agcggccccg gactggtcaa gccttcacag acactgagcc  1680
tgacatgcgc cattagcgga gatagcgtga gctcctacaa tgccgtgtgg aactggatca  1740
ggcagtctcc aagtcgagga ctggagtggc tgggacgaac atactataga tccgggtggt  1800
acaatgacta tgctgaatca gtgaaaagcc gaattactat caacccgat acctccaaga  1860
atcagttctc tctgcagctg aacagtgtga ccccctgagga cacagccgtg tactactgcg  1920
ccagaagcgg ccatatcacc gtctttggcg tcaatgtgat tgctttcgat atgtggggc  1980
aggggactat ggtcaccgtc tcttcaggtg agttggcttt ccttctgcct cctttctctg  2040
ggcccagcgt cctctgacct ggagctggga gataatgtcc gggggctcct tatcgtagga  2100
ctgcaagatc gctgcacagc agcgaatcgt gaaatatttt ctttagaatt atgaggtgcg  2160
ctgtgtgtca acctgcatct taaattcttt attggctgga aagagaactg tcggagtggg  2220
tgaatccagc caggagggac gcgtagcccc ggtcttgatg agagcagggt tgggggcagg  2280
ggtagcccag aaacggtggc tgccgtcctg acaggggctt agggaggctc caggacctca  2340
gtgccttgaa gctggtttcc atgagaaaag gattgtttat cttaggaggc atgcttactg  2400
ttaaaagaca ggatatgttt gaagtggctt ctgagaaaaa tggttaagaa aattatgact  2460
taaaaatgtg agagattttc aagtatatta atttttttaa ctgtccaagt atttgaaatt  2520
cttatcattt gattaacacc catg                                         2544
```

```
SEQ ID NO: 107          moltype = DNA  length = 2555
FEATURE                 Location/Qualifiers
misc_feature            1..2555
                        note = hu-emAb-AMM01-AAV
source                  1..2555
                        mol_type = other DNA
                        organism = synthetic construct
SEQUENCE: 107
tgtgacgccc ggagacagaa ggtctctggg tggctgggtt tttgtgggt gaggatggac    60
attctgccat tgtgattact actactacta ctacatggac gtctggggca aagggaccac   120
ggtcaccgtc tcctcaggta agaatggcca ctctagggcc tttgtttct gctactgcct    180
gtggggtttc ctgagggcat gttccgaggg gacctgggcg gactggccag gaggggatgg   240
gcactggggt gccttgagga tctgggagcc tctgtggatt ttccgatgcc tttggaaaat   300
gggactcagg ttgggtgcgt ctgatggagt aactgagcct gggggcttgg ggagccacat   360
ttggacgaga tgcctgaaca aaccagggg cttagtgatg gctgaggaat gtgtctcagg    420
agcggtgtct gatcgtaatc tttaggccaa taaaatgtgg gttcacagtg aggagtgcat   480
cctggggttg gggtttgttc tgcagcggga agagcgctgt gcacagaaag cttagaaatg   540
gggcaagaga tgcttttcct caggcaggat ttagggcttg gtctctcagc atcccacact   600
tgtacagctg atgtggcatc tgtgtttct ttctcatcct agatcaggct ttgagctgtg    660
aaataccctg cctcatgcat atgcaaataa cctgaggtct tctgagataa atatagatat   720
attggtgccc tgagagcatc acgccgccac catggctacc ggcagcagaa caagcctgct   780
gctcgctttt ggactgctct gtctccctg gttgcaagaa ggcagcgcct cctatgagct    840
gactcagcca ccctcagtgt cagtggcccc ggggcagagc gccacaatta cctgtgggag   900
acacaacatc ggagctaaaa atgtccactg gtaccagcag aagccaggcc aggcccctgt   960
cctggtcatc aatatgata gcgaccggcc tcaggggatc cctgagcgat tctctggctc   1020
caactctggg agcacggcca ccctgaccat cagcagggtc gaagccgggg atgaggccga  1080
ctattactgt caggtgtggg atagtggtcg tgggcatccc ctttatgtct tcggaggtgg  1140
gaccaaggtc accgtcctag gtcagcccaa ggccaacccc actgtcactc tgttcccacc  1200
ctcgagtgag gagcttcaag ccaacaaggc cacactggtg tgtctcataa gtgacttcta  1260
cccgggagcc gtgacagtgg cctggaaggc agatagcagc ccgtcaagg cgggagtgga   1320
gaccaccaca ccctccaaac aaagcaacaa caagtacgcg gccagcagct acctgagcct  1380
gacgcctgag cagtggaagt cccacagaag ctacagctgc caggtcacgc atgaagggag  1440
caccgtggag aagacagtgg ccctacaga atgttcagga ggaagtagtg gcagcgggag  1500
tgggtccaat tggagtcatc ctcaatttga gaaggaggg ggagggtcca attggtctca   1560
tccgcagttt gagaagggcg gcggcggctc caattggtcc catccccagt ttgaaaaagg  1620
ctctggtgga ggtggtagtg ctggtgggca ggttcagctg gtgcagtctg agctgatgt    1680
gaagaagcct ggggcctcag tgaaggtctc ctgcaaggct tctggttaca cctttattca  1740
ttttggtatc agttgggtgc ggcaggcccc tggacaaggg cttgagtgga tgggatggat  1800
```

```
cgacactaat aatggtaaca caaactatgc acagagtctc cagggcagag tcaccatgac  1860
cacagataca tccacgggca cagcctacat ggagctgagg agcctctcga ctgacgacac  1920
ggccgtgtat ttctgtgcgc gagctctgga aatggggcat agaagtggct tcccatttga  1980
ctactggggc cagggagtcc tggtcaccgt ctccccaggt gagttggctt tccttctgcc  2040
tcctttctct gggcccagcg tcctctgacc tggagctggg agataatgtc cggggggctcc  2100
ttatcgtagg actgcaagat cgctgcacag cagcgaatcg tgaaatattt tctttagaat  2160
tatgaggtgc gctgtgtgtc aacctgcatc ttaaattctt tattggctgg aaagagaact  2220
gtcggagtgg gtgaatccag ccaggaggga cgcgtagccc cggtcttgat gagagcaggg  2280
ttgggggcag gggtagccca gaaacggtgg ctgccgtcct gacagggct tagggaggct  2340
ccaggacctc agtgccttga agctggtttc catgagaaaa ggattgttta tcttaggagg  2400
catgcttact gttaaaagac aggatatgtt tgaagtggct tctgagaaaa atggttaaga  2460
aaattatgac ttaaaaatgt gagagatttt caagtatatt aattttttta actgtccaag  2520
tatttgaaat tcttatcatt tgattaacac ccatg                            2555
```

SEQ ID NO: 108          moltype = DNA   length = 2261
FEATURE                 Location/Qualifiers
misc_feature            1..2261
                        note = Balb/C mRSV-splice integration
source                  1..2261
                        mol_type = other DNA
                        organism = synthetic construct
SEQUENCE: 108

```
ctactggggt caaggaacct cagtcaccgt ctcctcaggt aagaatggcc tctccaggtc  60
tttattttta acctttgtta tggagttttc tgagcattgc agactaatct tggatatttg  120
tccctgaggg agccggctga gagaagttgg gaaataaact gtctagggat ctcagagcct  180
ttaggacaga ttatctccac atctttgaaa aactaagaat ctgtgtgatg gtgttggtgg  240
agtccctgga tgatgggata gggactttgg aggctcattt gaagaagatg ctaaaacaat  300
cctatggctg gagggatagt tggggctgta gttggagatt ttcagttttt agaataaaag  360
tattagttgt ggaatatact tcaggaccac ctctgtgaca gcatttatac agtatccgat  420
ggacaagtga gtgtctcagg ttaggattct attttaagat tgagatatta ggctttgata  480
ctacatctaa atggtctgta catgtctcga agaaagttct tcagacagag ttaggacttg  540
gatccaggag ttaggacttg gactgactca ggaggactct agtttcttct tctccagctg  600
gaatgtcctt atgtaagaaa agccttgcct catgagtatg caaatcatgt gcgactgtga  660
tgattaatat agggatatcc acaccaaaca tcatatgagc tcatcttct ctacagacac  720
tgaatctcaa ggtccttaca atggaaaccg acacactgct gctgtgggtg ctgcttcttt  780
gggtgcccgg aagcacaggc gacatccagc tgacacagag ccctgccatc atgtctgcta  840
gccctggcga gaaagtgaca atgacctgtt ccgccagcag ctccgtgggc tacatgcact  900
ggtatcagca gaagtctagc acaagcccca agctgtggat ctacgacacc tccaagctgg  960
cctctggcgt gccaggcaga ttttctggaa gcggcagcgg caacagctac agcctgacta  1020
tcagctccat ccaggccgag gatgtggcta cctactactg cttcagaggc agcggctacc  1080
ccttcacatt tggccagggc accaagctgg aaatcaaggc cgatgccgct cctaccgtgt  1140
ctatctttcc acctagcagc gagcagctga catctggcgg agcctctgtc gtgtgcttcc  1200
tgaacaactt ctaccctaag gacatcaacg tcaagtgaaa gatcgacggc tccgagagac  1260
agaacggcgt gctgaactct tggaccgacc aggacagcaa ggatagcacc tacagcatga  1320
gcagcactct gaccctgaca aaggacgagt acgagaggca caactcctac acatgcgagg  1380
ccacacacaa gaccagcaca tccccaatcg tgaagtcctt caaccggaac gagtgcgag  1440
gaagtagtgg cagcggggagt gggtccaatt ggagtcatcc tcaatttgag aaaggaggg  1500
gagggtccaa ttggtctcat ccgcagtttg agaaggcgg cggcggctcc aattggtccc  1560
atccccagtt tgaaaaaggc tctggtggag gtggtagtgc tggtgggcag gtggaactgc  1620
aagaaagcgg ccctggcatc ctgcagcctt ctcagacact gagcctgacc tgtagcttca  1680
gcggcttcag cctgagcaca agcggcatgt ctgtcggctg gatcagacag ccttctggcg  1740
aaggactgga atggctggcc gacatttggt gggacgacaa gaaggactac aaccccagcc  1800
tgaagtccag actgaccatc agcaaggaca ccagcagcaa ccaggtgttc ctgaagatca  1860
ccggcgtgga cacagccgat accgccacct attactgcgc cagatccatg atcaccaact  1920
ggtacttcga cgtgtggggc gctggcacca cagtgaccgt ctcctcaggt gagtcctaac  1980
ttctcccatt ctaaatgcat gttgggggga ttctgggcct tcaggaccac atagggacaa  2040
agagtggagt ggggcacttt ctttagattt gtgaggaatg ttccgcacta gattgtttaa  2100
aacttcattt gttggaagga gagctgtctt agtgattgag tcaagggaga aaggcatcta  2160
gcctcggtc caaaagggta gttgctgtct agagaggtc ggtggagcct gcaaaagtcc  2220
agctttcaaa ggaacacaga agtatgtgta tggaatatta g                     2261
```

SEQ ID NO: 109          moltype = DNA   length = 1707
FEATURE                 Location/Qualifiers
misc_feature            1..1707
                        note = TT-hRSV-T7-integrated
source                  1..1707
                        mol_type = other DNA
                        organism = synthetic construct
SEQUENCE: 109

```
gtcttagtga tggctgagga atgtgtctca ggagcggtgt ccgtaatctt taggccaata  60
aaatgtgggt tcacagtgag gagtgcatcc tggggttggg gtttgttctg cagcgggaag  120
agcgctgtgc acagaaagct tagaaatggg gcaagagatg ctttccctca ggcaggattt  180
agggcttggt ctctcagcat cccacacttg tacagctgat gtggcatctg tgttttcttt  240
ctcatcctag atcaggcttt gagctgtgaa ataccctgcc tcatgcatat gcaaataacc  300
tgaggtcttc tgagataaat atagatatat tggtgccctg aggtttaaac gccgccacca  360
tggctaccgg cagcagaaca agcctgctgc tcgctttttgg actgctctgt ctccctggt  420
tgcaagaagg cagcgccgac atccagatga cacagagccc tagcacactg tctgccagcg  480
tgggcgacag agtgaccatc acatgcaagt gccagcgag cgtgggctac atgcactggt  540
atcagcaaaa gcccggcaag gccccctaagc tgctgatcta cgataccctcc aagctggcct  600
```

-continued

```
ctggcgtgcc ctccagattt tctggcagcg gcagcggaac cgagttcacc ctgaccatct   660
caagcctgca gcctgacgac ttcgctacgt actactgctt ccaaggcagc ggctacccct   720
tcacatttgg cggcggaaca aagctggaaa tcaagcggac tgtggccgct cctagcgtgt   780
tcatctttcc acctagcgac gagcagctga agtctggcac tgcctctgtc gtgtgcctgc   840
tgaacaactt ctaccctcga gaggccaagg tgcagtgaca agtggacaat gccctgcaga   900
gcggcaacag ccaagagtct gtgaccgagc aggactccaa ggattccacc tacagcctgt   960
ctagcaccct gactctgagc aaggccgact acgagaagca caaggtgtac gcctgcgaag  1020
tgacacacca gggactgagc agccctgtga ccaagagctt caatcggggc gagtgcgag   1080
gaagtagtgg cagcgggagt gggtccaatt ggagtcatcc tcaatttgag aaaggagggg  1140
gagggtccaa ttggtctcat ccgcagtttg agaagggcgg cggcggctcc aattggtccc  1200
atccccagtt tgaaaaaggc tctggtggag gtggtagtgc tggtgggcaa gtgaccctga  1260
gagagtctgg acctgctctg gtcaagccca cacagaccct gacactgacc tgcaccttca  1320
gcggctttag cctgagcaca agcggcatga gcgtcggctg gattagacag cctcctggca  1380
aagccctgga atggctggcc gacatttggt gggacgaaca gaaggactac aaccccagcc  1440
tgaagtcccg gctgaccatc agcaaggaca ccagcaagaa ccaggtggtg ctgaaagtga  1500
ccaacatgga ccctgccgac accgccacct actactgtgc cagatccatg atcaccaact  1560
ggtacttcga cgtgtgggga gccggcacca caaccgtctc ttcaggtaag tctgctgtct  1620
ggggatagcg gggagccagg tgtactgggc caggcaaggg ctttggtgta ggactgcaag  1680
atcgctgcac agcagcgaat cgtgaaa                                     1707

SEQ ID NO: 110          moltype = DNA   length = 450
FEATURE                 Location/Qualifiers
source                  1..450
                        mol_type = genomic DNA
                        organism = Homo sapiens
SEQUENCE: 110
tgtgacgccc ggagacagaa ggtctctggg tggctgggtt tttgtggggt gaggatggac   60
attctgccat tgtgattact actactacta ctacatggac gtctgggca aagggaccac   120
ggtcaccgtc tcctcaggta agaatggcca ctctagggcc tttgttttct gctactgcct   180
gtggggtttc ctgagcattg caggttggtc ctcggggcat gttccgaggg gacctgggcg   240
gactggccag gaggggatgg gcactggggt gccttgagga tctggggagcc tctgtggatt   300
ttccgatgcc tttggaaaat gggactcagg ttgggtgcgt ctgatggagt aactgagcct   360
gggggcttgg ggagccacat ttggacgaga tgcctgaaca aaccaggggt cttagtgatg   420
gctgaggaat gtgtctcagg agcggtgtct                                    450

SEQ ID NO: 111          moltype = DNA   length = 300
FEATURE                 Location/Qualifiers
source                  1..300
                        mol_type = other DNA
                        organism = Homo sapiens
SEQUENCE: 111
gtaatcttta ggccaataaa atgtgggttc acagtgagga gtgcatcctg gggttggggt   60
ttgttctgca gcgggaagag cgctgtgcac agaaagctta gaaatggggc agagagatgct  120
tttcctcagg caggatttag ggcttggtct ctcagcatcc cacacttgta cagctgatgt  180
ggcatctgtg ttttctttct catcctagat caggctttga gctgtgaaat accctgcctc  240
atgcatatgc aaataacctg aggtcttctg agataaatat agatatattg gtgccctgag  300

SEQ ID NO: 112          moltype = DNA   length = 78
FEATURE                 Location/Qualifiers
misc_feature            1..78
                        note = Signal peptide coding sequence
source                  1..78
                        mol_type = other DNA
                        organism = synthetic construct
SEQUENCE: 112
atggctaccg gcagcagaac aagcctgctg ctcgcttttg gactgctctg tctcccctgg   60
ttgcaagaag gcagcgcc                                                 78

SEQ ID NO: 113          moltype = DNA   length = 717
FEATURE                 Location/Qualifiers
misc_feature            1..717
                        note = hRSV light chain coding sequence
source                  1..717
                        mol_type = other DNA
                        organism = synthetic construct
SEQUENCE: 113
atggctaccg gcagcagaac aagcctgctg ctcgcttttg gactgctctg tctcccctgg   60
ttgcaagaag gcagcgccga catccagatg acacagagcc ctagcacact gtctgccagc  120
gtgggcgaca gagtgaccat cacatgcaag tgccagctga gcgtgggcta catgcactgg  180
tatcagcaaa agcccggcaa ggcccctaag ctgctgatct acgatacctc caagctggcc  240
tctggcgtgc cctccagatt ttctggcagc ggcagcggaa ccgagttcac cctgaccatc  300
tcaagcctgc agcctgacga cttcgctacg tactactgct ccaaggcagc ggctacccc   360
ttcacatttg gcggcggaac aaagctggaa atcaagcgga ctgtggccgc tcctagcgtg  420
ttcatctttc cacctagcga cgagcagctg aagtctggca ctgcctctgt cgtgtgcctg  480
ctgaacaact ctaccctcg agaggccaag gtgcagtgga agtggacaa tgccctgcag   540
agcggcaaca gccaagagtc tgtgaccgag caggactcca aggattccac ctacagcctg  600
tctagcaccc tgactctgag caaggccgac tacgagaagc acaaggtgta cgcctgcgaa  660
gtgacacacc agggactgag cagccctgtg accaagagct tcaatcgggg cgagtgc     717
```

```
SEQ ID NO: 114              moltype = DNA   length = 321
FEATURE                     Location/Qualifiers
misc_feature                1..321
                            note = hRSV variable light chain coding sequence
source                      1..321
                            mol_type = other DNA
                            organism = synthetic construct
SEQUENCE: 114
gacatccaga tgacacagag ccctagcaca ctgtctgcca gcgtgggcga cagagtgacc   60
atcacatgca agtgccagct gagcgtgggc tacatgcact ggtatcagca aaagcccggc   120
aaggccccta agctgctgat ctacgatacc tccaagctgg cctctggcgt gccctccaga   180
ttttctggca gcggcagcgg aaccgagttc accctgacca tctcaagcct gcagcctgac   240
gacttcgcta cgtactactg cttccaaggc agcggctacc ccttcacatt tggcggcgga   300
acaaagctgg aaatcaagcg g                                             321

SEQ ID NO: 115              moltype = DNA   length = 318
FEATURE                     Location/Qualifiers
misc_feature                1..318
                            note = kappa constant light chain coding sequence
source                      1..318
                            mol_type = other DNA
                            organism = synthetic construct
SEQUENCE: 115
actgtggccg ctcctagcgt gttcatcttt ccacctagcg acgagcagct gaagtctggc   60
actgcctctg tcgtgtgcct gctgaacaac ttctaccctc gagaggccaa ggtgcagtgg   120
aaagtggaca atgccctgca gagcggcaac agccaaagt ctgtgaccga gcaggactcc   180
aaggattcca cctacagcct gtctagcacc ctgactctga gcaaggccga ctacgagaag   240
cacaaggtgt acgcctgcga agtgacacac cagggactga gcagccctgt gaccaagagc   300
ttcaatcggg gcgagtgc                                                 318

SEQ ID NO: 116              moltype = DNA   length = 171
FEATURE                     Location/Qualifiers
misc_feature                1..171
                            note = GSSG-streptag linker coding sequence
source                      1..171
                            mol_type = other DNA
                            organism = synthetic construct
SEQUENCE: 116
ggaggaagta gtggcagcgg gagtgggtcc aattggagtc atcctcaatt tgagaaagga   60
gggggagggt ccaattggtc tcatccgcag tttgagaagg cggcggcgg ctccaattgg   120
tcccatcccc agtttgaaaa aggctctggt ggaggtggta gtgctggtgg g           171

SEQ ID NO: 117              moltype = DNA   length = 357
FEATURE                     Location/Qualifiers
misc_feature                1..357
                            note = hRSV variable heavy chain coding sequence
source                      1..357
                            mol_type = other DNA
                            organism = synthetic construct
SEQUENCE: 117
caagtgaccc tgagagagtc tggacctgct ctggtcaagc ccacacagac cctgacactg   60
acctgcacct tcagcggctt tagcctgagc acaagcggca tgagcgtcgg ctggattaga   120
cagcctcctg gcaaagccct ggaatggctg gccgacattt ggtgggacga caagaaggac   180
tacaacccca gcctgaagtc ccggctgacc atcagcaagg acaccagcaa gaaccaggtg   240
gtgctgaaag tgaccaacat ggaccctgcc gacaccgcca cctactactg tgccagatcc   300
atgatcacca ctggtacttc cgacgtgtgg ggagccggca ccaacaccgt ctcttca      357

SEQ ID NO: 118              moltype = AA   length = 26
FEATURE                     Location/Qualifiers
REGION                      1..26
                            note = signal peptide amino acid sequence
source                      1..26
                            mol_type = protein
                            organism = synthetic construct
SEQUENCE: 118
MATGSRTSLL LAFGLLCLPW LQEGSA                                        26

SEQ ID NO: 119              moltype = AA   length = 239
FEATURE                     Location/Qualifiers
REGION                      1..239
                            note = hRSV light chain amino acid sequence
source                      1..239
                            mol_type = protein
                            organism = synthetic construct
SEQUENCE: 119
MATGSRTSLL LAFGLLCLPW LQEGSADIQM TQSPSTLSAS VGDRVTITCK CQLSVGYMHW   60
YQQKPGKAPK LLIYDTSKLA SGVPSRFSGS GSGTEFTLTI SSLQPDDFAT YYCFQGSGYP   120
FTFGGGTKLE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGEC    239
```

```
SEQ ID NO: 120              moltype = AA   length = 107
FEATURE                     Location/Qualifiers
REGION                      1..107
                            note = hRSV variable light chain amino acid sequence
source                      1..107
                            mol_type = protein
                            organism = synthetic construct
SEQUENCE: 120
DIQMTQSPST LSASVGDRVT ITCKCQLSVG YMHWYQQKPG KAPKLLIYDT SKLASGVPSR  60
FSGSGSGTEF TLTISSLQPD DFATYYCFQG SGYPFTFGGG TKLEIKR              107

SEQ ID NO: 121              moltype = AA   length = 106
FEATURE                     Location/Qualifiers
REGION                      1..106
                            note = kappa constant light chain amino acid sequence
source                      1..106
                            mol_type = protein
                            organism = synthetic construct
SEQUENCE: 121
TVAAPSVFIF PPSDEQLKSG TASVVCLLNN FYPREAKVQW KVDNALQSGN SQESVTEQDS  60
KDSTYSLSST LTLSKADYEK HKVYACEVTH QGLSSPVTKS FNRGEC              106

SEQ ID NO: 122              moltype = AA   length = 57
FEATURE                     Location/Qualifiers
REGION                      1..57
                            note = GSSG-streptag linker amino acid sequence
source                      1..57
                            mol_type = protein
                            organism = synthetic construct
SEQUENCE: 122
GGSSGSGSGS NWSHPQFEKG GGGSNWSHPQ FEKGGGGSNW SHPQFEKGSG GGGSAGG    57

SEQ ID NO: 123              moltype = AA   length = 119
FEATURE                     Location/Qualifiers
REGION                      1..119
                            note = hRSV variable heavy chain amino acid sequence
source                      1..119
                            mol_type = protein
                            organism = synthetic construct
SEQUENCE: 123
QVTLRESGPA LVKPTQTLTL TCTFSGFSLS TSGMSVGWIR QPPGKALEWL ADIWWDDKKD  60
YNPSLKSRLT ISKDTSKNQV VLKVTNMDPA DTATYYCARS MITNWYFDVW GAGTTTVSS  119

SEQ ID NO: 124              moltype = DNA   length = 67
FEATURE                     Location/Qualifiers
misc_feature                1..67
                            note = splice junction with flanking sequence in constructs
                             of disclosure
source                      1..67
                            mol_type = other DNA
                            organism = synthetic construct
SEQUENCE: 124
caggtaagtc tgctgtctgg ggatagcggg gagccaggtg tactgggcca ggcaagggct  60
ttggatc                                                           67

SEQ ID NO: 125              moltype = DNA   length = 450
FEATURE                     Location/Qualifiers
source                      1..450
                            mol_type = genomic DNA
                            organism = Homo sapiens
SEQUENCE: 125
gtaggactgc aagatcgctg cacagcagcg aatcgtgaaa tattttcttt agaattatga  60
ggtgcgctgt gtgtcaacct gcatcttaaa ttctttattg gctggaaaga gaactgtcgg  120
agtgggtgaa tccagccagg agggacgcgt agccccggtc ttgatgagag cagggttggg  180
ggcaggggta gcccagaaac ggtggctgcc gtcctgacag gggcttaggg aggctccagg  240
acctcagtgc cttgaagctg gtttccatga gaaaaggatt gtttatctta ggaggcatgc  300
ttactgttaa aagacaggat atgtttgaag tggcttctga gaaaaatggt taagaaaatt  360
atgacttaaa aatgtgagag attttcaagt atattaattt ttttaactgt ccaagtattt  420
gaaattctta tcatttgatt aacacccatg                                  450

SEQ ID NO: 126              moltype = AA   length = 415
FEATURE                     Location/Qualifiers
REGION                      1..415
                            note = signal peptide-light chain-streptag linker-variable
                             heavy chain amino acid sequence in human anti-RSV emAb AAV
source                      1..415
                            mol_type = protein
                            organism = synthetic construct
```

```
SEQUENCE: 126
MATGSRTSLL LAFGLLCLPW LQEGSADIQM TQSPSTLSAS VGDRVTITCK CQLSVGYMHW    60
YQQKPGKAPK LLIYDTSKLA SGVPSRFSGS GSGTEFTLTI SSLQPDDFAT YYCFQGSGYP   120
FTFGGGTKLE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGECG   240
GSSGSGSGSN WSHPQFEKGG GGSNWSHPQF EKGGGGSNWS HPQFEKGSGG GGSAGGQVTL   300
RESGPALVKP TQTLTLTCTF SGFSLSTSGM SVGWIRQPPG KALEWLADIW WDDKKDYNPS   360
LKSRLTISKD TSKNQVVLKV TNMDPADTAT YYCARSMITN WYFDVWGAGT TTVSS        415

SEQ ID NO: 127          moltype = DNA  length = 502
FEATURE                 Location/Qualifiers
source                  1..502
                        mol_type = genomic DNA
                        organism = Mus musculus
SEQUENCE: 127
ccaggggtga ttctagtcag actctggggt ttttgtcggg tatagaggaa aaatccacta    60
ttgtgattac tatgctatgg actactgggg tcaaggaacc tcagtcaccg tctcctcagg   120
taagaatggc ctctccaggt ctttattttt aacctttgtt atggagtttt ctgagcattg   180
cagactaatc ttggatattt gtccctgagg gagccggctg agagaagttg ggaaataaac   240
tgtctaggga tctcagagcc tttaggacag attatctcca catctttgaa aaactaagaa   300
tctgtgtgat ggtgttggtg gagtccctgg atgatgggat agggactttg gaggctcatt   360
tgaggggagat gctaaaacaa tcctatggct ggagggatag ttggggctgt agttggagat   420
tttcagtttt tagaataaaa gtattagttg tggaatatac ttcaggacca cctctgtgac   480
agcatttata cagtatccga tg                                           502

SEQ ID NO: 128          moltype = DNA  length = 319
FEATURE                 Location/Qualifiers
source                  1..319
                        mol_type = other DNA
                        organism = Mus musculus
SEQUENCE: 128
gacaagtgag tgtctcaggt taggattcta ttttaagatt gagatattag gctttgatac    60
tacatctaaa tggtctgtac atgtctcgaa gaaagttctt cagacagagt taggacttgg   120
atccaggagt taggacttgg actgactcag gaggactcga gtttcttctt ctccagctgg   180
aatgtcctta tgtaagaaaa gccttgcctc atgagtatgc aaatcatgtg cgactgtgat   240
gattaatata gggatatcca caccaaacat catatgagcc ctatcttctc tacagacact   300
gaatctcaag gtccttaca                                               319

SEQ ID NO: 129          moltype = DNA  length = 60
FEATURE                 Location/Qualifiers
misc_feature            1..60
                        note = Signal peptide coding sequence
source                  1..60
                        mol_type = other DNA
                        organism = synthetic construct
SEQUENCE: 129
atggaaaccg acacactgct gctgtgggtg ctgcttcttt gggtgcccgg aagcacaggc    60

SEQ ID NO: 130          moltype = DNA  length = 696
FEATURE                 Location/Qualifiers
misc_feature            1..696
                        note = mRSV kappa light chain coding sequence
source                  1..696
                        mol_type = other DNA
                        organism = synthetic construct
SEQUENCE: 130
atggaaaccg acacactgct gctgtgggtg ctgcttcttt gggtgcccgg aagcacaggc    60
gacatccagc tgacacagag ccctgccatc atgtctgcta gccctggcga aaaagtgaca   120
atgacctgtt ccgccagcag ctccgtgggc tacatgcact ggtatcagca gaagtctagc   180
acaagcccca agctgtggat ctacgacacc tccaagctgg cctctggcgt gccaggcaga   240
ttttctggaa gcggcagcgg caacagctac agcctgacta tcagctccat ccaggccgag   300
gatgtggcta cctactactg cttcagaggc agcggctacc ccttcacatt tggccagggc   360
accaagctgg aaatcaaggc cgatgccgct cctaccgtgt ctatctttcc acctagcagc   420
gagcagctga catctggcgg agcctctgtc gtgtgcttcc tgaacaactt ctaccctaag   480
gacatcaacg tcaagtggaa gatcgacggc tccgagagac agaacggcgt gctgaactct   540
tggaccgacc aggacagcaa ggatagcacc tacagcatga gcagcactct gaccctgaca   600
aaggacgagt acgagaggca caactcctac acatgcgagg ccacacacaa gaccagcaca   660
tccccaatcg tgaagtcctt caaccggaac gagtgc                            696

SEQ ID NO: 131          moltype = DNA  length = 318
FEATURE                 Location/Qualifiers
misc_feature            1..318
                        note = mPalivizumab variable light chain coding sequence
source                  1..318
                        mol_type = other DNA
                        organism = synthetic construct
SEQUENCE: 131
gacatccagc tgacacagag ccctgccatc atgtctgcta gccctggcga aaaagtgaca    60
atgacctgtt ccgccagcag ctccgtgggc tacatgcact ggtatcagca gaagtctagc   120
```

```
acaagcccca agctgtggat ctacgacacc tccaagctgg cctctggcgt gccaggcaga  180
ttttctggaa gcggcagcgg caacagctac agcctgacta tcagctccat ccaggccgag  240
gatgtggcta cctactactg cttcagaggc agcggctacc ccttcacatt tggccagggc  300
accaagctgg aaatcaag                                                 318

SEQ ID NO: 132        moltype = DNA   length = 318
FEATURE               Location/Qualifiers
misc_feature          1..318
                      note = mIgL kappa constant light chain coding sequence
source                1..318
                      mol_type = other DNA
                      organism = synthetic construct
SEQUENCE: 132
gccgatgccg ctcctaccgt gtctatcttt ccacctagca gcgagcagct gacatctggc  60
ggagcctctg tcgtgtgctt cctgaacaac ttctacccta aggacatcaa cgtcaagtgg  120
aagatcgacg gctccgagag acagaacggc gtgctgaact cttggaccga ccaggacagc  180
aaggatagca cctacagcat gagcagcact ctgaccctga caaaggacga gtacgagagg  240
cacaactcct acacatgcga ggccacacac aagaccagca tcccccaat cgtgaagtcc  300
ttcaaccgga acgagtgc                                                 318

SEQ ID NO: 133        moltype = DNA   length = 360
FEATURE               Location/Qualifiers
misc_feature          1..360
                      note = mPalivizumab variable heavy chain coding sequence
source                1..360
                      mol_type = other DNA
                      organism = synthetic construct
SEQUENCE: 133
caggtggaac tgcaagaaag cggccctggc atcctgcagc cttctcagac actgagcctg  60
acctgtagct tcagcggctt cagcctgagc acaagcggca tgtctgtcgg ctggatcaga  120
cagccttctg gcgaaggact ggaatggctg gccgacattt ggtgggacga caagaaggac  180
tacaacccca gcctgaagtc cagactgacc atcagcaagg acaccagcag caaccaggtg  240
ttcctgaaga tcaccggcgt ggacacagcc gataccgcca cctattactg cgccagatcc  300
atgatcacca ctggtactt cgacgtgtgg ggcgctggca ccacagtgac cgtctcctca  360

SEQ ID NO: 134        moltype = AA   length = 20
FEATURE               Location/Qualifiers
REGION                1..20
                      note = Signal peptide amino acid sequence
source                1..20
                      mol_type = protein
                      organism = synthetic construct
SEQUENCE: 134
METDTLLLWV LLLWVPGSTG                                                20

SEQ ID NO: 135        moltype = AA   length = 232
FEATURE               Location/Qualifiers
REGION                1..232
                      note = mRSV kappa light chain amino acid sequence
source                1..232
                      mol_type = protein
                      organism = synthetic construct
SEQUENCE: 135
METDTLLLWV LLLWVPGSTG DIQLTQSPAI MSASPGEKVT MTCSASSSVG YMHWYQQKSS  60
TSPKLWIYDT SKLASGVPGR FSGSGSGNSY SLTISSIQAE DVATYYCFRG SGYPFTFGQG  120
TKLEIKADAA PTVSIFPPSS EQLTSGGASV VCFLNNFYPK DINVKWKIDG SERQNGVLNS  180
WTDQDSKDST YSMSSTLTLT KDEYERHNSY TCEATHKTST SPIVKSFNRN EC           232

SEQ ID NO: 136        moltype = AA   length = 106
FEATURE               Location/Qualifiers
REGION                1..106
                      note = mPalivizumab variable light chain amino acid sequence
source                1..106
                      mol_type = protein
                      organism = synthetic construct
SEQUENCE: 136
DIQLTQSPAI MSASPGEKVT MTCSASSSVG YMHWYQQKSS TSPKLWIYDT SKLASGVPGR  60
FSGSGSGNSY SLTISSIQAE DVATYYCFRG SGYPFTFGQG TKLEIK                  106

SEQ ID NO: 137        moltype = AA   length = 106
FEATURE               Location/Qualifiers
REGION                1..106
                      note = mIgL kappa constant light chain amino acid sequence
source                1..106
                      mol_type = protein
                      organism = synthetic construct
SEQUENCE: 137
ADAAPTVSIF PPSSEQLTSG GASVVCFLNN FYPKDINVKW KIDGSERQNG VLNSWTDQDS  60
KDSTYSMSST LTLTKDEYER HNSYTCEATH KTSTSPIVKS FNRNEC                  106
```

-continued

```
SEQ ID NO: 138          moltype = AA   length = 120
FEATURE                 Location/Qualifiers
REGION                  1..120
                        note = mPalivizumab variable heavy chain amino acid sequence
source                  1..120
                        mol_type = protein
                        organism = synthetic construct
SEQUENCE: 138
QVELQESGPG ILQPSQTLSL TCSFSGFSLS TSGMSVGWIR QPSGEGLEWL ADIWWDDKKD    60
YNPSLKSRLT ISKDTSSNQV FLKITGVDTA DTATYYCARS MITNWYFDVW GAGTTVTVSS   120

SEQ ID NO: 139          moltype = DNA   length = 64
FEATURE                 Location/Qualifiers
misc_feature            1..64
                        note = splice junction with flanking sequence
source                  1..64
                        mol_type = other DNA
                        organism = synthetic construct
SEQUENCE: 139
caggtgagtc ctaacttctc ccattctaaa tgcatgttgg ggggattctg ggccttcagg    60
acca                                                                 64

SEQ ID NO: 140          moltype = DNA   length = 968
FEATURE                 Location/Qualifiers
source                  1..968
                        mol_type = genomic DNA
                        organism = Mus musculus
SEQUENCE: 140
cataggggaca aagagtggag tggggcactt tctttagatt tgtgaggaat gttccgcact    60
agattgttta aaacttcatt tgttggaagg agagctgtct tagtgattga gtcaagggag   120
aaaggcatct agcctcggtc tcaaaagggt agttgctgtc tagagaggtc tggtggagcc   180
tgcaaaagtc cagctttcaa aggaacacag aagtatgtgt atggaatatt agaagatgtt   240
gcttttactc ttaagttggt tcctaggaaa aatagttaaa tactgtgact ttaaaatgtg   300
agagggtttt caagtactca tttttttaaa tgtccaaaat ttttgtcaat cagtttgagg   360
tcttgtttgt gtagaactga tattacttaa agtttaaccg aggaatggga gtgaggctct   420
ctcataacct attcagaact gacttttaac aataataaat taagtttaaa atatttttaa   480
atgaattgag caatgttgag ttggagtcaa gatggccgat cagaaccaga acacctgcag   540
cagctggcag gaagcaggtc atgtggcaag gctatttggg gaagggaaaa taaaaccact   600
aggtaaactt gtagctgtgg tttgaagaag tggttttgaa acactctgtc cagccccacc   660
aaaccgaaag tccaggctga gcaaacacc acctgggtaa tttgcatttc taaaataagt   720
tgaggattca gccgaaactg gagaggtcct ctttttaactt attgagttca accttttaat   780
tttagcttga gtagttctag tttccccaaa cttaagttta tcgacttcta aaatgtattt   840
agaattcatt ttcaaaatta ggttatgtaa gaaattgaag gactttagtg tctttaatt   900
ctaatatatt tagaaaactt cttaaaatta ctctattatt cttccctctg attattggtc   960
tccattca                                                            968

SEQ ID NO: 141          moltype = AA   length = 409
FEATURE                 Location/Qualifiers
REGION                  1..409
                        note = signal peptide-light chain-streptag linker-variable
                         heavy chain amino acid sequence in mouse anti-RSV emAb AAV
source                  1..409
                        mol_type = protein
                        organism = synthetic construct
SEQUENCE: 141
METDTLLLWV LLLWVPGSTG DIQLTQSPAI MSASPGEKVT MTCSASSSVG YMHWYQQKSS    60
TSPKLWIYDT SKLASGVPGR FSGSGSGNSY SLTISSIQAE DVATYYCFRG SGYPFTFGQG   120
TKLEIKADAA PTVSIFPPSS EQLTSGGASV VCFLNNFYPK DINVKWKIDG SERQNGVLNS   180
WTDQDSKDST YSMSSTLTLT KDEYERHNSY TCEATHKTST SPIVKSFNRN ECGGSSGSGS   240
GSNWSHPQFE KGGGGSNWSH PQFEKGGGGS NWSHPQFEKG SGGGGSAGGQ VELQESGPGI   300
LQPSQTLSLT CSFSGFSLST SGMSVGWIRQ PSGEGLEWLA DIWWDDKKDY NPSLKSRLTI   360
SKDTSSNQVF LKITGVDTAD TATYYCARSM ITNWYFDVWG AGTTVTVSS              409

SEQ ID NO: 142          moltype = DNA   length = 39
FEATURE                 Location/Qualifiers
source                  1..39
                        mol_type = genomic DNA
                        organism = Mus musculus
SEQUENCE: 142
accacctctg tgacagcatt tatacagtat ccgatggat                          39

SEQ ID NO: 143          moltype = DNA   length = 39
FEATURE                 Location/Qualifiers
source                  1..39
                        mol_type = genomic DNA
                        organism = Mus musculus
SEQUENCE: 143
atccataggg acaaagagtg gagtggggca ctttccttta                          39
```

```
SEQ ID NO: 144              moltype = AA   length = 409
FEATURE                     Location/Qualifiers
REGION                      1..409
                            note = signal peptide-light chain-streptag linker-variable
                             heavy chain amino acid sequence in ms-emAb-RSV-dsDNA
source                      1..409
                            mol_type = protein
                            organism = synthetic construct
SEQUENCE: 144
METDTLLLWV LLLWVPGSTG DIQLTQSPAI MSASPGEKVT MTCSASSSVG YMHWYQQKSS  60
TSPKLWIYDT SKLASGVPGR FSGSGSGNSY SLTISSIQAE DVATYYCFRG SGYPFTFGQG  120
TKLEIKADAA PTVSIFPPSS EQLTSGGASV VCFLNNFYPK DINVKWKIDG SERQNGVLNS  180
WTDQDSKDST YSMSSTLTLT KDEYERHNSY TCEATHKTST SPIVKSFNRN ECGGSSGSGS  240
GSNWSHPQFE KGGGGSNWSH PQFEKGGGGS NWSHPQFEKG SGGGGSAGGQ VELQESGPGI  300
LQPSQTLSLT CSFSGFSLST SGMSVGWIRQ PSGEGLEWLA DIWWDDKKDY NPSLKSRLTI  360
SKDTSSNQVF LKITGVDTAD TATYYCARSM ITNWYFDVWG AGTTVTVSS              409

SEQ ID NO: 145              moltype = DNA   length = 708
FEATURE                     Location/Qualifiers
misc_feature               1..708
                            note = VRC01 light chain coding sequence
source                      1..708
                            mol_type = other DNA
                            organism = synthetic construct
SEQUENCE: 145
atggctaccg gcagcagaac aagcctgctg ctcgcttttg gactgctctg tctcccctgg  60
ttgcaagaag gcagcgccga aattgtgttg acacagtctc caggcaccct gtctttgtct  120
ccaggggaaa cagccatcat ctcttgtcgg accagtcagt atggttcctt agcctggtat  180
caacagaggc ccggccaggc ccccaggctc gtcatctatt cgggctctac tcgggccgct  240
ggcatcccag acaggttcag cggcagtcgg tgggggccag actacaatct caccatcagc  300
aacctggagt cgggagattt tggtgtttat tattgccagc agtatgaatt ttttggccag  360
gggaccaagt ccaggtcgaa cattaagcgc actgtggccg ctcctagcgt gttcatcttc  420
ccacctagcg acgagcagct gaagtctggc actgcctctg tcgtgtgcct gctgaacaac  480
ttctaccctc gagaggccaa ggtgcagtgg aaagtggaca atgccctgca gagcggcaac  540
agccaagagt ctgtgaccga gcaggactcc aaggattcca cctacagcct gtctagcacc  600
ctgactctga gcaaggccga ctacgagaag cacaaggtgt acgcctgcga agtgacacac  660
cagggactga gcagccctgt gaccaagagc ttcaatcggg gcgagtgc              708

SEQ ID NO: 146              moltype = DNA   length = 312
FEATURE                     Location/Qualifiers
misc_feature               1..312
                            note = VRC01 variable light chain coding sequence
source                      1..312
                            mol_type = other DNA
                            organism = synthetic construct
SEQUENCE: 146
gaaattgtgt tgacacagtc tccaggcacc ctgtctttgt ctccagggga aacagccatc  60
atctcttgtc ggaccagtca gtatggttcc ttagcctggt atcaacagag gcccggccag  120
gcccccaggc tcgtcatcta ttcgggctct actcgggccg ctggcatccc agacaggttc  180
agcggcagtc ggtggggggc agactacaat ctcaccatca gcaacctgga gtcgggagat  240
tttggtgttt attattgcca gcagtatgaa ttttttggcc aggggaccaa ggtccaggtc  300
gacattaagc gc                                                      312

SEQ ID NO: 147              moltype = DNA   length = 363
FEATURE                     Location/Qualifiers
misc_feature               1..363
                            note = VRC01 variable heavy chain coding sequence
source                      1..363
                            mol_type = other DNA
                            organism = synthetic construct
SEQUENCE: 147
caggtgcagc tggtgcagtc tggggggtcag atgaagaagc ctggcgagtc gatgagaatt  60
tcttgtcggg cttctggata tgaatttatt gattgtacgc taaattggat tcgtctggcc  120
cccggaaaaa ggcctgagtg gatgggatgg ctgaagcctc gaggtggcgc ggtcaactac  180
gcacgtccac ttcagggcag agtgaccatg actcgagacg tttattccga cacagccttt  240
ttggagctgc gctcgttgac agtagacgac acggccgtct acttttgtac taggggaaaa  300
aactgtgatt acaattggga cttcgaacac tggggccggg gcaccccggt catcgtctca  360
tca                                                                363

SEQ ID NO: 148              moltype = AA   length = 236
FEATURE                     Location/Qualifiers
REGION                      1..236
                            note = VRC01 light chain amino acid sequence
source                      1..236
                            mol_type = protein
                            organism = synthetic construct
SEQUENCE: 148
MATGSRTSLL LAFGLLCLPW LQEGSAEIVL TQSPGTLSLS PGETAIISCR TSQYGSLAWY  60
```

```
QQRPGQAPRL VIYSGSTRAA GIPDRFSGSR WGPDYNLTIS NLESGDFGVY YCQQYEFFGQ  120
GTKVQVDIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC       236

SEQ ID NO: 149        moltype = AA  length = 104
FEATURE               Location/Qualifiers
REGION                1..104
                      note = VRC01 variable light chain amino acid sequence
source                1..104
                      mol_type = protein
                      organism = synthetic construct
SEQUENCE: 149
EIVLTQSPGT LSLSPGETAI ISCRTSQYGS LAWYQQRPGQ APRLVIYSGS TRAAGIPDRF  60
SGSRWGPDYN LTISNLESGD FGVYYCQQYE FFGQGTKVQV DIKR                    104

SEQ ID NO: 150        moltype = AA  length = 121
FEATURE               Location/Qualifiers
REGION                1..121
                      note = VRC01 variable heavy chain amino acid sequence
source                1..121
                      mol_type = protein
                      organism = synthetic construct
SEQUENCE: 150
QVQLVQSGGQ MKKPGESMRI SCRASGYEFI DCTLNWIRLA PGKRPEWMGW LKPRGGAVNY  60
ARPLQGRVTM TRDVYSDTAF LELRSLTVDD TAVYFCTRGK NCDYNWDFEH WGRGTPVIVS  120
S                                                                   121

SEQ ID NO: 151        moltype = DNA  length = 87
FEATURE               Location/Qualifiers
misc_feature          1..87
                      note = splice junction with flanking sequence in constructs
                       of the disclosure
source                1..87
                      mol_type = other DNA
                      organism = synthetic construct
SEQUENCE: 151
caggtgagtt ggctttcctt ctgcctcctt tctctgggcc cagcgtcctc tgacctggag  60
ctgggagata atgtccgggg gctcctt                                       87

SEQ ID NO: 152        moltype = AA  length = 414
FEATURE               Location/Qualifiers
REGION                1..414
                      note = signal peptide-light chain-streptag linker-variable
                       heavy chain amino acid sequence in Hu-emAb-VRC01-AAV
source                1..414
                      mol_type = protein
                      organism = synthetic construct
SEQUENCE: 152
MATGSRTSLL LAFGLLCLPW LQEGSAEIVL TQSPGTLSLS PGETAIISCR TSQYGSLAWY  60
QQRPGQAPRL VIYSGSTRAA GIPDRFSGSR WGPDYNLTIS NLESGDFGVY YCQQYEFFGQ  120
GTKVQVDIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECGGSS  240
GSGSGSNWSH PQFEKGGGGS NWSHPQFEKG GGGSNWSHPQ FEKGSGGGGS AGGQVQLVQS  300
GGQMKKPGES MRISCRASGY EFIDCTLNWI RLAPGKRPEW MGWLKPRGGA VNYARPLQGR  360
VTMTRDVYSD TAFLELRSLT VDDTAVYFCT RGKNCDYNWD FEHWGRGTPV IVSS         414

SEQ ID NO: 153        moltype = DNA  length = 430
FEATURE               Location/Qualifiers
source                1..430
                      mol_type = genomic DNA
                      organism = Homo sapiens
SEQUENCE: 153
tgtgacgccc ggagacagaa ggtctctggg tggctgggtt tttgtggggt gaggatggac  60
attctgccat tgtgattact actactacta ctacatggac gtctgggca aagggaccac  120
ggtcaccgtc tcctcaggta agaatggcca ctctagggcc tttgtttct gctactgcct  180
gtggggtttc ctgagggcat gttccgaggg gacctgggcg gactggccag gaggggatgg  240
gcactggggt gccttgagga tctgggagcc tctgtggatt ttccgatgcc tttgaaaat  300
gggactcagg ttgggtgcgt ctgatggagt aactgagcct gggggcttgg ggagccacat  360
ttggacgaga tgcctgaaca aaccaggggt cttagtgatg gctgaggaat gtgtctcagg  420
agcggtgtct                                                          430

SEQ ID NO: 154        moltype = DNA  length = 708
FEATURE               Location/Qualifiers
misc_feature          1..708
                      note = Medi8852 light chain coding sequence
source                1..708
                      mol_type = other DNA
                      organism = synthetic construct
SEQUENCE: 154
```

```
atggctaccg gcagcagaac aagcctgctg ctcgcttttg gactgctctg tctcccctgg  60
ttgcaagaag gcagcgccga tattcagatg acccagagcc cttccagcct gtccgcttca  120
gtgggggatc gagtgaccat tacctgccga accagccaga gcctgagctc ctacacgcac  180
tggtatcagc agaagcccgg caaagcccct aagctgctga tctacgccgc ttctagtcgg  240
gggtccggag tgcaaagccg gttctccgga tctgggagtg gaaccgactt taccctgaca  300
atttcaagcc tgcagcccga ggatttcgct acatactact gtcagcgaga cagaactttc  360
gggcagggca ctaaggtgga gatcaaacg actgtggccg ctcctagcgt gttcatcttt  420
ccacctagcg acgagcagct gaagtctggc actgcctctg tcgtgtgcct gctgaacaac  480
ttctaccctc gagaggccaa ggtgcagtgg aaagtggaca atgccctgca gagcggcaac  540
agccaagagt ctgtgaccga gcaggactcc aaggattcca cctacagcct gtctagcacc  600
ctgactctga gcaaggccga ctacgagaag cacaaggtgt acgcctgcga agtgacacac  660
cagggactga gcagccctgt gaccaagagc ttcaatcggg gcgagtgc  708
```

```
SEQ ID NO: 155           moltype = DNA  length = 309
FEATURE                  Location/Qualifiers
misc_feature             1..309
                         note = MEDI8852-VK anti-stem HA variable light chain coding
                          sequence
source                   1..309
                         mol_type = other DNA
                         organism = synthetic construct
SEQUENCE: 155
gatattcaga tgacccagag cccttccagc ctgtccgctt cagtggggga tcgagtgacc  60
attacctgcc gaaccagcca gagcctgagc tcctacacgc actggtatca gcagaagccc  120
ggcaaagccc ctaagctgct gatctacgcc gcttctagtc gggggtccgg agtgccaagc  180
cggttctccg gatctgggag tggaaccgac tttaccctga caatttcaag cctgcagccc  240
gaggatttcg ctacatacta ctgtcagcag agcagaactt cgggcaggg cactaaggtg  300
gagatcaaa  309
```

```
SEQ ID NO: 156           moltype = DNA  length = 384
FEATURE                  Location/Qualifiers
misc_feature             1..384
                         note = anti-stem HA variable heavy chain coding sequence
source                   1..384
                         mol_type = other DNA
                         organism = synthetic construct
SEQUENCE: 156
caggtccagc tgcagcagag cggcccccgga ctggtcaagc cttcacagac actgagcctg  60
acatgcgcca ttagcggaga tagcgtgagc tcctacacaa tccgtgtgga actggatcagg  120
cagtctccaa gtcgaggact gggagtggctg ggacgaacat actatagatc cgggtggtac  180
aatgactatg ctgaatcagt gaaaagccga attactatca accccgatac ctccaagaat  240
cagttctctc tgcagctgaa cagtgtgacc cctgaggaca cagccgtgta ctactgcgcc  300
agaagcggcc atatcaccgt ctttggcgtc aatgtggatg ctttcgatat gtggggggcag  360
gggactatgg tcaccgtctc ttca  384
```

```
SEQ ID NO: 157           moltype = AA  length = 236
FEATURE                  Location/Qualifiers
REGION                   1..236
                         note = Medi8852 light chain amino acid sequence
source                   1..236
                         mol_type = protein
                         organism = synthetic construct
SEQUENCE: 157
MATGSRTSLL LAFGLLCLPW LQEGSADIQM TQSPSSLSAS VGDRVTITCR TSQSLSSYTH  60
WYQQKPGKAP KLLIYAASSR GSGVPSRFSG SGSGTDFTLT ISSLQPEDFA TYYCQQSRTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC  236
```

```
SEQ ID NO: 158           moltype = AA  length = 103
FEATURE                  Location/Qualifiers
REGION                   1..103
                         note = MEDI8852-VK anti-stem HA variable light chain amino
                          acid sequence
source                   1..103
                         mol_type = protein
                         organism = synthetic construct
SEQUENCE: 158
DIQMTQSPSS LSASVGDRVT ITCRTSQSLS SYTHWYQQKP GKAPKLLIYA ASSRGSGVPS  60
RFSGSGSGTD FTLTISSLQP EDFATYYCQQ SRTFGQGTKV EIK  103
```

```
SEQ ID NO: 159           moltype = AA  length = 128
FEATURE                  Location/Qualifiers
REGION                   1..128
                         note = anti-stem HA variable heavy chain amino acid sequence
source                   1..128
                         mol_type = protein
                         organism = synthetic construct
SEQUENCE: 159
QVQLQQSGPG LVKPSQTLSL TCAISGDSVS SYNAVWNWIR QSPSRGLEWL GRTYYRSGWY  60
```

-continued

```
NDYAESVKSR ITINPDTSKN QFSLQLNSVT PEDTAVYYCA RSGHITVFGV NVDAFDMWGQ   120
GTMVTVSS                                                            128

SEQ ID NO: 160           moltype = AA  length = 421
FEATURE                  Location/Qualifiers
REGION                   1..421
                         note = signal peptide-light chain-streptag linker-variable
                          heavy chain amino acid sequence in hu-emAb-Medi8852-AAV
source                   1..421
                         mol_type = protein
                         organism = synthetic construct
SEQUENCE: 160
MATGSRTSLL LAFGLLCLPW LQEGSADIQM TQSPSSLSAS VGDRVTITCR TSQSLSSYTH    60
WYQQKPGKAP KLLIYAASSR GSGVPSRFSG SGSGTDFTLT ISSLQPEDFA TYYCQQSRTF   120
GQGTKVEIKR TVAAPSVFIF PPSDEQLKSG TASVVCLLNN FYPREAKVQW KVDNALQSGN   180
SQESVTEQDS KDSTYSLSST LTLSKADYEK HKVYACEVTH QGLSSPVTKS FNRGECGGSS   240
GSGSGSNWSH PQFEKGGGGS NWSHPQFEKG GGGSNWSHPQ FEKGSGGGGS AGGQVQLQQS   300
GPGLVKPSQT LSLTCAISGD SVSSYNAVWN WIRQSPSRGL EWLGRTYYRS GWYNDYAESV   360
KSRITINPDT SKNQFSLQLN SVTPEDTAVY YCARSGHITV FGVNVDAFDM WGQGTMVTVS   420
S                                                                  421

SEQ ID NO: 161           moltype = DNA  length = 726
FEATURE                  Location/Qualifiers
misc_feature             1..726
                         note = AMM01 light chain coding sequence
source                   1..726
                         mol_type = other DNA
                         organism = synthetic construct
SEQUENCE: 161
atggctaccg gcagcagaac aagcctgctg ctcgcttttg gactgctctg tctcccctgg    60
ttgcaagaag gcagcgcctc ctatgagctg actcagccac cctcagtgtc agtggccccg   120
gggcagaggg ccacaattac ctgtggggga cacaacatcg gagctaaaaa tgtccactgg   180
taccagcaga agccaggcca ggcccctgtc ctggtcatcc aatatgatag cgaccggccc   240
tcagggatcc ctgagcgatt ctctggctcc aactctggga gcacggccac cctgaccatc   300
agcagggtcg aagccgggga tgaggccgac tattactgtc aggtgtggga tagtggtcgt   360
gggcatcccc tttatgtctt cggaggtggg accaaggtca ccgtcctagg tcagcccaag   420
gccaacccca ctgtcactct gttcccaccc tcgagtgagg agcttcaagc caacaaggcc   480
acactggtgt gtctcataag tgacttctac ccgggagccg tgacagtggc ctggaaggca   540
gatagcagcc ccgtcaaggc gggagtggag accaccacac cctccaaaca aagcaacaac   600
aagtacgcgg ccagcagcta cctgagcctg acgcctgagc agtggaagtc ccacagaagc   660
tacagctgcc aggtcacgca tgaagggagc accgtggaga agacagtggc ccctacagaa   720
tgttca                                                             726

SEQ ID NO: 162           moltype = DNA  length = 372
FEATURE                  Location/Qualifiers
misc_feature             1..372
                         note = AMM01 lambda variable light chain coding sequence
source                   1..372
                         mol_type = other DNA
                         organism = synthetic construct
SEQUENCE: 162
tcctatgagc tgactcagcc accctcagtg tcagtggccc cggggcagag ggccacaatt    60
acctgtgggg gacacaacat cggagctaaa aatgtccact ggtaccagca gaagccaggc   120
caggcccctg tcctggtcat ccaatatgat agcgaccggc cctcagggat ccctgagcga   180
ttctctggct ccaactctgg gagcacggcc accctgaccat tcagcaggt cgaagccggg   240
gatgaggccg actattactg tcaggtgtgg gatagtggtc gtgggcatcc cctttatgtct   300
ttcggaggtg ggaccaaggt caccgtccta ggtcagccca aggccaaccc cactgtcact   360
ctgttcccac cc                                                      372

SEQ ID NO: 163           moltype = DNA  length = 276
FEATURE                  Location/Qualifiers
misc_feature             1..276
                         note = lambda constant light chain coding sequence
source                   1..276
                         mol_type = other DNA
                         organism = synthetic construct
SEQUENCE: 163
tcgagtgagg agcttcaagc caacaaggcc acactggtgt gtctcataag tgacttctac    60
ccgggagccg tgacagtggc ctggaaggca gatagcagcc ccgtcaaggc gggagtggag   120
accaccacac cctccaaaca aagcaacaac aagtacgcgg ccagcagcta cctgagcctg   180
acgcctgagc agtggaagtc ccacagaagc tacagctgcc aggtcacgca tgaagggagc   240
accgtggaga agacagtggc ccctacagaa tgttca                            276

SEQ ID NO: 164           moltype = DNA  length = 369
FEATURE                  Location/Qualifiers
misc_feature             1..369
                         note = AMM01 variable heavy chain coding sequence
source                   1..369
                         mol_type = other DNA
```

-continued

```
                        organism = synthetic construct
SEQUENCE: 164
caggttcagc tggtgcagtc tggagctgat gtgaagaagc ctggggcctc agtgaaggtc   60
tcctgcaagg cttctggtta cacctttatt cattttggta tcagttgggt gcggcaggcc  120
cctggacaag ggcttgagtg gatgggatgg atcgacacta ataatggtaa cacaaactat  180
gcacagagtc tccagggcag agtcaccatg accacagata catccacggg cacagcctac  240
atggagctga ggagcctctc gactgacgac acggccgtgt atttctgtgc gcgagctctg  300
gaaatggggc atagaagtgg cttcccattt gactactggg gccagggagt cctggtcacc  360
gtctcccca                                                         369

SEQ ID NO: 165          moltype = AA  length = 242
FEATURE                 Location/Qualifiers
REGION                  1..242
                        note = AMM01 light chain amino acid sequence
source                  1..242
                        mol_type = protein
                        organism = synthetic construct
SEQUENCE: 165
MATGSRTSLL LAFGLLCLPW LQEGSASYEL TQPPSVSVAP GQRATITCGG HNIGAKNVHW   60
YQQKPGQAPV LVIQYDSDRP SGIPERFSGS NSGSTATLTI SRVEAGDEAD YYCQVWDSGR  120
GHPLYVFGGG TKVTVLGQPK ANPTVTLFPP SSEELQANKA TLVCLISDFY PGAVTVAWKA  180
DSSPVKAGVE TTTPSKQSNN KYAASSYLSL TPEQWKSHRS YSCQVTHEGS TVEKTVAPTE  240
CS                                                                242

SEQ ID NO: 166          moltype = AA  length = 124
FEATURE                 Location/Qualifiers
REGION                  1..124
                        note = AMM01 variable light chain amino acid sequence
source                  1..124
                        mol_type = protein
                        organism = synthetic construct
SEQUENCE: 166
SYELTQPPSV SVAPGQRATI TCGGHNIGAK NVHWYQQKPG QAPVLVIQYD SDRPSGIPER   60
FSGSNSGSTA TLTISRVEAG DEADYYCQVW DSGRGHPLYV FGGGTKVTVL GQPKANPTVT  120
LFPP                                                              124

SEQ ID NO: 167          moltype = AA  length = 92
FEATURE                 Location/Qualifiers
REGION                  1..92
                        note = AMM01 lambda constant light chain amino acid sequence
source                  1..92
                        mol_type = protein
                        organism = synthetic construct
SEQUENCE: 167
SSEELQANKA TLVCLISDFY PGAVTVAWKA DSSPVKAGVE TTTPSKQSNN KYAASSYLSL   60
TPEQWKSHRS YSCQVTHEGS TVEKTVAPTE CS                                92

SEQ ID NO: 168          moltype = AA  length = 123
FEATURE                 Location/Qualifiers
REGION                  1..123
                        note = AMM01 variable heavy chain amino acid sequence
source                  1..123
                        mol_type = protein
                        organism = synthetic construct
SEQUENCE: 168
QVQLVQSGAD VKKPGASVKV SCKASGYTFI HFGISWVRQA PGQGLEWMGW IDTNNGNTNY   60
AQSLQGRVTM TTDTSTGTAY MELRSLSTDD TAVYFCARAL EMGHRSGFPF DYWGQGVLVT  120
VSP                                                               123

SEQ ID NO: 169          moltype = AA  length = 422
FEATURE                 Location/Qualifiers
REGION                  1..422
                        note = signal peptide-light chain-streptag linker-variable
                         heavy chain amino acid sequence in hu-emAb-AMM01-AAV
source                  1..422
                        mol_type = protein
                        organism = synthetic construct
SEQUENCE: 169
MATGSRTSLL LAFGLLCLPW LQEGSASYEL TQPPSVSVAP GQRATITCGG HNIGAKNVHW   60
YQQKPGQAPV LVIQYDSDRP SGIPERFSGS NSGSTATLTI SRVEAGDEAD YYCQVWDSGR  120
GHPLYVFGGG TKVTVLGQPK ANPTVTLFPP SSEELQANKA TLVCLISDFY PGAVTVAWKA  180
DSSPVKAGVE TTTPSKQSNN KYAASSYLSL TPEQWKSHRS YSCQVTHEGS TVEKTVAPTE  240
CSGGGSGSGS GSNWSHPQFE KGGGGSNWSH PQFEKGGGGS NWSHPQFEKG SGGGGSAGGQ  300
VQLVQSGADV KKPGASVKVS CKASGYTFIH FGISWVRQAP GQGLEWMGWI DTNNGNTNYA  360
QSLQGRVTMT TDTSTGTAYM ELRSLSTDDT AVYFCARALE MGHRSGFPFD YWGQGVLVTV  420
SP                                                                422

SEQ ID NO: 170          moltype = DNA  length = 39
FEATURE                 Location/Qualifiers
```

-continued

```
source                  1..39
                        mol_type = genomic DNA
                        organism = Mus musculus
SEQUENCE: 170
aggaccacct ctgtgacagc atttatacag tatccgatg                                 39

SEQ ID NO: 171          moltype = DNA   length = 41
FEATURE                 Location/Qualifiers
source                  1..41
                        mol_type = genomic DNA
                        organism = Mus musculus
SEQUENCE: 171
cataggggaca aagagtggag tggggcactt tctttagatt t                             41

SEQ ID NO: 172          moltype = AA   length = 409
FEATURE                 Location/Qualifiers
REGION                  1..409
                        note = signal peptide-light chain-streptag linker-variable
                         heavy chain amino acid sequence in Balb/C mRSV-Splice
                         Integration
source                  1..409
                        mol_type = protein
                        organism = synthetic construct
SEQUENCE: 172
METDTLLLWV LLLWVPGSTG DIQLTQSPAI MSASPGEKVT MTCSASSSVG YMHWYQQKSS    60
TSPKLWIYDT SKLASGVPGR FSGSGSGNSY SLTISSGQAS DVATYYCFRG SGYPFTFGQG   120
TKLEIKADAA PTVSIFPPSS EQLTSGGASV VCFLNNFYPK DINVKWKIDG SERQNGVLNS   180
WTDQDSKDST YSMSSTLTLT KDEYERHNSY TCEATHKTST SPIVKSFNRN ECGGSSGSGS   240
GSNWSHPQFE KGGGGSNWSH PQFEKGGGGS NWSHPQFEKG SGGGGSAGGQ VELQESGPGI   300
LQPSQTLSLT CSFSGFSLST SGMSVGWIRQ PSGEGLEWLA DIWWDDKKDY NPSLKSRLTI   360
SKDTSSNQVF LKITGVDTAD TATYYCARSM ITNWYFDVWG AGTTVTVSS               409

SEQ ID NO: 173          moltype = DNA   length = 41
FEATURE                 Location/Qualifiers
source                  1..41
                        mol_type = genomic DNA
                        organism = Homo sapiens
SEQUENCE: 173
gtcttagtga tggctgagga atgtgtctca ggagcggtgt c                              41

SEQ ID NO: 174          moltype = DNA   length = 41
FEATURE                 Location/Qualifiers
source                  1..41
                        mol_type = genomic DNA
                        organism = Homo sapiens
SEQUENCE: 174
tgtaggactg caagatcgct gcacagcagc gaatcgtgaa a                              41

SEQ ID NO: 175          moltype = AA   length = 415
FEATURE                 Location/Qualifiers
REGION                  1..415
                        note = signal peptide-light chain-streptag linker-variable
                         heavy chain amino acid sequence in TT-hRSV-T7-integrated
source                  1..415
                        mol_type = protein
                        organism = synthetic construct
SEQUENCE: 175
MATGSRTSLL LAFGLLCLPW LQEGSADIQM TQSPSTLSAS VGDRVTITCK CQLSVGYMHW    60
YQQKPGKAPK LLIYDTSKLA SGVPSRFSGS GSGTEFTLTI SSLQPDDFAT YYCFQGSGYP   120
FTFGGGTKLE IKRTVAAPSV FIFPPSDEQL KSGTASVVCL LNNFYPREAK VQWKVDNALQ   180
SGNSQESVTE QDSKDSTYSL SSTLTLSKAD YEKHKVYACE VTHQGLSSPV TKSFNRGECG   240
GSSGSGSGSN WSHPQFEKGG GGSNWSHPQF EKGGGGSNWS HPQFEKGSGG GGSAGGQVTL   300
RESGPALVKP TQTLTLTCTF SGFSLSTSGM SVGWIRQPPG KALEWLADIW WDDKKDYNPS   360
LKSRLTISKD TSKNQVVLKV TNMDPADTAT YYCARSMITN WYFDVWGAGT TTVSS          415

SEQ ID NO: 176          moltype = AA   length = 21
FEATURE                 Location/Qualifiers
REGION                  1..21
                        note = T2A self-cleaving peptide
source                  1..21
                        mol_type = protein
                        organism = synthetic construct
SEQUENCE: 176
GSGEGRGSLL TCGDVEENPG P                                                     21

SEQ ID NO: 177          moltype = AA   length = 22
FEATURE                 Location/Qualifiers
REGION                  1..22
                        note = P2A self-cleaving peptide
```

-continued

```
source                 1..22
                       mol_type = protein
                       organism = synthetic construct
SEQUENCE: 177
GSGATNFSLL KQAGDVEENP GP                                          22

SEQ ID NO: 178         moltype = AA  length = 24
FEATURE                Location/Qualifiers
REGION                 1..24
                       note = E2A self-cleaving peptide
source                 1..24
                       mol_type = protein
                       organism = synthetic construct
SEQUENCE: 178
GSGQCTNYAL LKLAGDVESN PGPP                                        24

SEQ ID NO: 179         moltype = AA  length = 25
FEATURE                Location/Qualifiers
REGION                 1..25
                       note = F2A self-cleaving peptide
source                 1..25
                       mol_type = protein
                       organism = synthetic construct
SEQUENCE: 179
GSGVKQTLNF DLLKLAGDVE SNPGP                                       25

SEQ ID NO: 180         moltype =   length =
SEQUENCE: 180
000

SEQ ID NO: 181         moltype = AA  length = 4
FEATURE                Location/Qualifiers
REGION                 1..4
                       note = Gly-Ser linker
REGION                 1..4
                       note = MISC_FEATURE - Gly-Ser linker (GGGS)n, where n=1 to
                        100
source                 1..4
                       mol_type = protein
                       organism = synthetic construct
SEQUENCE: 181
GGGS                                                              4

SEQ ID NO: 182         moltype = AA  length = 5
FEATURE                Location/Qualifiers
REGION                 1..5
                       note = Gly-Ser linker
REGION                 1..5
                       note = MISC_FEATURE - Gly-Ser linker (GGGGS)n, where n=1 to
                        100
source                 1..5
                       mol_type = protein
                       organism = synthetic construct
SEQUENCE: 182
GGGGS                                                             5

SEQ ID NO: 183         moltype = AA  length = 18
FEATURE                Location/Qualifiers
REGION                 1..18
                       note = linker
REGION                 1..18
                       note = MISC_FEATURE - linker (KESGSVSSEQLAQFRSLD)n, where
                        n=1 to 100
source                 1..18
                       mol_type = protein
                       organism = synthetic construct
SEQUENCE: 183
KESGSVSSEQ LAQFRSLD                                               18

SEQ ID NO: 184         moltype = AA  length = 14
FEATURE                Location/Qualifiers
REGION                 1..14
                       note = linker
REGION                 1..14
                       note = MISC_FEATURE - linker (EGKSSGSGSESKST)n, where n=1
                        to 100
source                 1..14
                       mol_type = protein
                       organism = synthetic construct
```

-continued

```
SEQUENCE: 184
EGKSSGSGSE SKST                                                             14

SEQ ID NO: 185          moltype = AA  length = 19
FEATURE                 Location/Qualifiers
REGION                  1..19
                        note = exemplary signal peptide derived from human IgH
                         heavy chains
source                  1..19
                        mol_type = protein
                        organism = synthetic construct
SEQUENCE: 185
MELGLSWIFL LAILKGVQC                                                        19

SEQ ID NO: 186          moltype = AA  length = 19
FEATURE                 Location/Qualifiers
REGION                  1..19
                        note = exemplary signal peptide derived from human IgH
                         heavy chains
source                  1..19
                        mol_type = protein
                        organism = synthetic construct
SEQUENCE: 186
MELGLRWVFL VAILEGVQC                                                        19

SEQ ID NO: 187          moltype = AA  length = 19
FEATURE                 Location/Qualifiers
REGION                  1..19
                        note = exemplary signal peptide derived from human IgH
                         heavy chains
source                  1..19
                        mol_type = protein
                        organism = synthetic construct
SEQUENCE: 187
MKHLWFFLLL VAAPRWVLS                                                        19

SEQ ID NO: 188          moltype = AA  length = 19
FEATURE                 Location/Qualifiers
REGION                  1..19
                        note = exemplary signal peptide derived from human IgH
                         heavy chains
source                  1..19
                        mol_type = protein
                        organism = synthetic construct
SEQUENCE: 188
MDWTWRILFL VAAATGAHS                                                        19

SEQ ID NO: 189          moltype = AA  length = 19
FEATURE                 Location/Qualifiers
REGION                  1..19
                        note = exemplary signal peptide derived from human IgH
                         heavy chains
source                  1..19
                        mol_type = protein
                        organism = synthetic construct
SEQUENCE: 189
MDWTWRFLFV VAAATGVQS                                                        19

SEQ ID NO: 190          moltype = AA  length = 19
FEATURE                 Location/Qualifiers
REGION                  1..19
                        note = exemplary signal peptide derived from human IgH
                         heavy chains
source                  1..19
                        mol_type = protein
                        organism = synthetic construct
SEQUENCE: 190
MEFGLSWLFL VAILKGVQC                                                        19

SEQ ID NO: 191          moltype = AA  length = 19
FEATURE                 Location/Qualifiers
REGION                  1..19
                        note = exemplary signal peptide derived from human IgH
                         heavy chains
source                  1..19
                        mol_type = protein
                        organism = synthetic construct
SEQUENCE: 191
MEFGLSWVFL VALFRGVQC                                                        19
```

```
SEQ ID NO: 192              moltype = AA  length = 26
FEATURE                    Location/Qualifiers
REGION                     1..26
                           note = exemplary signal peptide derived from human IgH
                            heavy chains
source                     1..26
                           mol_type = protein
                           organism = synthetic construct
SEQUENCE: 192
MDLLHKNMKH LWFFLLLVAA PRWVLS                                                26

SEQ ID NO: 193              moltype = AA  length = 22
FEATURE                    Location/Qualifiers
REGION                     1..22
                           note = exemplary signal peptide derived from human IgL
                            light chains
source                     1..22
                           mol_type = protein
                           organism = synthetic construct
SEQUENCE: 193
MDMRVPAQLL GLLLLWLSGA RC                                                    22

SEQ ID NO: 194              moltype = AA  length = 22
FEATURE                    Location/Qualifiers
REGION                     1..22
                           note = exemplary signal peptide derived from human IgL
                            light chains
source                     1..22
                           mol_type = protein
                           organism = synthetic construct
SEQUENCE: 194
MKYLLPTAAA GLLLLAAQPA MA                                                    22

SEQ ID NO: 195              moltype = AA  length = 8
FEATURE                    Location/Qualifiers
REGION                     1..8
                           note = Strep tag II
source                     1..8
                           mol_type = protein
                           organism = synthetic construct
SEQUENCE: 195
WSHPQFEK                                                                    8

SEQ ID NO: 196              moltype = AA  length = 8
FEATURE                    Location/Qualifiers
REGION                     1..8
                           note = Flag tag
source                     1..8
                           mol_type = protein
                           organism = synthetic construct
SEQUENCE: 196
DYKDDDDK                                                                    8

SEQ ID NO: 197              moltype = AA  length = 8
FEATURE                    Location/Qualifiers
REGION                     1..8
                           note = Xpress tag
source                     1..8
                           mol_type = protein
                           organism = synthetic construct
SEQUENCE: 197
DLYDDDDK                                                                    8

SEQ ID NO: 198              moltype = AA  length = 15
FEATURE                    Location/Qualifiers
REGION                     1..15
                           note = Avi tag
source                     1..15
                           mol_type = protein
                           organism = synthetic construct
SEQUENCE: 198
GLNDIFEAQK IEWHE                                                            15

SEQ ID NO: 199              moltype = AA  length = 26
FEATURE                    Location/Qualifiers
REGION                     1..26
                           note = calmodulin tag
source                     1..26
```

-continued

```
                          mol_type = protein
                          organism = synthetic construct
SEQUENCE: 199
KRRWKKNFIA VSAANRFKKI SSSGAL                                        26

SEQ ID NO: 200        moltype = AA  length = 9
FEATURE               Location/Qualifiers
REGION                1..9
                      note = HA tag
source                1..9
                      mol_type = protein
                      organism = synthetic construct
SEQUENCE: 200
YPYDVPDYA                                                           9

SEQ ID NO: 201        moltype = AA  length = 10
FEATURE               Location/Qualifiers
REGION                1..10
                      note = Myc tag
source                1..10
                      mol_type = protein
                      organism = synthetic construct
SEQUENCE: 201
EQKLISEEDL                                                          10

SEQ ID NO: 202        moltype = AA  length = 13
FEATURE               Location/Qualifiers
REGION                1..13
                      note = Softag 1
source                1..13
                      mol_type = protein
                      organism = synthetic construct
SEQUENCE: 202
SLAELLNAGL GGS                                                      13

SEQ ID NO: 203        moltype = AA  length = 8
FEATURE               Location/Qualifiers
REGION                1..8
                      note = Softag 3
source                1..8
                      mol_type = protein
                      organism = synthetic construct
SEQUENCE: 203
TQDPSRVG                                                            8

SEQ ID NO: 204        moltype = AA  length = 14
FEATURE               Location/Qualifiers
REGION                1..14
                      note = V5 tag
source                1..14
                      mol_type = protein
                      organism = synthetic construct
SEQUENCE: 204
GKPIPNPLLG LDST                                                     14

SEQ ID NO: 205        moltype = AA  length = 106
FEATURE               Location/Qualifiers
REGION                1..106
                      note = variable light chain amino acid sequence of
                       exemplary mouse palivizumab
source                1..106
                      mol_type = protein
                      organism = synthetic construct
SEQUENCE: 205
DIQLTQSPAI MSASPGEKVT MTCSASSSVG YMHWYQQKLS TSPKLQIYDT SKLASGVPGR  60
FSGSGSGNSY SLTISSIQAE DVATYYCFRG SGYPFTFGQG TKLEIK                106

SEQ ID NO: 206        moltype = AA  length = 106
FEATURE               Location/Qualifiers
REGION                1..106
                      note = variable light chain amino acid sequence of
                       exemplary human anti-RSV antibody
source                1..106
                      mol_type = protein
                      organism = synthetic construct
SEQUENCE: 206
DIQMTQSPST LSASVGDRVT ITCKCQLSVG YMHWYQQKPG KAPKLLIYDT SKLASGVPSR  60
FSGSGSGTEF TLTISSLQPD FATYYCFQGS GYPFTFGGGT KLEIKR                106
```

-continued

```
SEQ ID NO: 207        moltype = AA   length = 12
FEATURE               Location/Qualifiers
REGION                1..12
                      note = CDRH1 of exemplary anti-RSV antibody
source                1..12
                      mol_type = protein
                      organism = synthetic construct SEQUENCE: 207
GASINSDNYY WT                                                          12

SEQ ID NO: 208        moltype = AA   length = 16
FEATURE               Location/Qualifiers
REGION                1..16
                      note = CDRH2 of exemplary anti-RSV antibody
source                1..16
                      mol_type = protein
                      organism = synthetic construct SEQUENCE: 208
HISYTGNTYY TPSLKS                                                      16

SEQ ID NO: 209        moltype = AA   length = 15
FEATURE               Location/Qualifiers
REGION                1..15
                      note = CDRH3 of exemplary anti-RSV antibody
source                1..15
                      mol_type = protein
                      organism = synthetic construct SEQUENCE: 209
CGAYVLISNC GWFDS                                                       15

SEQ ID NO: 210        moltype = AA   length = 11
FEATURE               Location/Qualifiers
REGION                1..11
                      note = CDRL1 of exemplary anti-RSV antibody
source                1..11
                      mol_type = protein
                      organism = synthetic construct SEQUENCE: 210
QASQDISTYL N                                                           11

SEQ ID NO: 211        moltype = AA   length = 7
FEATURE               Location/Qualifiers
REGION                1..7
                      note = CDRL2 of exemplary anti-RSV antibody
source                1..7
                      mol_type = protein
                      organism = synthetic construct SEQUENCE: 211
GASNLET                                                                7

SEQ ID NO: 212        moltype = AA   length = 9
FEATURE               Location/Qualifiers
REGION                1..9
                      note = CDRL3 of exemplary anti-RSV antibody
source                1..9
                      mol_type = protein
                      organism = synthetic construct SEQUENCE: 212
QQYQYLPYT                                                              9

SEQ ID NO: 213        moltype = AA   length = 8
FEATURE               Location/Qualifiers
REGION                1..8
                      note = CDRH1 of exemplary 10E8 anti-HIV antibody
source                1..8
                      mol_type = protein
                      organism = synthetic construct SEQUENCE: 213
GFDFDNAW                                                               8

SEQ ID NO: 214        moltype = AA   length = 10
FEATURE               Location/Qualifiers
REGION                1..10
                      note = CDRH2 of exemplary 10E8 anti-HIV antibody
source                1..10
                      mol_type = protein
                      organism = synthetic construct SEQUENCE: 214
ITGPGEGWSV                                                             10
```

-continued

```
SEQ ID NO: 215              moltype = AA  length = 20
FEATURE                     Location/Qualifiers
REGION                      1..20
                            note = CDRH3 of exemplary 10E8 anti-HIV antibody
source                      1..20
                            mol_type = protein
                            organism = synthetic construct
SEQUENCE: 215
TGKYYDFWSG YPPGEEYFQD                                                  20

SEQ ID NO: 216              moltype = AA  length = 11
FEATURE                     Location/Qualifiers
REGION                      1..11
                            note = CDRL1 of exemplary 10E8 anti-HIV antibody
source                      1..11
                            mol_type = protein
                            organism = synthetic construct
SEQUENCE: 216
TGDSLRSHYA S                                                           11

SEQ ID NO: 217              moltype = AA  length = 7
FEATURE                     Location/Qualifiers
REGION                      1..7
                            note = CDRL2 of exemplary 10E8 anti-HIV antibody
source                      1..7
                            mol_type = protein
                            organism = synthetic construct SEQUENCE: 217
GKNNRPS                                                                7

SEQ ID NO: 218              moltype = AA  length = 12
FEATURE                     Location/Qualifiers
REGION                      1..12
                            note = CDRL3 of exemplary 10E8 anti-HIV antibody
source                      1..12
                            mol_type = protein
                            organism = synthetic construct
SEQUENCE: 218
SSRDKSGSRL SV                                                          12

SEQ ID NO: 219              moltype = AA  length = 8
FEATURE                     Location/Qualifiers
REGION                      1..8
                            note = CDRH1 of exemplary VRC01 anti-HIV antibody
source                      1..8
                            mol_type = protein
                            organism = synthetic construct
SEQUENCE: 219
GYEFIDCT                                                               8

SEQ ID NO: 220              moltype = AA  length = 8
FEATURE                     Location/Qualifiers
REGION                      1..8
                            note = CDRH2 of exemplary VRC01 anti-HIV antibody
source                      1..8
                            mol_type = protein
                            organism = synthetic construct SEQUENCE: 220
KPRGGAVN                                                               8

SEQ ID NO: 221              moltype = AA  length = 14
FEATURE                     Location/Qualifiers
REGION                      1..14
                            note = CDRH3 of exemplary VRC01 anti-HIV antibody
source                      1..14
                            mol_type = protein
                            organism = synthetic construct
SEQUENCE: 221
RGKNCDYNWD FEHW                                                        14

SEQ ID NO: 222              moltype = AA  length = 5
FEATURE                     Location/Qualifiers
REGION                      1..5
                            note = CDRL3 of exemplary VRC01 anti-HIV antibody
source                      1..5
                            mol_type = protein
                            organism = synthetic construct
SEQUENCE: 222
```

-continued

```
QQYEF                                                         5

SEQ ID NO: 223          moltype = AA  length = 30
FEATURE                 Location/Qualifiers
REGION                  1..30
                        note = CDRH1 of exemplary anti-Dengue virus antibody
source                  1..30
                        mol_type = protein
                        organism = synthetic construct
SEQUENCE: 223
EVQLHQSGAE LVKPGASVKL SCTVSGFNIK                             30

SEQ ID NO: 224          moltype = AA  length = 13
FEATURE                 Location/Qualifiers
REGION                  1..13
                        note = CDRH2 of exemplary anti-Dengue virus antibody
source                  1..13
                        mol_type = protein
                        organism = synthetic construct
SEQUENCE: 224
WVKQRPEQGL EWI                                               13

SEQ ID NO: 225          moltype = AA  length = 31
FEATURE                 Location/Qualifiers
REGION                  1..31
                        note = CDRH3 of exemplary anti-Dengue virus antibody
source                  1..31
                        mol_type = protein
                        organism = synthetic construct
SEQUENCE: 225
ATIKADTSSN TAYLQLISLT SEDTAVYYCA F                           31

SEQ ID NO: 226          moltype = AA  length = 23
FEATURE                 Location/Qualifiers
REGION                  1..23
                        note = CDRL1 of exemplary anti-Dengue virus antibody
source                  1..23
                        mol_type = protein
                        organism = synthetic construct
SEQUENCE: 226
DIQMTQSPAS LSVSVGETVT ITC                                    23

SEQ ID NO: 227          moltype = AA  length = 15
FEATURE                 Location/Qualifiers
REGION                  1..15
                        note = CDRL2 of exemplary anti-Dengue virus antibody
source                  1..15
                        mol_type = protein
                        organism = synthetic construct
SEQUENCE: 227
WYQQKQGKSP QLLVY                                             15

SEQ ID NO: 228          moltype = AA  length = 32
FEATURE                 Location/Qualifiers
REGION                  1..32
                        note = CDRL3 of exemplary anti-Dengue virus antibody
source                  1..32
                        mol_type = protein
                        organism = synthetic construct
SEQUENCE: 228
GVPSRFSGSG SGTQYSLKIN SLQSEDFGTY YC                          32

SEQ ID NO: 229          moltype = AA  length = 9
FEATURE                 Location/Qualifiers
REGION                  1..9
                        note = CDRH1 of exemplary anti-Dengue virus antibody
source                  1..9
                        mol_type = protein
                        organism = synthetic construct
SEQUENCE: 229
YTFTDYAIT                                                    9

SEQ ID NO: 230          moltype = AA  length = 18
FEATURE                 Location/Qualifiers
REGION                  1..18
                        note = CDRH2 of exemplary anti-Dengue virus antibody
source                  1..18
                        mol_type = protein
                        organism = synthetic construct
```

-continued

```
SEQUENCE: 230
GLISTYYGDS FYNQKFKG                                                        18

SEQ ID NO: 231           moltype = AA   length = 10
FEATURE                  Location/Qualifiers
REGION                   1..10
                         note = CDRH3 of exemplary anti-Dengue virus antibody
source                   1..10
                         mol_type = protein
                         organism = synthetic construct
SEQUENCE: 231
TIRDGKAMDY                                                                 10

SEQ ID NO: 232           moltype = AA   length = 16
FEATURE                  Location/Qualifiers
REGION                   1..16
                         note = CDRL1 of exemplary anti-Dengue virus antibody
source                   1..16
                         mol_type = protein
                         organism = synthetic construct
SEQUENCE: 232
RSSQSLVHSN GNTYLH                                                          16

SEQ ID NO: 233           moltype = AA   length = 7
FEATURE                  Location/Qualifiers
REGION                   1..7
                         note = CDRL2 of exemplary anti-Dengue virus antibody
source                   1..7
                         mol_type = protein
                         organism = synthetic construct
SEQUENCE: 233
KVSNRFS                                                                    7

SEQ ID NO: 234           moltype = AA   length = 9
FEATURE                  Location/Qualifiers
REGION                   1..9
                         note = CDRL3 of exemplary anti-Dengue virus antibody
source                   1..9
                         mol_type = protein
                         organism = synthetic construct
SEQUENCE: 234
SQSTHVPYT                                                                  9

SEQ ID NO: 235           moltype = AA   length = 118
FEATURE                  Location/Qualifiers
REGION                   1..118
                         note = variable heavy chain of exemplary pertussis antibody
source                   1..118
                         mol_type = protein
                         organism = synthetic construct
SEQUENCE: 235
QVQLQQPGSE LVRPGASVKL SCKASGYKFT SYWMHWVKQR PGQGLEWIGN IFPGSGSTNY   60
DEKFNSKATL TVDTSSNTAY MQLSSLTSED SAVYYCTRWL SGAYFDYWGQ GTTVTVSS     118

SEQ ID NO: 236           moltype = AA   length = 106
FEATURE                  Location/Qualifiers
REGION                   1..106
                         note = variable light chain of exemplary pertussis antibody
source                   1..106
                         mol_type = protein
                         organism = synthetic construct
SEQUENCE: 236
QIVLTQSPAL MSASPGEKVT MTCSASSSVS FMYWYQQKPR SSPKPWIYLT SNLPSGVPAR   60
FSGSGSGTSY SLTISSMEAE DAATYYCQQW SSHPPTFGSG TKLEIK                  106

SEQ ID NO: 237           moltype = AA   length = 6
FEATURE                  Location/Qualifiers
REGION                   1..6
                         note = CDRH1 of exemplary anti-hepatitis C antibody
source                   1..6
                         mol_type = protein
                         organism = synthetic construct
SEQUENCE: 237
SYGMHW                                                                     6

SEQ ID NO: 238           moltype = AA   length = 18
FEATURE                  Location/Qualifiers
REGION                   1..18
                         note = CDRH2 of exemplary anti-hepatitis C antibody
```

-continued

```
source                      1..18
                            mol_type = protein
                            organism = synthetic construct
SEQUENCE: 238
VIWLDGSNTY YADSVKGR                                                  18

SEQ ID NO: 239              moltype = AA  length = 17
FEATURE                     Location/Qualifiers
REGION                      1..17
                            note = CDRH3 of exemplary anti-hepatitis C antibody
source                      1..17
                            mol_type = protein
                            organism = synthetic construct
SEQUENCE: 239
ARDIFTVARG VIIYFDY                                                   17

SEQ ID NO: 240              moltype = AA  length = 11
FEATURE                     Location/Qualifiers
REGION                      1..11
                            note = CDRL1 of exemplary anti-hepatitis C antibody
source                      1..11
                            mol_type = protein
                            organism = synthetic construct
SEQUENCE: 240
RASQSVSSYL A                                                         11

SEQ ID NO: 241              moltype = AA  length = 7
FEATURE                     Location/Qualifiers
REGION                      1..7
                            note = CDRL2 of exemplary anti-hepatitis C antibody
source                      1..7
                            mol_type = protein
                            organism = synthetic construct
SEQUENCE: 241
DASNRAT                                                              7

SEQ ID NO: 242              moltype = AA  length = 8
FEATURE                     Location/Qualifiers
REGION                      1..8
                            note = CDRL3 of exemplary anti-hepatitis C antibody
source                      1..8
                            mol_type = protein
                            organism = synthetic construct
SEQUENCE: 242
QQRSNWVT                                                             8

SEQ ID NO: 243              moltype = AA  length = 8
FEATURE                     Location/Qualifiers
REGION                      1..8
                            note = CDRH1 of exemplary anti-influenza virus antibody
source                      1..8
                            mol_type = protein
                            organism = synthetic construct
SEQUENCE: 243
GMTSNSLA                                                             8

SEQ ID NO: 244              moltype = AA  length = 8
FEATURE                     Location/Qualifiers
REGION                      1..8
                            note = CDRH2 of exemplary anti-influenza virus antibody
source                      1..8
                            mol_type = protein
                            organism = synthetic construct
SEQUENCE: 244
IIPVFETP                                                             8

SEQ ID NO: 245              moltype = AA  length = 16
FEATURE                     Location/Qualifiers
REGION                      1..16
                            note = CDRH3 of exemplary anti-influenza virus antibody
source                      1..16
                            mol_type = protein
                            organism = synthetic construct
SEQUENCE: 245
ATSAGGIVNY YLSFNI                                                    16

SEQ ID NO: 246              moltype = AA  length = 6
FEATURE                     Location/Qualifiers
REGION                      1..6
```

-continued

```
                              note = CDRL1 of exemplary anti-influenza virus antibody
source                        1..6
                              mol_type = protein
                              organism = synthetic construct
SEQUENCE: 246
QTITTW                                                                                6

SEQ ID NO: 247                moltype = AA  length = 9
FEATURE                       Location/Qualifiers
REGION                        1..9
                              note = CDRL3 of exemplary anti-influenza virus antibody
source                        1..9
                              mol_type = protein
                              organism = synthetic construct
SEQUENCE: 247
QQYSTYSGT                                                                             9

SEQ ID NO: 248                moltype = AA  length = 10
FEATURE                       Location/Qualifiers
REGION                        1..10
                              note = CDRH1 of exemplary anti-EBV AMM01 antibody
source                        1..10
                              mol_type = protein
                              organism = synthetic construct
SEQUENCE: 248
YTFIHFGISW                                                                            10

SEQ ID NO: 249                moltype = AA  length = 16
FEATURE                       Location/Qualifiers
REGION                        1..16
                              note = CDRH2 of exemplary anti-EBV AMM01 antibody
source                        1..16
                              mol_type = protein
                              organism = synthetic construct
SEQUENCE: 249
IDTNNGNTNY AQSLQG                                                                     16

SEQ ID NO: 250                moltype = AA  length = 15
FEATURE                       Location/Qualifiers
REGION                        1..15
                              note = CDRH3 of exemplary anti-EBV AMM01 antibody
source                        1..15
                              mol_type = protein
                              organism = synthetic construct
SEQUENCE: 250
RALEMGHRSG FPFDY                                                                      15

SEQ ID NO: 251                moltype = AA  length = 11
FEATURE                       Location/Qualifiers
REGION                        1..11
                              note = CDRL1 of exemplary anti-EBV AMM01 antibody
source                        1..11
                              mol_type = protein
                              organism = synthetic construct
SEQUENCE: 251
GGHNIGAKNV H                                                                          11

SEQ ID NO: 252                moltype = AA  length = 7
FEATURE                       Location/Qualifiers
REGION                        1..7
                              note = CDRL2 of exemplary anti-EBV AMM01 antibody
source                        1..7
                              mol_type = protein
                              organism = synthetic construct
SEQUENCE: 252
YDSDRPS                                                                               7

SEQ ID NO: 253                moltype = AA  length = 14
FEATURE                       Location/Qualifiers
REGION                        1..14
                              note = CDRL3 of exemplary anti-EBV AMM01 antibody
source                        1..14
                              mol_type = protein
                              organism = synthetic construct
SEQUENCE: 253
CQVWDSGRGH PLYV                                                                       14

SEQ ID NO: 254                moltype = AA  length = 19
FEATURE                       Location/Qualifiers
```

```
REGION                  1..19
                        note = beginning of heavy chain of infliximab
source                  1..19
                        mol_type = protein
                        organism = synthetic construct
SEQUENCE: 254
EVKLEESGGG LVQPGGSMK                                             19

SEQ ID NO: 255          moltype = AA  length = 18
FEATURE                 Location/Qualifiers
REGION                  1..18
                        note = beginning of light chain of infliximab
source                  1..18
                        mol_type = protein
                        organism = synthetic construct
SEQUENCE: 255
DILLTQSPAI LSVSPGER                                              18

SEQ ID NO: 256          moltype = AA  length = 6
FEATURE                 Location/Qualifiers
REGION                  1..6
                        note = CDRH1 of exemplary infliximab
source                  1..6
                        mol_type = protein
                        organism = synthetic construct
SEQUENCE: 256
IFSNHW                                                           6

SEQ ID NO: 257          moltype = AA  length = 10
FEATURE                 Location/Qualifiers
REGION                  1..10
                        note = CDRH2 of exemplary infliximab
source                  1..10
                        mol_type = protein
                        organism = synthetic construct
SEQUENCE: 257
RSKSINSATH                                                      10

SEQ ID NO: 258          moltype = AA  length = 7
FEATURE                 Location/Qualifiers
REGION                  1..7
                        note = CDRH3 of exemplary infliximab
source                  1..7
                        mol_type = protein
                        organism = synthetic construct
SEQUENCE: 258
NYYGSTY                                                          7

SEQ ID NO: 259          moltype = AA  length = 7
FEATURE                 Location/Qualifiers
REGION                  1..7
                        note = CDRL1 of exemplary infliximab
source                  1..7
                        mol_type = protein
                        organism = synthetic construct
SEQUENCE: 259
FVGSSIH                                                          7

SEQ ID NO: 260          moltype = AA  length = 7
FEATURE                 Location/Qualifiers
REGION                  1..7
                        note = CDRL2 of exemplary infliximab
source                  1..7
                        mol_type = protein
                        organism = synthetic construct
SEQUENCE: 260
KYASESM                                                          7

SEQ ID NO: 261          moltype = AA  length = 5
FEATURE                 Location/Qualifiers
REGION                  1..5
                        note = CDRL3 of exemplary infliximab
source                  1..5
                        mol_type = protein
                        organism = synthetic construct
SEQUENCE: 261
QSHSW                                                            5

SEQ ID NO: 262          moltype = AA  length = 6
```

-continued

```
FEATURE                  Location/Qualifiers
REGION                   1..6
                         note = CDRH1 of exemplary adalimumab
source                   1..6
                         mol_type = protein
                         organism = synthetic construct
SEQUENCE: 262
TFDDYA                                                              6

SEQ ID NO: 263           moltype = AA  length = 8
FEATURE                  Location/Qualifiers
REGION                   1..8
                         note = CDRH2 of exemplary adalimumab
source                   1..8
                         mol_type = protein
                         organism = synthetic construct
SEQUENCE: 263
TWNSGHID                                                            8

SEQ ID NO: 264           moltype = AA  length = 10
FEATURE                  Location/Qualifiers
REGION                   1..10
                         note = CDRH3 of exemplary adalimumab
source                   1..10
                         mol_type = protein
                         organism = synthetic construct
SEQUENCE: 264
VSYLSTASSL                                                         10

SEQ ID NO: 265           moltype = AA  length = 7
FEATURE                  Location/Qualifiers
REGION                   1..7
                         note = CDRL1 of exemplary adalimumab
source                   1..7
                         mol_type = protein
                         organism = synthetic construct
SEQUENCE: 265
GIRNYLA                                                             7

SEQ ID NO: 266           moltype = AA  length = 7
FEATURE                  Location/Qualifiers
REGION                   1..7
                         note = CDRL2 of exemplary adalimumab
source                   1..7
                         mol_type = protein
                         organism = synthetic construct
SEQUENCE: 266
YAASTLQ                                                             7

SEQ ID NO: 267           moltype = AA  length = 5
FEATURE                  Location/Qualifiers
REGION                   1..5
                         note = CDRL3 of exemplary adalimumab
source                   1..5
                         mol_type = protein
                         organism = synthetic construct
SEQUENCE: 267
RYNRA                                                               5

SEQ ID NO: 268           moltype = AA  length = 6
FEATURE                  Location/Qualifiers
REGION                   1..6
                         note = CDRH1 of exemplary certolizumab
source                   1..6
                         mol_type = protein
                         organism = synthetic construct
SEQUENCE: 268
VFTDYG                                                              6

SEQ ID NO: 269           moltype = AA  length = 8
FEATURE                  Location/Qualifiers
REGION                   1..8
                         note = CDRH2 of exemplary certolizumab
source                   1..8
                         mol_type = protein
                         organism = synthetic construct
SEQUENCE: 269
NTYIGEPI                                                            8
```

-continued

```
SEQ ID NO: 270          moltype = AA  length = 7
FEATURE                 Location/Qualifiers
REGION                  1..7
                        note = CDRH3 of exemplary certolizumab
source                  1..7
                        mol_type = protein
                        organism = synthetic construct
SEQUENCE: 270
GYRSYAM                                                        7

SEQ ID NO: 271          moltype = AA  length = 7
FEATURE                 Location/Qualifiers
REGION                  1..7
                        note = CDRL1 of exemplary certolizumab
source                  1..7
                        mol_type = protein
                        organism = synthetic construct
SEQUENCE: 271
NVGTNVA                                                        7

SEQ ID NO: 272          moltype = AA  length = 7
FEATURE                 Location/Qualifiers
REGION                  1..7
                        note = CDRL2 of exemplary certolizumab
source                  1..7
                        mol_type = protein
                        organism = synthetic construct
SEQUENCE: 272
YSASFLY                                                        7

SEQ ID NO: 273          moltype = AA  length = 5
FEATURE                 Location/Qualifiers
REGION                  1..5
                        note = CDRL3 of exemplary certolizumab
source                  1..5
                        mol_type = protein
                        organism = synthetic construct
SEQUENCE: 273
QYNIY                                                          5

SEQ ID NO: 274          moltype = DNA  length = 20
FEATURE                 Location/Qualifiers
misc_feature            1..20
                        note = mouse forward oligo for amplification of region
                         flanking cut site
source                  1..20
                        mol_type = other DNA
                        organism = synthetic construct
SEQUENCE: 274
ggctccacca gacctctcta                                         20

SEQ ID NO: 275          moltype = DNA  length = 20
FEATURE                 Location/Qualifiers
misc_feature            1..20
                        note = mouse reverse oligo for amplification of region
                         flanking cut site
source                  1..20
                        mol_type = other DNA
                        organism = synthetic construct
SEQUENCE: 275
aacctcagtc accgtctcct                                         20

SEQ ID NO: 276          moltype = DNA  length = 21
FEATURE                 Location/Qualifiers
misc_feature            1..21
                        note = human forward oligo for amplification of region
                         flanking cut site
source                  1..21
                        mol_type = other DNA
                        organism = synthetic construct
SEQUENCE: 276
acagtaagca tgcctcctaa g                                       21

SEQ ID NO: 277          moltype = DNA  length = 20
FEATURE                 Location/Qualifiers
misc_feature            1..20
                        note = human reverse oligo for amplification of region
                         flanking cut site
source                  1..20
```

```
                      mol_type = other DNA
                      organism = synthetic construct
SEQUENCE: 277
gccactctag ggcctttgtt                                               20

SEQ ID NO: 278          moltype = DNA  length = 65
FEATURE                 Location/Qualifiers
misc_feature            1..65
                        note = mouse forward primer to amplify anti-RSV-emAb
                          template
source                  1..65
                        mol_type = other DNA
                        organism = synthetic construct
SEQUENCE: 278
accacctctg tgacagcatt tatacagtat ccgatggaca agtgagtgtc tcaggttagg   60
attct                                                               65

SEQ ID NO: 279          moltype = DNA  length = 61
FEATURE                 Location/Qualifiers
misc_feature            1..61
                        note = mouse reverse primer to amplify anti-RSV-emAb
                          template
source                  1..61
                        mol_type = other DNA
                        organism = synthetic construct
SEQUENCE: 279
taaagaaagt gccccactcc actctttgtc cctatgcttg accacaatga atactcccac   60
c                                                                   61

SEQ ID NO: 280          moltype = DNA  length = 639
FEATURE                 Location/Qualifiers
misc_feature            1..639
                        note = hRSV light chain coding sequence without signal
                          sequence in human anti-RSV emAb AAV
source                  1..639
                        mol_type = other DNA
                        organism = synthetic construct
SEQUENCE: 280
gacatccaga tgacacagag ccctagcaca ctgtctgcca gcgtgggcga cagagtgacc   60
atcacatgca agtgccagct gagcgtgggc tacatgcact ggtatcagca aaagcccggc  120
aaggccccta agctgctgat ctacgatacc tccaagctgg cctctggcgt gccctccaga  180
ttttctggca gcggcagcgg aaccgagttc accctgacca tctcaagcct gcagcctgac  240
gacttcgcta cgtactactg cttccaaggc agcggctacc ccttcacatt tggcggcgga  300
acaaagctgg aaatcaagcg gactgtggcc gctcctagcg tgttcatctt ccacctagc  360
gacgagcagc tgaagtctgg cactgcctct gtcgtgtgcc tgctgaacaa cttctaccct  420
cgagaggcca aggtgcagtg gaaagtggac aatgccctgc agagcggcaa cagccaagag  480
tctgtgaccg agcaggactc caaggattcc acctacagcc tgtctagcac cctgactctg  540
agcaaggccg actacgagaa gcacaaggtg tacgcctgcg aagtgacaca ccagggactg  600
agcagccctg tgaccaagag cttcaatcgg ggcgagtgc                        639

SEQ ID NO: 281          moltype = DNA  length = 636
FEATURE                 Location/Qualifiers
misc_feature            1..636
                        note = mRSV kappa light chain coding sequence without
                          signal sequence in mouse anti-RSV emAb AAV
source                  1..636
                        mol_type = other DNA
                        organism = synthetic construct
SEQUENCE: 281
gacatccagc tgacacagag ccctgccatc atgtctgcta gccctggcga gaaagtgaca   60
atgacctgtt ccgccagcag ctccgtgggc tacatgcact ggtatcagca gaagtctagc  120
acaagcccca agctgtggat ctacgacacc tccaagctgg cctctggcgt gccaggcaga  180
ttttctggaa gcggcagcgg caacagctac agcctgacta tcagctccat ccaggccgag  240
gatgttggcta cctactactg cttcagaggc agcggctacc ccttcacatt tggcggcgga  300
accaagctgg aaatcaaggc cgatgccgct cctaccgtgt ctatctttcc acctagcagc  360
gagcagctga catctggcgg agcctctgtc gtgtgcttcc tgaacaactt ctaccctaag  420
gacatcaacg tcaagtggaa gatcgacggc tccgagagac agaacggcgt gctgaactct  480
tggaccgacc aggacagcaa ggatagcacc tacagcatga gcagcactct gaccctgaca  540
aaggacgagt acgagaggca caactcctac acatgcgagg ccacacacaa gaccagcaca  600
tccccaatcg tgaagtcctt caaccggaac gagtgc                           636

SEQ ID NO: 282          moltype = DNA  length = 630
FEATURE                 Location/Qualifiers
misc_feature            1..630
                        note = VRC01 light chain coding sequence without signal
                          sequence in Hu-emAb-VRC01-AAV
source                  1..630
                        mol_type = other DNA
                        organism = synthetic construct
```

```
SEQUENCE: 282
gaaattgtgt tgacacagtc tccaggcacc ctgtctttgt ctccagggga aacagccatc  60
atctcttgtc ggaccagtca gtatggttcc ttagcctggt atcaacagag gcccggccag  120
gccccccaggc tcgtcatcta ttcgggctct actcgggccg ctggcatccc agacaggttc  180
agcggcagtc ggtgggggcc agactacaat ctcaccatca gcaacctggg atcgggagat  240
tttggtgttt attattgcca gcagtatgaa ttttttggcc aggggaccaa ggtccaggtc  300
gacattaagc gcactgtggc cgctcctagc gtgttcatct ttccacctag cgacgagcag  360
ctgaagtctg gcactgcctc tgtcgtgtgc ctgctgaaca acttctaccc tcgagaggcc  420
aaggtgcagt ggaaagtgga caatgccctg cagagcggca cagccaaga gtctgtgacc  480
gagcaggact ccaaggattc cacctacagc ctgtctagca ccctgactct gagcaaggcc  540
gactacgaga agcacaaggt gtacgcctgc gaagtgacac accagggact gagcagccct  600
gtgaccaaga gcttcaatcg gggcgagtgc                                    630

SEQ ID NO: 283       moltype = DNA   length = 630
FEATURE              Location/Qualifiers
misc_feature         1..630
                     note = Medi8852 light chain coding sequence without signal
                     sequence in hu-emAb-Medi8852-AAV
source               1..630
                     mol_type = other DNA
                     organism = synthetic construct
SEQUENCE: 283
gatattcaga tgacccagag cccttccagc ctgtccgctt cagtggggga tcgagtgacc  60
attacctgcc gaaccagcca gagcctgagc tcctacacgc actggtatca gcagaagccc  120
ggcaaagccc ctaagctgct gatctacgcc gcttctagtc gggggtccgg agtgccaagc  180
cggttctccg gatctgggag tggaaccgac tttaccctga caatttcaag cctgcagccc  240
gaggatttcg ctacatacta ctgtcagcag agcagaactt tcgggcaggg cactaaggtg  300
gagatcaaac ggactgtggc cgctcctagc gtgttcatct ttccacctag cgacgagcag  360
ctgaagtctg gcactgcctc tgtcgtgtgc ctgctgaaca acttctaccc tcgagaggcc  420
aaggtgcagt ggaaagtgga caatgccctg cagagcggca cagccaaga gtctgtgacc  480
gagcaggact ccaaggattc cacctacagc ctgtctagca ccctgactct gagcaaggcc  540
gactacgaga agcacaaggt gtacgcctgc gaagtgacac accagggact gagcagccct  600
gtgaccaaga gcttcaatcg gggcgagtgc                                    630

SEQ ID NO: 284       moltype = DNA   length = 648
FEATURE              Location/Qualifiers
misc_feature         1..648
                     note = AMM01 light chain coding sequence without signal
                     sequence in hu-emAb-AMM01-AAV
source               1..648
                     mol_type = other DNA
                     organism = synthetic construct
SEQUENCE: 284
tcctatgagc tgactcagcc accctcagtg tcagtggccc cggggcagag ggccacaatt  60
acctgtgggg gacacaacat cggagctaaa aatgtccact ggtaccagca gaagccaggc  120
caggcccctg tcctggtcat ccaatatgat agcgaccggc cctcagggat ccctgagcga  180
ttctctcggct ccaactctgg gagcacggcc accctgacca tcagcaggct cgaagccggg  240
gatgaggccg actattactg tcaggtgtgg gatagtggtc gtgggcatcc cctttatgtc  300
ttcggaggtg ggaccaaggt caccgtccta ggtcagccca aggccaaccc cactgtcact  360
ctgttcccac cctcgagtga ggagcttcaa gccaacaagg ccacactggt gtgtctcata  420
agtgacttct acccgggagc cgtgacagtg gcctggaagg cagatagcag ccccgtcaag  480
gcgggagtgg agaccaccac accctccaaa caaagcaaca caagtacgc ggccagcagc  540
tacctgagcc tgacgcctga gcagtggaag tcccacagaa gctacagctg ccaggtcacg  600
catgaaggga gcaccgtgga gaagacagtg gcccctacag aatgttca              648

SEQ ID NO: 285       moltype = AA   length = 213
FEATURE              Location/Qualifiers
REGION               1..213
                     note = hRSV light chain amino acid sequence without signal
                     peptide in human anti-RSV emAb AAV
source               1..213
                     mol_type = protein
                     organism = synthetic construct
SEQUENCE: 285
DIQMTQSPST LSASVGDRVT ITCKCQLSVG YMHWYQQKPG KAPKLLIYDT SKLASGVPSR  60
FSGSGSGTEF TLTISSLQPD DFATYYCFQG SGYPPTFGGG TKLEIKRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GEC                                213

SEQ ID NO: 286       moltype = AA   length = 212
FEATURE              Location/Qualifiers
REGION               1..212
                     note = mRSV kappa light chain amino acid sequence without
                     signal peptide in mouse anti-RSV emAb AAV
source               1..212
                     mol_type = protein
                     organism = synthetic construct
SEQUENCE: 286
DIQLTQSPAI MSASPGEKVT MTCSASSSVG YMHWYQQKSS TSPKLWIYDT SKLASGVPGR  60
```

-continued

```
FSGSGSGNSY SLTISSIQAE DVATYYCFRG SGYPFTFGQG TKLEIKADAA PTVSIFPPSS  120
EQLTSGGASV VCFLNNFYPK DINVKWKIDG SERQNGVLNS WTDQDSKDST YSMSSTLTLT  180
KDEYERHNSY TCEATHKTST SPIVKSFNRN EC                                212

SEQ ID NO: 287          moltype = AA   length = 210
FEATURE                 Location/Qualifiers
REGION                  1..210
                        note = VRC01 light chain amino acid sequence without signal
                         peptide in Hu-emAb-VRC01-AAV
source                  1..210
                        mol_type = protein
                        organism = synthetic construct
SEQUENCE: 287
EIVLTQSPGT LSLSPGETAI ISCRTSQYGS LAWYQQRPGQ APRLVIYSGS TRAAGIPDRF  60
SGSRWGPDYN LTISNLESGD FGVYYCQQYE FFGQGTKVQV DIKRTVAAPS VFIFPPSDEQ  120
LKSGTASVVC LLNNFYPREA KVQWKVDNAL QSGNSQESVT EQDSKDSTYS LSSTLTLSKA  180
DYEKHKVYAC EVTHQGLSSP VTKSFNRGEC                                   210

SEQ ID NO: 288          moltype = AA   length = 210
FEATURE                 Location/Qualifiers
REGION                  1..210
                        note = Medi8852 light chain amino acid sequence without
                         signal peptide in hu-emAb-Medi8852-AAV
source                  1..210
                        mol_type = protein
                        organism = synthetic construct
SEQUENCE: 288
DIQMTQSPSS LSASVGDRVT ITCRTSQSLS SYTHWYQQKP GKAPKLLIYA ASSRGSGVPS  60
RFSGSGSGTD FTLTISSLQP EDFATYYCQQ SRTFGQGTKV EIKRTVAAPS VFIFPPSDEQ  120
LKSGTASVVC LLNNFYPREA KVQWKVDNAL QSGNSQESVT EQDSKDSTYS LSSTLTLSKA  180
DYEKHKVYAC EVTHQGLSSP VTKSFNRGEC                                   210

SEQ ID NO: 289          moltype = AA   length = 216
FEATURE                 Location/Qualifiers
REGION                  1..216
                        note = AMM01 light chain amino acid sequence without signal
                         peptide in hu-emAb-AMM01-AAV
source                  1..216
                        mol_type = protein
                        organism = synthetic construct
SEQUENCE: 289
SYELTQPPSV SVAPGQRATI TCGGHNIGAK NVHWYQQKPG QAPVLVIQYD SDRPSGIPER  60
FSGSNSGSTA TLTISRVEAG DEADYYCQVW DSGRGHPLYV FGGGTKVTVL GQPKANPTVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APTECS                           216

SEQ ID NO: 290          moltype = RNA   length = 20
FEATURE                 Location/Qualifiers
misc_feature            1..20
                        note = Human _1_gRNA_1 from FIG. 11B
source                  1..20
                        mol_type = other RNA
                        organism = synthetic construct
SEQUENCE: 290
ggtcctcggg gcatgttccg                                              20

SEQ ID NO: 291          moltype = RNA   length = 20
FEATURE                 Location/Qualifiers
misc_feature            1..20
                        note = Human _1_gRNA_2 from FIG. 11B
source                  1..20
                        mol_type = other RNA
                        organism = synthetic construct
SEQUENCE: 291
gggcatgttc cgaggggacc                                              20

SEQ ID NO: 292          moltype = RNA   length = 20
FEATURE                 Location/Qualifiers
misc_feature            1..20
                        note = Human _1_gRNA_4 from FIG. 11B
source                  1..20
                        mol_type = other RNA
                        organism = synthetic construct
SEQUENCE: 292
tcctcggggc atgttccgag                                              20

SEQ ID NO: 293          moltype = RNA   length = 20
FEATURE                 Location/Qualifiers
misc_feature            1..20
```

-continued

```
                             note = Human _1_gRNA_5 from FIG. 11B
source                       1..20
                             mol_type = other RNA
                             organism = synthetic construct
SEQUENCE: 293
ggcatgttcc gaggggacct                                                        20

SEQ ID NO: 294               moltype = RNA  length = 20
FEATURE                      Location/Qualifiers
misc_feature                 1..20
                             note = Human _1_gRNA_7 from FIG. 11B
source                       1..20
                             mol_type = other RNA
                             organism = synthetic construct
SEQUENCE: 294
agcattgcag gttggtcctc                                                        20

SEQ ID NO: 295               moltype = RNA  length = 20
FEATURE                      Location/Qualifiers
misc_feature                 1..20
                             note = Human _1_gRNA_8 from FIG. 11B
source                       1..20
                             mol_type = other RNA
                             organism = synthetic construct
SEQUENCE: 295
cctgggcgga ctggccagga                                                        20

SEQ ID NO: 296               moltype = RNA  length = 20
FEATURE                      Location/Qualifiers
misc_feature                 1..20
                             note = Human _1_gRNA_9 from FIG. 11B
source                       1..20
                             mol_type = other RNA
                             organism = synthetic construct
SEQUENCE: 296
actggggtgc cttgaggatc                                                        20

SEQ ID NO: 297               moltype = RNA  length = 20
FEATURE                      Location/Qualifiers
misc_feature                 1..20
                             note = Human _1_gRNA_10 from FIG. 11B
source                       1..20
                             mol_type = other RNA
                             organism = synthetic construct
SEQUENCE: 297
ccccagtgcc catcccctcc                                                        20

SEQ ID NO: 298               moltype = RNA  length = 20
FEATURE                      Location/Qualifiers
misc_feature                 1..20
                             note = Human _1_gRNA_11 from FIG. 11B
source                       1..20
                             mol_type = other RNA
                             organism = synthetic construct
SEQUENCE: 298
ctaagacccc tggtttgttc                                                        20

SEQ ID NO: 299               moltype = RNA  length = 20
FEATURE                      Location/Qualifiers
misc_feature                 1..20
                             note = Human _1_gRNA_12 from FIG. 11B
source                       1..20
                             mol_type = other RNA
                             organism = synthetic construct
SEQUENCE: 299
tgtggatttt ccgatgcctt                                                        20

SEQ ID NO: 300               moltype = RNA  length = 20
FEATURE                      Location/Qualifiers
misc_feature                 1..20
                             note = Human _1_gRNA_13 from FIG. 11B
source                       1..20
                             mol_type = other RNA
                             organism = synthetic construct
SEQUENCE: 300
aggaccaacc tgcaatgctc                                                        20

SEQ ID NO: 301               moltype = RNA  length = 20
FEATURE                      Location/Qualifiers
```

-continued

```
misc_feature        1..20
                    note = Human _1_gRNA_14 from FIG. 11B
source              1..20
                    mol_type = other RNA
                    organism = synthetic construct
SEQUENCE: 301
ctcaggttgg gtgcgtctga                                                      20

SEQ ID NO: 302      moltype = RNA  length = 20
FEATURE             Location/Qualifiers
misc_feature        1..20
                    note = Human _1_gRNA_15
source              1..20
                    mol_type = other RNA
                    organism = synthetic construct
SEQUENCE: 302
ccctcctggc cagtccgccc                                                      20

SEQ ID NO: 303      moltype = RNA  length = 20
FEATURE             Location/Qualifiers
misc_feature        1..20
                    note = Human _1_gRNA_16 from FIG. 11B
source              1..20
                    mol_type = other RNA
                    organism = synthetic construct
SEQUENCE: 303
ggccaggagg ggatgggcac                                                      20

SEQ ID NO: 304      moltype = RNA  length = 20
FEATURE             Location/Qualifiers
misc_feature        1..20
                    note = Human _1_gRNA_17
source              1..20
                    mol_type = other RNA
                    organism = synthetic construct
SEQUENCE: 304
gagatgcctg aacaaaccag                                                      20

SEQ ID NO: 305      moltype = RNA  length = 20
FEATURE             Location/Qualifiers
misc_feature        1..20
                    note = Human _1_gRNA_18 from FIG. 11B
source              1..20
                    mol_type = other RNA
                    organism = synthetic construct
SEQUENCE: 305
aggggtctta gtgatggctg                                                      20

SEQ ID NO: 306      moltype = RNA  length = 20
FEATURE             Location/Qualifiers
misc_feature        1..20
                    note = Human _1_gRNA_19 from FIG. 11B
source              1..20
                    mol_type = other RNA
                    organism = synthetic construct
SEQUENCE: 306
atgggcactg gggtgccttg                                                      20

SEQ ID NO: 307      moltype = RNA  length = 20
FEATURE             Location/Qualifiers
misc_feature        1..20
                    note = Human _1_gRNA_20 from FIG. 11B
source              1..20
                    mol_type = other RNA
                    organism = synthetic construct
SEQUENCE: 307
ttccgatgcc tttggaaaat                                                      20

SEQ ID NO: 308      moltype = RNA  length = 20
FEATURE             Location/Qualifiers
misc_feature        1..20
                    note = Human_2_gRNA_1 from FIG. 12B
source              1..20
                    mol_type = other RNA
                    organism = synthetic construct
SEQUENCE: 308
ctgacgccgc atcggtgatt                                                      20

SEQ ID NO: 309      moltype = RNA  length = 20
```

```
FEATURE                 Location/Qualifiers
misc_feature            1..20
                        note = Human_2_gRNA_2 from FIG. 12B
source                  1..20
                        mol_type = other RNA
                        organism = synthetic construct
SEQUENCE: 309
ttagacaagg gcgatgccag                                              20

SEQ ID NO: 310          moltype = RNA   length = 20
FEATURE                 Location/Qualifiers
misc_feature            1..20
                        note = Human_2_gRNA_3 from FIG. 12B
source                  1..20
                        mol_type = other RNA
                        organism = synthetic construct
SEQUENCE: 310
cgtgcgacct ctccttcaaa                                              20

SEQ ID NO: 311          moltype = RNA   length = 20
FEATURE                 Location/Qualifiers
misc_feature            1..20
                        note = Human_2_gRNA_4 from FIG. 12B
source                  1..20
                        mol_type = other RNA
                        organism = synthetic construct
SEQUENCE: 311
agcatatctt ctgcaccaag                                              20

SEQ ID NO: 312          moltype = RNA   length = 20
FEATURE                 Location/Qualifiers
misc_feature            1..20
                        note = Human_2_gRNA_5 from FIG. 12B
source                  1..20
                        mol_type = other RNA
                        organism = synthetic construct
SEQUENCE: 312
atattccacc caggtagtgg                                              20

SEQ ID NO: 313          moltype = RNA   length = 20
FEATURE                 Location/Qualifiers
misc_feature            1..20
                        note = Human_2_gRNA_6 from FIG. 12B
source                  1..20
                        mol_type = other RNA
                        organism = synthetic construct
SEQUENCE: 313
gtgcgacctc tccttcaaat                                              20

SEQ ID NO: 314          moltype = RNA   length = 20
FEATURE                 Location/Qualifiers
misc_feature            1..20
                        note = Human_2_gRNA_7 from FIG. 12B
source                  1..20
                        mol_type = other RNA
                        organism = synthetic construct
SEQUENCE: 314
aggtcccctt gctctagaag                                              20

SEQ ID NO: 315          moltype = RNA   length = 20
FEATURE                 Location/Qualifiers
misc_feature            1..20
                        note = Human_2_gRNA_8 from FIG. 12B
source                  1..20
                        mol_type = other RNA
                        organism = synthetic construct
SEQUENCE: 315
ctctagataa cagtcatcat                                              20

SEQ ID NO: 316          moltype = RNA   length = 20
FEATURE                 Location/Qualifiers
misc_feature            1..20
                        note = Human_2_gRNA_9 from FIG. 12B
source                  1..20
                        mol_type = other RNA
                        organism = synthetic construct
SEQUENCE: 316
ttgtctaagt cattgactgt                                              20
```

-continued

```
SEQ ID NO: 317        moltype = RNA   length = 20
FEATURE               Location/Qualifiers
misc_feature          1..20
                      note = Human_2_gRNA_10 from FIG. 12B
source                1..20
                      mol_type = other RNA
                      organism = synthetic construct
SEQUENCE: 317
ccaaagcgat ttatggtaaa                                              20

SEQ ID NO: 318        moltype = RNA   length = 20
FEATURE               Location/Qualifiers
misc_feature          1..20
                      note = Human_2_gRNA_11 from FIG. 12B
source                1..20
                      mol_type = other RNA
                      organism = synthetic construct
SEQUENCE: 318
tcttttgagt gaccattgtc                                              20

SEQ ID NO: 319        moltype = RNA   length = 20
FEATURE               Location/Qualifiers
misc_feature          1..20
                      note = Human_2_gRNA_12 from FIG. 12B
source                1..20
                      mol_type = other RNA
                      organism = synthetic construct
SEQUENCE: 319
ccatttacca taaatcgctt                                              20

SEQ ID NO: 320        moltype = RNA   length = 20
FEATURE               Location/Qualifiers
misc_feature          1..20
                      note = Human_2_gRNA_13 from FIG. 12B
source                1..20
                      mol_type = other RNA
                      organism = synthetic construct
SEQUENCE: 320
agggcgatgc cagtggggct                                              20

SEQ ID NO: 321        moltype = RNA   length = 20
FEATURE               Location/Qualifiers
misc_feature          1..20
                      note = Human_2_gRNA_14 from FIG. 12B
source                1..20
                      mol_type = other RNA
                      organism = synthetic construct
SEQUENCE: 321
agctaaagcc atctcattgc                                              20

SEQ ID NO: 322        moltype = RNA   length = 20
FEATURE               Location/Qualifiers
misc_feature          1..20
                      note = Human_2_gRNA_15 from FIG. 12B
source                1..20
                      mol_type = other RNA
                      organism = synthetic construct
SEQUENCE: 322
ccacaacctc tgaatgggga                                              20

SEQ ID NO: 323        moltype = RNA   length = 20
FEATURE               Location/Qualifiers
misc_feature          1..20
                      note = Human_2_gRNA_16 from FIG. 12B
source                1..20
                      mol_type = other RNA
                      organism = synthetic construct
SEQUENCE: 323
ttaattgctt gatgaagagc                                              20

SEQ ID NO: 324        moltype = RNA   length = 20
FEATURE               Location/Qualifiers
misc_feature          1..20
                      note = Human_2_gRNA_17 from FIG. 12B
source                1..20
                      mol_type = other RNA
                      organism = synthetic construct
SEQUENCE: 324
tagacaaggg cgatgccagt                                              20
```

-continued

```
SEQ ID NO: 325            moltype = RNA  length = 20
FEATURE                   Location/Qualifiers
misc_feature              1..20
                          note = Human_2_gRNA_18 from FIG. 12B
source                    1..20
                          mol_type = other RNA
                          organism = synthetic construct
SEQUENCE: 325
aagctgacct agactaaaca                                            20

SEQ ID NO: 326            moltype = RNA  length = 20
FEATURE                   Location/Qualifiers
misc_feature              1..20
                          note = Human_2_gRNA_19 from FIG. 12B
source                    1..20
                          mol_type = other RNA
                          organism = synthetic construct
SEQUENCE: 326
gcaggaaccc ggcaatgaga                                            20

SEQ ID NO: 327            moltype = RNA  length = 20
FEATURE                   Location/Qualifiers
misc_feature              1..20
                          note = Human_2_gRNA_20 from FIG. 12B
source                    1..20
                          mol_type = other RNA
                          organism = synthetic construct
SEQUENCE: 327
tctgttccga atcaccgatg                                            20

SEQ ID NO: 328            moltype = RNA  length = 20
FEATURE                   Location/Qualifiers
misc_feature              1..20
                          note = Mouse_1_gRNA_1 from FIG. 13B
source                    1..20
                          mol_type = other RNA
                          organism = synthetic construct
SEQUENCE: 328
caactaccct tttgagaccg                                            20

SEQ ID NO: 329            moltype = RNA  length = 20
FEATURE                   Location/Qualifiers
misc_feature              1..20
                          note = Mouse_1_gRNA_3 from FIG. 13B
source                    1..20
                          mol_type = other RNA
                          organism = synthetic construct
SEQUENCE: 329
tatacagtat ccgatgcata                                            20

SEQ ID NO: 330            moltype = RNA  length = 20
FEATURE                   Location/Qualifiers
misc_feature              1..20
                          note = Mouse_1_gRNA_4 from FIG. 13B
source                    1..20
                          mol_type = other RNA
                          organism = synthetic construct
SEQUENCE: 330
catctagcct cggtctcaaa                                            20

SEQ ID NO: 331            moltype = RNA  length = 20
FEATURE                   Location/Qualifiers
misc_feature              1..20
                          note = Mouse_1_gRNA_5 from FIG. 13B
source                    1..20
                          mol_type = other RNA
                          organism = synthetic construct
SEQUENCE: 331
cactctttgt ccctatgcat                                            20

SEQ ID NO: 332            moltype = RNA  length = 20
FEATURE                   Location/Qualifiers
misc_feature              1..20
                          note = Mouse_1_gRNA_6 from FIG. 13B
source                    1..20
                          mol_type = other RNA
                          organism = synthetic construct
SEQUENCE: 332
```

-continued

```
atctagcctc ggtctcaaaa                                                20

SEQ ID NO: 333          moltype = RNA  length = 20
FEATURE                 Location/Qualifiers
misc_feature            1..20
                        note = Mouse_1_gRNA_7 from FIG. 13B
source                  1..20
                        mol_type = other RNA
                        organism = synthetic construct
SEQUENCE: 333
aagtttttaaa caatctagtg                                               20

SEQ ID NO: 334          moltype = RNA  length = 20
FEATURE                 Location/Qualifiers
misc_feature            1..20
                        note = Mouse_1_gRNA_8 from FIG. 13B
source                  1..20
                        mol_type = other RNA
                        organism = synthetic construct
SEQUENCE: 334
aagatgctaa aacaatccta                                                20

SEQ ID NO: 335          moltype = RNA  length = 20
FEATURE                 Location/Qualifiers
misc_feature            1..20
                        note = Mouse_1_gRNA_9 from FIG. 13B
source                  1..20
                        mol_type = other RNA
                        organism = synthetic construct
SEQUENCE: 335
tgctaaaaca atcctatggc                                                20

SEQ ID NO: 336          moltype = RNA  length = 20
FEATURE                 Location/Qualifiers
misc_feature            1..20
                        note = Mouse_1_gRNA_10 from FIG. 13B
source                  1..20
                        mol_type = other RNA
                        organism = synthetic construct
SEQUENCE: 336
aagtccctat cccatcatcc                                                20

SEQ ID NO: 337          moltype = RNA  length = 20
FEATURE                 Location/Qualifiers
misc_feature            1..20
                        note = Mouse_1_gRNA_11 from FIG. 13B
source                  1..20
                        mol_type = other RNA
                        organism = synthetic construct
SEQUENCE: 337
gggagaaagg catctagcct                                                20

SEQ ID NO: 338          moltype = RNA  length = 20
FEATURE                 Location/Qualifiers
misc_feature            1..20
                        note = Mouse_1_gRNA_12 from FIG. 13B
source                  1..20
                        mol_type = other RNA
                        organism = synthetic construct
SEQUENCE: 338
tgagcattgc agactaatct                                                20

SEQ ID NO: 339          moltype = RNA  length = 20
FEATURE                 Location/Qualifiers
misc_feature            1..20
                        note = Mouse_1_gRNA_13 from FIG. 13B
source                  1..20
                        mol_type = other RNA
                        organism = synthetic construct
SEQUENCE: 339
ttagttgtgg aatatacttc                                                20

SEQ ID NO: 340          moltype = RNA  length = 20
FEATURE                 Location/Qualifiers
misc_feature            1..20
                        note = Mouse_1_gRNA_14 from FIG. 13B
source                  1..20
                        mol_type = other RNA
                        organism = synthetic construct
```

-continued

```
SEQUENCE: 340
tggtggagtc cctggatgat                                                20

SEQ ID NO: 341        moltype = RNA  length = 20
FEATURE               Location/Qualifiers
misc_feature          1..20
                      note = Mouse_1_gRNA_15 from FIG. 13B
source                1..20
                      mol_type = other RNA
                      organism = synthetic construct
SEQUENCE: 341
gtggagataa tctgtcctaa                                                20

SEQ ID NO: 342        moltype = RNA  length = 20
FEATURE               Location/Qualifiers
misc_feature          1..20
                      note = Mouse_1_gRNA_16 from FIG. 13B
source                1..20
                      mol_type = other RNA
                      organism = synthetic construct
SEQUENCE: 342
agtccctatc ccatcatcca                                                20

SEQ ID NO: 343        moltype = RNA  length = 20
FEATURE               Location/Qualifiers
misc_feature          1..20
                      note = Mouse_1_gRNA_17 from FIG. 13B
source                1..20
                      mol_type = other RNA
                      organism = synthetic construct
SEQUENCE: 343
atcttggata tttgtccctg                                                20

SEQ ID NO: 344        moltype = RNA  length = 20
FEATURE               Location/Qualifiers
misc_feature          1..20
                      note = Mouse_1_gRNA_18 from FIG. 13B
source                1..20
                      mol_type = other RNA
                      organism = synthetic construct
SEQUENCE: 344
gggatagttg gggctgtagt                                                20

SEQ ID NO: 345        moltype = RNA  length = 20
FEATURE               Location/Qualifiers
misc_feature          1..20
                      note = Mouse_1_gRNA_19 from FIG. 13B
source                1..20
                      mol_type = other RNA
                      organism = synthetic construct
SEQUENCE: 345
caggtaagaa tggcctctcc                                                20

SEQ ID NO: 346        moltype = RNA  length = 20
FEATURE               Location/Qualifiers
misc_feature          1..20
                      note = Mouse_1_gRNA_20 from FIG. 13B
source                1..20
                      mol_type = other RNA
                      organism = synthetic construct
SEQUENCE: 346
tctctcagcc ggctccctca                                                20

SEQ ID NO: 347        moltype = RNA  length = 20
FEATURE               Location/Qualifiers
misc_feature          1..20
                      note = MOUSE_2_gRNA__1 from FIG. 14B
source                1..20
                      mol_type = other RNA
                      organism = synthetic construct
SEQUENCE: 347
ccgaaaccag gcaccgcaaa                                                20

SEQ ID NO: 348        moltype = RNA  length = 20
FEATURE               Location/Qualifiers
misc_feature          1..20
                      note = MOUSE_2_gRNA__2 from FIG. 14B
source                1..20
                      mol_type = other RNA
```

```
                        organism = synthetic construct
SEQUENCE: 348
caccgcaaat ggtaagccag                                                20

SEQ ID NO: 349          moltype = RNA  length = 20
FEATURE                 Location/Qualifiers
misc_feature            1..20
                        note = MOUSE_2_gRNA__3 from FIG. 14B
source                  1..20
                        mol_type = other RNA
                        organism = synthetic construct
SEQUENCE: 349
ggcttaccat ttgcggtgcc                                                20

SEQ ID NO: 350          moltype = RNA  length = 20
FEATURE                 Location/Qualifiers
misc_feature            1..20
                        note = MOUSE_2_gRNA__4 from FIG. 14B
source                  1..20
                        mol_type = other RNA
                        organism = synthetic construct
SEQUENCE: 350
tgcggtgcct ggtttcggag                                                20

SEQ ID NO: 351          moltype = RNA  length = 20
FEATURE                 Location/Qualifiers
misc_feature            1..20
                        note = MOUSE_2_gRNA__5 from FIG. 14B
source                  1..20
                        mol_type = other RNA
                        organism = synthetic construct
SEQUENCE: 351
cagctatgct acgctgtgtt                                                20

SEQ ID NO: 352          moltype = RNA  length = 20
FEATURE                 Location/Qualifiers
misc_feature            1..20
                        note = MOUSE_2_gRNA__6 from FIG. 14B
source                  1..20
                        mol_type = other RNA
                        organism = synthetic construct
SEQUENCE: 352
aaggacagtg cttagatccg                                                20

SEQ ID NO: 353          moltype = RNA  length = 20
FEATURE                 Location/Qualifiers
misc_feature            1..20
                        note = MOUSE_2_gRNA__7 from FIG. 14B
source                  1..20
                        mol_type = other RNA
                        organism = synthetic construct
SEQUENCE: 353
tcagtcagtc agtgacgtga                                                20

SEQ ID NO: 354          moltype = RNA  length = 20
FEATURE                 Location/Qualifiers
misc_feature            1..20
                        note = MOUSE_2_gRNA__8 from FIG. 14B
source                  1..20
                        mol_type = other RNA
                        organism = synthetic construct
SEQUENCE: 354
catgctggtt ggtggttgag                                                20

SEQ ID NO: 355          moltype = RNA  length = 20
FEATURE                 Location/Qualifiers
misc_feature            1..20
                        note = MOUSE_2_gRNA__9 from FIG. 14B
source                  1..20
                        mol_type = other RNA
                        organism = synthetic construct
SEQUENCE: 355
tcttttgagt accgttgtct                                                20

SEQ ID NO: 356          moltype = RNA  length = 20
FEATURE                 Location/Qualifiers
misc_feature            1..20
                        note = MOUSE_2_gRNA__10 from FIG. 14B
source                  1..20
```

-continued

```
                        mol_type = other RNA
                        organism = synthetic construct
SEQUENCE: 356
tggcccattc aacaataagc                                        20

SEQ ID NO: 357         moltype = RNA  length = 20
FEATURE                Location/Qualifiers
misc_feature           1..20
                        note = MOUSE_2_gRNA__11 from FIG. 14B
source                 1..20
                        mol_type = other RNA
                        organism = synthetic construct
SEQUENCE: 357
ctgggccgct aagctaaact                                        20

SEQ ID NO: 358         moltype = RNA  length = 20
FEATURE                Location/Qualifiers
misc_feature           1..20
                        note = MOUSE_2_gRNA__12 from FIG. 14B
source                 1..20
                        mol_type = other RNA
                        organism = synthetic construct
SEQUENCE: 358
gccagcctag tttagcttag                                        20

SEQ ID NO: 359         moltype = RNA  length = 20
FEATURE                Location/Qualifiers
misc_feature           1..20
                        note = MOUSE_2_gRNA__13 from FIG. 14B
source                 1..20
                        mol_type = other RNA
                        organism = synthetic construct
SEQUENCE: 359
tgaagtagac tgtaatgaac                                        20

SEQ ID NO: 360         moltype = RNA  length = 20
FEATURE                Location/Qualifiers
misc_feature           1..20
                        note = MOUSE_2_gRNA__14 from FIG. 14B
source                 1..20
                        mol_type = other RNA
                        organism = synthetic construct
SEQUENCE: 360
gacctgggaa tgtatggttg                                        20

SEQ ID NO: 361         moltype = RNA  length = 20
FEATURE                Location/Qualifiers
misc_feature           1..20
                        note = MOUSE_2_gRNA__15 from FIG. 14B
source                 1..20
                        mol_type = other RNA
                        organism = synthetic construct
SEQUENCE: 361
ggtatggata cgcagaagga                                        20

SEQ ID NO: 362         moltype = RNA  length = 20
FEATURE                Location/Qualifiers
misc_feature           1..20
                        note = MOUSE_2_gRNA__16 from FIG. 14B
source                 1..20
                        mol_type = other RNA
                        organism = synthetic construct
SEQUENCE: 362
gttgagagcc ctagtaagcg                                        20

SEQ ID NO: 363         moltype = RNA  length = 20
FEATURE                Location/Qualifiers
misc_feature           1..20
                        note = MOUSE_2_gRNA__17 from FIG. 14B
source                 1..20
                        mol_type = other RNA
                        organism = synthetic construct
SEQUENCE: 363
gccgctaagc taaactaggc                                        20

SEQ ID NO: 364         moltype = RNA  length = 20
FEATURE                Location/Qualifiers
misc_feature           1..20
                        note = MOUSE_2_gRNA__18 from FIG. 14B
```

-continued

```
source              1..20
                    mol_type = other RNA
                    organism = synthetic construct
SEQUENCE: 364
tcagctatgc tacgctgtgt                                          20

SEQ ID NO: 365      moltype = RNA  length = 20
FEATURE             Location/Qualifiers
misc_feature        1..20
                    note = MOUSE_2_gRNA__19 from FIG. 14B
source              1..20
                    mol_type = other RNA
                    organism = synthetic construct
SEQUENCE: 365
ttttagagcc tcgcttacta                                          20

SEQ ID NO: 366      moltype = RNA  length = 20
FEATURE             Location/Qualifiers
misc_feature        1..20
                    note = MOUSE_2_gRNA__20 from FIG. 14B
source              1..20
                    mol_type = other RNA
                    organism = synthetic construct
SEQUENCE: 366
ctctatgatt attggttaac                                          20
```

SYSTEMS TO PRODUCE B CELLS GENETICALLY MODIFIED TO EXPRESS SELECTED ANTIBODIES

CROSS-REFERENCE TO RELATED APPLICATIONS

This application is a continuation of U.S. patent application Ser. No. 16/757,707, now U.S. Pat. No. 11,578,118,filed on Apr. 20, 2020, which claims priority to International Patent Application No. PCT/US2018/056789, filed on Oct. 19, 2018, which claims priority to U.S. Provisional Patent Application Nos. 62/575,275, filed on Oct. 20, 2017, 62/580, 303, filed on Nov. 1, 2017, and 62/623,371, filed on Jan. 29, 2018, each of which is incorporated herein by reference in its entirety as if fully set forth herein.

STATEMENT REGARDING SEQUENCE LISTING

The Sequence Listing associated with this application is provided in SML format in lieu of a paper copy, and is hereby incorporated by reference into the specification. The name of the file containing the Sequence Listing is 2U88774.xml. The file is 463 KB, was created on Feb. 2, 2023, and is being submitted electronically via Patent Center.

FIELD OF THE DISCLOSURE

The current disclosure provides systems and methods to genetically modify B cells to express selected antibodies. The systems and methods can be used to: obviate the need for classical vaccinations; provide protection against infectious agents for which no vaccinations are currently available; provide protection against infectious agents when patients are otherwise immune-suppressed; and/or provide a benefit provided by a therapeutic antibody, such as in the treatment of autoimmune disorders.

BACKGROUND OF THE DISCLOSURE

Vaccines are designed to increase the immunity of a subject against a particular infection by stimulating B cells to produce antibodies against the targeted infectious agent. Routine pediatric vaccination is a long established clinical intervention with comparatively low risk and high efficacy. Unfortunately, however, vaccinations are not available for all infectious agents. As one example, every year in the United States, millions of children visit a doctor or emergency room due to infections with Respiratory Syncytial Virus (RSV).

For decades, researchers have been trying to develop a vaccine that can induce B cells to produce antibodies that are effective to protect against viruses such as RSV, human immunodeficiency virus (HIV), and Zika virus. But all efforts to induce protective antibodies have failed. The only RSV vaccine tested widely actually made infection worse: antibodies generated following vaccination did not disable the virus, but instead, enhanced its ability to infect cells. Besides RSV, HIV, and Zika virus there are a number of other infectious agents for which no effective vaccines are available.

In addition to combating infections, antibodies can also be useful as treatments for other conditions such as autoimmune diseases. However, these antibody-based therapies typically require repeated injections of the antibodies to maintain protection.

Also of note, numerous patients undergo bone marrow or hematopoietic stem cell transplants as treatments for hematological malignancies (e.g., leukemia, lymphoma, myeloma). Other patients receive infusions of genetically-modified hematopoietic stem cells that provide a therapeutic gene that the patient lacks. All of these treatments require that the patient's existing immune system be removed before administration of the transplant or genetically-modified hematopoietic stem cells, leaving a dangerous window of immune suppression before the patient's immune system repopulates following the treatment. During this time of immune suppression, patients are incredibly susceptible to infections, such as RSV, influenza, parainfluenza, and metapneumovirus (MPV). These infections are a high risk factor and associated with numerous fatalities following these treatments.

SUMMARY OF THE DISCLOSURE

The current disclosure provides systems and methods to genetically modify B cells to express selected antibodies. In particular embodiments, the selected antibodies reduce or obviate the need for existing vaccinations. In particular embodiments, the selected antibodies protect against infection from viruses for which no effective vaccination strategies are currently available (e.g., RSV, HIV, Zika). In particular embodiments, the selected antibodies reduce or obviate the need for therapeutic antibody injections, such as those administered to treat various autoimmune disorders. In particular embodiments, the selected antibodies protect immune-suppressed patients from infections. In particular embodiments, methods of the disclosure can be used to reprogram B cells to protect against hundreds of different infectious agents or pathogens, all via a single laboratory manipulation encompassing a few days.

In particular embodiments, the current disclosure provides these benefits through the targeted insertion of a genetic construct into a particular area of the B cell's endogenous genome. Importantly, the genetic modification of B cells is difficult due to the high variability of genetic sequences within these cells that are required for antibody diversity. This high degree of genetic variability makes directly targeting antibody coding regions for genetic manipulation impractical. Moreover, removing and replacing coding portions of the B cell's genome is also not effective because this approach negatively affects B cell function.

Additional challenges regarding genetically modifying B cells to express selected antibodies arise because antibodies are formed from discrete protein units, referred to as heavy chains and light chains. The different chains are encoded by different portions of the B cell genome, yet must come together to form a functioning antibody.

The current disclosure overcomes the noted challenges, among others, by identifying a constant region of the B cell genome that can be reliably targeted for genetic insertion and that, when modified, results in preferential expression of an inserted genetic construct over corresponding portions of the B cell's natural genome. This strategy overcomes sequence variability associated with the B cell genome and also overcomes the need to remove and replace portions of the endogenous B cell genome to achieve functional expression of the selected antibody. Overcoming the need to remove and replace portions of the endogenous B cell genome preserves B cell function after the genetic manipulation.

In particular embodiments, the noted area targeted for genetic insertion is an intronic region upstream or downstream of an Eμ enhancer element of SEQ ID NO: 85 (human) or SEQ ID NO: 86 (mouse). In particular embodiments, the area targeted for genetic insertion is a constant intronic region selected from SEQ ID NO: 1 or 2 (human) or SEQ ID NO: 3 or 4 (mouse). In particular embodiments, human DNA sequences within SEQ ID NO: 1 to target for genetic insertion include SEQ ID NOs: 5-24. In particular embodiments, human DNA sequences within SEQ ID NO: 2 to target for genetic insertion include SEQ ID NOs: 25-44. In particular embodiments, mouse DNA sequences within SEQ ID NO: 3 to target for genetic insertion include SEQ ID NOs: 45-64. In particular embodiments, mouse DNA sequences within SEQ ID NO: 4 to target for genetic insertion include SEQ ID NOs: 65-84. Genetic sequences particularly capable of targeting these sites for genetic modification are described within the current disclosure as guide RNA (gRNA) SEQ ID NOs: 87-89, and 290-366.

In particular embodiments, the placement and components of an inserted genetic construct result in preferential expression of the inserted genetic construct over corresponding portions of the B cell's endogenous genome. These embodiments also include elements that overcome challenges associated with portions of antibodies being encoded by different regions of the endogenous B cell genome.

In particular embodiments, the genetic constructs are inserted into one of SEQ ID NO: 1, 2, 3, and 4 and include (i) a promoter; (ii) a signal peptide; (iii) a transgene encoding an entire light chain of a selected antibody; (iv) a flexible linker or a skipping element; (v) the variable portion of the heavy chain of a selected antibody; and (vi) a splice junction that results in expression of the B cell's endogenous heavy chain constant region. In these embodiments, expressing the selected antibody as a single construct overcomes challenges associated with portions of antibodies being encoded by different areas of the endogenous B cell genome. Inclusion of a flexible linker physically links the light chain portion and the heavy chain portion of the expressed selected antibody in a manner that allows them to form a functional unit and at the same time reduces the risk of the antibody portions binding with other potentially expressed antibody chains from the B cell's endogenous genome. Use of a skipping element does not physically link the light chain portion and the heavy chain portion, but their expression in close proximity also results in association to form a functional unit while at the same time reducing the risk of the antibody portions binding with other potentially expressed antibody chains from the B cell's endogenous genome. Inclusion of a splice junction results in the selected antibody including a heavy chain constant region appropriate for the B cell's current activation and/or maturation state. In other words, the selected expressed antibodies can be expressed having any of the B cell's endogenous heavy chain constant regions, and the heavy chain constant region expressed with the selected antibody can naturally change over time.

The current disclosure also provides methods to ensure that only B cells that have been effectively genetically modified to express a selected antibody are collected for formulation and administration to patients. For example, before genetic modification, a B cell will naturally express antibodies that include either a kappa light chain or a lambda light chain. The B cell can be modified to express a light chain that is different from the kappa or lambda chain that it naturally expresses, and only those B cells that express the replacement chain are selected for formulation and administration.

The current disclosure also provides numerous additional strategies to effectively modify B cells to provide the benefits described herein. These and other strategies are described more fully in the Detailed Description below.

BRIEF DESCRIPTION OF THE FIGURES

(FIG. 2A) formalin-inactivated RSV vaccine; (FIG. 2B) "improved" RSV vaccines; and (FIG. 2C) RSV epitope scaffold vaccine.

(FIG. 3A) palivizumab injection; (FIG. 3B) adenovirus-mediated palivizumab expression; and (FIG. 3C) stem cell genetic modification and differentiation.

(FIG. 4A) B cell modification to protect against RSV; and (FIG. 4B) strategy for simultaneous protection.

FIGS. 6A, 6B. The structure of (FIG. 6A) antibody genes and (FIG. 6B) antibody proteins, highlighting a technical challenge of the disclosure: that antibodies are proteins made from two separate gene products. In particular embodiments, synthetic genetic constructs encoding selected antibodies disclosed herein utilize skipping elements (e.g., self-cleaving peptides) to address this challenge.

(FIG. 8A) An approach for endogenous IgH targeting and a resulting chimera including portions of a selected antibody (e.g., Palivizumab). (FIG. 8B) An approach for IgL inactivation. In the depicted approaches, a stop codon can be placed upstream (or as part of) the inserted genetic construct.

In FIG. 9, the constant regions are individually denoted to highlight that the inserted genetic construct can be expressed with any of the potential heavy chain constant regions.

FIG. 11A, 11B. (FIG. 11A) the human Eμ intronic enhancer (SEQ ID NO: 85) and human DNA sequence to target for genetic insertion including from IGHJ6 to Eμ intronic enhancer (SEQ ID NO: 1); (FIG. 11B) exemplary associated gRNA (e.g., sgRNA) target sites (SEQ ID NOs. 5-24) and gRNA sequences (SEQ ID NOs: 88, 89, and 290-307).

FIGS. 12A, 12B. (FIG. 12A) Human DNA sequence to target for genetic insertion including from Eμ intronic enhancer to switch region (SEQ ID NO: 2); (FIG. 12B) exemplary associated gRNA (e.g., sgRNA) target sites (SEQ ID NOs. 25-44) and gRNA sequences (SEQ ID NOs: 308-327).

FIGS. 13A, 13B. (FIG. 13A) the mouse Eμ intronic enhancer (SEQ ID NO: 86) and mouse DNA sequence to target for genetic insertion including from IGHJ4 to Eμ intronic enhancer (SEQ ID NO: 3); (FIG. 13B) exemplary associated gRNA (e.g., sgRNA) target sites (SEQ ID NOs. 45-64) and gRNA sequences (SEQ ID NOs: 87, and 328-346).

FIGS. 14A, 14B. (FIG. 14A) Mouse DNA sequence to target for genetic insertion including from Eμ intronic enhancer to switch region (SEQ ID NO: 4); (FIG. 14B) exemplary associated gRNA (e.g., sgRNA) target sites (SEQ ID NOs. 65-84) and gRNA sequences (SEQ ID NOs: 347-366).

FIG. 15A is a schematic depicting insertion of a genetic construct encoding an anti-RSV antibody into an endogenous heavy chain locus, utilizing a CRISPR/Cas9 gene-editing system. The genetic construct can include homology arms or stitches, which are nucleotide overhangs that are homologous to genomic DNA at the insertion site. FIG. 15B depicts additional examples of DNA repair templates including sequences flanked by sgRNA target sites to generate double stranded DNA breaks flanking an inserted sequence in concert with Cas9/sgRNA cutting of the genome (top), single stranded DNA containing long homology arms flanking an inserted sequence (middle), and short homology arms flanking an inserted sequence produced by annealing of a DNA oligo (bottom).

FIGS. 18A-18C. Efficient Cas9 cutting of a targeted intronic region in mouse and human B cells. Electroporation with Cas9/sgRNA ribonuclear protein complexes mediated effective cutting in mouse and human B cells. Cells were electroporated with Cas9/sgRNA complexes. Editing efficiency was assessed at 3 days post electroporation by Tracking of Indels by Decomposition (TIDE) in: (FIG. 18A) mouse B cell line (A20); (FIG. 18B) primary B cells; and (FIG. 18C) human B cell line (Ramos).

(FIG. 22A) Primary B cells were primed 24 hours, co-incubated with adeno-associated virus (AAV) for 12 hours, washed and either electroporated or transferred directly into secondary culture for 3 days before analysis of mCherry expression. (FIG. 22B) Primary B cells were primed for 24 hours, mock electroporated, or electroporated with template+Cas9/sgRNA and transferred to secondary culture for 5 days before analysis of mCherry expression.

FIGS. 23A-23E. Insertion of a novel genetic construct encoding a functional antibody into mouse and human B cell lines enables expression of surface bound and secreted antibody. (FIG. 23A) Diagram of the IgH locus showing site for insertion of partial antibody construct, as well as depictions of a surface bound and secreted antibody. emAb=synthetic antibody, herein used interchangeably with synAb. (FIG. 23B) Staining of unmodified or anti-RSV synthetic antibody (αRSV synAb) modified mouse A20 B cell lines with the RSV-prefusion-F protein tetramer (RSV-Tetramer) and anti-Streptag II tetramer (αTagAb Tetramer). (FIG. 23C) Staining of unmodified or anti-RSV synAb modified human RAMOS B cell lines with the RSV-prefusion tetramer and anti-Streptag II antibody tetramer. (FIG. 23D) ELISA for binding of antibody to RSV prefusion F protein from the culture media of unmodified or anti-RSV synAb modified A20 cell cultures. Palivizumab was used as a positive control. (FIG. 23E) ELISA for binding of antibody to RSV prefusion F protein from the culture media of unmodified or anti-RSV synAb modified RAMOS cell cultures. Palivizumab was used as a positive control.

(FIG. 24A) Surface staining of mock treated (top) or anti-RSV synAb modified mouse B cell lines (bottom) with anti-Streptag II tetramer before enrichment (left panel) and after enrichment and expansion with anti-Streptag II tetramer (middle panel) and RSV-prefusion viral protein tetramers (right panel). (FIG. 24B) ELISA for binding of antibody to RSV prefusion F protein from the culture media of unmodified or anti-RSV synAb modified mouse B cell cultures. Palivizumab was used as a positive control. Antibody binding detected with a 1:1 mixture of polyclonal anti-human Ig and anti-mouse Ig bound to HRP. (24C) Rapid expansion of enriched B synAb cells in culture with 3T3-CD40L feeder cells and IL-21.

FIGS. 25A-25I. Exemplary sequences. (FIG. 25A) Exemplary sgRNA sequences (SEQ ID NOs: 87, 88, 89), genome homology regions (SEQ ID NOs: 90-95), and splicing oligonucleotides (SEQ ID NOs: 96-101); (FIG. 25B) human anti-RSV-emAb AAV (2531 bp (SEQ ID NO: 102) and associated nucleotide and protein sequences (SEQ ID NOs: 110-126, 280, 285)); (FIG. 25C) mouse anti-RSV-emAb AAV (3134 bp (SEQ ID NO: 103) and associated nucleotide and protein sequences (SEQ ID NOs: 127-141, 281, 286)); (FIG. 25D) mouse emAb-RSV-dsDNA (1736 bp (SEQ ID NO: 104) and associated nucleotide and protein sequences (SEQ ID NOs: 142-144)); (FIG. 25E) human emAb-VRC01-AAV (2551 bp (SEQ ID NO: 105) and associated nucleotide and protein sequences (SEQ ID NOs: 145-152, 282, 287)); (FIG. 25F) human-emAb-Medi8852-AAV (2544 bp (SEQ ID NO: 106) and associated nucleotide and protein sequences (SEQ ID NOs: 153-160, 283, 288)); (FIG. 25G) human-emAb-AMM01-AAV (2555 bp (SEQ ID NO: 107) and associated nucleotide and protein sequences (SEQ ID NOs: 161-169, 284, 289)); (FIG. 25H) Balb/C mRSV-splice integration sequence (2261 bp (SEQ ID NO: 108) and associated nucleotide and protein sequences (SEQ ID NOs: 170-172)); and (FIG. 25I) TT-hRSV-T7-integrated sequence (1707 bp (SEQ ID NO: 109) and associated nucleotide and protein sequences (SEQ ID NOs: 173-175)).

(FIG. 26A) Targeted area upstream of the Eμ enhancer for insertion of a new antibody cassette; by targeting this region, inserted emAb genes can be driven by a native (but inserted) IgH promoter, maximizing the native control of immunoglobin expression. To enable one-hit insertion and minimize off-target interactions, emAb constructs were expressed as a single chain fusion. This fusion consists of a full light chain sequence, linked to the variable region of the heavy chain with a 57 amino acid glycine-serine linker. Physically linking the light and heavy chains minimizes the possibility of misspairing between an inserted emAb and endogenous light chain. An optimized splice junction allows emAbs to splice to downstream endogenous IgH constant regions. This allows emAbs to be expressed as any of the heavy chain isotype classes. (FIG. 26B) The Burkitts-lymphoma derived B cell line natively expresses surface and secreted forms of IgM paired with a lambda light chain. Expression of an engineered αRSV-emAb derived from Palivizumab was detected using monomeric RSV-F protein and streptactin, a modified streptavidin with high affinity for the StreptagII motifs in the linker. αRSV-emAb modified RAMOS cells expressed the engineered RSV-specific antibody, which could be detected on the surface of cells. (FIG. 26C) The engineered RSV-specific antibody was also detected in secreted form in the supernatant. (FIG. 26D) αRSV-emAb modified cells but not control cells exhibited rapid and sustained calcium signaling in response to protein antigen.

FIGS. 27A-27G. Human B cells are efficiently genetically-modified to express single chain emAb by paired cas9-sgRNA and AAV template delivery. (FIG. 27A) Schematic representation of human cell engineering process. Day 0: B cells are isolated from PBMC and primed with CD40L, IL2, IL10, IL15, and CpG oligonucleotides. Day 2: cells are electroporated with cas9/sgRNA RNP and treated with AAV encoding the emAb HR template 1 hr post electroporation, followed by culture as described for day 0. Day 4: cells are selected on antigen binding or tag expression. Day 4-15L: selected cells are expanded on irradiated feeder cells expressing CD40L, IL2, and IL21, supplemented with IL15. Days 15-18: Cells transitioned to feeder-free differentiation culture with IL6, IL15, and IFNγ. (FIG. 27B) Indel frequency in B cells from 6 independent PBMC donors treated with emAb-targeting Cas9/sgRNA RNPs. (FIG. 27C) All human SNPs with an reported frequency across the targeting sgRNA site. (FIG. 27D) Representative FACS for binding of RSV-F prefusion monomer to control cultured or RSV-emAb genetically-modified human B cells at day 4 of culture. (FIG. 27E) Frequency of RSV-emAb B cells after engineering of B cells from 6 independent donors. (FIG. 27F) FACS for plasma cell markers (CD19, CD27, CD38 and CD138) in primed cells (Day 2) and cells differentiated in vitro (Day 18). (FIG. 27G) ELISA for secreted anti-HA-stem antibody in the culture media of control B cells or influenza targeted MED18852-emAb B cells at day 18 of culture.

(FIG. 29A) Diagram of RAMOS IgH alleles: one productive allele containing an emAb target site, and one allele with a c-myc translocation eliminating the emAb target site. (FIG. 29B) Flow cytometry showing surface expression of lambda light chain and RSV-F antigen binding in input RAMOS cells (gated on CD79b+), and αRSV-emAb engineered RAMOS cells (gated on CD79b+/RSV-F+). (FIG. 29C) Diagram of primary IgH alleles: one productive allele, and one non-productive allele without functional recombined VDJ, both of which contain an emAb target site. (FIG. 29D) Flow cytometry showing surface expression of A light chain and RSV-F antigen binding on input sorted A light chain+B cells (gated on CD79b+) and αRSV-emAb engineered B cells (gated on CD79b+/RSV-F+).

FIG. 30A-30E. Engineering of primary mouse B cells with an αRSV-emAb cassette (FIG. 30A) Schematic representation of the mouse B cell engineering process. Day 0: B cells are isolated from Spleen and peripheral lymph nodes (PLN) via negative selection and primed with CD40L-HA, anti-HA mAb, and IL4. Day 1: cells are electroporated with cas9/sgRNA RNP together with dsDNA (dsDNA condition), or cas9/sgRNA RNP alone followed by treatment with AAV containing the emAb HR template 1 hr post electroporation (AAV condition). Cells were then maintained in culture as described for day 0. Day 3: cells are selected on antigen binding or tag expression. Day 4-8L: selected cells are expanded on irradiated feeder cells expressing CD40L, supplemented with IL-21. (FIG. 30B) Indel percentage in B cells treated with IgH targeting cas9/sgRNA RNP. (FIG. 30C) Representative FACS for binding to monomeric pre-fusion-RSV-F protein in control B cells, or emAb B cells engineered using a dsDNA or AAV template. (FIG. 30D) Frequency of emAb cells in B cells engineered with dsDNA or AAV templates. (FIG. 30E) Anti-RSV specific secreted antibody in the supernatant of control B cells, or B cells engineered with using a dsDNA or AAV template.

(FIG. 31A) Schematic representation of antiviral protection by transferred emAb cells. Day 0: $1.5 \times 10^7$ enriched RSV-emAb B cells are transferred via I.P. injection. Day 5: Palivizumab I.P. injection at 15 mg/kg. Day 6: Blood draw to measure antiviral Ab titers.

Day 7: intranasal challenge with $10^6$ pfu RSV virus. Day 12: measurement of viral titer in lungs. (FIG. 31B) Surface expression of RSV-emAb receptor before or 24 hours after transfer of RSV-emAb cells measured with RSV-F monomer and streptactin tag binding. (FIG. 31C) Plasma titer of αRSV-F antibodies in mice at day 6. (FIG. 31D) Viral titers of RSV in the lungs of mice with no cells transferred, with αRSV-emAb B cells, with control B cells, or with 15 mg/kg Palivizumab delivered I.P. 48 hours prior to infection.

(FIG. 32B) ELISA for serum titers of anti-RSV-F and anti-HA-stem antibodies in mice which received emAb cells (Dual transfer) versus control serum (no transfer).

DETAILED DESCRIPTION

Vaccines are designed to increase the immunity of a subject against a particular infection by stimulating B cells to produce antibodies against the targeted infectious agent. Antibodies are proteins that can provide protection against pathogens. Antibodies can bind to a pathogen and are protective when this binding interferes with the normal function of a pathogen. For example, many protective antibodies bind to a portion of a pathogen that blocks the pathogen from entering cells. Antibodies can be attached to the surface of B cells (known as B cell receptors), but exert most of their protective functions when secreted into the blood.

Pathogen can refer to any substance that can cause disease, and pathogenic can refer to the ability of a substance to cause disease. Examples of pathogens include viruses, bacteria, and fungi that can infect a host and cause disease. Other examples of pathogens include host-derived proteins or other host-derived substances that cause disease, such as tumor necrosis factor alpha (TNFα), an inflammatory molecule associated with numerous autoimmune conditions (e.g., arthritis) and beta amyloid plaques, which are fibrous proteins that accumulate in the brain during Alzheimer's disease. In particular embodiments, cancer cells and/or tumors can also be referred to as pathogens or pathogenic substances, based on their ability to cause disease.

Upon exposure to a vaccine or a natural pathogen, an epitope provided in the vaccine and/or present on the pathogen can bind to a B cell receptor present on a naïve B cell. This binding can lead to activation of the B cell and production of protective antibodies.

Figure 1:
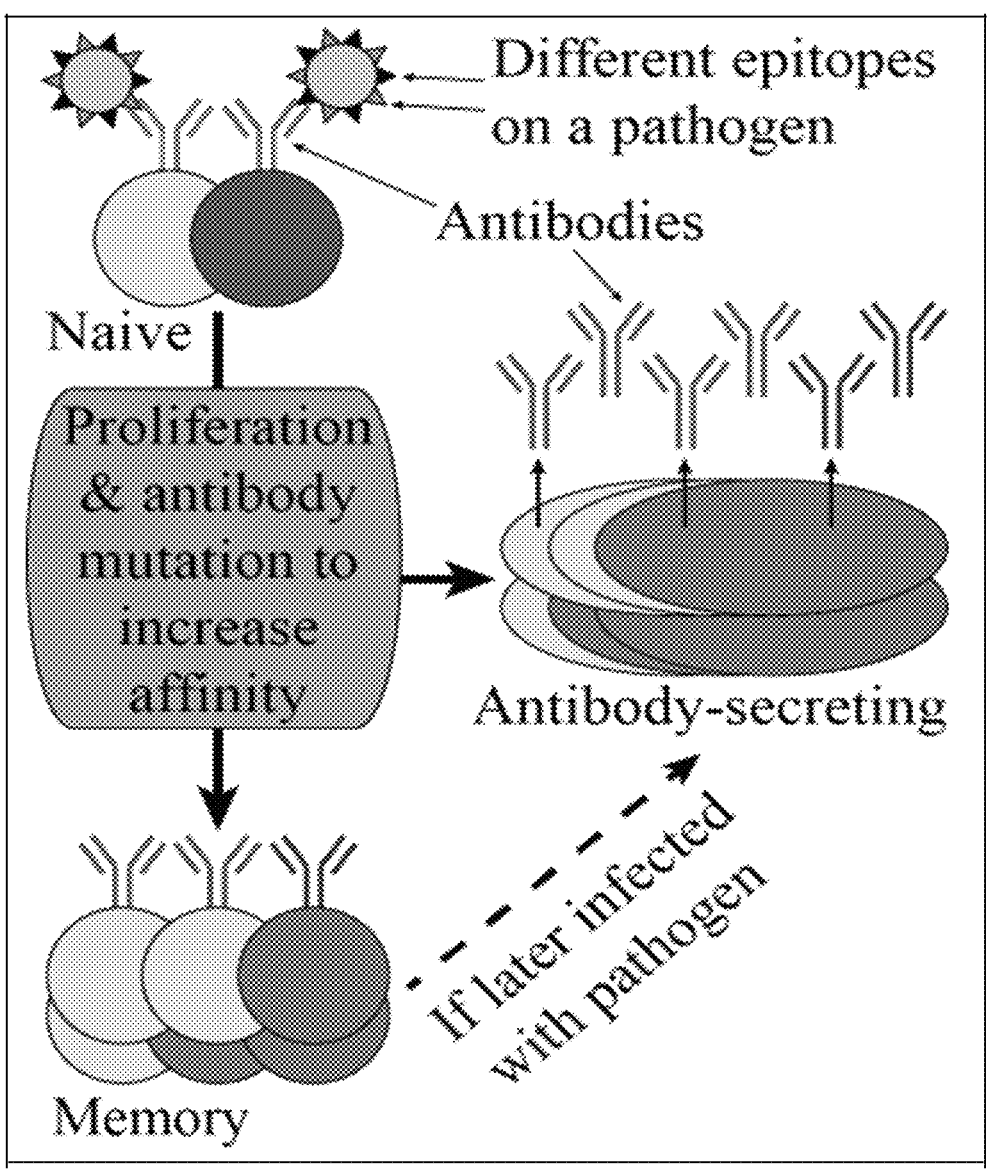
FIG. 1. Schematic of B cell response to classical vaccination strategies.

A naïve B cell refers to a B cell before it has come in contact with its epitope. Each naïve B cell expresses a unique antibody with unique epitope specificity. The unique antibody expressed by each naïve B cell is generated randomly through genetic recombination. Naïve B cells express membrane-bound antibodies (i.e., B cell receptors) and upon epitope binding, can rapidly proliferate. During proliferation and maturation, the antibody genes undergo somatic mutation, which serves to increase the affinity of epitope binding. The increase in affinity of epitope binding that occurs during B cell maturation is required for effective protection against the pathogen. A single naïve B cell is able to undergo dozens of cell divisions to create thousands of antibody-secreting B cells and memory B cells (FIG. 1) expressing the same antibody, or a related antibody that has been mutated to improve binding to the pathogen.

In addition to active antibody-secreting B cells, memory B cells are important for protection against pathogens. Memory B cells do not normally actively secrete antibodies but can rapidly differentiate into antibody-secreting cells. The rapid differentiation of memory B cells into antibody-secreting cells can help the immune system mount a rapid response to a secondary infection or a pathogen that has previously been encountered through vaccination (McHeyzer-Williams et al., Nat Rev Immunol. 2011; 12(1): 24-34; Taylor et al., Trends Immunol. 2012; 33(12):590-7). For example, memory B cells maintain protection against Hepatitis B virus when the level of antibody produced by antibody-secreting B cells has diminished (Williams et al., Vaccine. 2001; 19(28-29):4081-5; Bauer et al., Vaccine. 2006; 24(5):572-7). Thus, successful vaccines stimulate the generation of antibody-secreting B cells and long-lived memory B cells, all capable of expressing antibodies that bind to an epitope on the pathogen with high affinity.

Unfortunately, there are many infectious agents for which no vaccines are available. Examples of infectious agents without an available effective vaccine strategy include RSV, HIV, and Zika virus.

Figures 2A, 2B, 2C:
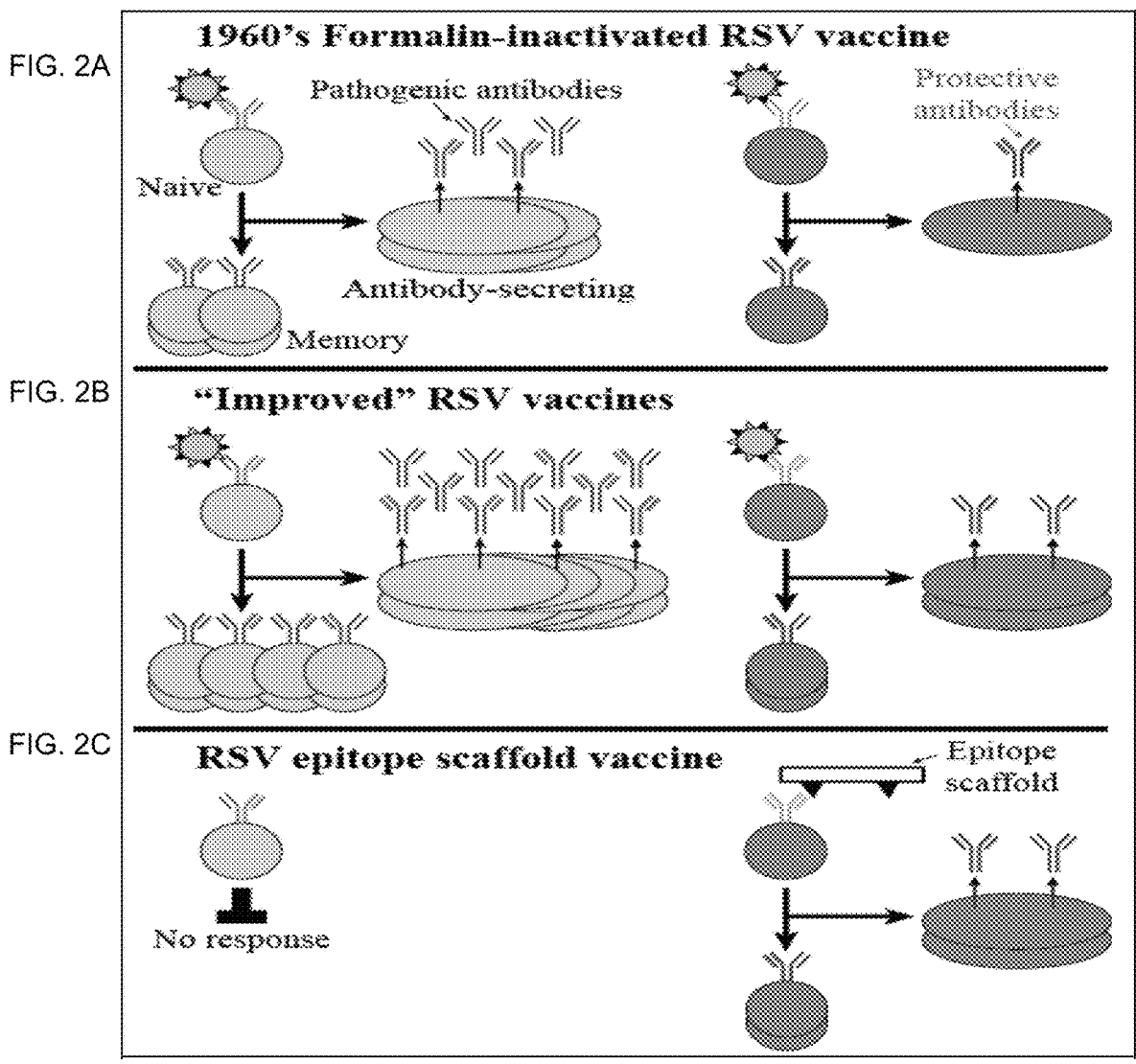
FIGS. 2A-2C. Schematics of prior art vaccination strategies against Respiratory Syncytial Virus (RSV)

Regarding RSV, the disastrous failure of a formalin-inactivated RSV vaccine in the 1960s was likely not due to a failure to induce antibody-secreting B cells and memory B cells targeting RSV. It is likely that the vaccine induced the production of antibodies that did not neutralize RSV, but instead enhanced RSV infection (FIG. 2A) (Blanco et al., Hum Vaccin. 2010; 6(6):482-92; Broadbent et al., Influenza Other Respir Viruses. 2015; 9(4):169-78). This highlights the delicate balance that must be achieved by vaccines: induction of the production of "protective" antibodies targeting certain epitopes while avoiding stimulating the production of "pathogenic" antibodies targeting the incorrect epitopes (FIG. 2A).

A 2015 analysis of the World Health Organization International Clinical Trials Registry Platform identified nine candidate RSV vaccines evaluated clinically since 2008, none of which progressed beyond Phase 2 of testing (Broadbent et al., Influenza Other Respir Viruses. 2015; 9(4):169-78). Amongst these, only three trials have been completed and only one has reported results. That vaccine, called MEDI-559, appears to reduce RSV infection, but respiratory symptoms were too high for further testing (Malkin et al., PLoS One. 2013; 8(10):e77104). These data suggest that while MEDI-559 induced the production of protective antibodies, it likely also induced the production of pathogenic antibodies (FIG. 2B).

Other "improved" vaccination strategies involve changing the formulation that is administered to patients. These include alternative methods to inactivate/attenuate the virus, and changes to the adjuvant aimed at increasing the inflammatory response (Broadbent et al., Influenza Other Respir Viruses. 2015; 9(4):169-78; Garg et al., The Journal of general virology. 2014; 95(Pt 5):1043-54; Swanson et al., J Virol. 2014; 88(20):11802-10; Widjaja et al., PLoS One.

2015; 10(6):e0130829; Stewart-Jones et al., PLoS One. 2015; 10(6):e0128779). Some of these approaches have yielded increases in protective antibodies in animal models, but the possibility of inducing pathogenic antibodies makes it likely that these "improved" RSV vaccines would suffer the same fate as MEDI-559.

In an effort to focus the immune response to the epitopes targeted by protective antibodies, a recent approach has been to graft a single RSV epitope onto a non-RSV scaffold (FIG. 2C). This approach eliminates the possibility of pathogenic antibodies specific for other RSV epitopes since they are absent from the scaffold. RSV epitope scaffold vaccination of rhesus macaque resulted in the production of neutralizing antibodies by some animals, but only after 3-5 injections (Correia et al., Nature. 2014; 507(7491):201-6).

Approaches to bypass vaccination and directly provide protective antibodies have also been developed. The only clinically approved prophylactic treatment for RSV is the injection of the high affinity RSV-specific protective antibody Palivizumab (FIG. 3A) (The PREVENT Study Group. Pediatrics. 1997; 99(1):93-9; The IMpact-RSV Study Group. Pediatrics. 1998; 102(3 Pt 1):531-7). Unfortunately, the $10,000 cost of a 5-month series of Palivizumab has limited its use to children at high-risk for severe RSV infection (Meissner & Kimberlin, Pediatrics. 2013; 132(5): 915-8). Other RSV-specific antibodies designed to last up to a year are currently undergoing clinical evaluation (Influenza Other Respir Viruses. 2015; 9(4):169-78). However, yearly antibody re-injection is not feasible for life-time protection.

To eliminate the need for life-long injections, methods have been developed in which an adenoviral vector is used to transfer a gene encoding a protective antibody into muscle cells (FIG. 3B) (Schnepp & Johnson, Curr Opin HIV AIDS. 2014; 9(3):250-6). Promisingly, adenovirus-mediated expression of Palivizumab partially protected mice from RSV infection (Skaricic et al., Virology. 2008; 378(1):79-85). A limitation of this approach, however, is the high costs of manufacturing the high doses of virus necessary to achieve protective levels of antibody (24). The high doses are necessary because the expression of antibody by a muscle cell is low compared to the estimated 10,000 antibodies secreted per second by a single B cell (Helmreich et al., J Biol Chem. 1961; 236:464-73; Hibi & Dosch, Eur J Immunol. 1986; 16(2):139-45). B cells achieve this high rate of secretion by completely reprogramming their protein production machinery to focus upon antibody secretion. Without a revolution in manufacturing capability, adenovirus-mediated antibody gene transfer into muscle cells is not a realistic option for RSV prevention.

Figures 3A, 3B, 3C:
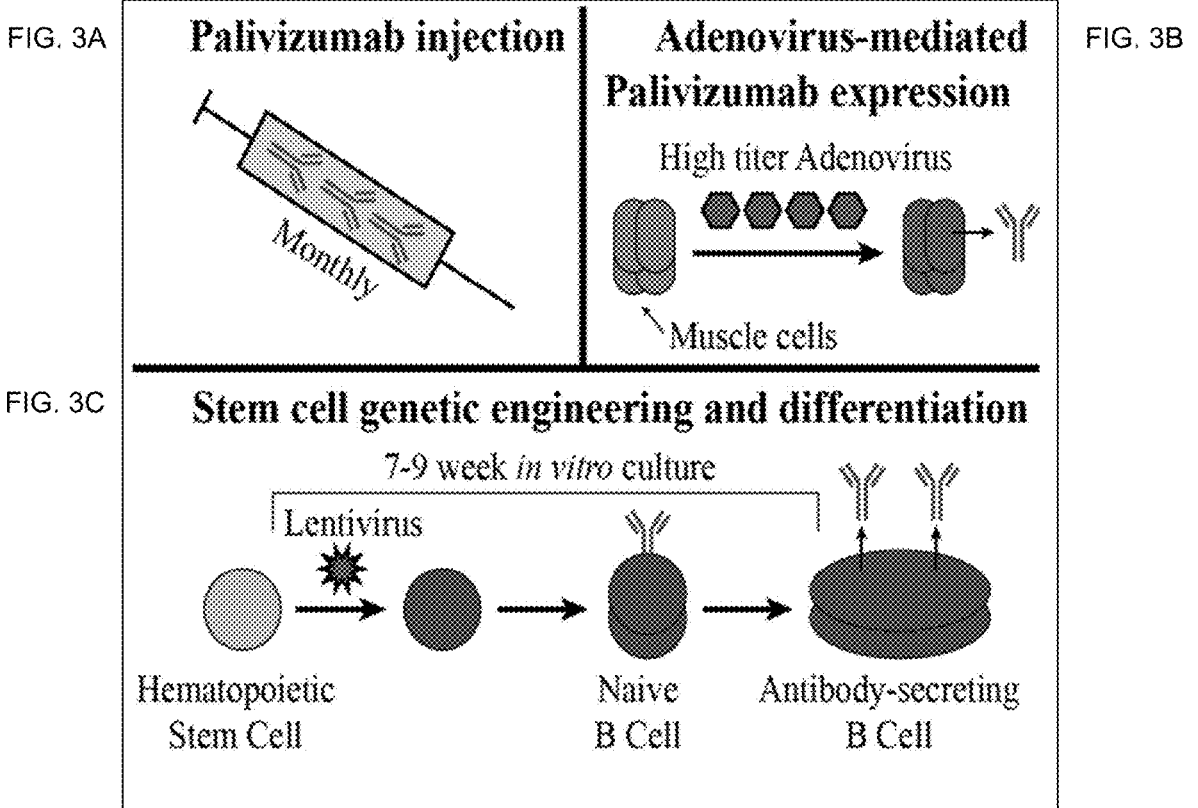
FIGS. 3A-3C. Summary of previous efforts to bypass vaccination and directly provide protective antibodies against RSV.
Figure 4A:
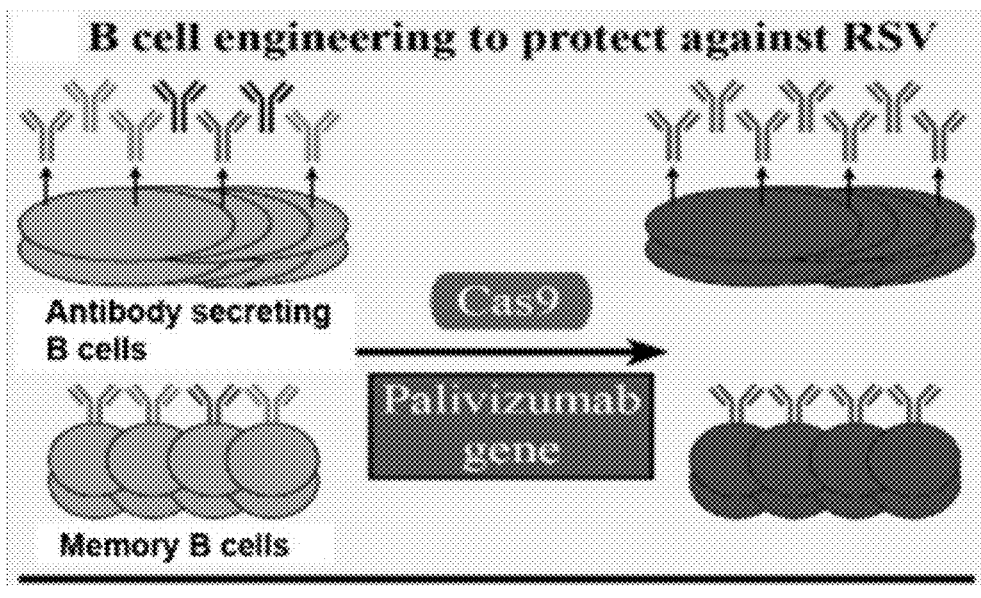
FIGS. 4A, 4B. Schematics for particular embodiments of protection strategies disclosed herein.
Figure 4B:
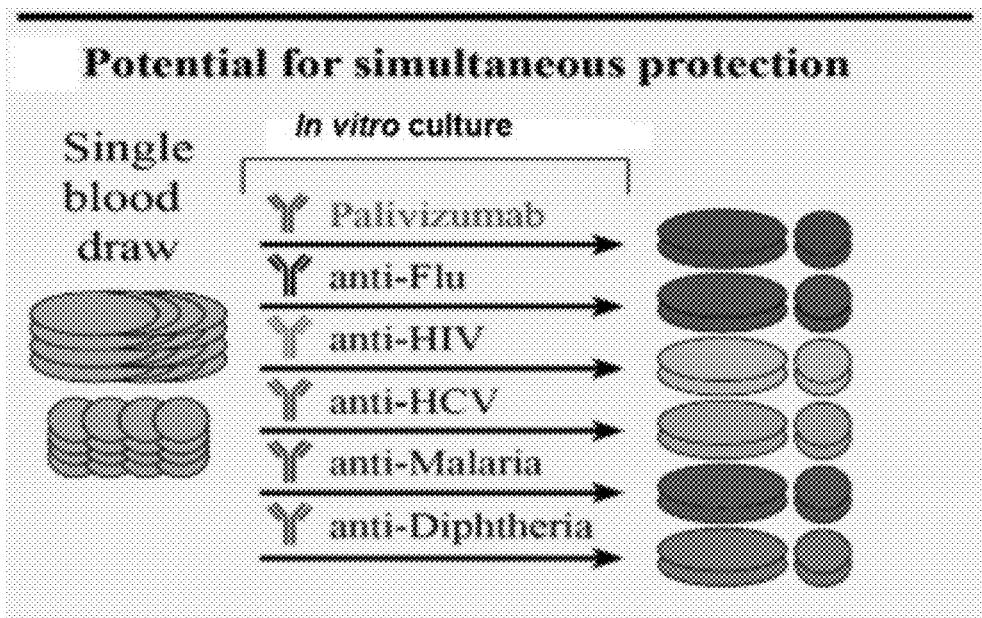
Figure 5:
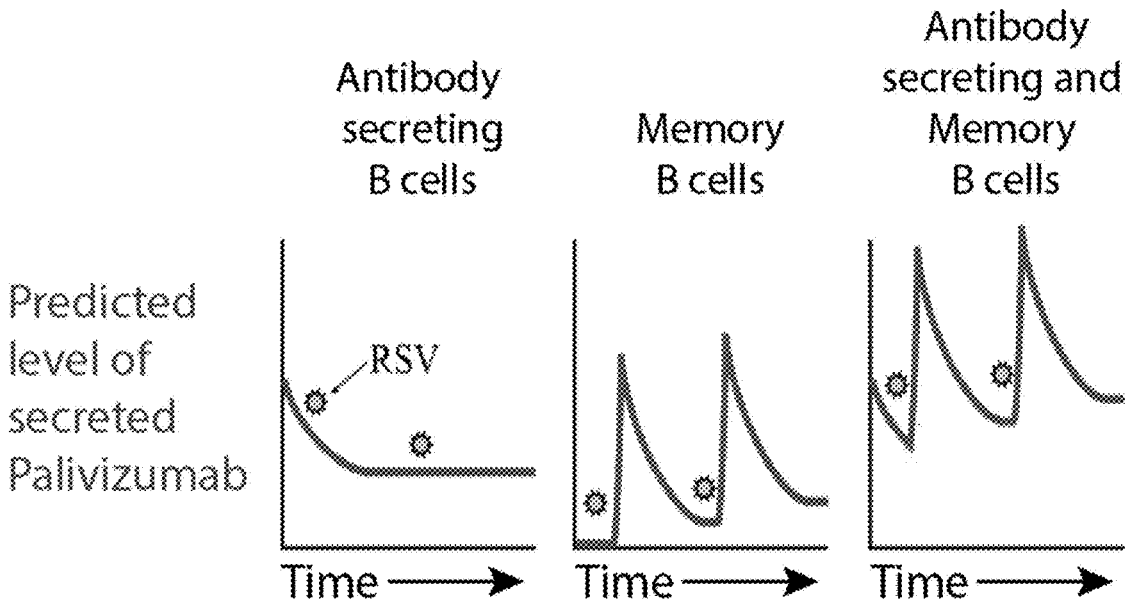
FIG. 5. Hypothesized secretion of palivizumab by B cell subtypes in the presence and absence of infection.

Another approach uses a lentiviral vector to incorporate the genes encoding protective antibodies into the genome of hematopoietic stem cells, which would be subsequently induced to differentiate into antibody-secreting B cells (FIG. 3C). One limitation of this approach is that antibody gene insertion is random, which introduces the risk of off-target genetic effects resulting in disease. A second limitation of this approach is the long two-month in vitro culture conditions necessary to induce differentiation of antibody-secreting cells from hematopoietic stem cells (Luo et al., Blood. 2009; 113(7):1422-31). A final limitation is that this strategy will not generate a source of antibody that can be augmented upon infection. Therefore, if the antibody-secreting cells are not present in high numbers, or are not long-lived, protection against infection will be inadequate In particular embodiments, the current disclosure provides bypassing vaccination and/or eliminating the need for repeated therapeutic antibody injections by genetically engineering B cells to express a selected antibody (e.g., an antibody against an infectious agent (e.g., palivizumab; FIG. 4A)). Types of B cells that are particularly useful to genetically engineer include existing antibody-secreting B cells, memory B cells, naïve B cells, B1 B cells, and marginal zone B cells. Naive B cells have the greatest proliferative and functional potential and can enter the germinal center response and improve their binding ability. B1 B cells express BCR and migrate to different locations such as the peritoneal cavity. B1 B cells rapidly differentiate into antibody-secreting cells upon stimulation through the BCR, and do not require signals for T cells for optimal function. Marginal zone B cells are largely located in the marginal zone of the spleen and rapidly differentiate into antibody-secreting cells upon stimulation through the BCR. Marginal zone B cells also do not require signals from T cells for optimal function. Genetically engineering one or more of these subsets of B cells can create a baseline level of antibody to treat ongoing or immediate infection, and a long-lived source of inducible antibody in case of future re-infection. FIG. 4B demonstrates an associated strategy for simultaneous protection against numerous pathogens utilizing the teachings of the current disclosure while FIG. 5 depicts hypothesized secretion of palivizumab by exemplary B cell subtypes in the presence and absence of infection.

The current disclosure provides genetic engineering of B cells by inserting a genetic construct including a transgene into an endogenous antibody gene locus specifically chosen to take advantage of the structure and function of the endogenous B cell genome. For example, inserting a transgene encoding at least a portion of a selected antibody into an endogenous antibody gene locus can allow for robust production of the selected antibody by taking advantage of the endogenous antibody expression regulatory machinery. Transgene may refer to a section of DNA that encodes a foreign (i.e., exogenous) protein. Genetic construct may refer to an artificially constructed segment of nucleic acid which is intended for introduction into a cell to allow expression of the foreign protein.

In particular embodiments, the current disclosure provides B cells that are modified to express a selected antibody. Antibodies are produced from two genes, a heavy chain gene and a light chain gene. Generally, an antibody includes two identical copies of a heavy chain, and two identical copies of a light chain (see, e.g., FIG. 6B). The heavy chains are the larger subunits of the two and each heavy chain includes a VDJ segment and a constant region (shown as "C" in FIG. 6B). The VDJ segment (or VDJ) refers to the unique pairing of V, D and J gene segments that encode the unique portion of the antibody heavy chains that bind to an epitope on a pathogen. Thus, V refers to one of the gene segments that randomly pairs with a D and J segment to encode the unique portion of the antibody heavy chain that binds to an epitope on the pathogen. Similarly, D refers to one of the gene segments that randomly pairs with a V and J segment to encode the unique portion of the antibody heavy chain that binds to an epitope on the pathogen. Finally, J refers to one of the gene segments that randomly pairs with a V and D segment to encode the unique portion of the antibody heavy chain that binds to an epitope on the pathogen. There are several V segments, D segments, and J segments that can come together in a variety of distinct combinations to form the particular VDJ segment of a particular heavy chain (see, e.g. FIG. 7).

Each B cell pairs just a single VDJ combination with a conserved constant, C, region to form a full-length heavy chain. The heavy chain C region can interact with other immune proteins, such as Fc receptors to activate other immune cells. All naive B cells express the same C region segments, but can change to express different C region segments following activation, and different C regions give antibodies different functions. For example, one C gene segment encodes ε, and antibodies expressing ε are "IgE". IgE-type antibodies bind to cells of the body and often mediate allergic reactions. Antibodies expressing an α C region are IgA antibodies; antibodies expressing a γ C region are IgG antibodies and antibodies expressing a μ C region are IgM antibodies. The human genome includes a single heavy chain locus, which is present on chromosome 14.

Again referring to FIG. 6B, the light chain of an antibody (IgL) includes a variable region and a constant region. The light chain variable region includes V and J gene segments, and the light chain constant region can include a single immunoglobulin constant domain. Humans express two different light chains: Igκ, which is encoded by the immunoglobulin kappa locus on chromosome 2; and Igλ, which is encoded by the immunoglobulin lambda locus on chromosome 22.

Figures 6A, 6B:
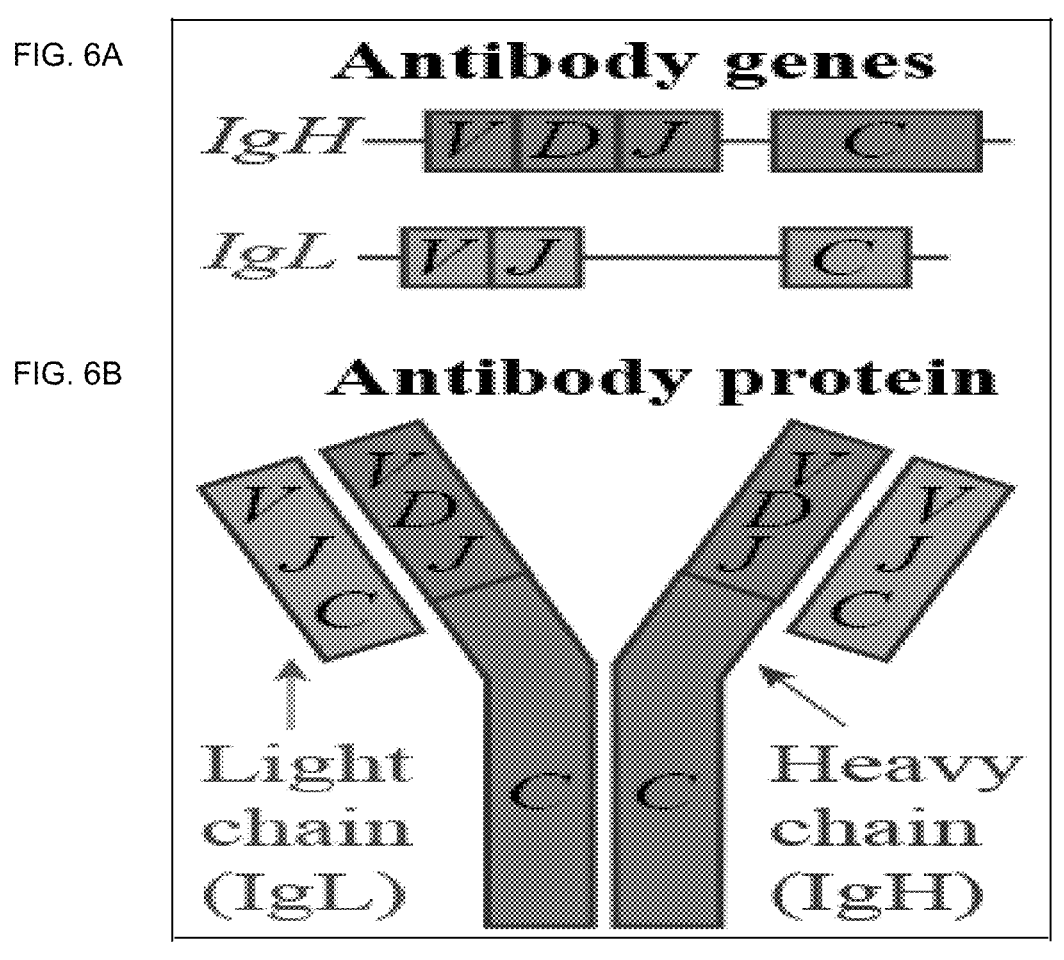
Figure 8A:
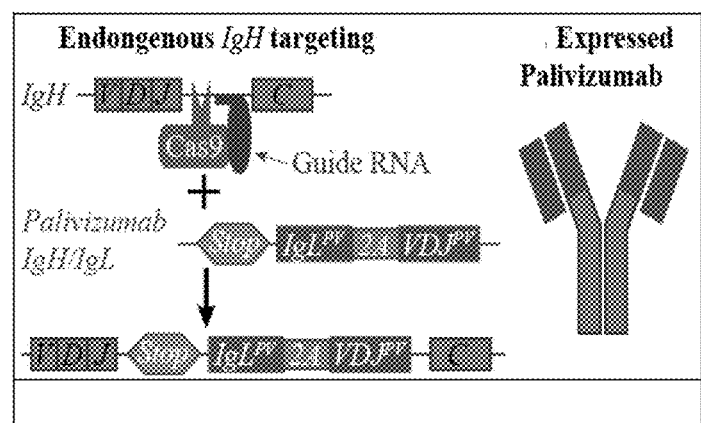
FIGS. 8A, 8B. Because two proteins come together to form an antibody, it can be desirable to target or inactivate the B cell's endogenous antibody heavy chain (IgH) and/or endogenous antibody light chain (IgL). In the absence of such targeting or inactivation, undesired hybrid antibodies could form (i.e., an endogenous light chain pairing with a selected antibody heavy chain or vice versa).
Figure 8B:
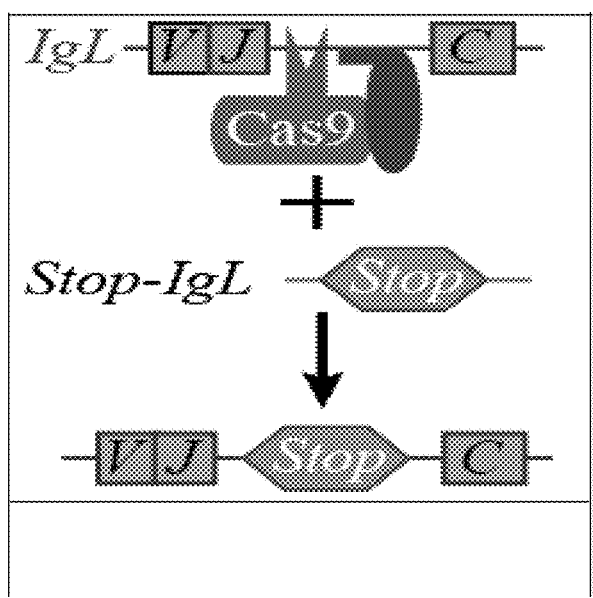

FIG. 6A depicts schematics of the endogenous B cell genome that encode an IgH chain and an IgL chain. FIGS. 8A and 8B depict initial schematics of where exogenous genetic constructs according to the current disclosure can be inserted to achieve expression of a selected antibody. FIG. 8A depicts inserting a genetic construct including [a stop signal, an IgL chain of a selected antibody (here, PV), a skipping element (here, 2A), and the VDJ segment of a heavy chain] into the endogenous IgH genome between the endogenous VDJ segment and the endogenous C region coding segments. This approach leads to expression of an entire exogenous IgL chain, an exogenous VDJ segment of a heavy chain, and an endogenous C region of the heavy chain. Expression of an antibody that includes an endogenous C region can be useful, for example, because it can allow a modified B cell to modulate C region expression based on natural B cell activation and maturation state. For example, alternative splicing in the constant region of the heavy chain gene locus can allow a modified B cell to switch between expression of a membrane-bound antibody and expression of a secreted antibody. This approach also allows expression of an exogenous VDJ without requiring excision of the endogenous VDJ. This feature is beneficial because the VDJ is a relatively large segment of DNA and its excision can negatively affect cellular function.

Figure 9:
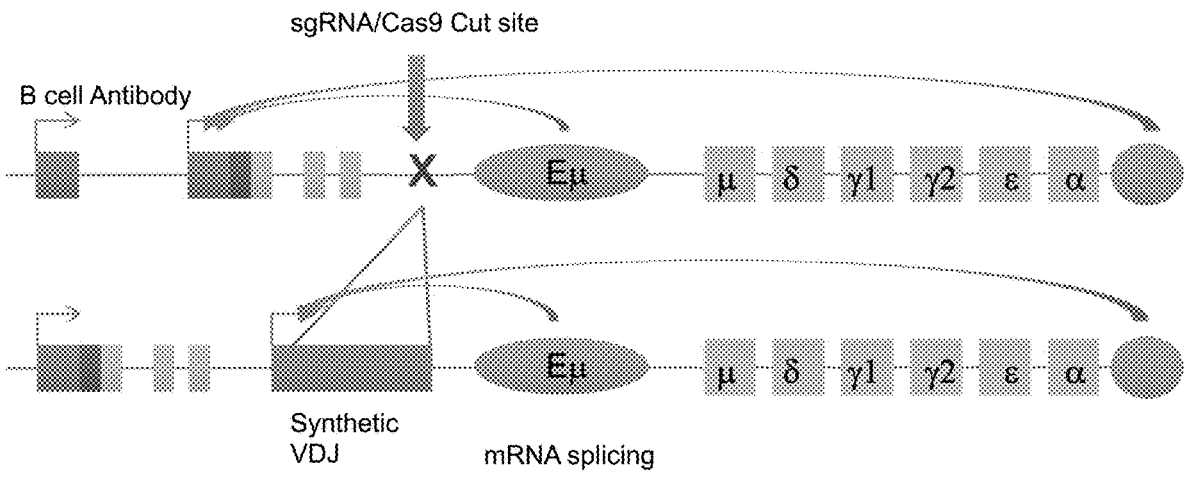
FIG. 9. Schematic depicting interactions of heavy chain enhancers with (top) an endogenous VDJ or (bottom) a synthetic VDJ encoded by an inserted genetic construct. Promoters are depicted as arrows. Nucleic acid is depicted as boxes. B cells naturally express nucleic acid that is downstream of the promoter that is closest to the Eμ enhancer. In the endogenous B cell genome depicted in FIG. 9, the first upstream promoter closest to the Eμ enhancer then drives expression of the endogenous heavy chain VDJ segments. Inserting a genetic construct that includes a promoter between the Eμ enhancer and the first endogenous promoter, results in the B cell expressing the inserted genetic construct rather than the endogenous heavy chain VDJ segments. This inserted gene could be a VDJ variable region of a heavy chain, a paired full antibody light chain together with the heavy chain variable VDJ, or another synthetic gene capable of being expressed as a fusion with a B cell heavy chain constant region.

FIG. 9 depicts a similar schematic with more detail regarding the structure and function of the endogenous B cell genome, and how the current disclosure utilizes this structure and function to achieve expression of selected antibodies. Promoter regions are necessary to achieve transcription of a gene segment. Heavy chain variable region ($V_H$) promoters are selectively active in the B cell lineage, and include a TATA box, an lnr element, and an octamer element within 100 base pair (bp) of the transcriptional initiation site. $V_H$ promoter activity is under proximity-dependent regulation by the endogenous B cell genome's Eμ enhancer element (gray oval), and an enhancer element positioned at the 3' end of the heavy chain gene locus, proximal to the heavy chain a constant gene (gray circle). The Eμ enhancer element is an intronic region of DNA (40 to 1500 bp in length) within the 700-bp intron between the J heavy chain segment and the C mu (μ) segment of the immunoglobulin heavy chain gene locus. It can bind an activator protein to increase or activate transcription of the heavy chain gene. The sequence of the human Eμ enhancer element is provided in FIG. 11A as SEQ ID NO: 85. The sequence of the mouse Eμ enhancer element is provided in FIG. 13A as SEQ ID NO: 86.

Inserting a genetic construct that includes a $V_H$ promoter between an endogenous heavy chain variable region and an endogenous Eμ enhancer may reduce or block transcription activation from the endogenous $V_H$ promoter because the Eμ enhancer will initiate transcription at the most proximal upstream promoter. In this manner, expression of the endogenous VDJ can be blocked without requiring the removal of such a large DNA segment (which, as indicated, is problematic for cell function and survival). In particular embodiments, VDJ recombination removes genetic material between the $V_H$ promoter and the Eμ enhancer, which positions the enhancer at the appropriate distance from an exogenous promoter of a genetic construct disclosed herein to activate transcription starting from the promoter in the inserted genetic construct. In particular embodiments, no endogenous genetic material is removed. In particular embodiments, less than 50 base pairs are removed. In particular embodiments, $V_H$ promoters within exogenous genetic constructs include the native light chain promoter for IgK or IgL, a native human IgH promoter, the spleen focus forming viral promoter SFFV, the J558 h10 promoter or the IgVH1-69 promoter.

Figure 10:
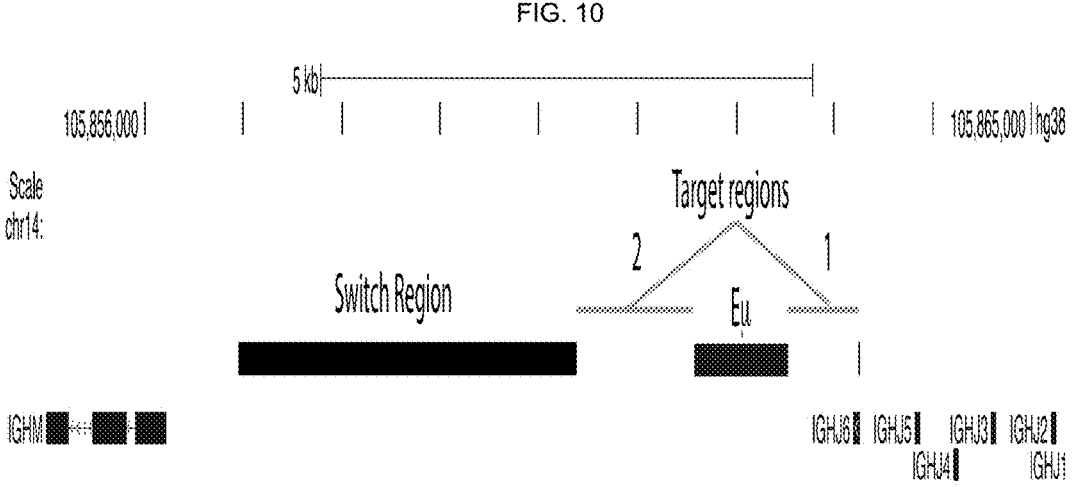
FIG. 10. Target regions for insertion (Human). Regions for genetic construct insertion into the genome: #1: From the terminal J region (IGHJ6 in human, IGHJ4 in mouse) to the Eμ enhancer, or #2: From the Eμ enhancer to the repetitive sequences of the constant domain switch region.

FIG. 10 provides an additional schematic for target areas for genetic construct insertion. These target areas encompass two conserved regions present in all B cells: from the terminal J gene segment (IGHJ6 in humans, IGHJ4 in mice) to the heavy chain intronic enhancer (Eμ), and from Eμ to the repetitive sequences associated with DNA switch recombination.

In particular embodiments, the area of the endogenous B cell genome that is targeted for insertion of the genetic construct is upstream of the Eμ enhancer of SEQ ID NOs: 85 or 86. FIGS. 11A-14B provide particular sequences that can be targeted for genetic construct insertion to achieve expression of a selected antibody as disclosed herein.

Figure 25C:
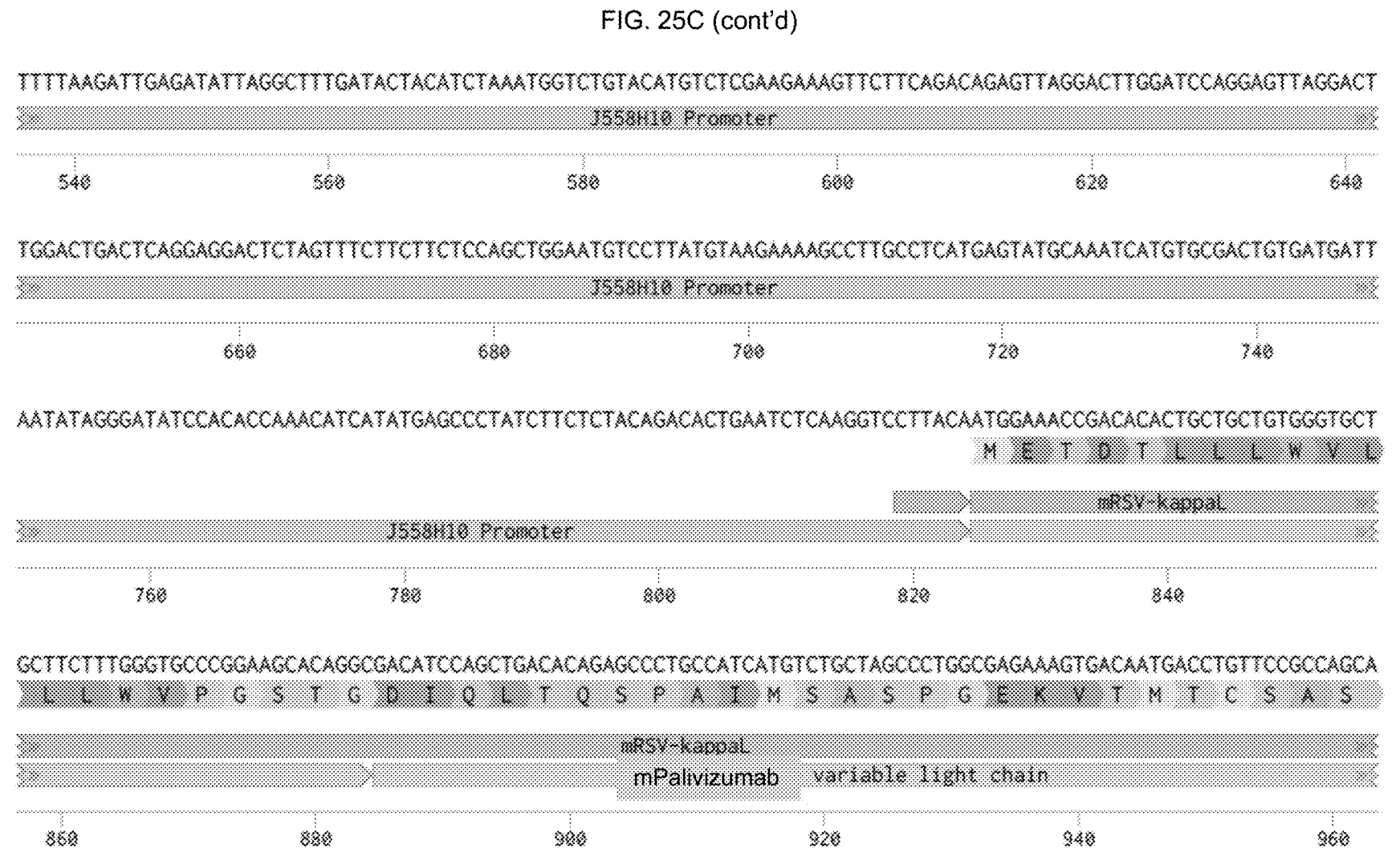
Figure 25H:
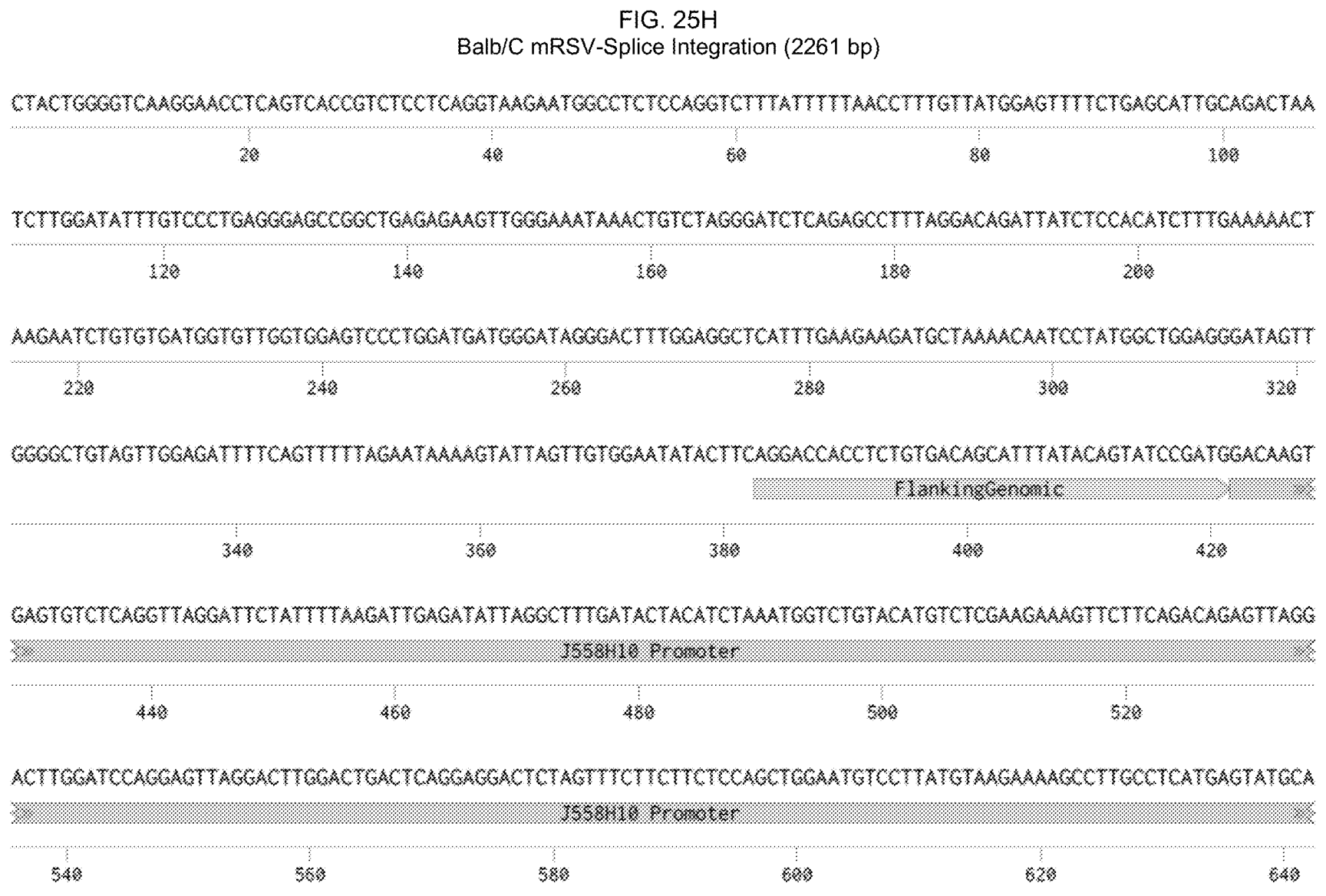

FIG. 11A provides the human DNA sequence of IGHJ6 to Eμ intronic enhancer (SEQ ID NO: 1; >hg38_dna range=chr14:105862523-105863244 5'pad=0 3'pad=0 strand=−repeatMasking=none). FIG. 11B provides exemplary ranges to target (e.g., gRNA sites) within this sequence including SEQ ID NOs: 5-24 and associated gRNA sequences (SEQ ID NOs: 88, 89, and 290-307). As examples, in particular embodiments, sgRNA of SEQ ID NO: 88 (see also FIG. 25A) can be used to target gRNA site of SEQ ID NO: 7. In particular embodiments, sgRNA of SEQ ID NO: 89 (see also FIG. 25A) can be used to target gRNA site of SEQ ID NO: 10.

FIG. 12A provides the human DNA sequence for Region 2: Eμ intronic enhancer to switch region (SEQ ID NO: 2; >hg38_dna range=chr14:105860383-105861690 5'pad=0 3'pad=0 strand=−). FIG. 12B provides exemplary ranges to target (e.g., gRNA sites) within this sequence including SEQ ID NOs: 25-44 and associated gRNA sequences (SEQ ID NOs: 308-327).

FIG. 13A provides the mouse DNA sequence for region 1: from IGHJ4 to Eμ intronic enhancer (SEQ ID NO: 3; >mm10_dna range=chr12:113427973-113428554 5'pad=0 3'pad=0 strand=− repeatMasking=none). FIG. 13B provides exemplary ranges to target (e.g., gRNA sites) within this sequence including SEQ ID NOs: 45-64 and associated gRNA sequences (SEQ ID NOs: 87, and 328-346). As an example, in particular embodiments, sgRNA of SEQ ID NO: 87 (see also FIG. 25A) can be used to target gRNA site of SEQ ID NO: 46.

FIG. 14A provides the Mouse DNA sequence for region 2: from Eμ intronic enhancer to switch region (SEQ ID NO: 4; >mm10_dna range=chr12:113425446-113426973 5'pad=0 3'pad=0 strand=– repeatMasking=none). FIG. 14B provides exemplary ranges to target (e.g., gRNA sites) within this sequence including SEQ ID NOs. 65-84 and associated gRNA sequences (SEQ ID NOs: 347-366).

Thus, in particular embodiments, the current disclosure provides targeted insertion of a genetic construct including (i) a promoter and (ii) a transgene encoding a portion of a selected antibody at an intronic region that is constant in all B cells (before and after recombination) and (i) positioned relative to an enhancer element that interacts with the promoter; and (ii) in a configuration such that the B cells' endogenous heavy chain VDJ sequence is not expressed. In particular embodiments, the encoded portion of the selected antibody includes the entire light chain of the antibody and the VDJ segment of the heavy chain. These portions of the selected antibody can be expressed with a heavy chain constant region expressed by the modified B cell at any given time. Particular embodiments of the genetic construct may also include or encode a signal peptide, a flexible linker, a skipping element, and or a splice junction.

One technical challenge of the current disclosure is that an antibody is a protein made from two separate gene products, the heavy chain (IgH) and the light chain (IgL) (FIGS. 6A, 6B). This means that, in particular embodiments, both genetic locations must be simultaneously modified in order to properly express a selected antibody. However, the current disclosure also provides strategies to produce functional selected antibodies without necessitating modifying both genetic locations. One approach that allows this is through the use of sequences that allow antibody expression through a single construct. In particular embodiments, this is achieved by including a skipping element within the genetic construct. One example of a skipping element is a self-cleaving peptide, such as a self-cleaving "2A" peptide. 2A peptides function by causing the ribosome to skip the synthesis of a peptide bond at a defined location, leading to production of two proteins from one mRNA. The 2A sequences are short (e.g., 20 amino acids), facilitating use in size-limited constructs, and proteins are produced at a 1:1 ratio. Particular examples include T2A (GSG) EGRGSLLTCGDVEENPGP (SEQ ID NO: 176); P2A (GSG)ATNFSLLKQAGDVEENPGP (SEQ ID NO: 177); E2A (GSG)QCTNYALLKLAGDVES NPGPP (SEQ ID NO: 178); and F2A (GSG)VKQTLNFDLLKLAGD-VESNPGP (SEQ ID NO: 179).

In particular embodiments, the genetic constructs include an internal ribosome entry site (IRES) sequence. The IRES can be positioned upstream of the heavy chain VDJ of the genetic construct. IRES are non-coding structured RNA sequences that allow ribosomes to initiate translation at a second internal site on a mRNA molecule, leading to production of two proteins from one mRNA. However, IRES driven translation is less efficient than 2A driven translation, leading to lower expression of the second protein in the transcript.

In particular embodiments, the genetic constructs encode a flexible linker between the light chain portion of the selected antibody and the heavy chain portion of the selected antibody. A linker can be a series of amino acids that flexibly link one protein domain to another protein domain in a way that allows the linked sequences to interact to form a functional unit.

In particular sequences, flexible linkers can include one or more series of combinations of glycine and serine, which provide flexibility to the linker sequence. Exemplary Gly-Ser linkers include (GGS)n (SEQ ID NO: 180), (GGGS)n (SEQ ID NO: 181), and (GGGGS)n (SEQ ID NO: 182) wherein n=1-100 and every integer therebetween. In particular embodiments, n=10, 11, 12, 13, 14, 15, 16, 17, 18, 19, 20, 21, 22, 23, 24, 25, 26, 27, 28, 29, or 30. In particular embodiments, a Gly-Ser linker includes 50-80 amino acids. In particular embodiments, the Gly-Ser linker includes 54, 57, or 60 amino acids. In particular embodiments, the Gly-Ser linker is encoded by SEQ ID NO: 116. In particular embodiments, the Gly-Ser linker includes SEQ ID NO: 122.

Additional examples of flexible linkers include (KES-GSVSSEQLAQFRSLD)n (SEQ ID NO: 183) and (EGKSSGSGSESKST)n (SEQ ID NO: 184). In these linkers the Gly and Ser residues in the linker were designed to provide flexibility, whereas Glu and Lys were added to improve the solubility. Bird, R E et al. Science, 1988; 242:423-426. In particular embodiments, n=1-100 and every integer therebetween. In particular embodiments, n=10, 11, 12, 13, 14, 15, 16, 17, 18, 19, 20, 21, 22, 23, 24, 25, 26, 27, 28, 29, or 30. In particular embodiments, these linkers includes 50-80 amino acids.

Particular embodiments include a splice junction that allows splicing between RNA encoded by the genetic construct and RNA encoded by the endogenous heavy chain constant region. In particular embodiments, the genetic constructs include a splice junction sequence at the 3' end. Splicing can refer to the removal of introns and joining together of exons by an RNA/protein complex known as the spliceosome. A splice junction refers to an intronic sequence directly flanking an exon. A splice junction at the 3' end of an exon can include a splice donor site. Splice donor site sequences typically begin with "GU". In particular embodiments, the splice junction may include 40-80 bp of an intron following the last exon of a VDJ. In particular embodiments, the splice junction includes 40-80 bp of the intron flaking the 3' end of the human IGHJ1 gene segment or the mouse IGHJ3 gene. In particular embodiments, the splice junction includes CAG/gtaagt, with the cut and splice taking place after the uppercase G (indicated by the "splice" annotation). In particular embodiments, the splice junction includes CAG/gtgagt. The CA form the end of a serine codon, and the G begins the first codon from the constant region. In particular embodiments, a splice junction with flanking sequence includes SEQ ID NOs: 124 or 151 in genetic constructs for insertion into a human locus. In particular embodiments, a splice junction with flanking sequence includes SEQ ID NO: 139 in genetic constructs for insertion into a mouse locus.

Genetic constructs disclosed herein can also encode signal peptides. Exemplary signal peptides include signal peptides derived from human IgH heavy chains, such as MELGLS-WIFLLAILKGVQC (SEQ ID NO: 185); MEL-GLRWVFLVAILEGVQC (SEQ ID NO: 186); MKHLWF-FLLLVAAPRWVLS (SEQ ID NO: 187); MDWTWRILFLVAAATGAHS (SEQ ID NO: 188); MDWTWRFLFVVAAATGVQS (SEQ ID NO: 189); MEFGLSWLFLVAILKGVQC (SEQ ID NO: 190); MEFGLSWVFLVALFRGVQC (SEQ ID NO: 191); and MDLLHKNMKHLWFFLLLVAAPRWVLS (SEQ ID NO: 192); and signal peptides derived from human IgL light chains, such as MDMRVPAQLLGLLLLWLSGARC (SEQ ID NO: 193); and MKYLLPTAAAGLLLLAAQPAMA (SEQ ID NO: 194). In particular embodiments, a signal peptide is encoded by SEQ ID NO: 112 and includes SEQ ID NO: 118 in genetic constructs for insertion into a human locus. In particular embodiments, a signal peptide is encoded by SEQ ID NO: 129 and includes SEQ ID NO: 134 in genetic constructs for insertion into a mouse locus. See also FIGS. 25B-25I and Haryadi R et al., tPLoS One v.10(2); 2015 PMC4338144.

As indicated, particular embodiments of the disclosure utilize insertion of exogenous genetic constructs at a targeted location within the endogenous B cell genome. In particular embodiments, such targeted insertion can be facilitated by including homology regions on one or both ends of the genetic construct. Homology regions (i.e., homology stitches or homology arms) are homologous to sequences at a desired insertion site. In particular embodiments, homology arms refer to segments of DNA included in a genetic construct that are 100% identical to a region of DNA that is being modified. In particular embodiments, 100% identity may not be required to achieve targeted insertion (e.g., at least 90% identity may be sufficient).

Figure 15A:
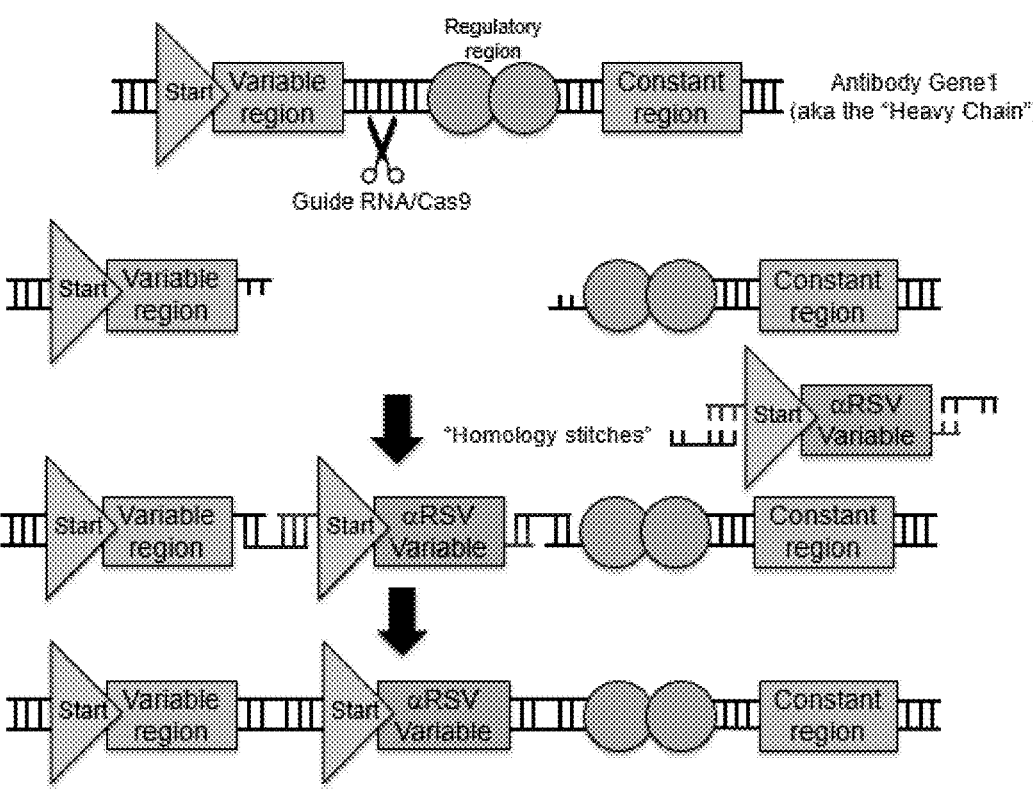
FIGS. 15A, 15B.

Homology regions cause the genetic construct to align next to the targeted genetic region, and portions of DNA from the genetic construct are swapped into the region cut by gene editing techniques. In particular embodiments, a genetic construct may include an upstream genome homology end with 20 to 1,500 bp of genome homology, and a downstream genome homology end with 20 to 1,500 bp of genome homology. The regions of homology may, for example, provide "homology stitches" as shown in FIG. 15A, which can mediate insertion of the genetic construct into the targeted insertion site. In particular embodiments, the upstream genome homology end and the downstream genome homology end may include sequences with homology to genome sequences between a heavy chain VDJ region and a heavy chain Eμ enhancer element. In particular embodiments, regions of homology may particularly include 20-50 base pairs; 300-500 base pairs; 350-550 base pairs; 900-1,000 base pairs, or 400-600 base pairs. In particular embodiments, regions of homology may particularly include 30-40 base pairs (e.g., 36 base pairs); 445-455 base pairs (e.g., 450 base pairs); 495-510 base pairs (e.g., 503 base pairs); and/or 960-980 base pairs (e.g., 968 base pairs). In particular embodiments, homology regions for use in mouse genetic constructs include SEQ ID NOs: 90, 91, 96, 97, 127, 140, 142, 143, 170, and 171. In particular embodiments, homology regions for use in human genetic constructs include SEQ ID NOs: 92-95, 98-101, 110, 125, 153, 173, and 174.

In particular embodiments, the genetic constructs also encode a tag sequence. Tag sequences may be useful, for example, so that cells expressing the genetic construct may be identified and/or sorted during genetic modification processes and/or so that they can be controlled following administration to a subject. For example, in particular embodiments, it may be useful to track and/or terminate genetically modified cells following administration to a subject. Exemplary tags include STREPTAG® (GmbH, LLC, Gottingen, DE), STREP® tag II (WSHPQFEK (SEQ ID NO: 195)), or any variant thereof; see, e.g., U.S. Pat. No. 7,981,632), His tag, Flag tag (DYKDDDDK (SEQ ID NO:196)), Xpress tag (DLYDDDDK (SEQ ID NO: 197)), Avi tag (GLNDIFEAQKIEWHE (SEQ ID NO: 198)), Calmodulin tag (KRRWKKNFIAVSAANRFKKISSSGAL (SEQ ID NO: 199)), Polyglutamate tag, HA tag (YPYDVPDYA (SEQ ID NO: 200)), Myc tag (EQKLISEEDL (SEQ ID NO: 201)), Nus tag, S tag, SBP tag, Softag 1 (SLAELLNAGLGGS (SEQ ID NO: 202)), Softag 3 (TQDPSRVG (SEQ ID NO: 203)), and V5 tag (GKPIPNPLLGLDST (SEQ ID NO: 204)).

In particular embodiments, the current disclosure provides a genetic construct for selected antibody expression including or encoding (i) a heavy chain promoter, and/or (ii) an immunoglobulin light chain, and/or (iii) a heavy chain variable region, and/or (iv) a stop codon; and/or (v) a skipping element and/or (vi) a splice junction and/or (vii) homology arms and/or (viii) a linker and/or (ix) a tag.

Particular embodiments include or encode: (i) a heavy chain promoter; (ii) a signal peptide; (iii) an entire light chain of a selected antibody; (iv) a flexible linker or a skipping element; (v) the variable region of a selected antibody heavy chain; and (vi) a splice junction.

Particular embodiments include or encode: (i) a heavy chain promoter; (ii) a signal peptide; (iii) an entire light chain of a selected antibody; (iv) a flexible linker or a skipping element; (v) the variable region of a selected antibody heavy chain; (vi) a splice junction, and (vii) homology arms.

Particular embodiments include or encode: (i) a heavy chain promoter; (ii) a signal peptide; (iii) an entire light chain of a selected antibody; (iv) a flexible linker or a skipping element; (v) the variable region of a selected antibody heavy chain; (vi) a splice junction, (vii) homology arms; and (viii) a tag.

Figure 15B:
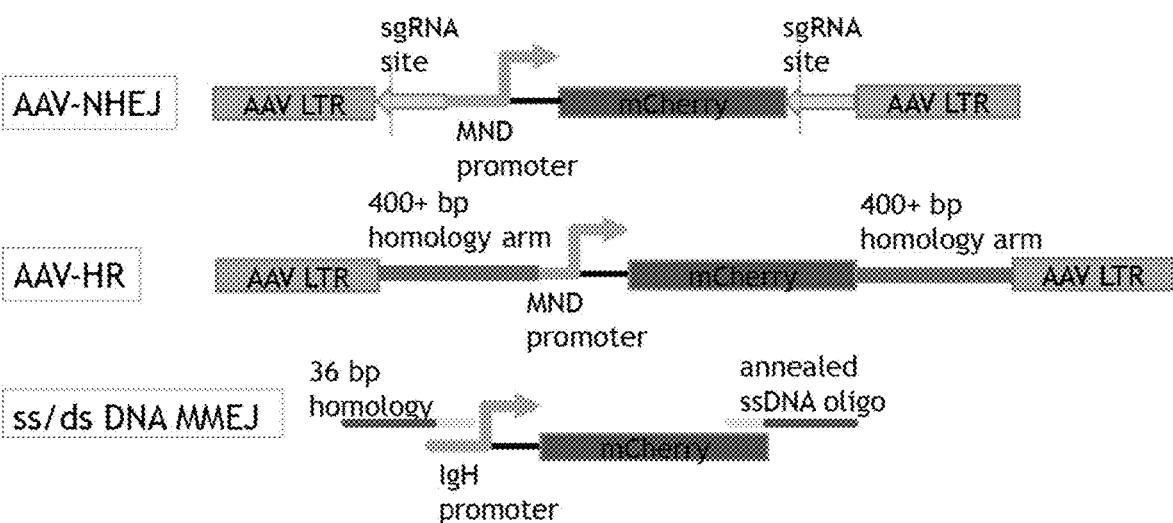

FIG. 15B depicts additional examples of DNA repair templates. Examples of DNA repair templates that can also be used include synthetic DNA templates and adeno-associated viruses. In particular embodiments, synthetic DNA templates can include double stranded DNA (dsDNA) including or encoding a promoter and selected antibody portion flanked by 20-1,500 base pairs of homology to the target site in the genome. In particular embodiments, synthetic DNA templates can include single stranded DNA (ssDNA) including or encoding a promoter and selected antibody portion flanked by 10-80 base pairs, or 400-1000 base pairs of homology to the target site in the genome. In particular embodiments, synthetic DNA templates can include both dsDNA and ssDNA, terminally modified by phosphorylation to increase DNA ligation efficiency. In particular embodiments, both dsDNA and ssDNA can be terminally modified with phosphorothioate bonds to increase stability and prevent endonuclease digestion.

In particular embodiments, an adeno-associated virus can include a segment encoding a synthetic antibody portion flanked by 20-1,500 base pairs of homology to the target site in the genome. In particular embodiments, the promoter and synthetic antibody portion encoding sequence can be flanked by matching homology sequences to the target site in the genome.

In particular embodiments, the genetic construct including a DNA repair mechanism (e.g., homology stitches, synthetic DNA template) may be delivered utilizing a gene editing system, such as CRISPR, TALENs, megaTALs, zinc finger nucleases and/or an adeno-associated virus as described in more detail below. For example, a genome targeting element, a genome cutting element, and a genetic construct described herein can be administered to a B cell.

As a particular example of an application of the current disclosure, B cells may be modified to express the palivizumab antibody. The B cells may be modified with a genetic construct that includes 80 bp homology arms flanking a heavy chain promoter upstream of the complete light chain (IgLPV) and VDJ heavy chain gene segments (VDJPV) from palivizumab separated by a 2A peptide. Here, the 2A peptide is included in order to induce a ribosomal skipping event (Donnelly et al., The Journal of general virology. 2001; 82(Pt 5):1013-25), which allows for the heavy chain and light chain to be produced as separate subunits that will associate normally to form the selected antibody. In particular embodiments, a stop codon can be included upstream of the inserted heavy chain promoter to halt any potential transcription of the endogenous heavy chain variable region.

Figure 16:
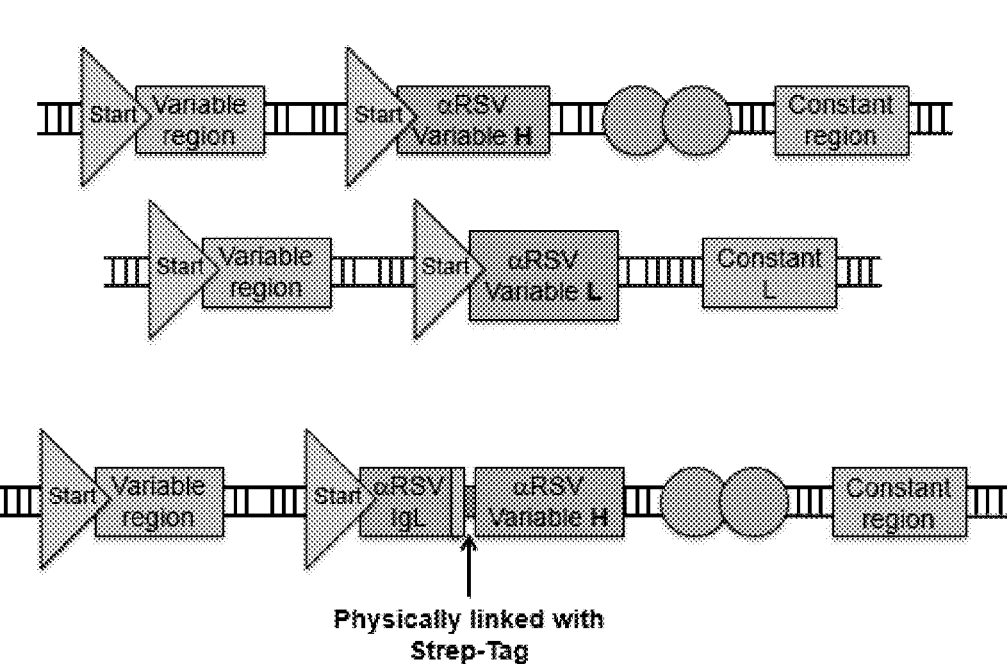
FIG. 16. Schematic depicting: (top) a modified heavy chain locus, modified with a genetic construct encoding a heavy chain variable region of an anti-RSV antibody; (middle) a modified light chain locus, modified with a genetic construct encoding a light chain variable region of an anti-RSV antibody; and (bottom) a modified heavy chain locus, modified with a genetic construct encoding a light chain (i.e., IgL) of an anti-RSV antibody, and a heavy chain variable region of an anti-RSV antibody, with a linker (including a Strep-Tag) between the light chain and the heavy chain variable region.
Figure 17:
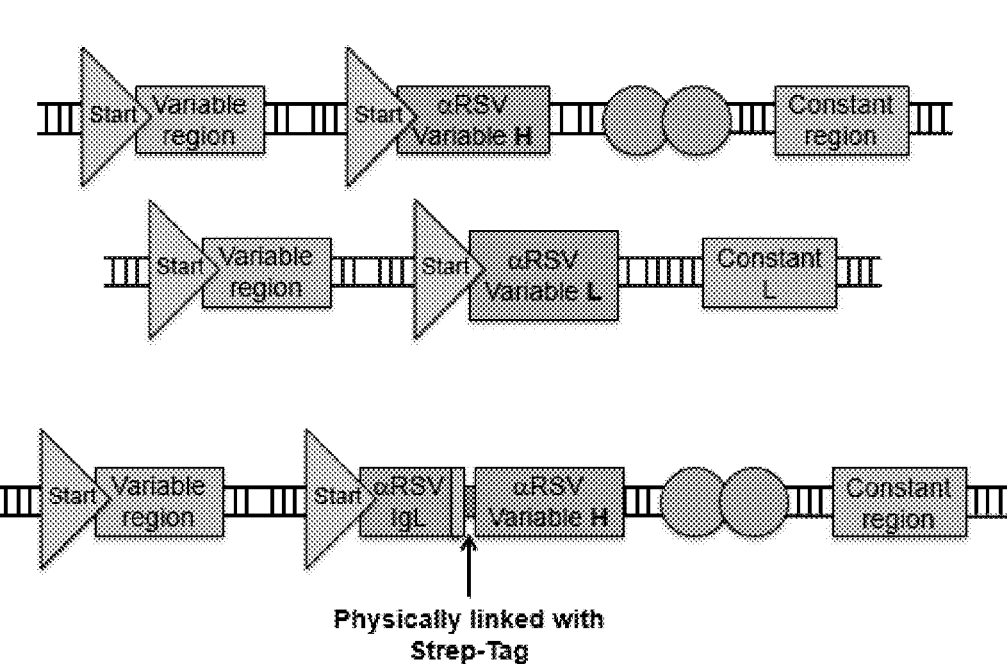
FIG. 17. Schematic of simultaneous protection against multiple pathogens by modified memory B cells and modified antibody-secreting B cells, as disclosed herein.

FIG. 16 depicts an example of an "as-modified" B cell genome, while FIG. 17 depicts resulting B cell populations expressing selected antibodies.

The following paragraphs provide a more detailed description regarding (i) Exemplary Selected Antibodies and Sequences; (ii) Gene Editing Techniques and Cell Sorting; (iii) Formulation of Modified B cells; and (iv) Methods of Use.

(i) Exemplary Selected Antibodies and Sequences. In particular embodiments, a selected antibody is an antibody that can provide a protective effect against a pathogen or condition (e.g., autoimmune disease). In particular embodiments, the selected antibody is an anti-RSV antibody, an anti-HIV antibody, an anti-Dengue virus antibody, an anti-*Bordatella pertussis* antibody, an anti-hepatitis C antibody, an anti-influenza virus antibody, an anti-parainfluenza virus antibody, an anti-metapneumovirus (MPV) antibody, an anti-cytomegalovirus antibody, an anti-Epstein Barr virus antibody; an anti-herpes simplex virus antibody, an anti-*Clostridium difficile* bacterial toxin antibody, or an anti-tumor necrosis factor (TNF) antibody.

In particular embodiments, the selected antibodies are chimeric antibodies. In particular embodiments, chimeric antibodies refer to a synthetic antibody that includes: (i) at least one portion that is encoded by a B cell's endogenous genome, and (ii) at least one portion that is encoded by an inserted genetic construct. In particular embodiments, the chimeric antibody includes an endogenous heavy chain constant domain, an exogenous immunoglobulin variable and constant light chain, and an exogenous variable heavy chain.

The following antibodies and sequences are useful to provide selected antibodies with targeted binding against pathogens or antigens of interest (unless noted, Kabat numbering is intended):

An exemplary anti-RSV antibody is palivizumab, which targets the RSV fusion protein and is used to prevent or reduce RSV infections.

In particular embodiments, an anti-RSV antibody is mouse palivizumab that includes a variable heavy chain sequence including: QVELQESGPGILQP-SQTLSLTCSFSGFSLSTSGMSVGWIRQPSGEGLEW-LADIWWDDKKDYN PSLKSRLTISKDTSSNQVFLKITGVDTADTATYYCAR-SMITNWYFDVWGAGTTVTVSS (SEQ ID NO: 138); and a variable light chain sequence including:

```
                                        (SEQ ID NO: 205)
DIQLTQSPAIMSASPGEKVTMTCSASSSVGYMHWYQQKLSTSPKLQIYD

TSKLASGVPGRFSGSGSGNSYSLTISSIQAEDVATYYCFRGSGYPFTFG

QGTKLEIK.
```

An additional exemplary anti-RSV antibody is human palivizumab and includes a variable light chain sequence including: DIQMTQSPSTLSASVGDRVTITCK-CQLSVGYMHWYQQKPGKAPKLLIYDTSK-LASGVPSRFSG SGSGTEFTLTISSLQPDFA-TYYCFQGSGYPFTFGGGTKLEIKR (SEQ ID NO: 206); and a variable heavy chain sequence including:

```
                                        (SEQ ID NO: 123)
QVTLRESGPALVKPTQTLTLTCTFSGFSLSTSGMSVGWIRQPPGKALEW

LADIWWDDKKDYNPSLKSRLTISKDTSKNQVVLKVTNMDPADTATYYCA

RSMITNWYFDVWGAGTT.
```

Within a variable heavy chain and variable light chain, segments referred to as complementary determining regions (CDRs) dictate epitope binding. Each heavy chain has three CDRs (i.e., CDRH1, CDRH2, and CDRH3) and each light chain has three CDRs (i.e., CDRL1, CDRL2, and CDRL3)

An additional exemplary anti-RSV antibody is described in U.S. Pat. No. 9,403,900. This anti-RSV antibody includes a variable heavy chain including a CDRH1 sequence including GASINSDNYYWT (SEQ ID NO: 207), a CDRH2 sequence including HISYTGNTYYTPSLKS (SEQ ID NO: 208), and a CDRH3 sequence including CGAYVLIS-NCGWFDS (SEQ ID NO: 209); and a variable light chain including a CDRL1 sequence including QASQDISTYLN (SEQ ID NO: 210), a CDRL2 sequence including GASN-LET (SEQ ID NO: 211), and a CDRL3 sequence including QQYQYLPYT (SEQ ID NO: 212).

Exemplary anti-RSV antibodies also include AB1128 (available from MILLIPORE) and ab20745 (available from ABCAM).

An example of an anti-HIV antibody is 10E8, which is a broadly neutralizing antibody that binds to gp41. The 10E8 anti-HIV antibody includes a variable heavy chain including a CDRH1 sequence including GFDFDNAW (SEQ ID NO: 213), a CDRH2 sequence including ITGPGEGWSV (SEQ ID NO: 214), and a CDRH3 sequence including TGKYYDFWSGYPPGEEYFQD (SEQ ID NO: 215); and a variable light chain including a CDRL1 sequence including TGDSLRSHYAS (SEQ ID NO: 216), a CDRL2 sequence including GKNNRPS (SEQ ID NO: 217), and a CDRL3 sequence including SSRDKSGSRLSV (SEQ ID NO: 218).

An additional example of an anti-HIV antibody is VRC01, which is a broadly neutralizing antibody that binds to the CD4 binding site of gp120. The VRC01 antibody includes a variable heavy chain including a CDRH1 sequence including GYEFIDCT (SEQ ID NO: 219), a CDRH2 sequence including KPRGGAVN (SEQ ID NO: 220), and a CDRH3 sequence including RGKNCDYNWD-FEHW (SEQ ID NO: 221); and a variable light chain including a CDRL1 sequence including QYGS, a CDRL2 sequence including SGS, and a CDRL3 sequence including QQYEF (SEQ ID NO: 222).

Exemplary anti-HIV antibodies also include ab18633 and 39/5.4A (available from ABCAM); and H81E (available from THERMOFISHER).

An example of an anti-Dengue virus antibody is antibody 55 described in U.S. 20170233460 and includes a variable heavy chain including a CDRH1 sequence including EVQLHQSGAELVKPGASVKLSCTVSGFNIK (SEQ ID NO: 223), a CDRH2 sequence including WVKQRPEQGLEWI (SEQ ID NO: 224), and a CDRH3 sequence including ATIKADTSSNTAYLQLISLTSED-TAVYYCAF (SEQ ID NO: 225); and a variable light chain including a CDRL1 sequence including DIQMTQSPASLSVSVGETVTITC (SEQ ID NO: 226), a CDRL2 sequence including WYQQKQGKSPQLLVY (SEQ ID NO: 227), and a CDRL3 sequence including GVPSRFSGSGSGTQYSLKINSLQSEDFGTYYC (SEQ ID NO: 228).

An additional example of an anti-Dengue virus antibody is DB2-3 described in U.S. Pat. No. 8,637,035 and includes a variable heavy chain including a CDRH1 sequence including YTFTDYAIT (SEQ ID NO: 229), a CDRH2 sequence including GLISTYYGDSFYNQKFKG (SEQ ID NO: 230), and a CDRH3 sequence including TIRDGKAMDY (SEQ ID NO: 231); and a variable light chain including a CDRL1 sequence including RSSQSLVHSNGNTYLH (SEQ ID NO: 232), a CDRL2 sequence including KVSNRFS (SEQ ID NO: 233), and a CDRL3 sequence including SQSTHVPYT (SEQ ID NO: 234). Examples of anti-Dengue virus antibodies also include ab155042 and ab80914 (both available from ABCAM).

An example of an anti-pertussis antibody is described in U.S. Pat. No. 9,512,204 and includes a variable heavy chain including QVQLQQPGSELVRPGASVKLSCK-ASGYKFTS YWMHWVKQRPGQGLEWIGNIFPGSG-STNYDEKFNSKATLTVDTSSNTAYMQLSSLTSEDSAV YYCTRWLSGAYFDYWGQGTTVTVSS (SEQ ID NO: 235) and a variable light chain including QIVLTQSPALM-SASPGEKVTMTCSASSSVSFMYWYQQKPRSSPKP-WIYLTSNLPSGVPARFSG SGSGTSYSLTISSMEAE-DAATYYCQQWSSHPPTFGSGTKLEIK (SEQ ID NO: 236).

An example of an anti-hepatitis C antibody includes a variable heavy chain including a CDRH1 sequence including SYGMHW (SEQ ID NO: 237), a CDRH2 sequence including VIWLDGSNTYYADSVKGR (SEQ ID NO: 238), and a CDRH3 sequence including ARDIFTVARGVIIYFDY (SEQ ID NO: 239); and a variable light chain including a CDRL1 sequence including RASQSVSSYLA (SEQ ID NO: 240), a CDRL2 sequence including DASNRAT (SEQ ID NO: 241), and a CDRL3 sequence including QQRSNWVT (SEQ ID NO: 242). Examples of anti-hepatitis C antibodies also include MAB8694 (available from MILLIPORE) and C7-50 (available from ABCAM).

An example of an anti-influenza virus antibody is described U.S. Pat. No. 9,469,685 and includes a variable heavy chain including a CDRH1 sequence including GMTSNSLA (SEQ ID NO: 243), a CDRH2 sequence including IIPVFETP (SEQ ID NO: 244), and a CDRH3 sequence including ATSAGGIVNYYLSFNI (SEQ ID NO: 245); and a variable light chain including a CDRL1 sequence including QTITTW (SEQ ID NO: 246), a CDRL2 sequence including KTS, and a CDRL3 sequence including QQYSTYSGT (SEQ ID NO: 247). An example of an anti-influenza virus antibody also includes C102 (available from THERMOFISHER).

An exemplary anti-MPV antibody includes MPE8.

Exemplary anti-CMV antibodies includes MCMV5322A, MCMV3068A, LJP538, and LJP539. RG7667 includes a mixture of MCMV5322A and MCMV3068A while CSJ148 includes a mixture of LJP538, and LJP539. See also, for example, Deng et al., Antimicrobial Agents and Chemotherapy 62(2) e01108-17 (February 2018); and Dole et al., Antimicrobial Agents and Chemotherapy 60(5) 2881-2887 (May 2016).

An example of an anti-EBV antibody includes a variable heavy chain including an AMM01 CDRH1 sequence including YTFIHFGISW (SEQ ID NO: 248), an AMM01 CDRH2 sequence including IDTNNGNTNYAQSLQG (SEQ ID NO: 249), and an AMM01 CDRH3 sequence including RALEMGHRSGFPFDY (SEQ ID NO: 250); and a variable light chain including an AMM01 CDRL1 sequence including GGHNIGAKNVH (SEQ ID NO: 251), an AMM01 CDRL2 sequence including YDSDRPS (SEQ ID NO: 252), and an AMM01 CDRL3 sequence including CQVWDS-GRGHPLYV (SEQ ID NO: 253).

An example of an anti-HSV antibody includes HSV8-N and MB66.

Exemplary anti-*Clostridium difficile* antibodies include actoxumab and bezlotoxumab. See also, for example, Wilcox et al., N Engl J Med 376(4) 305-317 (2017).

Commercially available anti-TNF antibodies include infliximab (Remicade® Centocor, Inc., Malvern, PA. with biosimilars Inflectra® Pfizer, Kent, UK and Ixifi® Pfizer, New York, NY), adalimumab (Humira® Abbott Laboratories, Abbott Park, IL with biosimilars Amjevita® Amgen, Thousand Oaks, CA and Cyltezo® Boehringer Ingelheim Int'l, Ingelheim, DE), golimumab (Simponi® Johnson & Johnson Corp., New Brunswick, NJ), etanercept (Enbrel® Immunex Corp, Thousand Oaks, CA with biosimilar Erelzi® Novartis AG, Basel, CH), and certolizumab-pegol (Cimzia® UCB Pharma, Brussels, BE).

In particular embodiments, the CDRs of infliximab include: heavy chain residues 26-37, 52-70, and 103-116 and light chain residues 24-39, 55-61, and 94-102. In particular embodiments, the heavy chain of infliximab begins with EVKLEESGGGLVQPGGSMK (SEQ ID NO: 254) and the light chain begins with DILLTQSPAILSVSPGER (SEQ ID NO: 255).

In particular embodiments, infliximab includes a variable heavy chain including a CDRH1 sequence including IFSNHW (SEQ ID NO: 256), a CDRH2 sequence including RSKSINSATH (SEQ ID NO: 257), and a CDRH3 sequence including NYYGSTY (SEQ ID NO: 258); and a variable light chain including a CDRL1 sequence including FVGSSIH (SEQ ID NO: 259), a CDRL2 sequence including KYASESM (SEQ ID NO: 260), and a CDRL3 sequence including QSHSW (SEQ ID NO: 261).

In particular embodiments, adalimumab includes a variable heavy chain including a CDRH1 sequence including TFDDYA (SEQ ID NO: 262), a CDRH2 sequence including TWNSGHID (SEQ ID NO: 263), and a CDRH3 sequence including VSYLSTASSL (SEQ ID NO: 264); and a variable light chain including a CDRL1 sequence including GIR-NYLA (SEQ ID NO: 265), a CDRL2 sequence including YAASTLQ (SEQ ID NO: 266), and a CDRL3 sequence including RYNRA (SEQ ID NO: 267).

In particular embodiments, certolizumab includes a variable heavy chain including a CDRH1 sequence including VFTDYG (SEQ ID NO: 268), a CDRH2 sequence including NTYIGEPI (SEQ ID NO: 269), and a CDRH3 sequence including GYRSYAM (SEQ ID NO: 270); and a variable light chain including a CDRL1 sequence including NVGTNVA (SEQ ID NO: 271), a CDRL2 sequence including YSASFLY (SEQ ID NO: 272), and a CDRL3 sequence including QYNIY (SEQ ID NO: 273).

Numerous additional antibody sequences are available and known to those of ordinary skill in the art that can be used within the teachings of the current disclosure. Sequence information for commercially available antibodies may be found in the Drug Bank database, the CAS Registry, and/or the RSCB Protein Data Bank. Moreover, nucleic acid sequences encoding portions of selected antibodies described herein can be easily derived by one of ordinary skill in the art.

(ii) Gene Editing Techniques and Cell Sorting. Gene editing systems allow control over the target sites of genetic therapies. Within the teachings of the current disclosure, any gene editing system capable of precise sequence targeting and modification can be used. These systems typically include a targeting element for precise targeting and a cutting element for cutting the targeted genetic site. Guide RNA is one example of a targeting element while various nucleases provide examples of cutting elements. Targeting elements and cutting elements can be separate molecules or linked, for example, by a nanoparticle. Alternatively, a targeting element and a cutting element can be linked together into one dual purpose molecule. When insertion of a therapeutic nucleic acid sequence is intended, the systems can also include homology-directed repair templates (i.e., homology arms as described above) associated with the genetic construct. As detailed further below, however, different gene editing systems can adopt different components and configurations while maintaining the ability to precisely target, cut, and modify selected genomic sites.

Particular embodiments utilize zinc finger nucleases (ZFNs) as gene editing agents. ZFNs are a class of site-specific nucleases engineered to bind and cleave DNA at specific positions. ZFNs are used to introduce double strand breaks (DSBs) at a specific site in a DNA sequence which enables the ZFNs to target unique sequences within a genome in a variety of different cells. Moreover, subsequent to double-stranded breakage, homology-directed repair (HDR) or non-homologous end joining (NHEJ) takes place to repair the DSB, thus enabling genome editing.

ZFNs are synthesized by fusing a zinc finger DNA-binding domain to a DNA cleavage domain. The DNA-binding domain includes three to six zinc finger proteins which are transcription factors. The DNA cleavage domain includes the catalytic domain of, for example, FokI endonuclease. The FokI domain functions as a dimer requiring two constructs with unique DNA binding domains for sites on the target sequence. The FokI cleavage domain cleaves within a five or six base pair spacer sequence separating the two inverted half-sites.

For additional information regarding ZFNs, see Kim, et al. Proceedings of the National Academy of Sciences of the United States of America 93, 1156-1160 (1996); Wolfe, et al. Annual review of biophysics and biomolecular structure 29, 183-212 (2000); Bibikova, et al. Science 300, 764 (2003); Bibikova, et al. Genetics 161, 1169-1175 (2002); Miller, et al. The EMBO journal 4, 1609-1614 (1985); and Miller, et al. Nature biotechnology 25, 778-785 (2007).

Particular embodiments can use transcription activator like effector nucleases (TALENs) as gene editing agents. TALENs refer to fusion proteins including a transcription activator-like effector (TALE) DNA binding protein and a DNA cleavage domain. TALENs are used to edit genes and genomes by inducing DSBs in the DNA, which induce repair mechanisms in cells. Generally, two TALENs must bind and flank each side of the target DNA site for the DNA cleavage domain to dimerize and induce a DSB. The DSB is repaired in the cell by NHEJ or HDR if an exogenous double-stranded donor DNA fragment is present.

As indicated, TALENs have been engineered to bind a target sequence of, for example, an endogenous genome, and cut DNA at the location of the target sequence. The TALEs of TALENs are DNA binding proteins secreted by *Xanthomonas* bacteria. The DNA binding domain of TALEs include a highly conserved 33 or 34 amino acid repeat, with divergent residues at the $12^{th}$ and $13^{th}$ positions of each repeat. These two positions, referred to as the Repeat Variable Diresidue (RVD), show a strong correlation with specific nucleotide recognition. Accordingly, targeting specificity can be improved by changing the amino acids in the RVD and incorporating nonconventional RVD amino acids.

Examples of DNA cleavage domains that can be used in TALEN fusions are wild-type and variant FokI endonucleases. For additional information regarding TALENs, see Boch, et al. Science 326, 1509-1512 (2009); Moscou, &

Bogdanove, Science 326, 1501 (2009); Christian, et al. Genetics 186, 757-761 (2010); and Miller, et al. Nature biotechnology 29, 143-148 (2011).

Particular embodiments utilize MegaTALs as gene editing agents. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

In particular embodiments, the endogenous B cell genome can be targeted using CRISPR gene editing systems. The CRISPR nuclease system is a prokaryotic immune system that confers resistance to foreign genetic elements such as plasmids and phages and provides a form of acquired immunity. CRISPRs are DNA loci containing short repetitions of base sequences. In the context of a prokaryotic immune system, each repetition is followed by short segments of spacer DNA belonging to foreign genetic elements that the prokaryote was exposed to. This CRISPR array of repeats interspersed with spacers can be transcribed into RNA. The RNA can be processed to a mature form and associate with a nuclease, such as cas (CRISPR-associated) nuclease. A CRISPR-Cas system including an RNA having a sequence that can hybridize to the foreign genetic elements and Cas nuclease can then recognize and cut these exogenous genetic elements in the genome.

A CRISPR-Cas system does not require the generation of customized proteins to target specific sequences, but rather a single Cas enzyme can be programmed by a short guide RNA molecule (crRNA) to recognize a specific DNA target. The CRISPR-Cas systems of bacterial and archaeal adaptive immunity show extreme diversity of protein composition and genomic loci architecture. The CRISPR-Cas system loci have more than 50 gene families and there are no strictly universal genes, indicating fast evolution and extreme diversity of loci architecture. So far, adopting a multi-pronged approach, there is comprehensive cas gene identification of 395 profiles for 93 Cas proteins. Classification includes signature gene profiles plus signatures of locus architecture. A new classification of CRISPR-Cas systems is proposed in which these systems are broadly divided into two classes, Class 1 with multi-subunit effector complexes and Class 2 with single-subunit effector modules exemplified by the Cas9 protein.

At least three different Cas9 nucleases have been developed for genome editing. The first is the wild type Cas9 which introduces double strand breaks (DSBs) at a specific DNA site, resulting in the activation of DSB repair machinery. DSBs can be repaired by non-homologous end joining (NHEJ), homology-directed repair (HDR), or microhomology mediated repair (MMEJ). NHEJ can involve repair of a DSB with no homology (<5 bp) between the two ends joined during repair; HDR can involve repair of a DSB with a large region of homology between the ends joined during repair (100 or more nucleotides); and MMEJ can involve repair of a DSB with a small (5 to 50 bp) region of homology between the ends joined during repair. Another type of Cas9 includes a mutant Cas9, known as the Cas9D10A, with only nickase activity, which means that it only cleaves one DNA strand and does not activate NHEJ. Thus, the DNA repairs proceed via the HDR pathway only. The third is a nuclease-deficient Cas9 (dCas9) which does not have cleavage activity but is able to bind DNA. Therefore, dCas9 is able to target specific sequences of a genome without cleavage. By fusing dCas9 with various effector domains, dCas9 can be used either as a gene silencing or activation tool.

In addition to the Class 1 and Class 2 CRISPR-Cas systems, more recently a putative Class 2, Type V CRISPR-Cas class exemplified by Cpf1 has been identified Zetsche et al. (2015) Cell 163(3): 759-771. The Cpf1 nuclease particularly can provide added flexibility in target site selection by means of a short, three base pair recognition sequence (TTN), known as the protospacer-adjacent motif or PAM. Cpf1's cut site is at least 18 bp away from the PAM sequence, thus the enzyme can repeatedly cut a specified locus after indel (insertion and deletion) formation, increasing the efficiency of HDR. Moreover, staggered DSBs with sticky ends permit orientation-specific donor template insertion.

Additional information regarding CRISPR-Cas systems and components thereof are described in, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

Particular embodiments combine tracrRNA and crRNA into a single synthetic single guide RNA (sgRNA utilizing e.g., SEQ ID NOs: 87-89, or 290-366). In particular embodiments, an sgRNA can include a twenty nucleotide sequence that is analogous to the crRNA, and a tracrRNA sequence. For certain gene editing systems, the target sequence may be adjacent to a PAM (e.g., 5'-20 nt target-NGG-3'). In particular embodiments, a target sequence can include a PAM (SEQ ID NOs: 5-84). In particular embodiments, guide RNA (gRNA) includes a target site adjacent to the PAM targeted by the genome editing complex. The gRNA can include at least the 16, 17, 18, 19, 20, 21, or 22 nucleotides adjacent to the PAM.

In particular embodiments, a cutting element is directed to the targeted DNA location with the assistance of engineered gRNAs (FIG. 25A (Sternberg et al., Mol Cell. 2015; 58(4): 568-74)). Genetic constructs with homology arms flanking the cut genomic region are efficiently inserted into this location by the homology-directed DNA repair mechanism (see, e.g., FIG. 15B (Elliott et al., Mol Cell Biol. 1998; 18(1):93-101). Using this approach expression of the endogenous antibody will be eliminated and genes encoding the selected antibody will be inserted into the targeted genetic location. This targeted insertion eliminates or significantly reduces the possibility of off-target effects resulting from random genetic insertion.

Figure 7:
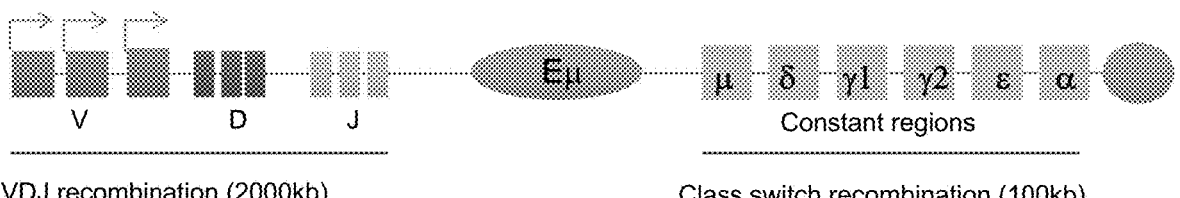
FIG. 7. Schematic depicting an endogenous heavy chain gene locus, including V, D, and J segments that recombine, enhancer elements, shown as a circle and an oval, and 6 potential constant regions that can be expressed. B cells start by expressing the μ/δ constant regions, but can switch to using γ, α, or ε constant regions by deleting intervening DNA. Also note that each V segment is associated with a heavy chain promoter denoted by an arrow that drives expression of the heavy chain following recombination.

In particular embodiments, sgRNA targeting the mouse or human IgH of each endogenous antibody targets the region 100 bp downstream of the J region (FIG. 9). In the experimental examples, this region was targeted to express a version of the selected antibody palivizumab containing the C region from the endogenous genome (FIGS. 7 and 9). The crispr.mit.edu algorithm (Hsu et al., Nat Biotechnol. 2013; 31(9):827-32) identified 22 targeting sequences for this region that are predicted to have little, if any, off-target binding. Individual targeting sequences can be inserted into the full-length sgRNA and mixed with a nuclease such as Cas9 immediately prior to incubation as described (Schumann et al., Proc Natl Acad Sci USA. 2015; 112(33):10437-42) and electroporated into B cells (Kim et al., J Immunol. 1979; 122(2):549-54). Since cellular repair of DNA cut by Cas9 often results in loss of gene function (Symington & Gautier, Annu Rev Genet. 2011; 45:247-71), efficient sgRNAs targeting antibody coding regions are expected to result in the appearance of some B cells lacking antibody, which can be easily assessed by flow cytometry. The activity of sgRNAs targeting intronic sequences can be assessed by sequencing, or through enzymatic assays such as the T7 endonuclease assay.

In particular embodiments, genome targeting and cutting elements can be administered through electroporation, nanoparticle-mediated delivery and/or viral vector delivery. Electroporation can be useful, for example, to deliver targeting elements and/or cutting elements because the membrane of the cell does not normally allow such foreign molecules into the cell. Electroporation sends an electric shock to the cells that temporarily allows such foreign molecules to pass through the cell membrane.

In particular embodiments, genetic constructs for insertion can be administered through electroporation, nanoparticle-mediated delivery and/or viral vector delivery. Adeno-associated viral vectors include those derived from e.g., adenovirus 5 (Ad5), adenovirus 35 (Ad35), adenovirus 11 (Ad11), adenovirus 26 (Ad26), adenovirus 48 (Ad48) or adenovirus 50 (Ad50)), and adeno-associated virus (AAV; see, e.g., U.S. Pat. No. 5,604,090; Kay et al., Nat. Genet. 24:257 (2000); Nakai et al., Blood 91:4600 (1998)).

In particular embodiments, genome targeting and cutting elements can be administered through electroporation and genetic constructs for insertion can be administered through AAV-mediated delivery. In particular embodiments, genome targeting and cutting elements can be administered through nanoparticle-mediated delivery and genetic constructs for insertion can be administered through AAV-mediated delivery.

In particular embodiments, the genetic construct including a transgene can be mixed with a targeting element (e.g., sgRNA) and a cutting element (e.g., Cas9 or cpf1) immediately or shortly before electroporation. Selected antibody expression can be confirmed later (e.g., 3 days later) by measuring cell binding to fluorescently tagged target proteins by flow cytometry. Enrichment and analysis methodologies for detecting and analyzing epitope-specific B cells can be used. Pape et al., Science. 2011; 331(6021):1203-7; Taylor et al., J Exp Med. 2012; 209(3):597-606; Taylor et al., J Exp Med. 2012; 209(11):2065-77; Haasken et al., J Immunol. 2013; 191(3):1055-62; Taylor et al., J Immunol Methods. 2014; 405:74-86; Nanton et al., Eur J Immunol. 2015; 45(2):428-41; Hamilton et al., J Immunol. 2015; 194(10): 5022-34; Taylor et al., Science. 2015; 347(6223):784-7). These methodologies allow detection of selected antibody-expressing B cells at frequencies as extraordinarily low as 0.00002% of the total B cell population (Taylor et al., Science. 2015; 347(6223):784-7).

In particular embodiments, cells can be identified and/or sorted based on marker expression, before or after delivering the genetic construct. For example, it may be useful to isolate a particular type of B cells (e.g., memory B cells, antibody-secreting B cells, naïve B cells, B1 B cells, marginal zone B cells) from a sample prior to delivering the genetic construct. As another example, it may be useful to isolate B cells from other cells present in a blood sample.

CD19 is an example of a protein expressed by B cells but few other cells of the body. By marking CD19 with a fluorescent molecule, B cells can be specifically identified. B220 is a useful marker to identify mouse B cells.

CD27 is an example of a protein expressed by memory but not naive human B cells. By marking CD27 with a fluorescent molecule, memory B cells can be identified.

CD21 is an example of a protein not expressed (or expressed to a low degree) by some memory human B cells with the capacity to quickly secrete antibody following infection. Low CD21 expression can be used to define B cells primed for plasma cell differentiation. By marking CD21 with a fluorescent molecule, these B cells can be specifically identified by for example, negative selection.

Human naïve B cells can be identified by the marker profile IgM+ IgD+ CD27−. Mouse naïve B cells can be identified by the marker profile CD38+ GL7− IgM+ IgD+. Human B1 B cells can be identified by the marker profile CD5+ CD43+. Mouse B1 B cells can be identified by the marker profile CD43+ B220LOW. Human marginal zone B cells can be identified by the marker profile CD21+++ IgM++ IgD− CD27+. Mouse marginal zone B cells can be identified by the marker profile CD21+++ IgM++ IgD−.

Particular embodiments may utilize the $CD19^+CD27^+$ $CD21^{lo}$ marker profile.

CD45 is a marker used for identifying and/or isolating cell types used in the experiments described herein. Different mouse strains express different versions of the protein called CD45, termed CD45.1 and CD45.2. In experiments disclosed herein, B cells from a mouse that expresses CD45.2 will be taken and transferred into a mouse that expresses CD45.1. By marking CD45.1 and CD45.2 with different fluorescent molecules, one can identify the cells that came from the donor animal because they express CD45.2 but not CD45.1.

Particular embodiments include sorting B cells after genetic modification based on expression of an exogenous light chain. For example, B cells that naturally express a kappa light chain can be modified to express a selected antibody that includes a lambda light chain. B cells that naturally express a lambda light chain can be modified to express a selected antibody that includes a kappa light chain. Sorting based on expression of an exogenous light chain will allow for isolation of only those B cells expressing the selected antibody. In particular embodiments, only those B cells that completely lack surface expression of their endogenous light chain are isolated for formulation and administration to a subject.

In particular embodiments, cells may be identified and/or isolated using flow cytometry. Flow cytometry is a sensitive and powerful analysis approach that uses lasers to individually analyze the fluorescent molecules marking millions of individual cells. By analyzing the combination of fluorescent molecules each cell is marked with, different B cell subtypes can be identified. Flow cytometry can be used to identify B cell subsets and analyze the expression of selected antibodies (e.g., palivizumab) within these cells.

In particular embodiments, methods of modifying B cells can include obtaining hematopoietic stem cells (HSC), and/or delivering the genetic constructs to HSC. HSC can refer to a type of stem cell that naturally produces B cells as well as all other cells of the immune system. HSC can be obtained, for example, from cord blood.

Particular experimental results described herein utilized A20 cells to develop the genetic modification methodology prior to moving on to freshly-isolated B cells. A20 is an immortalized cell line made from a mouse B cell.

In particular embodiments, B cells may be obtained from a human subject and obtained B cells or a subset thereof may be modified ex vivo.

Formulations of Modified B Cells. Once modified, cells can be harvested from a culture medium, and washed and concentrated into a carrier in a therapeutically-effective amount. Exemplary carriers include saline, buffered saline, physiological saline, water, Hanks' solution, Ringer's solution, Nonnosol-R (Abbott Labs), PLASMA-LYTE A® (Baxter Laboratories, Inc., Morton Grove, IL), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% hyaluronic acid sodium salt (HAS) or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, formulations can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Formulations can include, for example, greater than $10^2$ modified B cells, greater than $10^3$ modified B cells, greater than $10^4$ modified B cells, greater than $10^5$ modified B cells, greater than $10^6$ modified B cells, greater than $10^7$ modified B cells, greater than $10^8$ modified B cells, greater than $10^9$ modified B cells, greater than $10^{10}$ modified B cells, or greater than $10^{11}$ modified B cells.

Methods of Use. Methods disclosed herein include treating subjects (e.g., humans, veterinary animals (dogs, cats, reptiles, birds) livestock (e.g., horses, cattle, goats, pigs, chickens) and research animals (e.g., monkeys, rats, mice, fish) with formulations disclosed herein. Treating subjects includes delivering therapeutically effective amounts.

Therapeutically effective amounts include those that provide effective amounts, prophylactic treatments and/or therapeutic treatments.

An "effective amount" is the amount of a composition necessary to result in a desired physiological change in the subject. Effective amounts are often administered for research purposes. Effective amounts disclosed herein can cause a statistically-significant effect in an animal model or in vitro assay relevant to the assessment of a condition's development, progression, and/or resolution.

A "prophylactic treatment" includes a treatment administered to a subject who does not display signs or symptoms of a condition or displays only early signs or symptoms of a condition such that treatment is administered for the purpose of diminishing or decreasing the risk of developing the condition. Thus, a prophylactic treatment functions as a preventative treatment against a condition. In particular embodiments, prophylactic treatments reduce, delay, or prevent the worsening of a condition. Particular embodiments include administration of a formulation described herein as prophylactic protection in the absence of a currently effective vaccine. Particular embodiments include administration of a formulation described herein as prophylactic protection as a replacement for conventional vaccination strategies. Particular embodiments include administration of a formulation described herein as prophylactic protection as a supplement to conventional vaccination strategies.

A "therapeutic treatment" includes a treatment administered to a subject who displays symptoms or signs of a condition and is administered to the subject for the purpose of diminishing or eliminating those signs or symptoms of the condition. The therapeutic treatment can reduce, control, or eliminate the presence or activity of the condition and/or reduce control or eliminate side effects of the condition.

In particular embodiments, the condition is an infection.

Function as an effective amount, prophylactic treatment or therapeutic treatment are not mutually exclusive, and in particular embodiments, administered dosages may accomplish more than one treatment type.

In particular embodiments, therapeutically effective amounts provide anti-pathogen effects. Anti-pathogen effects can include anti-infection effects. Anti-infection effects can include a decrease in the occurrence of infections, a decrease in the severity of infections, a decrease in the duration of infections, a decrease in the number of infected cells, a decrease in volume of infected tissue, an increase in life expectancy, induced sensitivity of infected cells to immune clearance, reduced infection-associated pain, and/or reduction or elimination of a symptom associated with the treated infection.

In particular embodiments, therapeutically effective amounts provide anti-inflammatory effects. Anti-inflammatory effects can include reduced inflammation-associated pain, heat, redness, swelling and/or loss of function.

In particular embodiments, therapeutically effective amounts provide anti-Crohn's disease effects or anti-ulcerative colitis effects. Anti-Crohn's disease effects or anti-ulcerative colitis effects can include reduced diarrhea, reduced rectal bleeding, reduced unexplained weight loss, reduced fever, reduced abdominal pain and cramping, reduced fatigue and feelings of low energy, and/or restored appetite.

In particular embodiments, therapeutically effective amounts provide anti-arthritis effects. Anti-arthritis effects can include reduced pain, stiffness, swelling, redness in the joints and/or a restored range of motion. Types of arthritis include rheumatoid arthritis (RA), ankylosing spondylitis, and psoriatic arthritis.

In particular embodiments, therapeutically effective amounts provide anti-plaque psoriasis effects. Anti-plaque psoriasis effects can include reduced red patches, scaling spots, itching, burning, soreness, nail bed abnormalities and/or swollen or stiff joints.

In particular embodiments, B cells may be obtained from a subject, a subset of the B cells may be modified ex vivo, and then the modified B cells may be formulated and administered to the subject. In particular embodiments, a first subset of the subject's B cells may be modified with a first genetic construct to produce a selected antibody against a first pathogen, and a second subset of the subject's B cells may be modified with a second genetic construct to produce a selected antibody against a second pathogen, thereby providing protective antibodies against two pathogens. As indicated, B cells against any number of pathogens can be formed and administered to a subject. In particular embodiments, the selected antibodies can be an anti-RSV antibody, an anti-HIV antibody, an anti-Dengue virus antibody, an anti-*Bordatella pertussis* antibody, an anti-hepatitis C antibody, an anti-influenza virus antibody, an anti-parainfluenza virus antibody, an anti-MPV antibody, an anti-cytomegalovirus antibody, an anti-Epstein Barr virus antibody; an anti-herpes simplex virus antibody, an anti-*Clostridium difficile* bacterial toxin antibody, and/or an anti-TNF antibody. In particular embodiments, the selected antibodies can be one or more of an anti-RSV antibody, an anti-influenza virus antibody, an anti-parainfluenza virus antibody, and/or an anti-MPV antibody. In particular embodiments, the selected antibodies can be an anti-RSV antibody, an anti-influenza virus antibody, an anti-parainfluenza virus antibody, and an anti-MPV antibody. In particular embodiments, the selected antibody is palivizumab.

In particular embodiments, B cells may be obtained from a bone marrow donor or a hematopoietic stem cell donor that has been immunologically matched to a recipient. In particular embodiments, a first subset of the donor's B cells may be modified with a first genetic construct to produce a selected antibody against a first pathogen, and a second subset of the donor's B cells may be modified with a second genetic construct to produce a selected antibody against a second pathogen, thereby providing protective antibodies against two pathogens. As indicated, B cells against any number of pathogens can be formed and administered to a subject. In particular embodiments, the selected antibodies can be an anti-RSV antibody, an anti-HIV antibody, an anti-Dengue virus antibody, an anti-*Bordatella pertussis* antibody, an anti-hepatitis C antibody, an anti-influenza virus antibody, an anti-parainfluenza virus antibody, an anti-MPV antibody, an anti-cytomegalovirus antibody, an anti-Epstein Barr virus antibody; an anti-herpes simplex virus antibody, an anti-*Clostridium difficile* bacterial toxin antibody, and/or an anti-TNF antibody. In particular embodiments, the selected antibodies can be one or more of an anti-RSV antibody, an anti-influenza virus antibody, an anti-parainfluenza virus antibody, and/or an anti-MPV antibody. In particular embodiments, the selected antibodies can be an anti-RSV antibody, an anti-influenza virus antibody, an anti-parainfluenza virus antibody, and an anti-MPV antibody. In particular embodiments, the selected antibody is palivizumab. The genetically-modified B cells can be administered to the recipient to provide protection against infection (e.g., an anti-infection effect) until the transplanted cells repopulate the recipient's own immune system.

In particular embodiments, the recipient is receiving bone marrow from a donor or a hematopoietic stem cell transplant as a treatment for a hematological malignancy. Examples of hematological malignancies include acute lymphocytic leukemia, B-cell prolymphocytic leukemia, Burkitt lymphoma/leukemia, chronic lymphocytic leukemia (CLL), diffuse large B-cell lymphoma, follicular lymphoma (grades I, II, III, or IV), Hodgkin's lymphoma, intravascular large B-cell lymphoma, lymphoma, lymphoplasmocytic lymphoma, mantle cell lymphoma, marginal zone lymphoma (extranodal and nodal), mediastinal (thymic) large B-cell lymphoma, multiple myeloma, non-Hodgkin's lymphoma, POEMS syndrome/osteosclerotic myeloma, primary effusion lymphoma, splenic marginal zone lymphoma, small lymphocytic lymphoma, smoldering multiple myeloma (SMM), and Waldenstrom's macroglobulinemia.

In particular embodiments, the recipient is receiving genetically-modified hematopoietic stem cells that provide a gene the recipient is lacking. These recipients may have a primary or secondary immunodeficiency that can be treated with the provision of a therapeutic gene through hematopoietic stem cells. More than 80 primary immune deficiency diseases are recognized by the World Health Organization. These diseases are characterized by an intrinsic defect in the immune system in which, in some cases, the body is unable to produce any or enough antibodies against infection. In other cases, cellular defenses to fight infection fail to work properly. Typically, primary immune deficiencies are inherited disorders. X-linked severe combined immunodeficiency (SCID-X1) is another example of a primary immune deficiency. X-linked SCID results in both a cellular and humoral immune depletion caused by mutations in the common gamma chain gene (γC), which result in the absence of T and natural killer (NK) lymphocytes.

Secondary, or acquired, immune deficiencies are not the result of inherited genetic abnormalities, but rather occur in individuals in which the immune system is compromised by factors outside the immune system. Examples include trauma, viruses, chemotherapy, toxins, and pollution. Acquired immunodeficiency syndrome (AIDS) is an example of a secondary immune deficiency disorder caused by a virus, the human immunodeficiency virus (HIV), in which a depletion of T lymphocytes renders the body unable to fight infection.

In particular embodiments, B cells may be obtained from a subject, a subset of the B cells may be modified ex vivo, and then the modified B cells may be formulated and administered to the subject. In particular embodiments, a first subset of the subject's B cells may be modified with a first genetic construct to produce a selected antibody against an inflammatory molecule, such as an inflammatory cytokine, thereby providing antibodies that protect against inflammation. In particular embodiments, the selected antibodies can be anti-TNF antibodies and/or anti-IL-1 antibodies. In particular embodiments, the selected antibody is infliximab, adalimumab, and/or golimumab and/or an approved biosimilar thereof.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including age, previous vaccinations (if any), target, body weight, severity of condition, type of condition, stage of condition, previous or concurrent therapeutic interventions, idiopathy of the subject and route of administration.

As indicated, in particular embodiments, modified B cells express a tag that allows, for example, tracking and/or elimination after administration to a subject Exemplary doses can include greater than $10^2$ modified B cells, greater than $10^3$ modified B cells, greater than $10^4$ modified B cells, greater than $10^5$ modified B cells, greater than $10^6$ modified B cells, greater than $10^7$ modified B cells, greater than $10^8$ modified B cells, greater than $10^9$ modified B cells, greater than $10^{10}$ modified B cells, or greater than $10^{11}$ modified B cells.

In particular embodiments, the effects of selected antibodies can be measured using viral titers. Viral titer refers to the amount of virus that can be detected. High viral titers mean high levels of infection. An optimal protective response is observed with titers that fall to zero.

As will be understood by one of ordinary skill in the art, while particular embodiments have been described, additional embodiments may also be utilized within the scope of the disclosure. The following description provides description and enablement of representative additional embodiments.

Exemplary Embodiments

1. A method of genetically engineering B cells to express a selected antibody including targeted insertion of a genetic construct including (i) a promoter and (ii) a transgene encoding a portion of a selected antibody at an intronic region that is constant in all B cells and that is (i) positioned relative to an enhancer element that interacts with the promoter to drive expression of the transgene; and (ii) in a configuration such that a portion of the B cells' endogenous antibody-encoding genome is not expressed.

2. A method of genetically engineering B cells to express a selected antibody including inserting into SEQ ID NO: 1, SEQ ID NO: 2, SEQ ID NO: 3, or SEQ ID NO: 4, a genetic construct including or encoding (i) a heavy chain promoter, (ii) a signal peptide, (iii) the full length light chain of the selected antibody; (iv) a flexible linker or a skipping element; (v) the variable region of the heavy chain of the selected antibody; and (vi) a splice junction, thereby genetically engineering the B cells to express the selected antibody.

3. A method of embodiment 1 or 2, wherein the B cells' endogenous variable heavy chain encoding genome is not excised during the genetic modification.

4. A method of any of embodiments 1-3, wherein the selected antibody is an anti-Respiratory Syncytial Virus (RSV) antibody, an anti-human immunodeficiency virus (HIV) antibody, an anti-Dengue virus antibody, an anti-*Bordatella pertussis* antibody, an anti-hepatitis C antibody, an anti-influenza virus antibody, an anti-parainfluenza virus antibody, an anti-metapneumovirus (MPV) antibody, an anti-cytomegalovirus antibody, an anti-Epstein Barr virus antibody; an anti-herpes simplex virus antibody, an anti-*Clostridium difficile* bacterial toxin antibody, or an anti-tumor necrosis factor (TNF) antibody.

5. A method of any of embodiments 1-4, wherein the genetic construct includes SEQ ID NOs: 102-175, 278, 279, or 280-289.

6. A method of any of embodiments 2-5, wherein the flexible linker is between the full length light chain of the selected antibody and the variable region of the heavy chain of the selected antibody.

7. A method of any of embodiments 2-6, wherein the flexible linker is selected from SEQ ID NOs: 180-184.

8. A method of any of embodiments 2-7, wherein the flexible linker is a Gly-Ser linker including 50-80 amino acids.

9. A method of any of embodiments 2-8, wherein the flexible linker is a Gly-Ser linker including 57 amino acids.

10. A method of any of embodiments 2-6, 8, or 9, wherein the flexible linker is SEQ ID NO: 122.

11. A method of any of embodiments 2-10, wherein the skipping element is between the full length light chain of the selected antibody and the variable region of the heavy chain of the selected antibody.

12. A method of any of embodiments 2-11, wherein the skipping element is a self-cleaving peptide.

13. A method of embodiment 12, wherein the self-cleaving peptide is selected from SEQ ID NOs: 176-179.

14. A method of any of embodiments 2-13, wherein the skipping element is an internal ribosome entry site (IRES).

15. A method of any of embodiments 2-14, wherein the heavy chain promoter is selected from SEQ ID NOs: 111 and 128.

16. A method of any of embodiments 2-15, wherein the heavy chain promoter is IgVH1-69 or J558H10.

17. A method of any of embodiments 2-16, wherein the signal peptide is selected from SEQ ID NOs: 118, 134, and 185-194.

18. A method of any of embodiments 2-17, wherein the signal peptide is derived from human IgH heavy chain or human IgL light chain.

19. A method of any of embodiments 1-18, wherein the genetic construct includes homology arms.

20. A method of embodiment 19, wherein the homology arms include SEQ ID NOs: 90-101, 110, 125, 127, 140, 142, 143, 153, 170, 171, 173, 174, 278, or 279.

21. A method of any of embodiments 1-20, wherein the genetic construct encodes a tag.

22. A method of embodiment 21, wherein the tag includes STREPTAG®, STREP® tag II, His tag, Flag tag, Xpress tag, Avi tag, calmodulin tag, polyglutamate tag, HA tag, Myc tag, Nus tag, S tag, SBP tag, Softag 1, Softag 3, or V5 tag.

23. A method of embodiment 21 or 22, wherein the tag includes SEQ ID NOs: 122, or 195-204.

24. A method of any of embodiments 1-23, further including delivering a guide RNA (gRNA) sequence selected from one or more of SEQ ID NOs: 87-89, and 290-366, and a nuclease to the B cells.

25. A method of embodiment 24, wherein the delivering is through electroporation, a nanoparticle, or viral-mediated delivery.

26. A method of any of embodiments 1-25, wherein the genetic construct is part of an adeno-associated viral vector.

27. A method of any of embodiments 24-26, wherein the gRNA and nuclease are delivered through electroporation and the genetic construct is delivered as part of an adeno-associated viral vector.

28. A method of any of embodiments 24-27, wherein the nuclease is Cas9 or Cpf1.

29. A method of any of embodiments 24-28, wherein a target sequence targeted by one or more of the gRNA sequence is selected from one or more of SEQ ID NOs: 5-84 and the gRNA is selected from one or more of SEQ ID NOs: 87-89, and 290-366.

30. A method of any of embodiments 1-29, wherein the selected antibody is an anti-RSV antibody including palivizumab, AB1128, or ab20745.

31. A method of any of embodiments 1-30, wherein the selected antibody is: palivizumab including a heavy chain including SEQ ID NO: 138 and a light chain including SEQ ID NO: 136; palivizumab including a heavy chain including SEQ ID NO: 138 and a light chain including SEQ ID NO: 205; an anti-RSV antibody including a heavy chain including SEQ ID NO: 123 and a light chain including SEQ ID NO: 120; or an anti-RSV antibody including a heavy chain including SEQ ID NO: 123 and a light chain including SEQ ID NO: 206.

32. A method of any of embodiments 1-30, wherein the selected antibody is an anti-RSV antibody including a CDRH1 including SEQ ID NO: 207, a CDRH2 including SEQ ID NO: 208, a CDRH3 including SEQ ID NO: 209; a CDRL1 including SEQ ID NO: 210, a CDRL2 including SEQ ID NO: 211, and a CDRL3 including SEQ ID NO: 212.

33. A method of any of embodiments 1-29, wherein the selected antibody is an anti-HIV antibody including 10E8, VRC01, ab18633 or 39/5.4A.

34. A method of any of embodiments 1-29 or 33, wherein the selected antibody is an anti-HIV antibody including a heavy chain including SEQ ID NO: 150 and a light chain including SEQ ID NO: 149.

35. A method of any of embodiments 1-29 or 33, wherein the selected antibody is an anti-HIV antibody including a CDRH1 including SEQ ID NO: 213, a CDRH2 including SEQ ID NO: 214, a CDRH3 including SEQ ID NO: 215, a CDRL1 including SEQ ID NO: 216, a CDRL2 including SEQ ID NO: 217, and a CDRL3 including SEQ ID NO: 218 or a CDRH1 including SEQ ID NO: 219, a CDRH2 including SEQ ID NO: 220, a CDRH3 including SEQ ID NO: 221, a CDRL1 including QYGS, a CDRL2 including SGS, and a CDRL3 including SEQ ID NO: 222.

36. A method of any of embodiments 1-29, wherein the selected antibody is an anti-Dengue virus antibody including antibody 55, DB2-3, ab155042 or ab80914.

37. A method of any of embodiments 1-29 or 36, wherein the selected antibody is an anti-Dengue virus antibody including a CDRH1 including SEQ ID NO: 223, a CDRH2 including SEQ ID NO: 224, a CDRH3 including SEQ ID NO: 225; a CDRL1 including SEQ ID NO: 226, a CDRL2 including SEQ ID NO: 227, and a CDRKL3 including SEQ ID NO: 228 or a CDRH1 including SEQ ID NO: 229, a CDRH2 including SEQ ID NO: 230, a CDRH3 including SEQ ID NO: 231, a CDRL1 including SEQ ID NO: 232, a CDRL2 including SEQ ID NO: 233, and a CDRL3 including SEQ ID NO: 234.

38. A method of any of embodiments 1-29, wherein the selected antibody is an anti-pertussis antibody including a heavy chain including SEQ ID NO: 235 and a light chain including SEQ ID NO: 236.

39. A method of any of embodiments 1-29, wherein the selected antibody is an anti-hepatitis C antibody including MAB8694 or C7-50.

40. A method of any of embodiments 1-29 or 39, wherein the selected antibody is an anti-hepatitis C antibody including a CDRH1 including SEQ ID NO: 237, a CDRH2 including SEQ ID NO: 238, a CDRH3 including SEQ ID NO: 239, a CDRL1 including SEQ ID NO: 240, a CDRL2 including SEQ ID NO: 241, and a CDRL3 including SEQ ID NO: 242.

41. A method of any of embodiments 1-29, wherein the selected antibody is an anti-influenza virus antibody including C102.

42. A method of any of embodiments 1-29 or 41, wherein the selected antibody is an anti-influenza virus antibody including a heavy chain including SEQ ID NO: 159 and a light chain including SEQ ID NO: 158.

43. A method of any of embodiments 1-29 or 41, wherein the selected antibody is an anti-influenza virus antibody including a CDRH1 including SEQ ID NO: 243, a CDRH2 including SEQ ID NO: 244, a CDRH3 including SEQ ID NO: 245, a CDRL1 including SEQ ID NO: 246, a CDRL2 including KTS, and a CDRL3 including SEQ ID NO: 247.

44. A method of any of embodiments 1-29, wherein the selected antibody is an anti-MPV antibody including MPEG.

45. A method of any of embodiments 1-29, wherein the selected antibody is an anti-CMV antibody including MCMV5322A, MCMV3068A, LJP538, or LJP539.

46. A method of any of embodiments 1-29, wherein the selected antibody is an anti-EBV antibody including a heavy chain including SEQ ID NO: 168 and a light chain including SEQ ID NO: 166.

47. A method of any of embodiments 1-29, wherein the selected antibody is an anti-EBV antibody including a CDRH1 including SEQ ID NO: 248, a CDRH2 including SEQ ID NO: 249, a CDRH3 including SEQ ID NO: 250, a CDRL1 including SEQ ID NO: 251, a CDRL2 including SEQ ID NO: 252, and a CDRL3 including SEQ ID NO: 253.

48. A method of any of embodiments 1-29, wherein the selected antibody is an anti-HSV antibody including HSV8-N and MB66.

49. A method of any of embodiments 1-29, wherein the selected antibody is an anti-*Clostridium difficile* antibody including actoxumab or bezlotoxumab.

50. A method of any of embodiments 1-29, wherein the selected antibody is an anti-TNF antibody including inflix-imab, adalimumab, etanercept, certolizumab, or accepted biosimilars thereof.

51. A method of any of embodiments 1-29 or 50, wherein the selected antibody is an anti-TNF antibody including a heavy chain including SEQ ID NO: 254 and a light chain including SEQ ID NO: 255; a CDRH1 including SEQ ID NO: 256, a CDRH2 including SEQ ID NO: 257, and a CDRH3 includ-ing SEQ ID NO: 258; a CDRL1 including SEQ ID NO: 259, a CDRL2 including SEQ ID NO: 260, and a CDRL3 including SEQ ID NO: 261; a CDRH1 including SEQ ID NO: 262, a CDRH2 including SEQ ID NO: 263, and a CDRH3 including SEQ ID NO: 264; a CDRL1 including SEQ ID NO: 265, a CDRL2 including SEQ ID NO: 266, and a CDRL3 including SEQ ID NO: 267; a CDRH1 including SEQ ID NO: 268, a CDRH2 including SEQ ID NO: 269, and a CDRH3 including SEQ ID NO: 270; or a CDRL1 includ-ing SEQ ID NO: 271, a CDRL2 including SEQ ID NO: 272, and a CDRL3 including SEQ ID NO: 273.

52. A method of any of embodiments 1-51, wherein the genetic modification utilizes a sequence including any of SEQ ID NOs: 87, 88, 89, 90-175, 278-366.

53. A method of any of embodiments 1-52, wherein the B cell is an antibody-producing B cell, a memory B cell, a naïve B cell, a B1 B cell or a marginal zone B cell.

54. A B cell modified according to a method of any one of embodiments 1-53.

55. A B cell of embodiment 54, wherein the B cell is an antibody-secreting B cell, a memory B cell, a naïve B cell, a B1 B cell or a marginal zone B cell.

56. A method of providing an anti-infection effect in a subject in need thereof including administering a therapeu-tically effective amount of a B cell of embodiment 54 or 55 to the subject thereby providing an anti-infection effect.

57. A method of embodiment 56, wherein the providing obviates the need for a vaccination.

58. A method of embodiment 56 or 57, wherein the admin-istering replaces a vaccination protocol.

59. A method of any of embodiments 56-58, wherein the subject is immune-suppressed.

60. A method of any of embodiments 56-59, wherein the subject is immune-suppressed as part of a treatment regimen including a bone marrow transplant, hematopoietic stem cell transplant, or administration of genetically modified hema-topoietic stem cells.

61. A method of providing an anti-inflammatory effect in a subject in need thereof including administering a therapeu-tically effective amount of a B cell of embodiment 54 or 55 to the subject thereby providing an anti-inflammatory effect.

62. A genetic construct for modifying a B cell to express a selected antibody, the genetic construct including or encod-ing (i) a heavy chain promoter, (ii) a signal peptide, (iii) the full length light chain of the selected antibody; (iv) a flexible linker or a skipping element; (v) the variable region of the heavy chain of the selected antibody; and (vi) a splice junction.

63. A genetic construct of embodiment 62, including SEQ ID NOs: 102-175, or 280-289.

64. A genetic construct of embodiment 62 or 63, wherein the flexible linker is between the full length light chain of the selected antibody and the variable region of the heavy chain of the selected antibody.

65. A genetic construct of any of embodiments 62-64, wherein the flexible linker is selected from SEQ ID NOs: 180-184.

66. A genetic construct of any of embodiments 62-65, wherein the flexible linker is a Gly-Ser linker including 50-80 amino acids.

67. A genetic construct of any of embodiments 62-66, wherein the flexible linker is a Gly-Ser linker includes 57 amino acids.

68. A genetic construct of any of embodiments 62-64, 66 or 67, wherein the flexible linker is SEQ ID NO: 122.

69. A genetic construct of any of embodiments 62-68, wherein the skipping element is between the full length light chain of the selected antibody and the variable region of the heavy chain of the selected antibody.

70. A genetic construct of any of embodiments 62-69, wherein the skipping element is a self-cleaving peptide.

71. A genetic construct of embodiment 70, wherein the self-cleaving peptide is selected from SEQ ID NOs: 176-179.

72. A genetic construct of any of embodiments 62-69, wherein the skipping element is an internal ribosome entry site (IRES).

73. A genetic construct of any of embodiments 62-72, wherein the heavy chain promoter is selected from SEQ ID NOs: 111 and 128.

74. A genetic construct of any of embodiments 62-73, wherein the heavy chain promoter is IgVH1-69 or J558H10.

75. A genetic construct of any of embodiments 62-74, wherein the signal peptide is selected from SEQ ID NOs: 118, 134, and 185-194.

76. A genetic construct of any of embodiments 62-75, wherein the signal peptide is derived from human IgH heavy chain or human IgL light chain.

77. A genetic construct of any of embodiments 62-76, wherein the genetic construct includes homology arms.

78. A genetic construct of embodiment 77, wherein the homology arms include SEQ ID NOs: 90-101, 110, 125, 127, 140, 142, 143, 153, 170, 171, 173, 174, 278, or 279.

79. A genetic construct of any of embodiments 62-78, wherein the genetic construct encodes a tag.

80. A genetic construct of embodiment 79, wherein the tag includes STREPTAG®, STREP® tag II, His tag, Flag tag, Xpress tag, Avi tag, calmodulin tag, polyglutamate tag, HA tag, Myc tag, Nus tag, S tag, SBP tag, Softag 1, Softag 3, or V5 tag.

81. A genetic construct of embodiment 79 or 80, wherein the tag includes SEQ ID NOs: 122, or 195-204.

82. A genetic construct of any of embodiments 62-81, wherein the selected antibody is an anti-RSV antibody including palivizumab, AB1128, or ab20745.

83. A genetic construct of any of embodiments 62-82, wherein the selected antibody is: palivizumab including a heavy chain including SEQ ID NO: 138 and a light chain including SEQ ID NO: 136; palivizumab including a heavy chain including SEQ ID NO: 138 and a light chain including SEQ ID NO: 205; an anti-RSV antibody including a heavy chain including SEQ ID NO: 123 and a light chain including SEQ ID NO: 120; or an anti-RSV antibody including a heavy chain including SEQ ID NO: 123 and a light chain including SEQ ID NO: 206.

84. A genetic construct of any of embodiments 62-82, wherein the selected antibody is an anti-RSV antibody including a CDRH1 including SEQ ID NO: 207, a CDRH2 including SEQ ID NO: 208, a CDRH3 including SEQ ID NO: 209; a CDRL1 including SEQ ID NO: 210, a CDRL2 including SEQ ID NO: 211, and a CDRL3 including SEQ ID NO: 212.

85. A genetic construct of any of embodiments 62-81, wherein the selected antibody is an anti-HIV antibody including 10E8, VRC01, ab18633 or 39/5.4A.

86. A genetic construct of any of embodiments 62-81 or 85, wherein the selected antibody is an anti-HIV antibody including a heavy chain including SEQ ID NO: 150 and a light chain including SEQ ID NO: 149.

87. A genetic construct of any of embodiments 62-81 or 85, wherein the selected antibody is an anti-HIV antibody including a CDRH1 including SEQ ID NO: 213, a CDRH2 including SEQ ID NO: 214, a CDRH3 including SEQ ID NO: 215, a CDRL1 including SEQ ID NO: 216, a CDRL2 including SEQ ID NO: 217, and a CDRL3 including SEQ ID NO: 218 or a CDRH1 including SEQ ID NO: 219, a CDRH2 including SEQ ID NO: 220, a CDRH3 including SEQ ID NO: 221, a CDRL1 including QYGS, a CDRL2 including SGS, and a CDRL3 including SEQ ID NO: 222.

88. A genetic construct of any of embodiments 62-81, wherein the selected antibody is an anti-Dengue virus antibody including antibody 55, DB2-3, ab155042 or ab80914.

89. A genetic construct of any of embodiments 62-81 or 88, wherein the selected antibody is an anti-Dengue virus antibody including a CDRH1 including SEQ ID NO: 223, a CDRH2 including SEQ ID NO: 224, a CDRH3 including SEQ ID NO: 225; a CDRL1 including SEQ ID NO: 226, a CDRL2 including SEQ ID NO: 227, and a CDRKL3 including SEQ ID NO: 228 or a CDRH1 including SEQ ID NO: 229, a CDRH2 including SEQ ID NO: 230, a CDRH3 including SEQ ID NO: 231, a CDRL1 including SEQ ID NO: 232, a CDRL2 including SEQ ID NO: 233, and a CDRL3 including SEQ ID NO: 234.

90. A genetic construct of any of embodiments 62-81, wherein the selected antibody is an anti-pertussis antibody including a heavy chain including SEQ ID NO: 235 and a light chain including SEQ ID NO: 236.

91. A genetic construct of any of embodiments 62-81, wherein the selected antibody is an anti-hepatitis C antibody including MAB8694 or C7-50.

92. A genetic construct of any of embodiments 62-81 or 91, wherein the selected antibody is an anti-hepatitis C antibody including a CDRH1 including SEQ ID NO: 237, a CDRH2 including SEQ ID NO: 238, a CDRH3 including SEQ ID NO: 239, a CDRL1 including SEQ ID NO: 240, a CDRL2 including SEQ ID NO: 241, and a CDRL3 including SEQ ID NO: 242.

93. A genetic construct of any of embodiments 62-81, wherein the selected antibody is an anti-influenza virus antibody including C102.

94. A genetic construct of any of embodiments 62-81 or 93, wherein the selected antibody is an anti-influenza virus antibody including a heavy chain including SEQ ID NO: 159 and a light chain including SEQ ID NO: 158.

95. A genetic construct of any of embodiments 62-81 or 93, wherein the selected antibody is an anti-influenza virus antibody including a CDRH1 including SEQ ID NO: 243, a CDRH2 including SEQ ID NO: 244, a CDRH3 including SEQ ID NO: 245, a CDRL1 including SEQ ID NO: 246, a CDRL2 including KTS, and a CDRL3 including SEQ ID NO: 247.

96. A genetic construct of any of embodiments 62-81, wherein the selected antibody is an anti-MPV antibody including MPEG.

97. A genetic construct of any of embodiments 62-81, wherein the selected antibody is an anti-CMV antibody including MCMV5322A, MCMV3068A, LJP538, or LJP539.

98. A genetic construct of any of embodiments 62-81, wherein the selected antibody is an anti-EBV antibody including a heavy chain including SEQ ID NO: 168 and a light chain including SEQ ID NO: 166.

99. A genetic construct of any of embodiments 62-81, wherein the selected antibody is an anti-EBV antibody including a CDRH1 including SEQ ID NO: 248, a CDRH2 including SEQ ID NO: 249, a CDRH3 including SEQ ID NO: 250, a CDRL1 including SEQ ID NO: 251, a CDRL2 including SEQ ID NO: 252, and a CDRL3 including SEQ ID NO: 253.

100. A genetic construct of any of embodiments 62-81, wherein the selected antibody is an anti-HSV antibody including HSV8-N and MB66.

101. A genetic construct of any of embodiments 62-81, wherein the selected antibody is an anti-*Clostridium difficile* antibody including actoxumab or bezlotoxumab.

102. A genetic construct of any of embodiments 62-81, wherein the selected antibody is an anti-TNF antibody including infliximab, adalimumab, etanercept, certolizumab, or accepted biosimilars thereof.

103. A genetic construct of any of embodiments 62-81 or 102, wherein the selected antibody is an anti-TNF antibody including a heavy chain including SEQ ID NO: 254 and a light chain including SEQ ID NO: 255; a CDRH1 including SEQ ID NO: 256, a CDRH2 including SEQ ID NO: 257, and a CDRH3 including SEQ ID NO: 258; a CDRL1 including SEQ ID NO: 259, a CDRL2 including SEQ ID NO: 260, and a CDRL3 including SEQ ID NO: 261; a CDRH1 including SEQ ID NO: 262, a CDRH2 including SEQ ID NO: 263, and a CDRH3 including SEQ ID NO: 264; a CDRL1 including SEQ ID NO: 265, a CDRL2 including SEQ ID NO: 266, and a CDRL3 including SEQ ID NO: 267; a CDRH1 including SEQ ID NO: 268, a CDRH2 including SEQ ID NO: 269, and a CDRH3 including SEQ ID NO: 270; or a CDRL1 including SEQ ID NO: 271, a CDRL2 including SEQ ID NO: 272, and a CDRL3 including SEQ ID NO: 273.

104. A kit for genetically modifying a B cell including a genetic construct of any of embodiments 62-103 and a gRNA targeting SEQ ID NO: 1, SEQ ID NO: 2, SEQ ID NO: 3, or SEQ ID NO: 4.

105. A kit of embodiment 104, wherein the gRNA is selected from one or more of SEQ ID NOs: 87, 88, 89, and 290-366.

106. A kit of embodiment 104 or 105, further including a nuclease.

107. A kit of embodiment 106, wherein the nuclease is Cas9 or Cpf1.

108. A kit of any of embodiments 104-107, further including a nanoparticle or adeno-associated viral vector.

109. A kit of any of embodiments 104-108, wherein the gRNA and nuclease are associated with a nanoparticle.

110. A kit of any of embodiments 104-109, wherein the genetic construct is part of an adeno-associated viral vector.

Example 1. Providing Life-Long Protection Against Respiratory Syncytial Virus Infection without a Vaccine. Respiratory syncytial virus (RSV) is a leading cause of severe respiratory illness in young children, particularly infants with chronic lung disease, congenital heart disease or born prematurely. Humoral immunity can mediate effective protection against RSV, demonstrated by the therapeutic effects of the recombinant antibody Synagis® (MedImmune, Inc.)/palivizumab. However, both natural infection and previous vaccine trials have failed to induce a fully protective immune response against RSV.

For RSV and other difficult to vaccinate against diseases, bypassing vaccination through engineering primary B cells to elicit expression of a desired therapeutic antibody is extremely attractive. The immunoglobin (Ig) loci are extremely large, diverse, and subject to extensive genomic recombination and editing. In addition, the transcription of immunoglobin genes to produce both membrane and secreted forms relies on the regulation of mRNA splicing and polyadenylation by regulatory DNA elements. This complexity has made viral transduction, the traditional approach for cellular engineering of lymphocytes, technically impractical for the production of therapeutic B cells.

Particular embodiments include a platform for rapid and selective reprogramming of primary B cell antibody specificity by single hit immunogenetic engineering. This platform takes advantage of the high activity of the microhomology mediated end joining DNA repair pathway in primary B cells to insert a fully synthetic hybrid double stranded/single stranded DNA template after creation of DNA breaks by Cas9/sgRNA riboproteins. Key to this approach is preservation of endogenous regulatory elements, which allows for native control of surface bound and secreted antibody expression. Moreover, the strategy is not restricted to RSV. It can be possible to express antibodies protective against virtually any pathogen with just a single blood draw and subsequent cell infusion a few days later.

Materials and Methods. Design of sgRNA. sgRNAs targeting intronic sequences in the mouse and human IgH locus were designed using CrispRGold (crisprgold.mdc-berlin.de) and produced in a synthetic form incorporating 2'-O-methyl analogs and 3' phosphorothioate internucleotide linkages at the first three 5' and 3' terminal RNA residues (Synthego). Genome targeting sequences are as follows:

```
Mouse:
                              (SEQ ID NO: 87)
UUAUACAGUAUCCGAUGCAU

Human:
                              (SEQ ID NO: 89)
GUCUCAGGAGCGGUGUCUGU
```

Design and assembly of template sequences.

Human: Antibody construct included the IgVH1-69 heavy chain promoter region (SEQ ID NO: 111), the full-length codon optimized light chain of palivizumab (SEQ ID NO:

113 (nucleotide) and SEQ ID NO: 120 (amino acid)), a 57-amino acid glycine-serine linker containing 3 tandem copies of the Streptag II motif (SEQ ID NO: 116 (nucleotide) and SEQ ID NO: 122 (amino acid)), the codon optimized variable region of the palivizumab heavy chain (SEQ ID NO: 117 (nucleotide) and SEQ ID NO: 123 (amino acid)), and a splice junction with 60 bp of flanking sequence derived from the human IGHJ1 gene segment (SEQ ID NO: 124).

Mouse: mCherry template included the J5558H10 heavy chain promoter, the full codon optimized mCherry open reading frame, and the sv40 polyadenylation site. Antibody constructs included the J5558H10 heavy chain promoter (SEQ ID NO: 128, V. A Love et. al Molecular Immunology 2000), full length codon optimized antibody light chain (SEQ ID NO: 130 (nucleotide) and SEQ ID NO: 135 (amino acid)), a 57 amino acid glycine-serine linker containing two tandem copies of the Streptag II sequence (SEQ ID NO: 116 (nucleotide) and SEQ ID NO: 122 (amino acid)), codon optimized variable region of the heavy antibody chain (SEQ ID NO: 133 (nucleotide) and SEQ ID NO: 138 (amino acid)), and a splice junction with 60 bp of flanking sequence derived from the mouse IGHJ3 gene segment (SEQ ID NO: 139).

Annealing of stitching oligonucleotides (i.e., splicing oligonucleotides). Stitching oligonucleotides with 36 bp of complementarity to the pam-distal and pam-proximal non-target DNA strand and 50-100 bp of complementarity to the inserted template were produced synthetically, and pre-annealed to the DNA template before use (e.g., SEQ ID Nos: 96-101). The splicing oligonucleotides can provide "homology stitches" as shown in FIG. 15.

Adeno-associated virus (AAV) viral vector template delivery. AAV viral vectors contained the MND promoter, full codon optimized mCherry open reading frame, and the sv40 polyadenylation site flanked by either 2 mouse sgRNA recognition sites or 400 bp of homology. AAV virions were produced in 293T cells pseudotyped with AAV6 viral capsid, and purified by sucrose gradient centrifugation and stored at –80° C. For viral delivery of template DNA, concentrated AAV virus was added to a final volume of 10% of total culture volume 12 hrs before electroporation.

Mouse B cell culture and electroporation. Base B cell medium included RPMI medium with 10% Fetal calf serum (Hyclone), 10 mM HEPES (Gibco), 1 mM sodium pyruvate, (Gibco), 55 μM p-mercaptoethanol (Sigma), and 100 U/ml penicillin plus 100 μg/mL streptomycin (Gibco) except in antibiotic free steps as noted.

B cells were isolated from spleen and lymph nodes via negative selection with magnetic beads (Miltenyi) and cultured for 24 hours at $2 \times 10^6$/ml in B cell medium supplemented with 100 ng/ml recombinant carrier free HA-tagged mouse CD40L (R&D systems), 100 ng/ml anti-HA antibody (clone 543851, R&D systems), and 4 ng/ml mouse IL-4 (R&D systems). Next, the B cells were electroporated using the Neon transfection system and 10-μl tip as follows. Cas9 protein (Invitrogen) and synthetic sgRNA (Synthego) were mixed at a ratio of 3 μg Cas9/900 ng sgRNA and incubated at room temperature for at least 10 minutes. B cells were washed with PBS and suspended in Neon Buffer T at a final density of $2.5 \times 10^7$ cells/ml with Cas9/sgRNA and the pre-assembled DNA template. Cells were electroporated (1675 V, 10 milliseconds, 3 pulses) and immediately dispensed into pre-warmed antibiotic free medium.

For cell expansion, B cells were co-cultured with irradiated (80 gy) 3T3-CD40L feeder cell in the presence of 20 ng/ml mouse IL-21.

Assessment of sgRNA activity by Tracking of Indels by Decomposition (TIDE). Total genomic DNA was isolated from mock and Cas9 treated cells at 3-5 days post electroporation. The 500-600 bp region flanking the cut site was amplified by PCR using the following oligos:

```
Mouse:
Forward:
                           (SEQ ID NO: 274)
GGCTCCACCAGACCTCTCTA Reverse:
                           (SEQ ID NO: 275)
AACCTCAGTCACCGTCTCCT Human:
Forward:
                           (SEQ ID NO: 276)
ACAGTAAGCATGCCTCCTAAG Reverse:
                           (SEQ ID NO: 277)
GCCACTCTAGGGCCTTTGTT
```

Figures 18A, 18B, 18C:
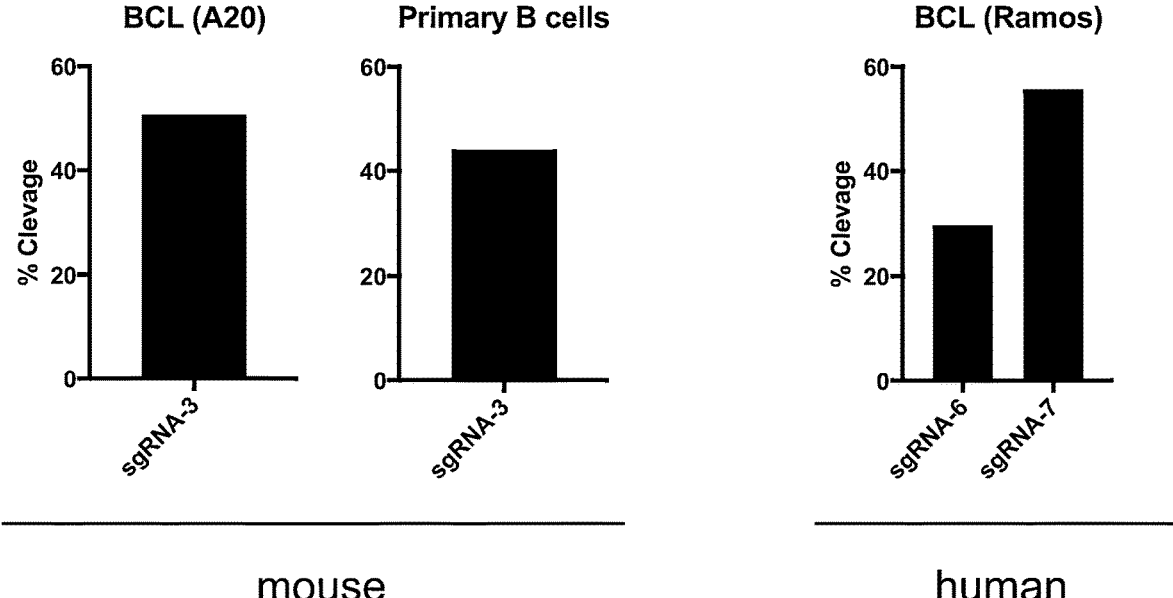
Figure 19:
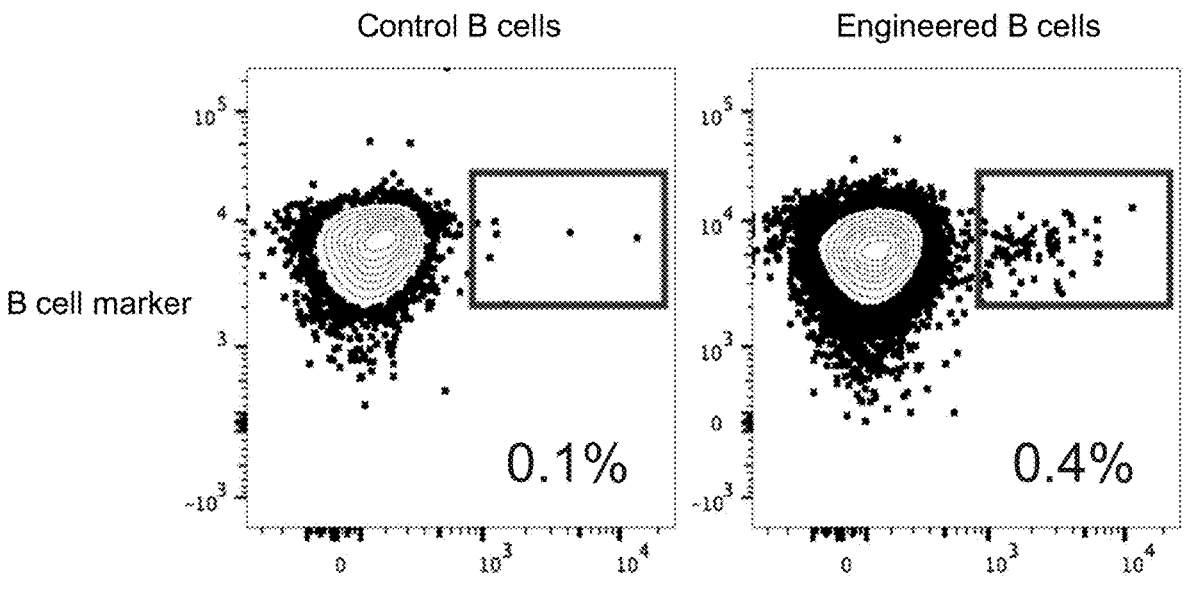
FIG. 19. Insertion of a genetic construct encoding an RSV-specific antibody into mouse B cells.
Figure 20:
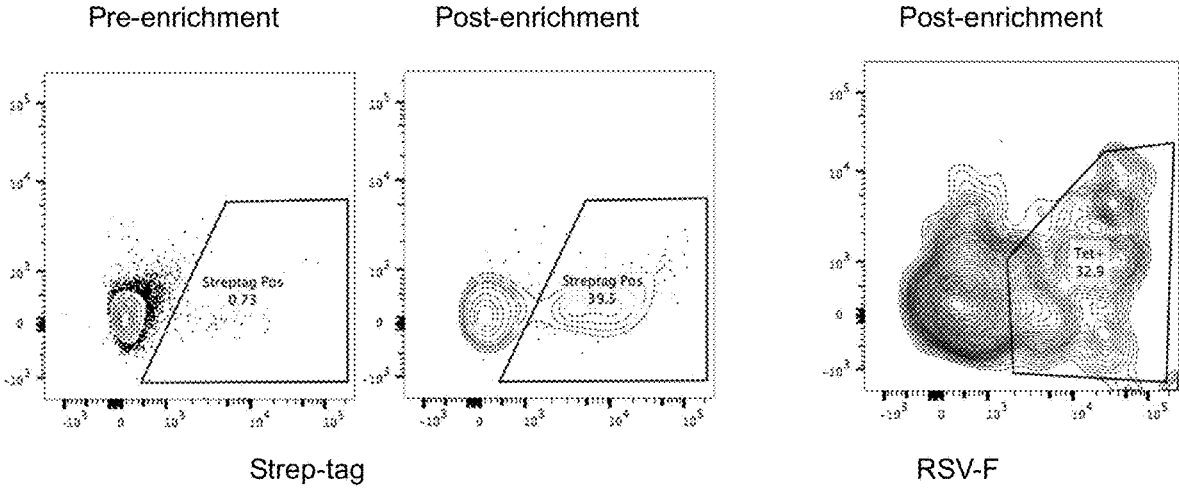
FIG. 20. Enrichment and analysis of genetically-modified B cells.
Figure 21:
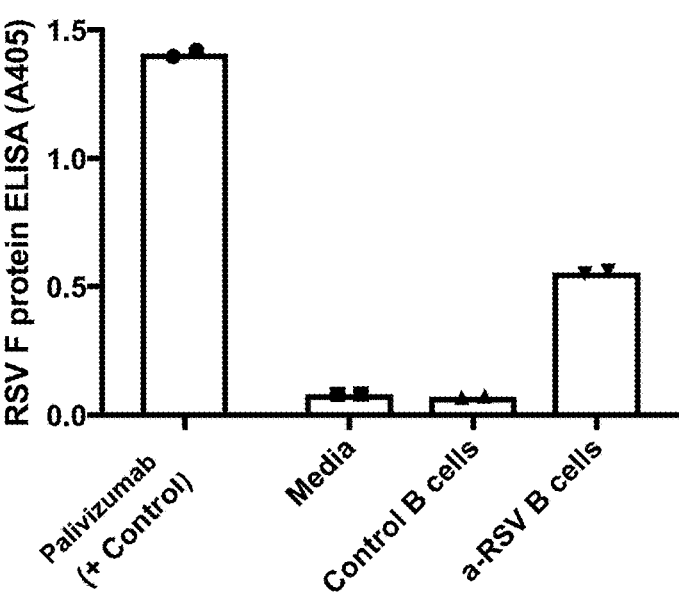
FIG. 21. Genetically-modified B cells secrete RSV binding antibody.
Figure 22A:
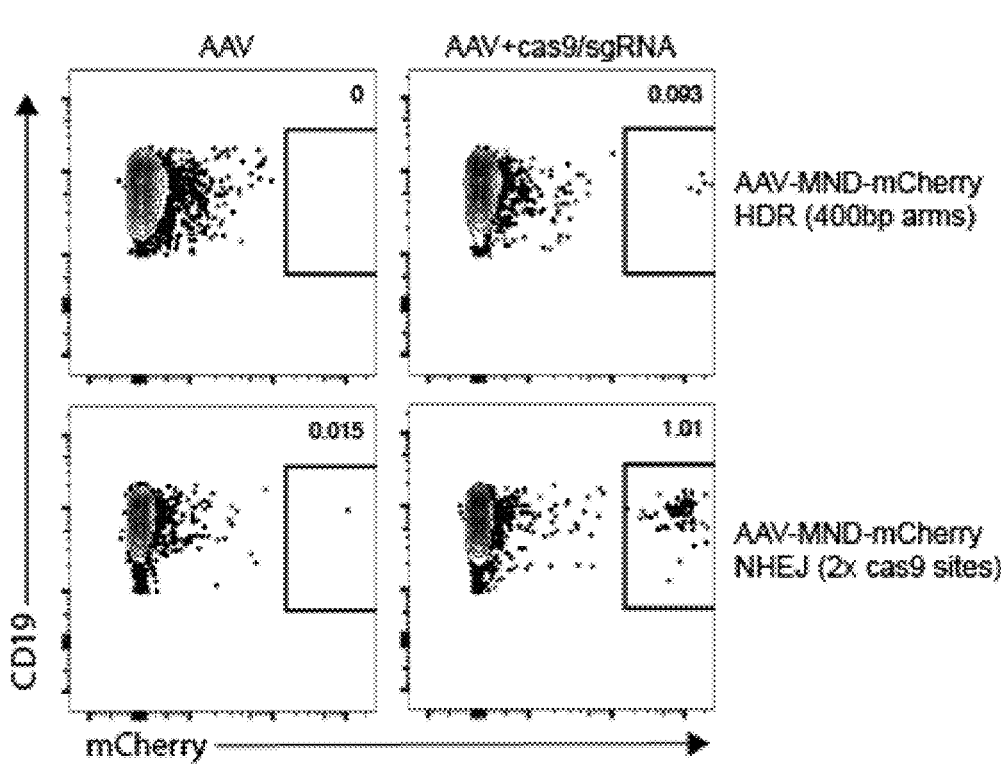
FIGS. 22A, 22B. Non-homologous end joining (NHEJ) and micro-homology mediated end joining (MMEJ) approaches offer alternatives to long-homology-directed repair (HDR) for genome engineering of primary mouse B cells.
Figure 22B:
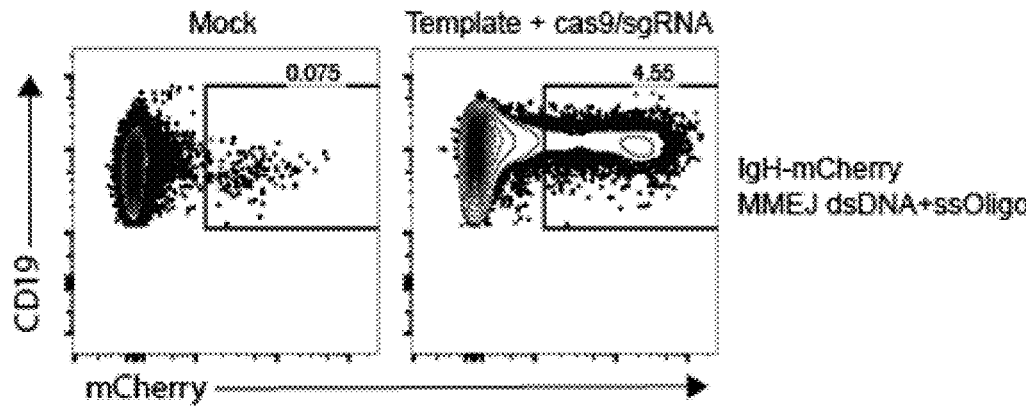
Figure 23B:
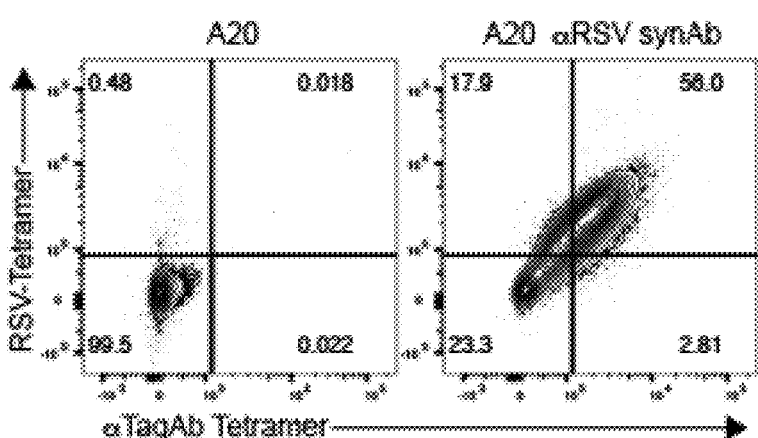
Figure 23C:
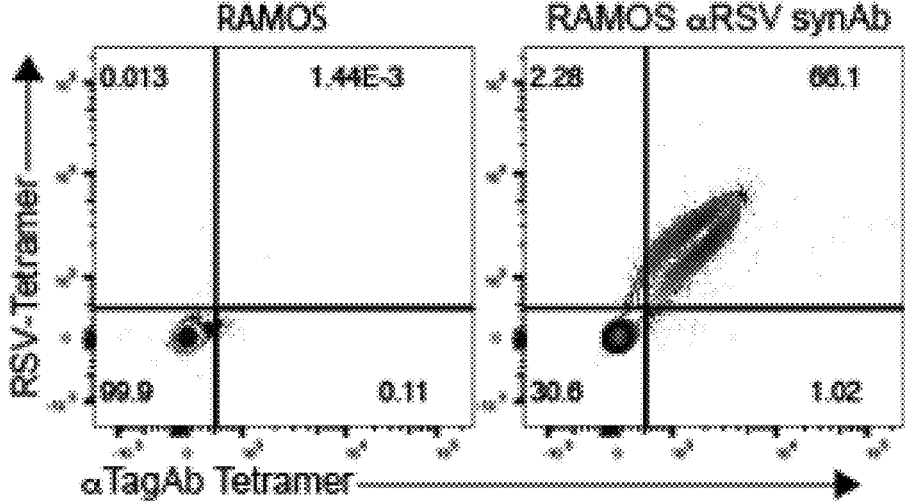
Figure 23D:
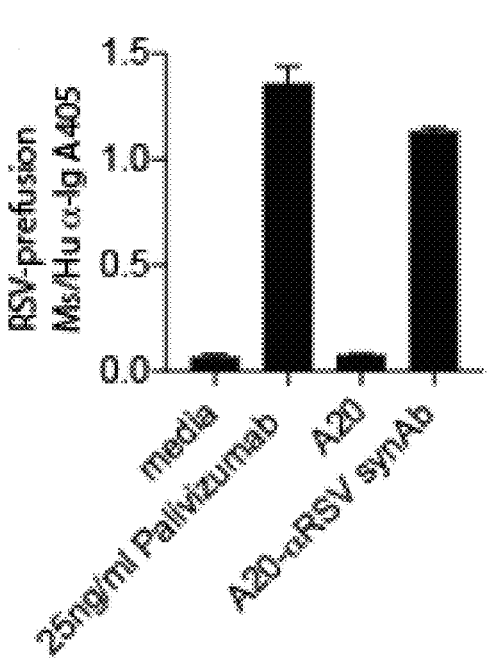
Figure 23E:
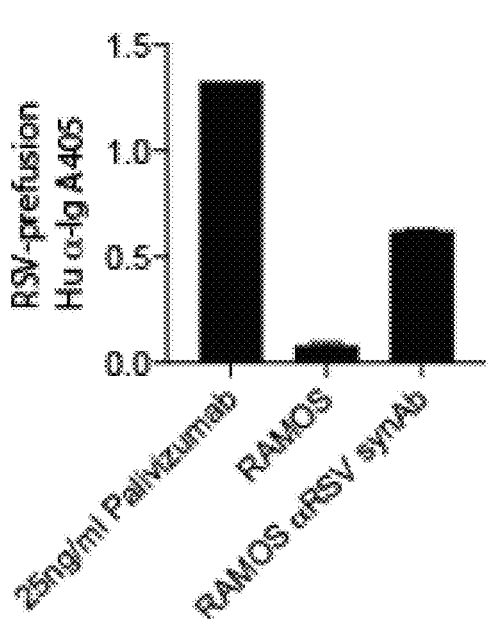
Figures 24A, 24B:
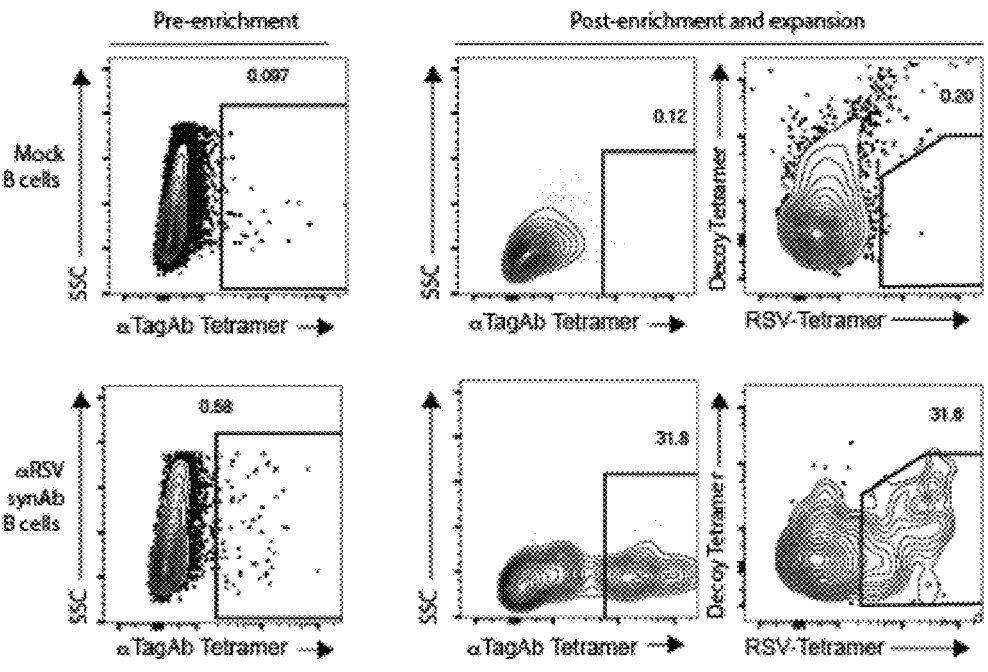
FIGS. 24A-24C. Production of primary mouse B cells with a novel specificity.
Figure 24C:
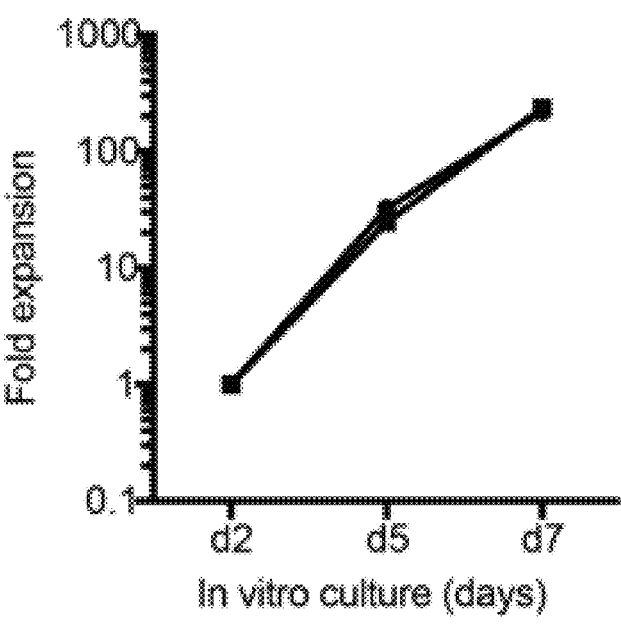

Results. Results are shown in FIGS. 18A-18C, FIGS. 22A & 22B, FIGS. 23B-23E, and FIGS. 24A-24C. FIGS. 18A, 18B, and 18C demonstrate successful cutting of mouse B cell line A20, primary mouse B cells, and human B cell line RAMOS, respectively, at the target IgH loci after electroporation of cells with Cas9/sgRNA ribonuclear proteins. FIGS. 22A and 22B depict insertion of a mCherry fluorescent protein reporter into the IgH locus of primary mouse B cells. FIGS. 23B and 23C demonstrate surface expression of an anti-RSV antibody after insertion of a partial antibody cassette into A20 mouse B cell lines (FIG. 23B) and RAMOS human B cell lines (FIG. 23C). FIGS. 23D and 23E demonstrates secretion of an anti-RSV antibody after insertion of a partial antibody cassette into A20 mouse B cell lines (FIG. 23D) and RAMOS human B cell lines (FIG. 23E). FIG. 24A demonstrates surface expression of an anti-RSV antibody after insertion of a partial antibody cassette into primary mouse B cells, initially (left panels) and after enrichment and expansion in vitro (right panels). FIG. 24B demonstrates secretion of an anti-RSV antibody after insertion of a partial antibody cassette into primary mouse B cell lines. FIG. 24C demonstrates the in vitro proliferative potential of engineered B cells.

Example 2. The goal of this example was to produce genetically-modified B cells with a defined specificity which maintain native control of secreted and surface Ig expression through genome engineering of the IgH locus. The IgH locus in B cells is a difficult region to target for genome engineering, due to the highly variable sequences present in B cells. B cell development results in recombination of V, D, and J elements over more than 1 megabase of DNA to generate the VDJ variable regions fundamental to antibody diversity. Later in B cell ontogeny, class switch between different constant regions results in loss of DNA over a similar sequence range (Reviewed in Watson, et al., (2017). Trends Immunol 38(7): 459-470).

Figure 26A:
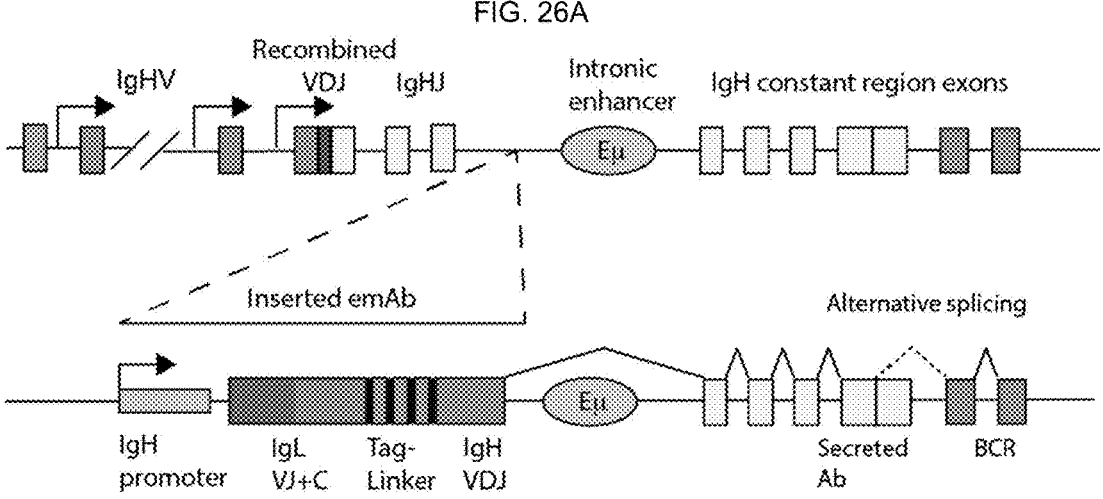
FIGS. 26A-26D.

This sequence variability makes directly targeting antibody coding regions impractical. However, a small DNA region between the last J gene segment and the switch region involved in class switch is present in all B cells. This universal target contains the critical intronic Eμ enhancer, one of several strong enhancer elements which cooperate to drive high level expression of IgH genes, despite their weak promoters. Activity of these enhancers is regulated in part by the proximity of promoters relative to the Eμ enhancer, and insertion of a transgene between the recombined VDJ segments and the Eμ enhancer can completely block VDJ transcription (Delpy, et al., (2002). J Immunol 169(12): 6875-6882). For this reason, methods used in this example targeted the area upstream of the Eμ enhancer for insertion of a new antibody cassette (FIG. 26A). By targeting this region, inserted emAb genes can be driven by a native (but inserted) IgH promoter, maximizing the native control of immunoglobin expression.

To enable one-hit insertion and minimize off-target interactions, emAb constructs were expressed as a single chain fusion. This fusion consists of a full light chain sequence, linked to the variable region of the heavy chain with a 57 amino acid glycine-serine linker as has been described for single chain F(ab) fragments. (Koerber, et al., (2015). J Mol Biol 427(2): 576-586) (FIG. 26A). This linker contains 3 tandem repeats of the StreptagII motif, to facilitate the detection and enrichment of genetically-modified cells (Schmidt & Skerra (2007). Nat Protoc 2(6): 1528-1535). Physically linking the light and heavy chains minimizes the possibility of misspairing between an inserted emAb and endogenous light chain. An optimized splice junction allows emAbs to splice to downstream endogenous IgH constant regions. This allows emAbs to be expressed as any of the heavy chain isotype classes.

Figures 26B, 26C, 26D:
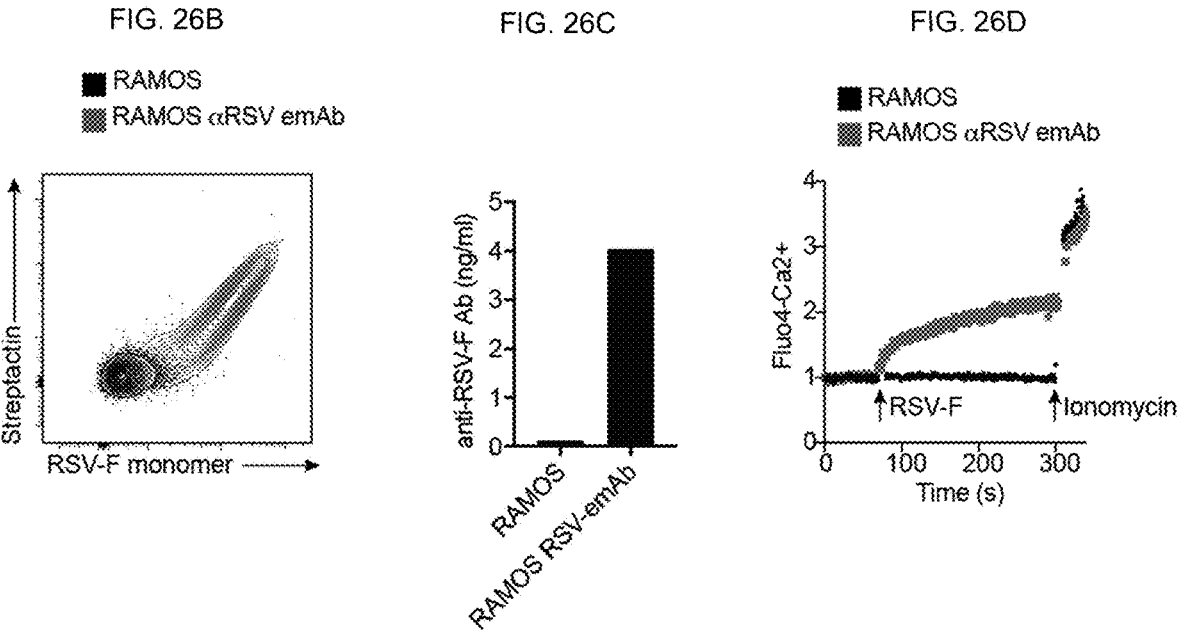

The strategy was tested in the RAMOS human B cell line. This Burkitts-lymphoma derived B cell line natively expresses surface and secreted forms of IgM paired with a lambda light chain. In these experiments, expression of an engineered αRSV-emAb derived from Palivizumab was detected using monomeric RSV-F protein and streptactin, a modified streptavidin with high affinity for the Streptag II motifs in the linker. αRSV-emAb genetically-modified RAMOS cells expressed the engineered RSV-specific antibody, which could be detected on the surface of cells (FIG. 26B) and as a secreted form in the supernatant (FIG. 26C). To confirm that an emAb BCR assembles with secondary protein complexes crucial for BCR signaling, RAMOS cells were exposed to stimulation with multimerized RSV-F antigen. αRSV-emAb engineered but not control cells exhibited rapid and sustained calcium signaling in response to protein antigen (FIG. 26D). These data served to confirm the viability of the emAb engineering approach.

Next, human primary B cells were genetically-modified using a multistep process of expansion and differentiation (FIG. 27A). Electroporation of pre-complexed guide RNA and Cas9 lead to highly efficient cutting of genomic DNA, resulting in faulty repairs of this region in 70% of the target alleles analyzed across multiple independent donors (FIG. 27B). The sgRNA target site is strongly conserved in humans, with no reported single nucleotide polymorphisms reported at a frequency above 1% (FIG. 27C). Addition of an AAV delivered αRSV-emAb cassette efficiently reprogrammed human B cells to bind RSV-F protein (FIG. 27D). Notably, emAb B cells have been successfully produced from every human donor tested, with an average engineering rate of 24% (FIG. 27E). In vitro culture and differentiation during the production of emAb increased antibody secretion potential. Primed cells at day 2 expressed high levels of CD19, and low amounts of the plasma cell markers CD138, CD27, and CD138, in contrast to cells at day 18, which had lower levels of CD19, and increased CD38, CD27, and CD138 (FIG. 27F). Corresponding to these alterations in cell surface markers, differentiated emAb engineered B cells secrete substantial amount of targeted antibody (FIG. 27G).

Taken together, these data demonstrate the ability to rapidly and efficiently engineer primary B cells to produce specific protective antibodies.

Figure 28:
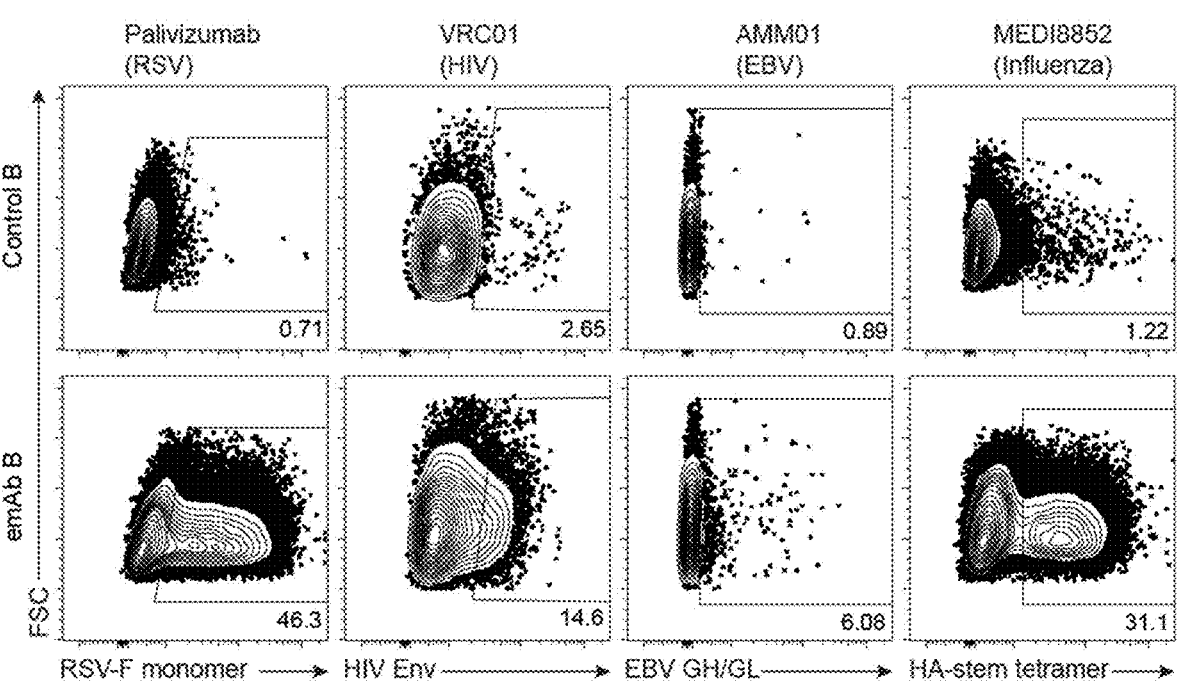
FIG. 28. Single chain emAb is a flexible platform for expression of antiviral antibodies. Human B cells were mock electroporated (Control B, top row) or genetically-modified with emAb constructs (bottom row) derived from the variable regions of the indicated broadly neutralizing antibody constructs and human kappa (Palivizumab, VRC01, and MEDI8852) or lambda (AMM01) light chains. Control and emAb engineered cells were stained with a matching antigen derived from the indicated pathogen: RSV-F monomer, or tetramers of HIV-ENV, EBV GH/GL, or HA-stem.

To demonstrate the flexible aspect of the platform, emAb cassettes derived from 3 additional broadly neutralizing anti-viral antibodies were tested, including the anti-HIV targeted VRC01, the EBV targeted AMM01, and the influenza HA-stem targeted MED18852. Primary B cells were efficiently reprogrammed with all 4 constructs, which included antibodies with both kappa (Palivizumab, VRC01, Medi8852) and lambda (AMM01) light chains (FIG. 28). These data demonstrate the flexible and broadly applicable nature of the emAb platform.

Figure 29A:
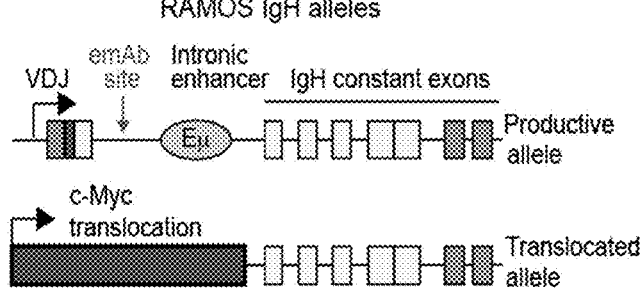
FIGS. 29A-29D. emAb insertion on the productive IgH allele can block endogenous IgH production.
Figure 29B:
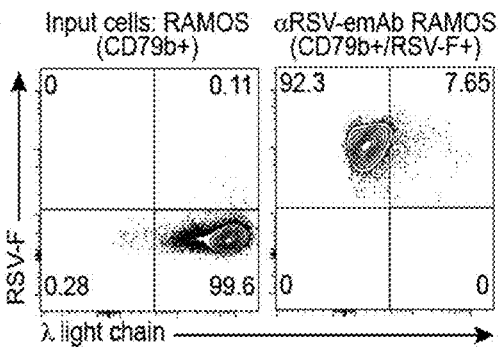
Figure 29C:
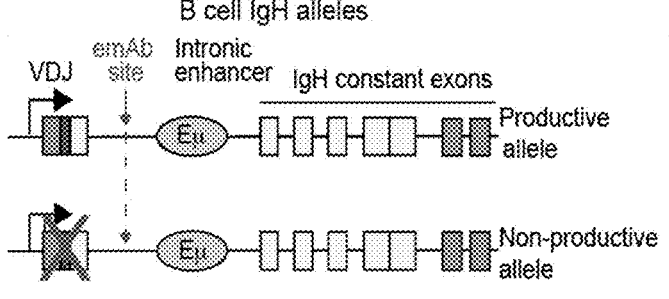
Figure 29D:
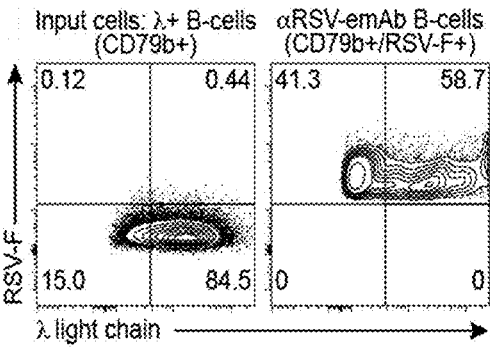

Blocking production of the endogenous Ig heavy chain is important to maximize the production of emAb and minimize the potential for production of unknown endogenous antibodies from genetically-modified cells. The RAMOS B cell line endogenously expresses an IgH paired with a lambda light chain. Engineering these cells with an αRSV-emAb linked to a kappa light chain enables use of surface lambda light chain expression as an effective measure of IgH expression. In addition, RAMOS cells have undergone a c-myc translocation, disrupting one IgH allele, such that any emAb insertion will by necessity be in the productive allele (FIG. 29A). Input RAMOS cells express high levels of lambda light chain on the surface, whereas cells expressing the αRSV-emAb have almost completely lost lambda expression (FIG. 29B). These data indicate that emAb insertion on the productive allele can effectively block expression of an endogenous IgH. In almost all primary B cells, one IgH allele possesses a productive VDJ rearrangement, whereas the other allele did not undergo VDJ recombination, or was unproductively recombined. However, both these alleles possess potential sites for emAb insertion (FIG. 29C). To test the effects of emAb insertion, purified lambda light chain expressing primary B cells were genetically-modified with αRSV-emAb. Input cells continued to express the endogenous antibody paired with lambda light chain on the surface. In contrast, half of αRSV-emAb engineered B cells have lost lambda light chain expression (FIG. 29D). The differential patterns of expression seen in RAMOS and primary B cells suggest that emAb insertion can block endogenous IgH expression if inserted into the productive allele. Differential expression of surface light chain is an avenue for purification of cells which exclusively express an emAb construct. Alternatively, the potential for insertion at either allele offers the possibility of producing dual-antibody expressing emAb cells by either selection of initial pool of anti-viral memory B cells for engineering, or by insertion of a different cassette on each allele.

Figure 30D:
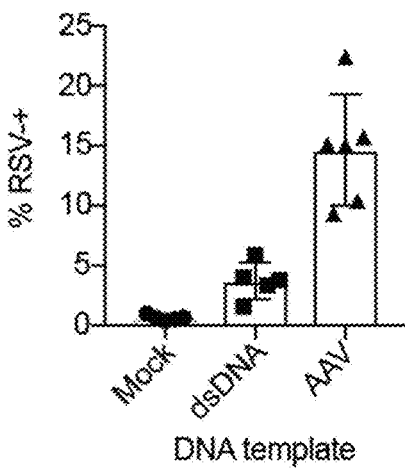
Figure 30E:
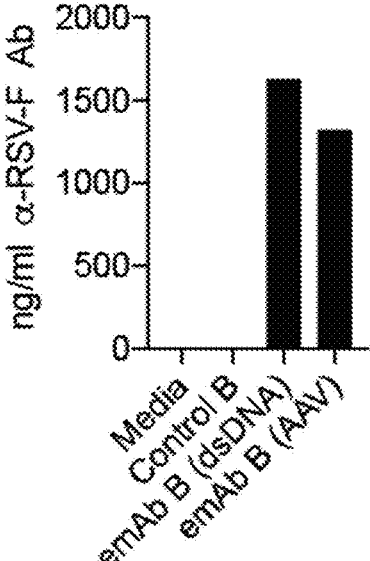

Having demonstrated the ability to engineer B cells, the protective capability of the cells in murine models of viral infection was next confirmed. Murine emAb B cells were produced using a process of priming, electroporation+emAb cassette delivery, and expansion similar to that used in human primary B cells (FIG. 30A). Electroporation in combination with pre-complexed guide RNA and Cas9, cutting was highly efficient, resulting in faulty repairs of this region in 80% of the DNA analyzed (FIG. 30B). Delivery of a murine αRSV-emAb cassette via AAV reproducibly modified mouse B cells, with 8-24% of murine B cells binding RSV-F (FIG. 30C, 30D). Insertion in 1-7% of cells was also achieved using double stranded DNA (dsDNA) containing short homology regions instead of AAV (FIG. 30C, 30D (see also Example 1), offering a potential for emAb engineering of B cells using purely synthetic components. High titers of secreted engineered antibodies could also be detected in culture supernatants produced by both methodologies (FIG. 30E).

Figures 31A, 31B, 31C, 31D:
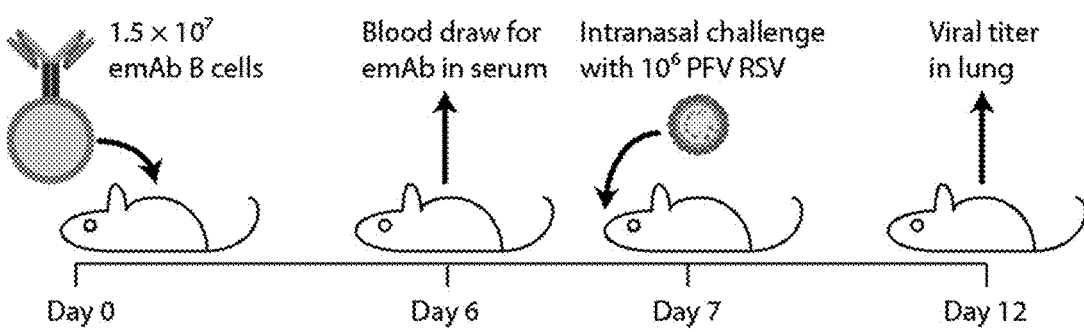
FIGS. 31A-31D. Protection from viral infection by engineered αRSV-emAb B cells.
Figure 32A:
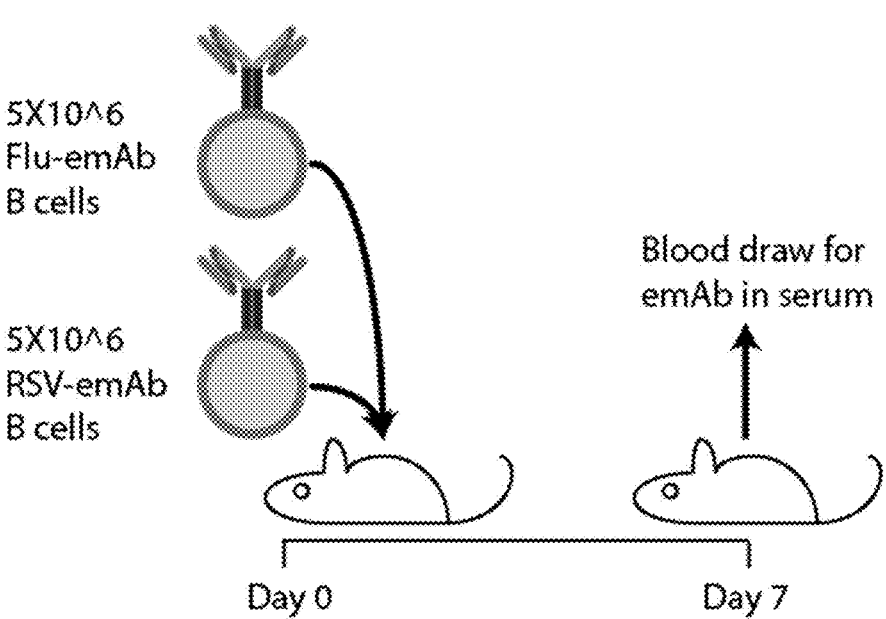
FIGS. 32A, 32B. Mutiplex transfer of human antibody secreting cells to NSG mice (FIG. 32A) Schematic of transfer of human emAb B cells into NSG mice. Day 0: $5 \times 10^6$ anti-Flu emAb B cells and $5 \times 10^6$ anti-RSV emAb B produced as described in FIG. 27 were transferred via I.P. injection. Day 7: Blood draw for antibody production in serum.
Figure 32B:
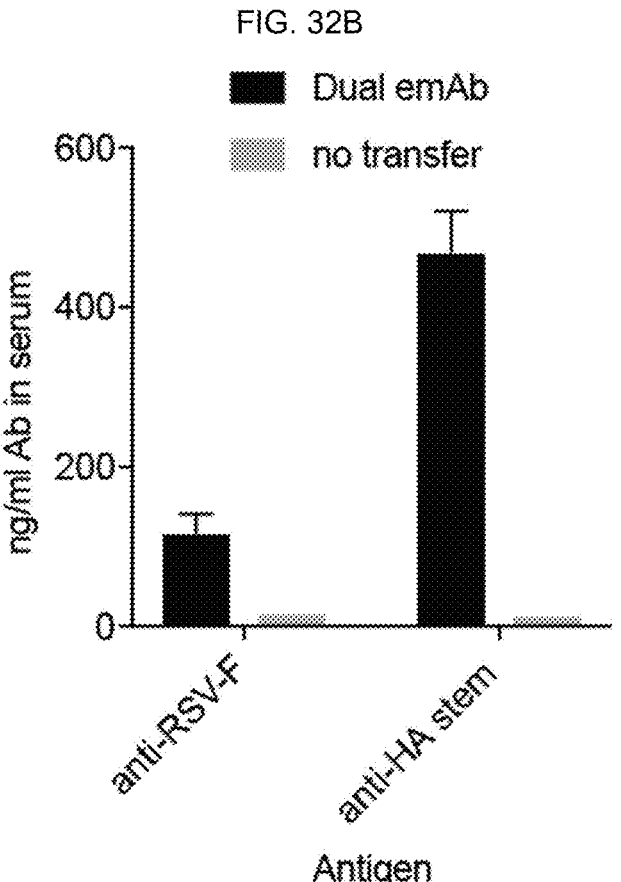
Figure 33A:
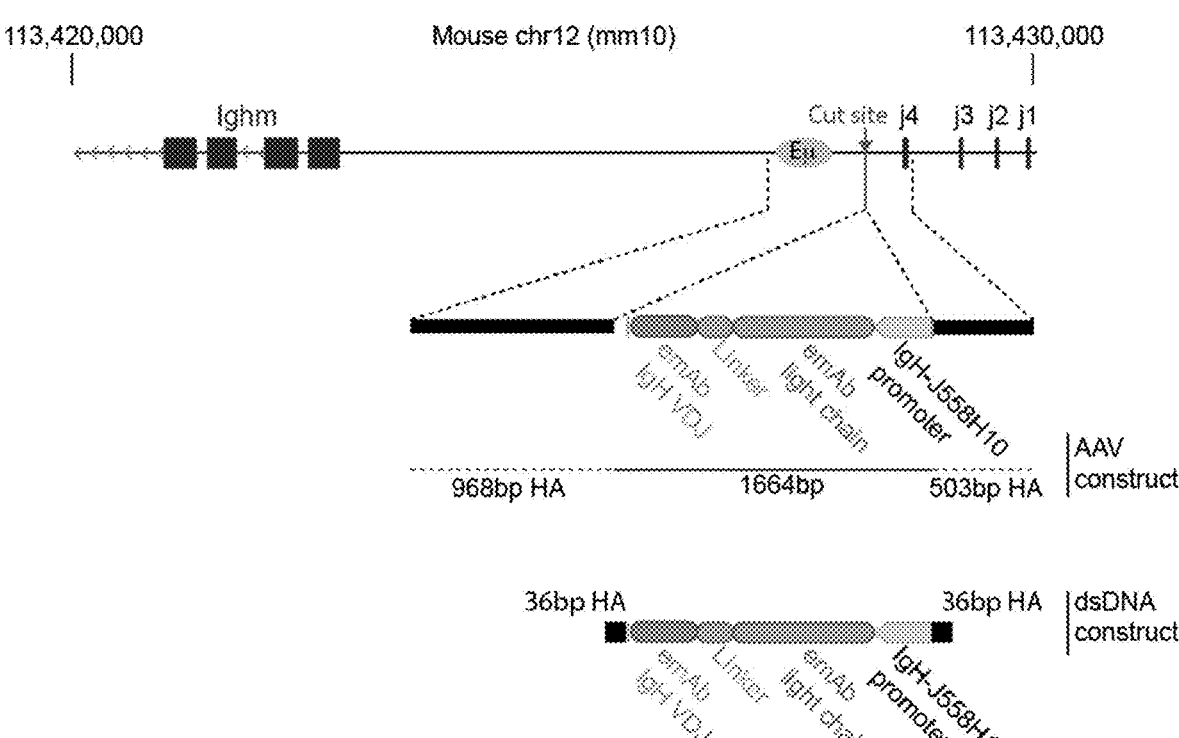
FIGS. 33A, 33B. Templates for long insertion of emAb cassettes into the mouse (FIG. 33A) and human (FIG. 33B) IgH locus. Indicated on the top row for each genome are the position of elements in germline IgH loci, including the final J regions, the Eμ intronic enhancer element, and the beginning of the p constant domain. The position of the cas9/sgRNA target site is indicated (Cut site). Below is shown the positions of the targeting arms targeting homology arms included in the mouse AAV and dsDNA construct (FIG. 33A) as well as the human AAV construct (FIG. 33B). Also shown is the emAb cassette as inserted in the genome.
Figure 33B:
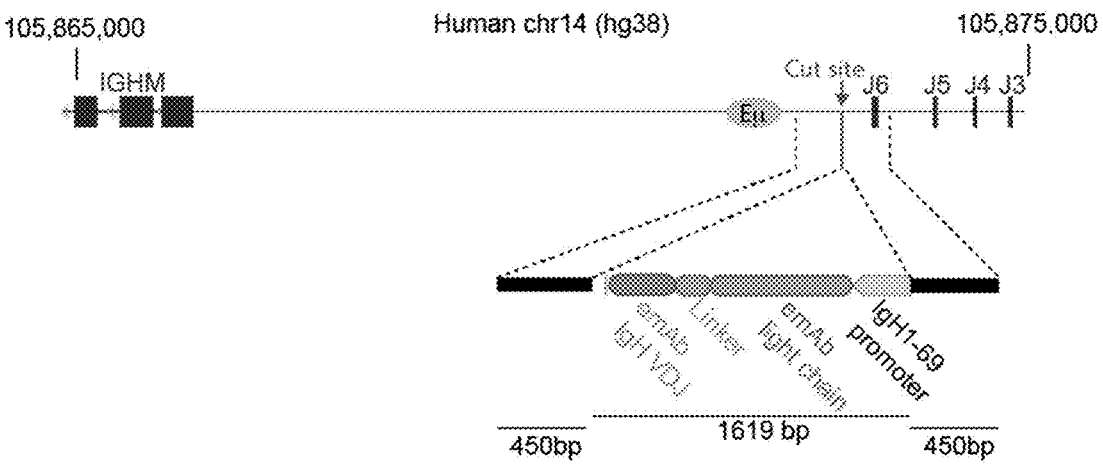

To test the potential for antiviral protection $1.5 \times 10^7$ genetically-modified mouse B cells were infused into wild-type Balbc/byJ mice, followed by a blood draw and RSV challenge (FIG. 31A). RSV-specific antibodies and genetically-modified B cells were present in the blood 6 days following the transfer of genetically-modified B cells (FIG. 31B, 31C). Importantly, mice receiving genetically-modified B cells were almost completely protected against RSV infection (FIG. 31D). This protection approached that afforded by the injection of Palivizumab 2 days before infection (FIG. 31D). Transfer of mixed human emAb cells targeting RSV and influenza to NOD-scid IL2Rgammanull (NSG) mice lead to serum titers of antibodies targeting both viruses (FIGS. 32A, 32B). These results show that genetically-modified B cells disclosed herein protect against viral infection.

Methods. Design of single-chain antibody templates sequences. Human: Antibody constructs included the IgVH1-69 heavy chain promoter region (SEQ ID NO: 111), full-length antibody light chain (e.g., SEQ ID NOs: 113, 145, 154, and 161 (nucleotide) and SEQ ID NOs: 119, 148, 157, and 165 (amino acid)), a 57 amino acid glycine-serine linker containing 3 tandem copies of the StreptagII motif (SEQ ID NO: 116 (nucleotide) and SEQ ID NO: 122 (amino acid)), variable region of the heavy chain (e.g., SEQ ID NOs: 117, 147, 156, and 164 (nucleotide) and SEQ ID NOs: 123, 150, 159, and 168 (amino acid)), and a splice junction with 60 base pairs of flanking sequence derived from matching IgHJ variable regions (e.g., SEQ ID NOs: 124 and 151).

Mouse: Antibody constructs included the J5558H10 heavy chain promoter (SEQ ID NO: 128, V. A Love et. al Molecular Immunology 2000), full length codon optimized antibody light chain (e.g., SEQ ID NO: 130 (nucleotide) and SEQ ID NO: 135 (amino acid)), a 57 amino acid glycine-serine linker containing three tandem copies of the streptag II sequence (SEQ ID NO: 116 (nucleotide) and SEQ ID NO: 122 (amino acid)), codon optimized variable region of the heavy antibody chain (e.g., SEQ ID NO: 133 (nucleotide) and SEQ ID NO: 138 (amino acid)), and a splice junction with 60 base pairs of flanking sequence derived from the mouse IGHJ3 gene segment (e.g., SEQ ID NO: 139).

Full sequences of exemplary antibody constructs are available in FIG. 25B-25I.

Production of recombinant AAV vectors. AAV vectors were generated by triple transfection of AAV vector, serotype 6 capsid, and adenoviral helper plasmids (pHelper) into HEK293T cells using PEI. At 24 hours post-transfection, media was changed to serum-free DMEM, and after 72 hours cells were collected, lysed by freeze-thaw, benzonase treated, purified over iodixanol gradient followed by concentration into PBS using an Amicon Ultra-15 column (EMD Millipore) (Choi, et al., (2007). Curr Protoc Mol Biol Chapter 16: Unit 16 25). Titers of the viral stock were determined by qPCR of AAV genomes, and ranged from $5 \times 10^{10}$ to $1 \times 10^{12}$ per microliter (Aurnhammer, et al., (2012). Hum Gene Ther Methods 23(1): 18-28).

Production of Murine dsDNA emAb Templates.

αRSV-emAb templates were amplified and short homology regions added by modified DNA oligos as follows:

Forward primer:
(contains a 5' phosphate, mouse genomic homology region in bold)
                                                          (SEQ ID NO: 278)
/5Phos/ACCACCTCTGTGACAGCATTTATACAGTATCCGATGGACAAGTGAGTGTCTCAGG

TTAGGATTCT

Reverse primer
(contains phosphorothioate stabilized DNA bonds (*) mouse genomic homology
region in bold)
                                                          (SEQ ID NO: 279)
**T*A*A*AGAAAGTGCCCCACTCCACTCTTTGTCCCTATGC**TTGACCACAATGAATACTCCCA

CC dsDNA template was amplified by PCR, purified and concentrated using minElute PCR cleanup columns (Qiagen).

Cell lines. 3T3-msCD40L were obtained from Dr. Mark Connors at the NIH AIDS Reagent Program, Division of AIDS, NIAID, NIH: Cat#12535. 3T3 cells were cultured in DMEM medium with 10% fetal calf serum (Gibco), 100 U/ml penicillin plus 100 µg/mL streptomycin (Gibco), and G418 (350 µg/mL).

RAMOS cells were obtained from ATCC (CRL-1596™). RAMOS cells were cultured in RPMI medium with 10% Fetal calf serum (Gibco) and 100 U/ml penicillin plus 100 µg/mL streptomycin (Gibco).

Mouse B cell culture and electroporation. Base B cell medium included RPMI medium with 10% Fetal calf serum (Gemini Biosciences), 10 mM HEPES (Gibco), 1 mM sodium pyruvate, (Gibco), 55 µM Beta-mercaptoethanol (Sigma), and 100 U/ml penicillin plus 100 µg/mL streptomycin (Gibco) except in antibiotic free steps as noted.

B cells were isolated from spleen and lymph nodes via negative selection with magnetic beads (Miltenyi) and cultured for 24 hours at $2\times10^6$/ml in B cell medium supplemented with 100 ng/ml recombinant carrier free HA-tagged mouse CD40L (R&D systems), 100 ng/ml anti-HA antibody (clone 543851, R&D systems), and 4 ng/ml mouse IL-4 (R&D systems). Next, the B cells were electroporated using the Neon transfection system as follows. Cas9 protein (Invitrogen) and synthetic sgRNA (Synthego) were mixed at a ratio of 1 µg Cas9 to 300 ng sgRNA and incubated at room temperature for at least 10 minutes. B cells were washed with PBS and suspended in Neon Buffer T at a final density of $2.5\times10^7$ cells/ml with 12 µg of Cas9 RNP/$10^6$ cells. For dsDNA conditions, 7.5 µg dsDNA template/$10^6$ cells was also included in the electroporation. Cells were electroporated (1675 V, 10 milliseconds, 3 pulses) and immediately dispensed into pre-warmed antibiotic free medium. For AAV conditions, concentrated AAV in PBS was added up to 15% of final culture volume. After electroporation, B cells were expanded for an additional 48 hours with B cell medium supplemented with 100 ng/ml recombinant carrier free HA-tagged mouse CD40L (R&D systems), 100 ng/ml anti-HA antibody (clone 543851, R&D systems), 4 ng/ml mouse IL-4 (R&D systems), and 20 ng/ml mouse IL-21. (Biolegend). For secondary expansion, B cells were co-cultured with irradiated (80 gy) NIH 3T3-CD40L feeder cells in the presence of 20 ng/ml mouse IL-21. (Biolegend).

Human B cell culture and electroporation. Basal media for human B cell culture (hBCM) was in IMDM media, with 10% FBS (Gemini Biosciences), 100 U/ml penicillin and 100 µg/mL streptomycin (Gibco), except in antibiotic free steps as noted.

Human PBMCs were obtained through the Fred Hutchinson Cancer Research Center. Cells were thawed, and isolated using negative selection using the Militenyi B Cell Isolation Kit II (Human), according to the manufacturer's protocol. Isolated cells were resuspended at 0.5-1.0*10^6 cells/mL in hBCM supplemented with 100 ng/mL MEGACD40L (Enzo Life Sciences), 50 ng/mL recombinant IL-2 (Biolegend), 50 ng/mL IL-10 (Shenendoah Biotech), 10 ng/mL IL-15 (Shenandoah Biotech), 1 µg/mL CpG ODN 2006 (IDT).

After 48 hours of stimulation, cells were electroporated using the Neon Transfection System. Cas9 protein (Invitrogen) and H7 sgRNA (Synthego) were precomplexed at a 2:1 ratio in Buffer T for 20 minutes at room temperature. Cells were washed with PBS (Gibco) and resuspended in Buffer T at a final concentration of 2.5*10^7 cells/ml in Buffer T containing pre-complexed Cas9 RNP. The Cell-RNP mixture was loaded into a 10 uL Neon Transfection Tip, and electroporated according to the manufacturer's protocol with the settings of 1750V, 20 ms, and 1 pulse. Immediately after electroporation, cells were plated into stimulation media as described above, without antibiotics. After 30 minutes, AAV was added to a final concentration of 10-15% culture volume and mixed thoroughly. After 2-4 hours, cells were transferred to a larger culture dish to allow for further expansion.

Two days after electroporation, cells were stained with fluorochrome labeled antigen or streptactin and genetically-modified cells were selected. For secondary expansion, B cells were co-cultured with irradiated (80 gy) NIH 3T3-CD40L feeder cells in hBCM containing 5 µg/mL Human recombinant Insulin (Sigma), 50 µg/mL Transferrin (Sigma), 50 ng/mL recombinant IL-2 (Biolegend), 20 ng/mL IL-21 (Biolegend), and 10 ng/mL IL-15 (Shenandoah Biotech).

In order to promote differentiation to plasma cells, cells were transferred from expansion conditions into fresh feeder-free culture conditions containing hBCM supplemented with 5 µg/mL Human recombinant Insulin (Sigma), 50 µg/mL Transferrin (Sigma), 500 U/mL Universal Type I IFN Protein (R&D Systems), 50 ng/mL IL-6 (Shenendoah Biotech), 10 ng/mL IL-15 (Shenendoah Biotech).

Assessment of sGRNA activity by TIDE. Total genomic DNA was isolated from mock and cas9/sgRNA treated cells at 3-5 days post electroporation. The 500-600 base pair region flanking the sgRNA target site was amplified by PCR using the following oligos:

```
Mouse:
Forward:
                         (SEQ. ID NO: 274)
GGCTCCACCAGACCTCTCTA Reverse:
                         (SEQ ID NO: 275)
AACCTCAGTCACCGTCTCCT
```

-continued
Human:
Forward:

(SEQ ID NO: 276)

ACAGTAAGCATGCCTCCTAAG

Reverse:

(SEQ ID NO: 277)

GCCACTCTAGGGCCTTTGTT

Purified PCR product was Sanger sequenced, and the frequency of indels in Cas9/sgRNA electroporated cells relative to mock electroporated cells was determined using the ICE algorithm (Hsiau, et al., (2018). "Inference of CRISPR Edits from Sanger Trace Data." bioRxiv).

Protein antigens. Pre-fusion RSV-F protein, EBV gh/gl complex, and modified HIV env antigen (426c TM4 d1-3) were produced as described (McLellan, et al., (2013). Science 342(6158): 592-598; McGuire, et al., (2016). Nat Commun 7: 10618; Snijder, et al., (2018). Immunity 48(4): 799-811 e799). Stabilized influenza HA-stem was produced from VRC clone 3925, derived from strain H1 1999 NC as described (Yassine, et al., (2015). Nat Med 21(9): 1065-1070). Monomeric prefusion RSV-F protein was labeled with Alexa-488 (Thermo Fisher). All other proteins were conjugated to biotin using a molar ratio of biotin:protein between 0.8 to 2, followed by tetramerization with strepta-vidin-PE or -APC (prozyme)

Flow Cytometry. Flow cytometric analysis was done on an FACSymphony machine (BD bioscience), cells were sorted on Aria II (BD bioscience), and data analyzed using FlowJo software (Tree Star).

EmAb therapeutic studies in mice. Animal studies were approved and conducted in accordance with the Fred Hutchinson Cancer Center Institutional Animal Care and Use Committee.

For RSV challenge, EmAb or control B cells were administered as a single intraperitoneal (IP) dose of $1.5 \times 10^7$ cells. For passive transfer of palivizumab, mice received a single dose of 15 mg/kg i.p. GFP-expressing RSV (here-in referred to as RSV for simplicity) was generously provided (Munir, et al., (2008). J Virol 82(17): 8780-8796). Age matched BALB/cByJ mice (Jackson Labs) were inoculated intranasally with 106 pfu of sucrose purified RSV in 40 μL PBS. Lungs were harvested on day 5 post-infection and the titer was determined as previously described by plaque assay (Murphy, et al., (1990). Vaccine 8(5): 497-502). In brief, lungs were homogenized in 2 mls media in a GentleMACS dissociator, clarified by centrifugation at 400×g for 10 minutes, then flash frozen and stored at −80° C. The supernatant was diluted 1:10 and 1:20 in DMEM media in duplicate. 100 μL of each dilution was added to confluent Vero cells in 24 well plates for 2 hours at 37° C. An overlay of 0.8% methylcellulose was then added, and plates incubated for 5 days prior to imaging on a Typhoon imager with filter settings for GFP. The titer in pfu/lung was calculated by counting the number of plaques in the highest positive dilution and correcting for the dilution factor.

For engraftment of human cells, human emAb B cells were administered as a single IP dose of $5 \times 10^6$ cells/emAb specificity ($1 \times 10^7$ total) to NOD-scid IL2Rgamma$^{null}$ (NSG) mice (produced by FHCRC breeding facility). 7 days post transfer, blood was drawn, and human emAb titers to RSV-F and HA-stem in serum determined by ELISA.

Statistical Analysis. Statistical analysis were performed using GraphPad Prism 7. Pairwise comparisons were performed using unpaired t-test with Welch's correction.

Nucleic acid sequences described herein are shown using standard letter abbreviations for nucleotide bases, as defined in 37 C.F.R. § 1.822. In some instances, only one strand of each nucleic acid sequence is shown, but the complementary strand is understood as included in embodiments where it would be appropriate. By way of example, sequences complementary to target sites including SEQ ID NOs: 5-84 provide gRNA targeting sequences to target these sites.

Any nucleic acid that encodes a selected antibody construct as described herein may be utilized. Variants of nucleic acid sequences disclosed herein include various sequence polymorphisms, mutations, and alterations wherein the differences in the sequence do not substantially affect the function of the encoded protein. The term nucleic acid or "gene" may include not only coding sequences but also regulatory regions such as promoters, enhancers, and termination regions. The term further can include all introns and other DNA sequences spliced from the mRNA transcript, along with variants resulting from alternative splice sites. Encoding nucleic acid can be DNA or RNA that directs the expression of the one or more selected antibody constructs. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Nucleic acid sequences encoding selected antibody constructs can be readily prepared from the relevant amino acid sequence of a selected antibody construct.

"Variants" of protein sequences include those having one or more amino acid additions, deletions, stop positions, or substitutions, as compared to a protein sequence disclosed elsewhere herein.

An amino acid substitution can be a conservative or a non-conservative substitution. Variants of protein sequence disclosed herein can include those having one or more conservative amino acid substitutions. A "conservative substitution" or "conservative amino acid substitution" involves a substitution found in one of the following conservative substitutions groups: Group 1: A, G, S, T; Group 2: D, E; Group 3: N, Q; Group 4: R, K, H; Group 5: I, L, M, V; and Group 6: F, Y, W.

Additionally, amino acids can be grouped into conservative substitution groups by similar function, chemical structure, or composition (e.g., acidic, basic, aliphatic, aromatic, or sulfur-containing). For example, an aliphatic grouping may include, for purposes of substitution, G, A, V, L, and I. Other groups including amino acids that are considered conservative substitutions for one another include: sulfur-containing: M and C; acidic: D, E, N, and Q; small aliphatic, nonpolar or slightly polar residues: A, S, T, P, and G; polar, negatively charged residues and their amides: D, N, E, and Q; polar, positively charged residues: H, R, and K; large aliphatic, nonpolar residues: M, L, I, V, and C; and large aromatic residues: F, Y, and W.

Non-conservative substitutions include those that significantly affect: the structure of the peptide backbone in the area of the alteration (e.g., the alpha-helical or beta-sheet structure); the charge or hydrophobicity of the molecule at the target site; or the bulk of the side chain. Non-conservative substitutions which in general are expected to produce the greatest changes in the protein's properties are those in which (i) a hydrophilic residue (e.g. S or T) can be substituted for (or by) a hydrophobic residue (e.g. L, I, F, V, or A);

(ii) a C or P can be substituted for (or by) any other residue; (iii) a residue having an electropositive side chain (e.g. K, R, or H) can be substituted for (or by) an electronegative residue (e.g. Q or D); or (iv) a residue having a bulky side chain (e.g. F), can be substituted for (or by) one not having a bulky side chain, (e.g. G). Additional information is found in Creighton (1984) Proteins, W.H. Freeman and Company.

Variants of nucleic acid and protein sequences disclosed herein also include sequences with at least 70% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to a reference sequence disclosed herein.

"Percent (%) sequence identity" with respect to the sequences identified herein is defined as the percentage of nucleic acid or amino acid residues in a candidate sequence that are identical with the nucleic acid or amino acid residues in a reference sequence after aligning the sequences and introducing gaps, if necessary, to achieve the maximum percent sequence identity. Alignment for purposes of determining percent nucleic acid or amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, % sequence identity values generated using the WU-BLAST-2 computer program (Altschul et al., Methods in Enzymology, 266:460-480 (1996)) uses several search parameters, most of which are set to the default values. Those that are not set to default values (i.e., the adjustable parameters) are set with the following values: overlap span=1, overlap fraction=0.125, word threshold (T)=11 and scoring matrix BLOSUM62.

Variants will typically exhibit the same qualitative biological activity and elicit a substantially similar biological response as a reference nucleic acid or peptide sequence, although variants can be selected to modify the characteristics of a reference nucleic acid or peptide as needed. Screening of variants can be performed using experimental protocols described herein.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in B cell expression of a selected antibody.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A genetic construct comprising or encoding (i) a heavy chain promoter, (ii) a signal peptide, (iii) a full-length light chain of a selected antibody; (iv) a flexible linker or a skipping element; (v) a variable region of a heavy chain of the selected antibody; and (vi) a splice junction comprising the sequence CAGGTAAGT or CAGGTGAGT and 40-80 base pairs of the intron following the last exon of a variable-diversity-joining (VDJ).

2. The genetic construct of claim 1, wherein the flexible linker is between the full-length light chain of the selected antibody and the variable region of the heavy chain of the selected antibody.

3. The genetic construct of claim 1, wherein the flexible linker is encoded by the nucleotide sequence as set forth in SEQ ID NO: 116; has the amino acid sequence as set forth in one of SEQ ID NOs: 122, 180-184; and/or is a Gly-Ser linker comprising 50-80 amino acids.

4. The genetic construct of claim 1, wherein the skipping element is between the full-length light chain of the selected antibody and the variable region of the heavy chain of the selected antibody.

5. The genetic construct of claim 1, wherein the skipping element comprises an internal ribosome entry site (IRES) or a self-cleaving peptide having the sequence as set forth in SEQ ID NOs: 176, 177, 178, or 179.

6. The genetic construct of claim 1, wherein the heavy chain promoter is IgVH1-69 or J558H10.

7. The genetic construct of claim 1, wherein the signal peptide is selected from the sequence as set forth in one of SEQ ID NOs: 118, 134, and 185-194.

8. The genetic construct of claim 1, wherein the signal peptide is a signal peptide of a human IgH heavy chain or a human IgL light chain.

9. The genetic construct of claim 1, wherein the genetic construct further comprises homology arms.

10. The genetic construct of claim 9, wherein the homology arms have the sequence as set forth in SEQ ID NO: 90-101, 110, 125, 127, 140, 142, 143, 153, 170, 171, 173, 174, 278, or 279.

11. The genetic construct of claim 1, wherein the genetic construct further encodes a tag having the sequence as set forth in SEQ ID NOs: 122, 195, 196, 197, 198, 199, 200, 201, 202, 203, or 204.

12. The genetic construct of claim 1, wherein the selected antibody is an anti-RSV antibody comprising
  (a) a variable heavy chain comprising the sequence as set forth in SEQ ID NO: 138 and a variable light chain comprising the sequence as set forth in SEQ ID NO: 136,
  (b) a variable heavy chain comprising the sequence as set forth in SEQ ID NO: 138 and a variable light chain comprising the sequence as set forth in SEQ ID NO: 205,
  (c) a variable heavy chain comprising the sequence as set forth in SEQ ID NO: 123 and a light chain comprising the sequence as set forth in SEQ ID NO: 120, or
  (d) a variable heavy chain comprising the sequence as set forth in SEQ ID NO: 123 and a variable light chain comprising the sequence as set forth in SEQ ID NO: 206;

an anti-human immunodeficiency virus (HIV) antibody comprising a variable heavy chain comprising the sequence as set forth in SEQ ID NO: 150 and a variable light chain comprising the sequence as set forth in SEQ ID NO: 149;

an anti-pertussis antibody comprising a variable heavy chain comprising the sequence as set forth in SEQ ID NO: 235 and a variable light chain comprising the sequence as set forth in SEQ ID NO: 236;

an anti-influenza virus antibody comprising a variable heavy chain comprising the sequence as set forth in SEQ ID NO: 159 and a variable light chain comprising the sequence as set forth in SEQ ID NO: 158;

anti-Epstein Barr virus (EBV) antibody comprising a variable heavy chain comprising the sequence as set forth in SEQ ID NO: 168 and a variable light chain comprising the sequence as set forth in SEQ ID NO: 166; or an anti-tumor necrosis factor (TNF) antibody comprising a variable heavy chain comprising the sequence as set forth in SEQ ID NO: 254 and a variable light chain comprising the sequence as set forth in SEQ ID NO: 255.

13. A kit comprising a genetic construct of claim 1 and a gRNA that binds a genomic region comprising SEQ ID NO: 1, SEQ ID NO: 2, SEQ ID NO: 3, or SEQ ID NO: 4.

14. The kit of claim 13, wherein the gRNA has the sequence as set forth in SEQ ID NO: 88, 89, 290, 291, 292, 293, 294, 295, 296, 297, 298, 299, 300, 301, 302, 303, 304, 305, 306, or 307 when the genomic region comprises SEQ ID NO: 1;

SEQ ID NO: 308, 309, 310, 311, 312, 313, 314, 315, 316, 317, 318, 319, 320, 321, 322, 323, 324, 325, 326, or 327 when the genomic region comprises SEQ ID NO: 2;

SEQ ID NO: 87, 328, 329, 330, 331, 332, 333, 334, 335, 336, 337, 338, 339, 340, 341, 342, 343, 344, 345, or 346 when the genomic region comprises SEQ ID NO: 3; or SEQ ID NO: 347, 348, 349, 350, 351, 352, 353, 354, 355, 356, 357, 358, 359, 360, 361, 362, 363, 364, 365, or 366 when the genomic region comprises SEQ ID NO: 4.

15. The kit of claim 13, further comprising a nuclease.

16. The kit of claim 15, wherein the nuclease is Cas9 or Cpf1.

17. The kit of claim 13, further comprising a nanoparticle or adeno-associated viral vector.

18. The kit of claim 15, wherein the gRNA and nuclease are associated with a nanoparticle and the genetic construct is part of an adeno-associated viral vector.

19. Am isolated B cell comprising the genetic construct of claim 1, wherein the genetic construct is inserted into a genomic region having the sequence of SEQ ID NO: 1, SEQ ID NO: 2, SEQ ID NO: 3, or SEQ ID NO: 4.

20. The B cell of claim 19, wherein the B cell is an antibody-secreting B cell, a memory B cell, a naïve B cell, a B1 B cell or a marginal zone B cell.

* * * * *